(12) United States Patent
Crowne et al.

(10) Patent No.: US 12,427,185 B2
(45) Date of Patent: Sep. 30, 2025

(54) FORMULATIONS OF MANP AND USES THEREOF

(71) Applicant: E-Star Biotech, LLC, New York, NY (US)

(72) Inventors: Jesse Crowne, Salt Lake City, UT (US); Elizabeth John, Richland, WA (US); Mark C. Manning, Johnstown, CO (US); Robert W. Payne, Fort Collins, CO (US)

(73) Assignee: E-Star Biotech, LLC, New York, NY (US)

( * ) Notice: Subject to any disclaimer, the term of this patent is extended or adjusted under 35 U.S.C. 154(b) by 0 days.

(21) Appl. No.: 18/824,445

(22) Filed: Sep. 4, 2024

(65) Prior Publication Data

US 2025/0073310 A1 Mar. 6, 2025

Related U.S. Application Data

(60) Provisional application No. 63/588,186, filed on Oct. 5, 2023, provisional application No. 63/580,623, filed on Sep. 5, 2023.

(51) Int. Cl.

| *A61K 38/22* | (2006.01) |
| *A61K 9/19* | (2006.01) |
| *A61K 47/12* | (2006.01) |
| *A61K 47/26* | (2006.01) |
| *A61P 9/12* | (2006.01) |

(52) U.S. Cl.
CPC ............ *A61K 38/2242* (2013.01); *A61K 9/19* (2013.01); *A61K 47/12* (2013.01); *A61K 47/26* (2013.01); *A61P 9/12* (2018.01)

(58) Field of Classification Search
None
See application file for complete search history.

(56) References Cited

U.S. PATENT DOCUMENTS

| 4,034,074 A | 7/1977 | Miles |
| 4,098,876 A | 7/1978 | Piasio et al. |
| 4,161,521 A | 7/1979 | Veber et al. |
| 4,233,402 A | 11/1980 | Maggio et al. |
| 4,683,195 A | 7/1987 | Mullis et al. |
| 4,728,721 A | 3/1988 | Yamamoto et al. |
| 4,757,048 A | 7/1988 | Lewicki et al. |
| 4,935,492 A | 6/1990 | Lewicki et al. |
| 4,938,763 A | 7/1990 | Dunn et al. |
| 5,226,325 A | 7/1993 | Komurasaki et al. |
| 5,278,201 A | 1/1994 | Dunn et al. |
| 5,278,202 A | 1/1994 | Dunn et al. |
| 5,296,347 A | 3/1994 | LaMotte, III |
| 5,410,016 A | 4/1995 | Hubbell et al. |
| 5,501,863 A | 3/1996 | Rössling et al. |
| 5,529,914 A | 6/1996 | Hubbell et al. |
| 5,580,859 A | 12/1996 | Felgner et al. |
| 5,589,466 A | 12/1996 | Felgner et al. |
| 5,691,310 A | 11/1997 | Vesely |
| 5,698,213 A | 12/1997 | Jamiolkowski et al. |
| 6,013,630 A | 1/2000 | Shimkets |
| 6,165,458 A | 12/2000 | Foldvari et al. |
| 6,312,679 B1 | 11/2001 | Tomalia et al. |
| 6,407,211 B1 | 6/2002 | Burnett, Jr. et al. |
| 6,410,044 B1 | 6/2002 | Chudzik et al. |
| 6,818,619 B2 | 11/2004 | Burnett, Jr. et al. |
| 6,833,447 B1 | 12/2004 | Goldman et al. |
| 7,022,673 B2 | 4/2006 | Drummond et al. |
| 7,026,293 B2 | 4/2006 | Kitakaze |
| 7,276,481 B2 | 10/2007 | Golembo et al. |
| 7,345,142 B2 | 3/2008 | Cohen et al. |
| 7,384,917 B2 | 6/2008 | Burnett, Jr. et al. |
| 7,754,852 B2 | 7/2010 | Burnett, Jr. et al. |
| 7,795,221 B2 | 9/2010 | Sharma et al. |
| 7,803,901 B2 | 9/2010 | Burnett, Jr. et al. |
| 7,964,564 B2 | 6/2011 | Burnett, Jr. et al. |
| 8,063,191 B2 | 11/2011 | Burnett, Jr. et al. |
| 8,198,242 B2 | 6/2012 | Wendt et al. |
| 8,283,318 B2 | 10/2012 | Chen et al. |
| 8,324,162 B2 | 12/2012 | Simari et al. |
| 8,357,656 B2 | 1/2013 | Simari et al. |
| 8,455,438 B2 | 6/2013 | Burnett, Jr. et al. |
| 8,530,422 B2 | 9/2013 | Chen et al. |
| 8,642,550 B2 | 2/2014 | Dickey et al. |

(Continued)

FOREIGN PATENT DOCUMENTS

| EP | 0 045 665 A1 | 2/1982 |
| JP | 5031964 B2 | 9/2012 |

(Continued)

OTHER PUBLICATIONS

Carey et al., JAMA 328:1849-1861 (2022) (Year: 2022).*
Kamerzell et al., Adv. Drug Delivery Rev. 63:1118-1159 (2011) (Year: 2011).*
Chi, EY, "Excipients and their Effects on the Quality of Biologics," VA, USA: American Association of Pharmaceutical Scientists. FDD Tech Corner (2012) (Year: 2012).*
Antalfy et al., Adv. Ther. 40:4758-4776 (Sep. 2023) (Year: 2023).*
Ahn et al., "MondoA coordinately regulates skeletal myocyte lipid homeostasis and Insulin signaling," *The Journal of Clinical Investigation*, 126(9):3567-3579 (Sep. 2016).

(Continued)

*Primary Examiner* — Thea D'Ambrosio
(74) *Attorney, Agent, or Firm* — Arnold & Porter Kaye Scholer LLP

(57) ABSTRACT

The present disclosure provides for, and includes, pharmaceutical formulations comprising an MANP peptide, methods of preparing such formulations, and uses of such formulations in the treatment of diseases and conditions for which use of the peptide contained in such formulations is indicated. The present disclosure further provides for, and includes, methods for increasing the stability by a peptide formulation and for reducing aggregation during production of a peptide formulation.

39 Claims, 53 Drawing Sheets
Specification includes a Sequence Listing.

(56) References Cited

U.S. PATENT DOCUMENTS

| | | | |
|---|---|---|---|
| 8,741,842 | B2 | 6/2014 | Burnett, Jr. et al. |
| 8,835,601 | B2 | 9/2014 | Chen et al. |
| 9,079,973 | B2 | 7/2015 | Burnett, Jr. et al. |
| 9,102,707 | B2 | 8/2015 | Lee et al. |
| 9,102,757 | B2 | 8/2015 | Chen et al. |
| 9,193,777 | B2 | 11/2015 | Burnett, Jr. et al. |
| 9,857,382 | B2 | 1/2018 | Sangaralingham et al. |
| 11,628,217 | B2 | 4/2023 | Demopulos et al. |
| 2004/0086976 | A1 | 5/2004 | Fleer et al. |
| 2007/0042957 | A1 | 2/2007 | Burnett et al. |
| 2009/0163421 | A1* | 6/2009 | Gupta ............... A61P 9/04 514/1.1 |
| 2010/0266704 | A1 | 10/2010 | Ahlheim et al. |
| 2011/0152194 | A1 | 6/2011 | Burnett, Jr. et al. |
| 2011/0223230 | A1 | 9/2011 | Hersel et al. |
| 2012/0010142 | A1 | 1/2012 | Burnett, Jr. et al. |
| 2012/0053123 | A1 | 3/2012 | Burnett, Jr. et al. |
| 2012/0108514 | A1 | 5/2012 | Burnett, Jr. et al. |
| 2012/0277155 | A1 | 11/2012 | VanAntwerp et al. |
| 2013/0303454 | A1 | 11/2013 | Burnett, Jr. et al. |
| 2014/0005358 | A1 | 1/2014 | Lee et al. |
| 2014/0066367 | A1 | 3/2014 | Chen et al. |
| 2014/0274901 | A1 | 9/2014 | Ichiki et al. |
| 2017/0020899 | A1 | 1/2017 | Geimer |
| 2018/0369341 | A1 | 12/2018 | Chang et al. |
| 2021/0139555 | A1 | 5/2021 | Mayer-Bartschmid et al. |
| 2022/0118054 | A1 | 4/2022 | Burnett, Jr. et al. |

FOREIGN PATENT DOCUMENTS

| | | |
|---|---|---|
| MX | 302200 | 9/2012 |
| WO | WO 93/16687 A1 | 9/1993 |
| WO | WO 98/20165 A2 | 5/1998 |
| WO | WO 99/57318 A2 | 11/1999 |
| WO | WO 2004/047871 A2 | 6/2004 |
| WO | WO 2004/071736 A2 | 8/2004 |
| WO | WO 2006/017852 A2 | 2/2006 |
| WO | WO 2007/035600 A2 | 3/2007 |
| WO | WO 2008/061355 A1 | 5/2008 |
| WO | WO 2009/086126 A2 | 7/2009 |
| WO | WO 2011/005939 A2 | 1/2011 |
| WO | WO 2012/058585 A2 | 5/2012 |
| WO | WO 2013/041591 A1 | 3/2013 |
| WO | WO 2013/103896 A1 | 7/2013 |
| WO | WO 2016/077143 A1 | 5/2016 |
| WO | WO 2018/089601 A1 | 5/2018 |
| WO | WO 2020/097421 A1 | 5/2020 |
| WO | WO 2024/030615 A1 | 2/2024 |
| WO | WO 2024/178072 A1 | 8/2024 |

OTHER PUBLICATIONS

Allen et al., "Management of acute decompensated heart failure," *Can Med Assoc J*, 176(6):797-805 (Mar. 13, 2007).

Almquist et al., "Synthesis and Biological Activity of a Ketomethylene Analogue of a Tripeptide Inhibitor of Angiotensin Converting Enzyme," *J. Med. Chem.*, 23(12):1392-1398 (1980).

Arora et al., "Atrial natriuretic peptide is negatively regulated by microRNA-425," *The Journal of Clinical Investigation*, 123(8):3378-3382 (Aug. 2013).

Australian Examination Report dated May 17, 2024 in Australian Patent Application No. 2019375988, 6 pages.

Ausubel et al., "Mutagenesis of Cloned DNA," *Short Protocols in Molecular Biology*. Green Publishing Associates and John Wiley & Sons, Chapter 8, pp. 8-1 to 8-25, 1992.

Bailey et al., "Novel Use of Kaplan-Meier Methods to Explain Age and Gender Differences in Hypertension Control Rates," *Hypertension*, 51(4):841-847 (Apr. 2008).

Bailey, "Detecting Fabrication of Data in a Multicenter Collaborative Animal Study," *Controlled Clinical Trials*, 12(6):741-752 (Dec. 1991).

Bailey, "Generalizing the Results of Randomized Clinical Trials," *Controlled Clinical Trials*, 15(1):15-23 (Feb. 1994).

Bailey, "Inter-Study Differences: How Should They Influence the Interpretation and Analysis of Results?," Statistical in Medicine, 6(3):351-358 (Apr./May 1987).

Banga, "Theme Section: Transdermal Delivery of Proteins," *Pharmaceutical Research*, 24(7): 1357-1359 (Jul. 2007).

Bestle et al., "Cardiovascular, endocrine, and renal effects of urodilatin in normal humans," *Am J Physiol.*, 276(3):R684-R695 (Mar. 1999).

Bild et al., "Multi-Ethnic Study of Atherosclerosis: Objectives and Design," *American Journal Epidemiology*, 156(9):871-881 (Nov. 2002).

Bloch et al., "A serum protease cleaves proANF into a 14-kilodalton peptide and ANF," *Am J Physiol.*, 252(1 Pt 1):E147-E151 (Jan. 1987).

Blood Pressure UK, "Diuretics - blood pressure medication," Blood Pressure UK [online], 2008, [retrieved on Nov. 6, 2013]. Retrieved from the Internet: <URL: http://www.bloodpressureuk.org/BloodPressureandyou/Medicines/Medicinetypes/Diuretics>, 4 pages.

Boerrigter et al., "Targeting Heme-Oxidized Soluble Guanylate Cyclase in Experimental Heart Failure," *Hypertension*, 49(5):1128-1133 (May 2007).

Bowie et al., "Deciphering the Message in Protein Sequences: Tolerance to Amino Acid Substitutions," *Science*, 247(4948):1306-1310 (1990).

Braunwald, "Shattuck Lecture: Cardiovascular Medicine at the Turn of the Millennium: Triumphs, Concerns and Opportunities," *The New England Journal of Medicine*, 337(19):1360-1369 (Nov. 1997).

Brugada et al., "Identification of a Genetic Locus for Familial Atrial Fibrillation," *The New England Journal of Medicine*, 336(13):905-911 (Mar. 1997).

Buglioni et al., "Aldosterone Predicts Cardiovascular, Renal and Metabolic Disease in the General Community: A 4-Year Follow-Up," *Journal of the American Heart Association*, 4(12):e002505 (Dec. 2015).

Buglioni et al., "Circulating Aldosterone and Natriuretic Peptides in the General Community: Relationship to Cardiorenal and Metabolic Disease," *Hypertension*, 65(1):45-53 (Jan. 2015).

Buglioni et al., "New Pharmacological Strategies to Increase cGMP," *Annu. Rev. Med.*, 67:229-243 (Jan. 2016).

Buglioni et al., "Structural insights into C-terminus and N-terminus of a designer cGMP activating ANP-based antihypertensive peptide: ZD100," Abstract presented at American Heart Association Meeting Nov. 2016, 1 page, Available on or after Nov. 11, 2016.

Burnett, Jr. et al., "Atrial Natriuretic Peptide Elevation in Congestive Heart Failure in the Human," *Science*, 231:1145-1147 (Mar. 1986).

Burnett, Jr., "Vasopeptidase inhibition," *Current Opinion in Nephrology and Hypertension*, 9(5):465-468 (Sep. 2000).

Burnett, Jr., et al., "MANP: A Novel Particulate Guanylyl Cyclase A Receptor/cGMP Activator for Resistant Hypertension: Preliminary First in Human Clinical Trial Results," BMC Pharmacology & Toxicology, 16(Suppl.1):A3, 2pp. (2015).

Calhoun et al., "Resistant Hypertension: Diagnosis, Evaluation, and Treatment: A Scientific Statement from the American Heart Association Professional Education Committee of the Council for High Blood Pressure Research," *Circulation*, 117(25):e510-e526 (Jun. 2008).

Calhoun, "Aldosteronism and Hypertension," *Clin. J. Am. Soc. Nephrology*, 1(5):1039-1045 (Sep. 2006).

Campese et al., "Salt Intake and Plasma Atrial Natriuretic Peptide and Nitric Oxide in Hypertension," *Hypertension*, 28(3):335-340 (Sep. 1996).

Cannone et al., "A genetic variant of the atrial natriuretic peptide gene is associated with cardiometabolic protection in the general community," *J Am Coll Cardiol.*, 58(6):629-636 (Aug. 2011).

Cannone et al., "Atrial natriuretic peptide genetic variant rs5065 and risk for cardiovascular disease in the general community: a 9-year follow-up study," *Hypertension*, 62(5):860-865 (Nov. 2013).

Cannone et al., "MANP: A Novel Designer Natriuretic Peptide for Cardiometabolic Disease," *J. Card. Failure*, 18(8S):019, 1 pp. (Aug. 2012).

(56) References Cited

OTHER PUBLICATIONS

Cannone et al., "The ANP genetic variant Rs5068 and circulating levels of natriuretic peptides in patients with chronic heart failure," *Int. J. Cardiology*, 176(3):1249-1251 (Oct. 2014).
Cannone et al., "The atrial natriuretic peptide genetic variant rs5068 is associated with a favorable cardiometabolic phenotype in a Mediterranean population," *Diabetes Care.*, 36(9):2850-2856 (Sep. 2013).
Carstens et al., "Metabolism and action of urodilatin infusion in healthy volunteers," *Clinical Pharmacology & Therapeutics*, 64(1):73-86 (Jul. 1998).
Cataliotti et al., "Chronic actions of a novel oral B-type natriuretic peptide conjugate in normal dogs and acute actions in angiotensin II-mediated hypertension," *Circulation*, 118:1729-1736 (Oct. 2008).
Cataliotti et al., "Long-term cardiac pro-B-type natriuretic peptide gene delivery prevents the development of hypertensive heart disease in spontaneously hypertensive rats," *Circulation*, 123(12):1297-1305 (Mar. 2011).
Cataliotti et al., "Oral Brain Natriuretic Peptide: A Novel Strategy for Chronic Protein Therapy for Cardiovascular Disease," *Trends Cardiovasc. Med.*, 17:10-14 (Nov. 2007).
Chaurand et al., "Peptide and Protein Identification by Matrix-Assisted Laser Desorption Ionization (MALDI) and MALDI-Post-Source Decay Time-of-Flight Mass Spectrometry," *J. Am. Soc. Mass Spectrom.*, 10:91-103 (Sep. 1999).
Chen et al., "A first-in-human trial of a novel designer natriuretic peptide ZD100 in human hypertension," *J. Am. Coll. Cardiol.*, 67(13):1946 (Apr. 2016).
Chen et al., "Biochemistry, therapeutics, and biomarkers implications of neprilysin cardiorenal disease," *Clinical Chemistry*, 63(1):108-115 (Jan. 2017).
Chen et al., "Equimolar doses of atrial and brain natriuretic peptides and urodilatin have differential renal actions in overt experimental heart failure," *Am J Physiol Regul Integr Comp. Physiol.*, 288(5):R1093-R1097, Epub Dec. 30, 2004.
Chen et al., "First-in-Human Study of MANP: A Novel ANP (Atrial Natriuretic Peptide) Analog in Human Hypertension," *Hypertension*, 78:1859-1867 (Dec. 2021).
Chen et al., "KCNQ1 Gain-of-function mutation in familial atrial fibrillation," *Science*, 299:251-254 (Jan. 2003).
Chen et al., "Local renal delivery of a natriuretic peptide a renal-enhancing strategy for B-type natriuretic peptide in overt experimental heart failure," *J Am Coll Cardiol.*, 53(15):1302-1308 (Apr. 2009).
Chen et al., "Subcutaneous administration of brain natriuretic peptide in experimental heart failure," *J Am Coll Cardiol.*, 36(5):1706-1712 (Nov. 2000).
Chen et al., "Subcutaneous BNP administration in symptomatic human heart failure: a novel therapeutic strategy for congestive heart failure," *J Am Coll Cardiol.*, 35(2sl):240A, 1 page (Feb. 2000).
Cheng et al., "Temporal analysis of signaling pathways activated in a murine model of two-Kidney, one- Clip hypertension," *Am. J. Physiol. Renal. Physiology*, 297(4):F1055-F1068 (Oct. 2009).
Cole et al., "The EBV-Hybridoma Technique and its application to human lung cancer," *Monoclonal Antibodies and Cancer Therapy*, pp. 77-96 (1985).
Costello-Boerrigter et al., "Renal and anti-aldosterone actions of vasopressin-2 receptor antagonism and B-type natriuretic peptide in experimental heart failure," *Circ Heart Fail.*, 3(3):412-419 (May 2010).
Cote et al., "Generation of human monoclonal antibodies reactive with cellular antigens," *Proc. Natl. Acad. Sci. USA*, 80:2026-2030 (Apr. 1983).
Darbar et al., "Familial atrial fibrillation is a genetically heterogeneous disorder," *J. Am. Coll. Cardiol.*, 41(12):2185-2192 (Jun. 2003).
Davidov et al., "Antihypertensive Properties of Furosemide," *Circulation*, vol. 36, pp. 125-135 (Jul. 1967).

De Bold et al., "A rapid and potent natriuretic response to intravenous injection of atrial myocardial extract in rats," *Life Sci.*, 28(1):89-94 (Jan. 1981).
De Bold, "Atrial natriuretic factor of the rat heart. Studies on isolation and properties," *Proc Soc Exo Biol Med.*, 170(2):133-138 (Jun. 1982).
De Palo et al., "Circulating immunoreactive proANP(1-30) and proANP(31-67) in sedentary subjects and athletes," *Clin. Chem.*, 46(6 Pt. 1):843-847 (Jun. 2000).
Deckard et al., "Therapeutic hypothermia after cardiac arrest: What, why, who, and how," American Nurse Today, 6(7):23-28 (Jul. 2011).
Dickey et al., "A familial mutation renders atrial natriuretic peptide resistant to proteolytic degradation," *J. Biol. Chem.*, 284:19196-19202 (Jul. 2009).
Dietz et al., "Evidence supporting a physiological role for proANP-(1-30) in the regulation of renal excretion," *Am J Physiol Regulatory Integrative Comp Physiol.*, 280(5):R1510-R1517 (May 2001).
Dietz, "Mechanisms of atrial natriuretic peptide secretion from the atrium," *Cardiovasc Res.*, 68(1):8-17 (Oct. 2005).
Dong et al., "Plasma soluble corin in patients with heart failure," *Circ. Heart Failure*, 3(2):207-211 (Mar. 2010).
Dzhoyashvili et al., "Abstract 14450: Challenging Hypertension: M-Atrial Natriuretic Peptide Enhances Antihypertensive Actions of Furosemide and Attenuates the Activation of Aldosterone," *Circulation*, 138(S1):A14450, 5 pages (Nov. 2018).
Dzhoyashvili et al., "Challenging Hypertension: M-atrial Natriuretic Peptide Enhances Antihypertensive Actions of Furosemide and Attenuates the Activation of Aldosterone," Poster, Presented at Proceedings of the American Heart Association Scientific Sessions, Chicago, IL, USA, Nov. 10-12, 2018, 1 page.
Eirin et al., "A mitochondrial permeability transition pore inhibitor improves renal outcomes after revascularization in experimental atherosclerotic renal artery stenosis," *Hypertension*, 60(5):1242-1249 (Nov. 2012).
Eirin et al., "Adipose tissue-derived mesenchymal stem cells improve revascularization outcomes to restore renal function in swine atherosclerotic renal artery stenosis," *Stem Cells*, 30(5):1030-1041 (May 2012).
Eirin et al., "Inflammatory and injury signals released from the post-stenotic human kidney," *Eur. Heart Journal*, 34(7):540-548a (Feb. 2013).
Eirin et al., "Renal vein cytokine release as an index of renal parenchymal inflammation in chronic experimental renal artery stenosis," *Nephrol. Dial. Transplantation*, 29(2):274-282 (Feb. 2014).
Elsner et al., "Efficacy of prolonged infusion of urodilatin [ANP-(95-126)] in patients with congestive heart failure," *Am Heart J.*, 129(4):766-773 (Apr. 1995).
Espiner et al., "Atrial natriuretic peptide: An Important Factor in Sodium and Blood Pressure Regulation," Lancet, 1(8640):707-710 (Apr. 1989).
European Supplementary Search Report dated Jun. 28, 2022, in EP Application No. 19881216.6, 7 pages.
Extended European Search Report in European Application No. 17870165.2 dated May 29, 2020, 7 pages.
Fenelon et al., "Examination of the In Vivo Cardiac Electrophysiological Effects of Nesiritide (Human Brain Natriuretic Peptide) in Conscious Dogs," *J. Cardiac Failure*, 8(5):320-325 (2002).
Fonarow et al., "Factors identified as precipitating hospital admissions for heart failure and clinical outcomes: findings from OPTIMIZE-HF," *Arch Intern Med.*, 168(8):847-854 (Apr. 2008).
Forssmann et al., "The renal urodilatin system: clinical implications," *Cardiovasc Res.*, 51(3):450-462 (Aug. 2001).
Fox et al., "Association of plasma B-type natriuretic peptide concentrations with longitudinal blood pressure tracking in African Americans: findings from the Jackson Heart Study," *Hypertension*, 61(1):48-54 (Jan. 2013).
Fox et al., "Parental atrial fibrillation as a risk factor for atrial fibrillation in offspring," *JAMA*, 291(23):2851-2855 (Jun. 2004).
Freitag et al., "Plasma brain natriuretic peptide levels and blood pressure tracking in the Framingham Heart Study," *Hypertension*, 41(4):978-983 (Apr. 2003).

(56) References Cited

OTHER PUBLICATIONS

From et al., "Relationship between low bone mineral density and exercise-induced myocardial ischemia," *Mayo Clin. Proceedings*, 82(6):679-685 (Jun. 2007).
Fuhr et al., "A simple colorimetrical method for inuline determination for nieral clearance examinations in substance changing healths and diabetics," *Klin. Wochenschrift*, 33(29-30):729-730, Aug. 1955 (with English Translation).
Funder et al., "Aldosterone: a cardiovascular risk factor?" *Biochimica et Biophysica Acta.*, 1802(12):1188-1192 (2010).
"Furosemide", Drugs.com accessed Oct. 21, 2024 at URL ttps:/web.archive.org/web/20140903053410/http://www.drugs com/monograph/furosemide html?printable=1, (2014).
Gaddam et al., "Aldosterone and Cardiovascular Disease," *Curr Probl Cardiol.*, 34(2):51-84 (Feb. 2009).
Garbers et al., "Membrane guanylyl cyclase receptors: an update," *Trends Endocrinol Metab.*, 17(6):251-258 (Epub Jun. 30, 2006).
GenBank Accession No. BC005893, "*Homo sapiens* natriuretic peptide precursor A, mRNA (cDNA clone MGC:14467 Image:4273949), complete cds," dated Jul. 15, 2006, 3 pgs.
GenBank Entry AJ712145 CMPD01 Homo sapiens cDNA clone CMPD10397, mRNA sequence-database entry date Jun. 30, 2004.
Gevaert et al., "Protein identification based on matrix assisted laser desorption/ionization-post source decay-mass spectrometry," *Electrophoresis*, 22:1645-1651 (2001).
Gloviczki et al., "Blood oxygen level-dependent magnetic resonance imaging identifies cortical hypoxia in severe renovascular disease," *Hypertension*, 58(6):1066-1072 (Dec. 2011).
Gloviczki et al., "Comparison of 1.5 and 3 T BOLD MR to study oxygenation of kidney cortex and medulla in human renovascular disease," *Invest. Radiology*, 44(9):566-571 (Sep. 2009).
Gloviczki et al., "TGF expression and macrophage accumulation in atherosclerotic renal artery stenosis," *Clin. J. Am. Soc. Nephrology*, 8(4):546-553 (Apr. 2013).
Goebel et al., "Dermal Peptide Delivery Using Colloidal Carrier Systems," *Skin Pharmacol. Physiol.*, 21:3-9 (2008).
Gollob et al., "Somatic Mutations in the Connexin 40 Gene (GJA5) in Atrial Fibrillation," *N. Engl. J. Med.*, 354:2677-2688 (Jun. 2006).
Graves et al., "Limited (6-h) ambulatory blood pressure monitoring is a valid replacement for the office blood pressure by trained nurse clinician in the diagnosis of hypertension," *Blood Press Monitoring*, 10(4):169-174 (Aug. 2005).
Guatelli et al., "Isothermal, in vitro amplification of nucleic acids by a multienzyme reaction modeled after retroviral replication," *Proc. Natl. Acad. Sci. USA*, 87(5):1874-1878 (Mar. 1990).
Gudbjartsson et al., "Variants conferring risk of atrial fibrillation on chromosome 4q25," *Nature*, 448:353-357 (Jul. 2007).
Gupta et al., "Racial differences in circulating natriuretic peptide levels: The atherosclerosis risk in communities study," *J. Am. Heart Assoc.*, 4(5):e001831, 8 pages (May 2015).
Gupta et al., "Racial differences in natriuretic peptide levels: The Dallas Heart Study," *JACC Heart Failure*, 3(7):513-519 (Jul. 2015).
Hann et al., "On the Double Bond Isostere of the Peptide Bond: Preparation of an Enkephalin Analogue," *J. Chem. Soc. Perkin Trans.*, 1:307-314 (1982).
Hata et al., "Effects of carperitide on the long-term prognosis of patients with acute decompensated chronic heart failure: the PROTECT multicenter randomized controlled study," *Circulation Journal*, 72(11):1787-1793, (Nov. 2008).
Hawkridge et al., "Quantitative mass spectral evidence for the absence of circulating brain natriuretic peptide (BNP-32) in severe human heart failure," *Proc Natl Acad Sci USA.*, 102(48):17442-17447 (Nov. 2005).
Hershberger et al., "Probing the CXCR6/CXCL16 Axis: Targeting prevention of prostate cancer metastasis," *Probe Reports from the NIH Molecular Libraries Program* [Internet], Dec. 15, 2012, 24 pages.
Heublein et al., "Immunoreactivity and guanosine 3',5'-cyclic monophosphate activating actions of various molecular forms of human B-type natriuretic peptide," *Hypertension*, 49(5):1114-1119, Epub Mar. 19, 2007.
Hoare et al., "Single amino acid residue determinants of non-peptide antagonist binding to the corticotropin-releasing factor1 (CRF1) receptor," *Biochemical Pharmacology*, 72(2):244-255 (Jul. 2006).
Hodgson-Zingman et al., "Atrial natriuretic peptide frameshift mutation in familial atrial fibrillation," *N Engl J Med.*, 359(2):158-165 (Jul. 2008).
Holladay et al., "Synthesis of Hydroxyethylene and Ketomethylene Dipeptide Isosteres," *Tetrahedron Letters*, 24(41):4401-4404 (1983).
Hruby, "Conformational Restrictions of Biologically Active Peptides via Amino Acid Side Chain Groups," *Life Sci.*, 31(3):189-199 (1982).
Hudson et al., "Methionine Enkephalin and Isosteric Analogues," *Int. J. Pept. Prot. Res.*, 14:177-185 (1979).
Hunt et al., "Hypotension and bradycardia during caloric restriction in mice are independent of salt balance and do not require ANP receptor," *Am. J. Physiol. Heart Circ. Physiol.*, 287(4):H1446-H1451 (2004).
Hunter et al., "Measurement of the total proANP product in mammals by processing independent analysis," *J Immunol Methods.*, 370(1-2):104-110, (Jun. 2011).
Huntley et al., "Pro-B-type natriuretic peptide-1-108 processing and degradation in human heart failure," *Circ. Heart Failure*, 8(1):89-97 (Jan. 2015).
Huse et al., "Generation of a Large Combinatorial Library of the Immunoglobulin Repertoire in Phage Lambda," *Science*, 246:1275-1281 (Dec. 1989).
Hutcheon et al., "Diuretic and Antihypertensive Actions of Furosemide," *The Journal of Clinical Pharmacology*, 7(1):26-33 (Jan. 1967).
Ibebuogu et al., "Decompensated heart failure is associated with reduced corin levels and decreased cleavage of pro-atrial natriuretic peptide," *Circ Heart Fail.*, 4(2):114-120 (Mar. 2011).
Ichiki et al., "Protein therapeutics for cardiovascular disease: it is all about delivery," *J Am Coll Cardiol.*, 60(24):2558-2560, Epub Nov. 24, 2012.
Ichiki et al., "Abstract 11349: The natriuretic peptide prohormones are processed into active peptides in the normal human circulation and the processing is preserved in heart failure," *Circulation*, 126: A11349, 2012.
Ichiki et al., "All three NP pre/prohormones are processed in human blood into biologically active mature peptides," *16th Annual Scientific Meeting of Heart Failure Society of America*, Sep. 10, 2012 [slideshow].
Ichiki et al., "All three NP pre/prohormones are processed in human blood into biologically active mature peptides," *J Card Fail.*, 18(8):S3, Abstract 008 (Aug. 2012).
Ichiki et al., "Cardiac fibrosis in end-stage human heart failure and the cardiac natriuretic peptide guanylyl cyclase system: regulation and therapeutic implications," *J. Mol. Cell Cardiology*, 75:199-205 (Oct. 2014).
Ichiki et al., "Corin is present in the normal human heart, kidney, and blood, with pro-B-type natriuretic peptide processing in the circulation," *Clinical Chemistry*, 57(1):40-47 (2011).
Ichiki et al., "Differential expression of the pro-natriuretic peptide convertases corin and furin in experimental heart failure and atrial fibrosis," *Am J Physiol Regul Integr Comp Physiol.*, 304(2):R102-R109, Jan. 15, 2013.
Ichiki et al., "Pro-atrial natriuretic peptide in vitro and in vivo normal canines: A selective renal enhancing therapeutic," *17th Annual Scientific Meeting of the Heart Failure Society of America*, S27: Abstract 074, Orland FL, USA, Sep. 23, 2013, 1 page [abstract].
Ichiki et al., "Pro-Atrial Natriuretic Peptide: A Novel Guanylyl Cyclase-A Receptor Activator That Goes Beyond Atrial and B-Type Natriuretic Peptides," *JACC Heart Failure*, 3(9):715-723 (Sep. 2015).
Ichiki et al., "Pro-atrial natriuretic peptide1-126 is processed in the human circulation to a mature GC-A activating peptide with therapeutic potential in heart failure," *Eur Heart J.*, 34: doi: 10.1093/eurheartj/eht307.66, Aug. 31, 2013 [abstract].

(56) References Cited

OTHER PUBLICATIONS

Ichiki et al., "The natriuretic peptide prohormones are processed into active peptides in the normal human circulation and the processing is preserved in heart failure," *American Heart Association Scientific meeting*, Nov. 7, 2012, [poster], 1 page.
Ichiki et al., "The processing and degradation of preproANP in the circulation in normal human and patients with heart failure," *The 77th Annual Scientific Meeting of Japanese Circulation Society (JCS 2013)*, Yokohama, Japan, Mar. 16, 2013, 1 page.
International Preliminary Report on Patentability in International Application No. PCT/US2010/041339, dated Jan. 19, 2012, 7 pages.
International Preliminary Report on Patentability in International Application No. PCT/US2017/060808, dated May 23, 2019, 8 pages.
International Preliminary Report on Patentability in International Application No. PCT/US2019/060401, dated May 11, 2021, 6 pages.
International Search Report and Written Opinion dated Nov. 20, 2008, in International Application No. PCT/US2006/036227, 5 pages.
International Search Report and Written Opinion in International Application No. PCT/US2010/041339, dated Mar. 15, 2011, 11 pages.
International Search Report and Written Opinion in International Application No. PCT/US24/16662, mailed Jun. 6, 2024, 13 pages.
International Search Report and Written Opinion in International Application No. PCT/2017/060808, dated Mar. 26, 2018, 12 pages.
International Search Report and Written Opinion in International Application No. PCT/US2019/060401, dated Feb. 5, 2020, 9 pages.
International Search Report mailed Dec. 7, 2023, in International Application PCT/US2023/074449, 6 pages.
Jennings-White et al., "Synthesis of ketomethylene analogs of dipeptides," *Tetrahedron Letters*, 23(25):2533-2534 (Mar. 1982).
Jiang et al., "Ectodomain shedding and autocleavage of the cardiac membrane protease corin," *J Biol Chem.*, 286(12):10066-10072 (Mar. 2011).
Jordan et al., "Natriuretic Peptides in Cardiovascular and Metabolic Crosstalk," *Hypertension*, 72:270-276 (2018).
Kenny et al., "Role of endopeptidase-24.11 in the inactivation of atrial natriuretic peptide," *FEBS Letters*, 232(1):1-8 (May 1988).
Kenny et al., "Hydrolysis of human and pig brain natriuretic peptides, urodilatin, C-type natriuretic peptide and some C-receptor ligands by endopeptidase-24.11," *Biochem J.*, 291:83-88 (Apr. 1993).
Kerkela et al., "Natriuretic Peptides in the Regulation of Cardiovascular Physiology and Metabolic Events," *Journal of the American Heart Association*, Web, Oct. 27, 2015, pp. 1-13.
Kirby et al., "Assessment of drug-induced arrhythmic risk using limit cycle and autocorrelation analysis of human iPSC-cardiomyocyte contractility," *Toxicol. Appl. Pharmacology*, 305:250-258 (Aug. 2016).
Kohler et al., "Continuous cultures of fused cells secreting antibody of predefined specificity," *Nature*, 256:495-497 (1975).
Komatsu et al., "C-type natriuretic peptide (CNP) in rats and humans," *Endocrinol.*, 129(2):1104-1106 (Aug. 1991).
Kozbor et al., "The production of monoclonal antibodies from human lymphocytes," *Immunology Today*, 4(3):72-79 (1983).
Kuhn, "Structure, regulation, and function of mammalian membrane guanylyl cyclase receptors, with a focus on guanylyl cyclase-A," *Circ. Res.*, 93(8):700-709 (Oct. 2003).
Lambert et al., "The question of vertical or nonvertical participation of silicon beta to a cation in the antiperiplanar stereochemistry," *J. Am. Chem. Society*, 115(4):1317-1320 (Feb. 1993).
Lanier et al., "N-[6-Amino-2-(heteroaryl)pyrimidin-4-yl]acetamides as A2A Receptor Antagonists with Improved Drug Like Properties and in Vivo Efficacy," *J. Med. Chemistry*, 52(3):709-717 (Jan. 2009).
Lasix, package insert, Sanofi-furosemide tablet and injection, available at www.sanofi.in/dam/jcr:1e827e3a-a60a-40e7-8510-ad465f673631/Lasix_PI.pdf. pp. 1-9 (Sep. 2017).
Lebl et al., "Synthesis of Cyclic Peptides By Solid Phase Methodology", *Tetrahedron Letters*, 25(20):2067-2068 (1984).
Lee et al., "Cenderitide: Structural Requirements for the Creation of a Novel Dual Particulate Guanylyl Cyclase Receptor Agonist with Renal-Enhancing In Vivo And Ex Vivo Actions," *Eur. Heart J. Cardiovasc. Pharmacotherapy*, 2(2):98-105 (Apr. 2016).
Lee et al., "Pharmacodynamics of a novel designer natriuretic peptide, CD-NP, in a first-in-human clinical trial in healthy subjects," *J. Clin. Pharmacology*, 49(6):668-673 (Jun. 2009).
Lerman et al., "Animal Models of Hypertension: A Scientific Statement From the American Heart Association," *Hypertension*, 73(6):e87-e120 (Jun. 2019).
Leung et al., "An ultra high-throughput, whole-animal screen for small molecule modulators of a specific genetic pathway in Caenorhabditis elegans," *PLoS One*, 8(4):e62166, 12 pages (Apr. 2013).
Levin et al., "Natriuretic Peptides," *N. Engl. J. Med.*, 339(5):321-328 (1998).
Lewis, "PCR's Competitors Are Alive and Well and Moving Rapidly Towards Commercialization," *Genetic Engineering News*, 12(9):1, 3 pages (1992).
Lloyd-Jones et al., "Lifetime risk for development of atrial fibrillation: The framingham heart study," *Circulation*, 110(9):1042-1046 (Aug. 2004).
Luss et al., "Renal effects of ularitide in patients with decompensated heart failure," *Am Heart J.*, 155(6):1012.e1-8 (Jun. 2008).
Ma et al., "MANP in Hypertension With Metabolic Syndrome," *JACC: Basic To Translational Science*, 9(1):18-29 (Jan. 2024).
Macheret et al., "Human hypertension is characterized by a lack of activation of the antihypertensive cardiac hormones ANP and Bnp," *J. Am. Coll. Cardiology*, 60(16):1558-1565 (Oct. 2012).
Malany et al., "Analytical method for simultaneously measuring ex vivo drug receptor occupancy and dissociation rate: application to (R)-dimethindene occupancy of central histamine H1 receptors," *J. Recept. Signal Transduction*, 29(2):84-93 (Apr. 2009).
Malany et al., "Orientation of alpha-neurotoxin at the subunit interfaces of the nicotinic acetylcholine receptor," *Biochemistry*, 39(50):15388-15398 (Dec. 2000).
Malany et al., "Theoretical and experimental investigations of electrostatic effects on acetylcholinesterase catalysis and inhibition," *Chem. Biol. Interactions*, 119-120:99-110 (May 1999).
Malany et al., "Transition State Structure and Rate Determination for the Acylation Stage of Acetylcholinesterase Catalyzed Hydrolysis of (Acetylthio)choline," *J. Am. Chem. Society*, 122(13):2981-2987 (Mar. 2000).
Malik et al., "Recent advances in protein and peptide drug delivery systems," *Curr. Drug Deliv.*, 4(2):141-151 (2007).
Mandal, "What is a diuretic?," News Medical Life Sciences and Medicine, 1 p. (2014), available at http://news-medical.net/health/What-is-a-Diuretic.aspx#:-:text=Diuretics%20are%20drugs$20that%20can,a%20different%20mechanism%20of%20action.
Mangiafico et al., "Neutral endopeptidase inhibition and the natriuretic peptide system: an evolving strategy in cardiovascular therapeutics," *Eur Heart J.*, 34(12):886-893 (Mar. 2013).
Martin et al., "CD-NP: a novel engineered dual guanylyl cyclase activator with anti- fibrotic actions in the heart," *PLoS One*, 7(12):e52422, 7 pages (Dec. 2012).
Martin et al., "Experimental mild renal insufficiency mediates early cardiac apoptosis, fibrosis, and diastolic dysfunction: a kidney-heart connection," *Am. J. Physiol. Regul. Integr. Comp. Physiology*, 302(2):R292-299 (Jan. 2012).
McKie et al., "A human atrial natriuretic peptide gene mutation reveals a novel peptide with enhanced blood pressure-lowering, renal-enhancing, and aldosterone-suppressing actions," *J. Am. Coll. Cardiol.*, 54(11):1024-1032 (Sep. 2009).
McKie et al., "A novel atrial natriuretic peptide based therapeutic in experimental angiotensin II mediated acute hypertension," *Hypertension*, 56:1152-1159 (2010).
McKie et al., "Abstract 15205: Manp: A Novel ANP Analog for Hypertension Associated With Obesity and Metabolic Syndrome," *Circulation*, Web, Nov. 12, 2020 (Abstract).

(56) References Cited

OTHER PUBLICATIONS

McKie et al., "Amino-terminal pro-B-type natriuretic peptide and B-type natriuretic peptide: biomarkers for mortality in a large community-based cohort free of heart failure," *Hypertension*, 47(5):874-880 (May 2006).

McKie et al., "B-type natriuretic peptide as a biomarker beyond heart failure: speculations and opportunities," Mayo Clin. Proceedings, 80(8):1029-1036 (Aug. 2005).

McKie et al., "Chronic subcutaneous BNP therapy in asymptomatic systolic heart failure," Eur. J. Heart Failure, 18(4):433-441 (Apr. 2016).

McKie et al., "High-sensitivity troponin I and amino-terminal pro-B-type natriuretic peptide predict heart failure and mortality in the general population," Clin. Chemistry, 60(9):1225-1233 (Sep. 2014).

McKie et al., "Impaired natriuretic and renal endocrine response to acute vol. expansion in pre-clinical systolic and diastolic dysfunction," *J. Am. Coll. Cardiology*, 58(20):1-18 (Nov. 2011).

McKie et al., "M-Atrial Natriuretic Peptide and Nitroglycerin in a Canine Model of Experimental Acute Hypertensive Heart Failure: Differential Actions of 2 cGMP Activating Therapeutics," *J. Am. Heart Association*, 3(1):e000206, 9 pages (Jan. 2013).

McKie et al., "M-atrial natriuretic peptide: a novel antihypertensive protein therapy," *Curr. Hypertens. Reports*, 14(1):62-69 (Feb. 2012).

McKie et al., "Predictive Utility of Atrial, N-Terminal Pro-Atrial, and N-Terminal Pro-B-Type Natriuretic Peptides for Mortality and Cardiovascular Events in the General Community: A Nine-Year Follow-Up Study," Mayo Clin. Proceedings, 86(12):1154-1160 (Dec. 2011).

McKie et al., "The Prognostic Value of N-terminal pro-B-type Natriuretic Peptide for Death and Cardiovascular Events in Healthy Normal and Stage A/B Heart Failure Subjects," *J. Am. Coll. Cardiology*, 55(19):2140-2147 (May 2010).

McKie, "MANP in Hypertension and Metabolic Syndrome (MANP-HTN-MS)," ClinicalTrials.gov Web, pp. 1-11 (2020).

Meems et al., "Innovative therapeutics: designer natriuretic peptides," *JACC: basic to Translational Science*, 1(7):557-567 (Dec. 2016).

Miller et al., "Amphiphilic Conjugates of Human Brain Natriuretic Peptide Designed for Oral Delivery: In Vitro Activity Screening," *Bioconjugate Chem.*, 17: 267-274 (2006).

Miller et al., "Comparison of novel pro-BNP(1-108) and standard BNP assays in heart failure patients," *Clin Chim Acta.*, 413(9-10):920-926 (Feb. 2012).

Mitrovic et al., "Effects of the renal natriuretic peptide urodilatin (ularitide) in patients with decompensated chronic heart failure: a double-blind, placebo-controlled, ascending-dose trial," *Am Heart J.*, 150(6):1239e1-e8 (Dec. 2005).

Mitrovic et al., "Haemodynamic and clinical effects of ularitide in decompensated heart failure," *Eur Heart J.*, 27(23):2823-2832 (2006).

Miyasaka et al., "Secular trends in incidence of atrial fibrillation in Olmsted County, Minnesota, 1980 to 2000, and implications on the projections for future prevalence," *Circulation*, 114(2):119-125 (Jul. 2006).

Moree et al., "Characterization of novel selective H1-antihistamines for clinical evaluation in the treatment of insomnia," *J. Med. Chemistry*, 52(17):5307-5310 (Sep. 2009).

Morley et al., "K+ channel openers and suppression of airway hyperreactivity," *Trends Pharmacol Sci.*, 15(12):463-468 (Dec. 1994).

Morley, "Modulation of the action of regulatory peptides by structural modification," *Trends Pharm. Sci.*, 463-468 (Dec. 1980).

Morris et al., "A duplexed high-throughput screen to identify allosteric modulators of the glucagon-like peptide 1 and glucagon receptors," *J. Biomol. Screening*, 19(6):847-858 (Jul. 2014).

Morrison et al., "Combinatorial Alanine Scanning," *Curr. Opin. Chem. Biol.*, 5:302-307 (2001).

Moussaud et al., "Targeting α-synuclein oligomers by protein-fragment complementation for drug discovery in synucleinopathies," *Expert Opin. Ther. Targets*, 19(5):589-603 (May 2015).

Mukoyama et al., "Brain natriuretic peptide as a novel cardiac hormone in humans. Evidence for an exquisite dual natriuretic peptide system, atrial natriuretic peptide and brain natriuretic peptide," *J Clin Invest.*, 87(4):1402-1412 (Apr. 1991).

Myakishev et al., "High-Throughput SNP Genotyping by Allele-Specific PCR with Universal Energy-Transfer-Labeled Primers," *Genome Res.*, 11:163-169 (2001).

Nemer et al., "Gene structure of human cardiac hormone precursor, pronatriodilatin," *Nature*, 312(5995):654-656 (Dec. 1984).

Newton-Cheh et al., "Association of common variants in NPPA and NPPB with circulating natriuretic peptides and blood pressure," *Nat Genet.*, 41(3):348-353 (Mar. 2009).

Ng et al., "Cenderitide-eluting film for potential cardiac patch applications," *PLoS One*, 8(7):e68346, pp. 1-10 (Jul. 2013).

Ngo et al., "Computational Complexity, Protein Structure Prediction, and the Levinthal Paradox," *The Protein Folding Problem and Tertiary Structure Prediction*, Merz, Jr. and Grand, Eds, Birkhauser, Boston, pp. 433-506 (1994).

Niederkofler et al., "Detection of endogenous b-type natriuretic peptide at very low concentrations in patients with heart failure," *Circ Heart Fail.*, 1(4):258-264 (Nov. 2008).

Nieminen et al., "Executive summary of the guidelines on the diagnosis and treatment of acute heart failure: the Task Force on Acute Heart Failure of the European Society of Cardiology," *Eur Heart J.*, 26(4):384-416 (Jan. 2005).

Nishida et al., "Effects of brain natriuretic peptide on hemodynamics and renal function in dogs," *Japanese Journal of Physiology*, 40(4):531-540 (1990).

Nomura et al., "Multicenter prospective investigation on efficacy and safety of carperitide as a first-line drug for acute heart failure syndrome with preserved blood pressure: COMPASS: Carperitide Effects Observed Through Monitoring Dyspnea in Acute Decompensated Heart Failure Study," *Circ J.*, 72(11):1777-1786 (Nov. 2008).

O'Connor et al., "Effect of nesiritide in patients with acute decompensated heart failure," N Engl J Med., 365(1):32-43 (Jul. 7, 2011).

Oikawa et al., "Cloning and sequence analysis of cDNA encoding a precursor for human atrial natriuretic polypeptide," *Nature*, 309(5970):724-726 (Jun. 21-27, 1984).

Olson et al., "Kv1.5 channelopathy due to KCNA5 loss-of-function mutation causes human atrial fibrillation," *Hum. Mol. Genet.*, 15(14):2185-2191 (Jun. 2006).

Olson et al., "Sodium channel mutations and susceptibility to heart failure and atrial fibrillation," *JAMA*, 293:447-454 (2005).

Olson et al., "The Mayo Clinic Biobank: a building block for individualized medicine," Mayo Clin. Proceedings, 88(9):952-962 (Sep. 2013).

Osaka et al., "Pairwise electrostatic interactions between alpha-neurotoxins and gamma, delta, and epsilon subunits of the nicotinic acetylcholine receptor," *J. Biol. Chemistry*, 275(8):5478-5484 (Feb. 2000).

Osaka et al., "Subunit interface selectivity of the alpha-neurotoxins for the nicotinic acetylcholine receptor," *J. Biol. Chemistry*, 274(14):9581-9586 (Apr. 1999).

Pan et al., "Biodesign of a renal-protective peptide based on alternative splicing of B-type natriuretic peptide," *Proc. Natl. Acad. Sci. USA*, 106(27):11282-11287 (Jul. 7, 2009).

Parker et al., "Optimization of Combinatorial Mutagenesis," *Journal of Computational Biology*, 18(11):1743-1756 (2011).

Patel et al., "Cardiac-specific attenuation of natriuretic peptide A receptor activity accentuates adverse cardiac remodeling and mortality in response to pressure overload," *Am. J. Physiol. Heart Circ. Physiology*, 289(2):H777-784 (Aug. 2005).

Peddibhotla et al., "Discovery of ML358, a Selective Small Molecule Inhibitor of the SKN-1 Pathway Involved in Drug Detoxification and Resistance in Nematodes," *ACS Chem. Biology*, 10(8):1871-1879 (May 2015).

Pereira et al., "Circulating atrial natriuretic peptide genetic association study identifies a novel gene cluster associated with stroke in whites," *Circ. Cardiovasc. Genetics*, 8(1):141-149 (Feb. 2015).

(56) References Cited

OTHER PUBLICATIONS

Petrilli et al., "A chemical biology approach identified PI3K as a potential therapeutic target for neurofibromatosis type 2," *Am. J. Transl. Research*, 6(5):471-493 (Oct. 15, 2014).
Potter et al., "Natriuretic peptides, their receptors, and cyclic guanosine monophosphate-dependent signaling functions," *Endocr Rev.*, 27(1):47-72 (Feb. 2006).
Potter, "Natriuretic peptide metabolism, clearance and degradation," *FEBS J.*, 278(11):1808-1817 (Apr. 7, 2011).
Prausnitz, "A Peptide chaperone for transdermal drug delivery," *Nat. Biotechnol.*, 24(4):416-417 (Apr. 2006).
Prince et al., "Robust and accurate single nucleotide polymorphism genotyping by dynamic allele-specific hybridization (DASH): design criteria and assay validation," *Genome Res.*, 11:152-162 (2001).
PubMed search for atrial natriuretic peptide; Nov. 24, 2009, 5 pages.
PubMed search for brain natriuretic peptide; Nov. 24, 2009, 3 pages.
PubMed search for C-type natriuretic peptide; Nov. 24, 2009, 4 pages.
PubMed search for DNP; Nov. 24, 2009, 4 pages.
Ralat et al., "Insulin-degrading enzyme modulates the natriuretic peptide-mediated signaling response," *J Biol Chem.*, 286(6):4670-4679 (Feb. 11, 2011).
Redfield et al., "Burden of systolic and diastolic ventricular dysfunction in the community: appreciating the scope of the heart failure epidemic," *JAMA*, 289(2):194-202 (Jan. 2003).
Ronco et al., "Cardio-renal syndromes: report from the consensus conference of the acute dialysis quality initiative," *Eur Heart J.*, 31(6):703-711, print Mar. 2010 (Dec. 25, 2009).
Rossi et al., "Natriuretic peptide levels in atrial fibrillation: a prospective hormonal and Doppler-echocardiographic study," *J. Am. Coll. Cardiol.*, 35(5):1256-1262 (Apr. 2000).
Saad et al., "Human Renovascular Disease: Estimating fractional tissue hypoxia to analyze Blood Oxygen Level Dependent (BOLD) MR1," *Radiology*, 268(3):770-778 (Sep. 2013).
Sabrane et al., "Vascular endothelium is critically involved in the hypotensive and hypovolemic actions of atrial natriuretic peptide," *J Clin Invest.*, 115(6):1666-1674 (Jun. 2005).
Safian et al., "Renal-Artery Stenosis," *N. Engl. J. Medicine*, 344(6):431-442 (Feb. 8, 2001).
Sangaralingham et al., "Cardiorenal Fibrosis and Dysfunction in Aging: Imbalance in Mediators and Regulators of Collagen," *Peptides*, 76:108-114 (Feb. 2016).
Sangaralingham et al., "Circulating C-type natriuretic peptide and its relationship to cardiovascular disease in the general population," *Hypertension*, 65(6):1187-1194 (Jun. 2015).
Sangaralingham et al., "Estrogen Delays the Progression of Salt-Induced Cardiac Hypertrophy by Influencing the Renin-Angiotensin System in Heterozygous proANP Gene-Disrupted Mice," *Mol. Cell. Biochemistry*, 306(1-2):221-230 (Aug. 23, 2007).
Sangaralingham et al., "Estrogen Protects Against the Development of Salt-Induced Cardiac Hypertrophy in Heterozygous proANP Gene-Disrupted Mice," *J. Endocrinology*, 194(1):143-152 (Jul. 2007).
Sangaralingham et al., "Rationale and Design of a Randomized, Double-Blind, Placebo-Controlled Clinical Trial to Evaluate the Efficacy of B-type Natriuretic Peptide For the Preservation of Left Ventricular Function Post Anterior Myocardial Infarction," *J. Card. Failure*, 19(8):533-539 (Aug. 2013).
Sangaralingham et al., "The Aging Heart, Myocardial Fibrosis and its Relationship to Circulating C-Type Natriuretic Peptide," *Hypertension*, 57(2):201-207 (Feb. 2011).
Sangaralingham et al., "Urinary C-Type Natriuretic Peptide Excretion: A Potential Novel Biomarker for Renal Fibrosis during Aging," *Am. J. Physiol. Renal Physiology*, 301(5):F943-F952 (Nov. 2011).
Schafer et al., "DNA variation and the future of human genetics," *Nat. Biotechnol.*, 16:33-39 (Jan. 1998).
Schiller et al., "A novel cyclic opioid peptide analog showing high preference for u-receptors," *Biochem. Biophy. Res. Comm.*, 127(2):558-564 (Mar. 1985).
Schiller et al., "Synthesis of side-chain to side-chain cyclized peptide analogs on solid supports," *Int. J. Peptide Protein Res.*, 25:171-177 (1985).
Schulz-Knappe et al., "Isolation and Structural Analysis of "Urodilatin", a New Peptide of the Cardiodilatin-(ANP)-Family, Extracted from Human Urine," *Klin Wochenschr.*, 66(17):752-759 (Sep. 1988).
Spatola et al., "Structure-activity relationships of enkephalins containing serially replaced thiomethylene amide bond surrogates," *Life Sci.*, 38(14):1243-1249 (Apr. 1986).
Spatola, "Peptide backbone modifications: A structure-activity analysis of peptides containing amide bond surrogates, conformational constraints and related backbone re-placements" Chemistry and Biochemistry of Amino Acid Peptides and Proteins, B. Weinstein, Ed., Marcel Dekker, New York, 7:267-357 (1983).
Steen et al., "The abc's (and xyz's) of peptide sequencing," *Nat Rev Mol Cell Biol.*, 5:699-711 (Sep. 2004).
Steiner et al., "The Measurement of Cyclic Nucleotides by Radioimmunoassay," *Adv. Biochem. Psychopharmacol.*, 3:89-111 (1970).
Stoneking et al., "Population variation of human mtDNA control region sequences detected by enzymatic amplification and sequence-specific oligonucleotide probes," *Am. J. Hum. Genet.*, 48:370-382 (1991).
Sugarman et al., "Identification of Inhibitors of Triacylglyceride Accumulation in Muscle Cells: Comparing HTS Results from 1536-Well Plate-Based and High-Content Platforms," *J. Biomol. Screening*, 19(1):77-87 (Jan. 2014).
Suwa et al., "Multicenter Prospective Investigation on Efficacy and Safety of Carperitide for Acute Heart Failure in the 'Real World' of Therapy," *Circ J.*, 69(3):283-290 (Mar. 2005).
Takagi et al., "Alpha-human atrial natriuretic peptide, carperitide, reduces infarct size but not arrhythmias after coronary occlusion/reperfusion in dogs," *J. Cardiovasc. Pharmacol.*, 36:22-30 (Jul. 2000).
Takata et al., "The beneficial effects of atrial natriuretic peptide on arrhythmias and myocardial high-energy phosphates after reperfusion," *Cardiovascular Research*, 32:286-293 (Aug. 1996).
Tawaragi et al., "Gene and Precursor structures of human c-type natriuretic peptide," *Biochem. Biophys. Res. Commun.*, 175(2):645-651 (Mar. 1991).
Textor et al., "Altered pressor responses to NE and ANG II during cyclosporin A administration to conscious rats," *Am. J. Physiology*, 258(3 Pt 2):H854-H860 (Mar. 1990).
Textor et al., "Converting enzyme inhibition during chronic angiotensin II infusion in rats: Evidence against a non-angiotensin mechanism," *Hypertension*, 3(2):269-276, (Mar./Apr. 1981).
Textor et al., "Critical perfusion pressure for renal function in patients with bilateral atherosclerotic renal vascular disease," *Ann. Intern. Medicine*, 102(3):308-314 (Mar. 1985).
Textor et al., "De-Novo accelerated hypertension during sequential cyclosporine and prednisone therapy in normotensive bone marrow transplant recipients," *Transplant Proceedings*, 20(3 Suppl 3):480-486 (Jun. 1988).
Textor et al., "Regulation of renal hemodynamics and glomerular filtration in patients with renovascular hypertension during converting enzyme inhibition with captopril," *Am. J. Medicine*, 76(5B):29-37 (May 31, 1984).
Textor et al., "Renal hemodynamics, urinary eicosanoids, and endothelin after liver transplantation," *Transplantation*, 54(1):74-80 (Jul. 1992).
Textor et al., "Responses of the stenosed and contralateral kidneys to (Sar-1, Thr-8) All in human renovascular hypertension," *Hypertension*, 5(5):796-804 (Sep. 1983).
Textor et al., "The use of magnetic resonance to evaluate tissue oxygenation in renal artery stenosis," *J. Am. Soc. Nephrology*, 19(4):780-788 (Apr. 2008).
Textor et al., "Urinary endothelin and renal vasoconstriction with cyclosporine or FK506 after liver transplantation," *Kidney International*, 47(5):1426-1433 (May 1995).
The SPRINT Research Group, "A randomized trial of intensive versus standard blood pressure control," *N. Engl. J. Medicine*, 373(22):2103-2116 (Nov. 26, 2015).
Thiesson et al., "Inhibition of cGMP-specific phosphodiesterase type 5 reduces sodium excretion and arterial blood pressure in

(56) References Cited

OTHER PUBLICATIONS patients with NaCl retention and ascites," *Am. J. Physiol. Renal Physiology*, 288(5):F1044-F1052 (May 2005).
Tsuruda et al., "Brain natriuretic peptide is produced in cardiac fibroblasts and induces matrix metalloproteinases," *Circ. Res.*, 91:1127-1134 (Dec. 2002).
Turner et al., "Power to identify a genetic predictor of antihypertensive drug response using different methods to measure blood pressure response," *J. Transl. Medicine*, 10:47, 9 pages (Mar. 13, 2012).
Underhill et al., "Detection of numerous Y chromosome biallelic polymorphisms by denaturing high-performance liquid chromatography," *Genome Research*, 7(10):996-1005 (1997).
Van den Akker, "Structural insights into the ligand binding domains of membrane bound guanylyl cyclases and natriuretic peptide receptors," *J Mol Biol.*, 311(5):923-937, (Aug. 31, 2001).
Van den Berg et al., "Depletion of atrial natriuretic peptide during longstanding atrial fibrillation," *Europace*, 6(5):433-437 (2004).
Veronese et al., "The impact of PEGylation on biological therapies," *Biodrugs*, 22(5):315-329 (2008).
Veronese et al., "PEGylation, successful approach to drug delivery," *Drug Discov. Today*, 10(21):1451-1458 (Nov. 2005).
Vesely DL, "Atrial natriuretic peptides in pathophysiological diseases," *Cardiovascular Research*, 51:647-658 (2001).
Vesely DL, "Atrial Natriuretic Peptide Prohormone Gene Expression: Hormones and Diseases That Upregulate its Expression," *Life*, 53:153-159 (2002).
Vesely DL, "Natriuretic peptides and acute renal failure," *Am. J. Physiol. Renal. Physiol.*, 285(2):F167-F177 (2003).
Von Lueder et al., "Angiotensin receptor neprilysin inhibitor LCZ696 attenuates cardiac remodeling and dysfunction after myocardial infarction by reducing cardiac fibrosis and hypertrophy," *Circ. Heart Failure*, 8(1):71-78 (Jan. 2015).
Von Lueder et al., "Renin-Angiotensin Blockade Combined With Natriuretic Peptide System Augmentation: Novel Therapeutic Concepts to Combat Heart Failure," *Circ. Heart Failure*, 6(3):594-605 (May 2013).
Wan et al., "Chronic Peptide Therapy With B-Type Natriuretic Peptide in Patients With Preclinical Diastolic Dysfunction (Stage B Heart Failure)," *JACC Heart Failure*, 4(7):539-547 (Jul. 2016).
Wang et al., "A single amino acid determines lysophospholipid specificity of the S1P1 (EDG1) and LPA1 (EDG2) phospholipid growth factor receptors," *J. Biol. Chem.*, 276(52):49213-49220, (Oct. 2001).
Wang et al., "AlbuBNP, a recombinant B-type natriuretic peptide and human serum albumin fusion hormone, as a long-term therapy of congestive heart failure," *Pharm. Res.*, 21(11):2105-2111 (Nov. 2004).
Warner et al., "Genetic deficiency of Smad3 protects the kidneys from atrophy and interstitial fibrosis in 2K1C hypertension," *Am. J. Physiol. Renal Physiology*, 302(11):F1455-F1464 (Jun. 2012).
Weiss, "Hot prospect for new gene amplifier," *Science*, 254(5036):1292-1293 (Nov. 1991).
Wells, "Additivity of mutational effects in proteins," *Biochemistry*, 29(37):8509-8517 (Sep. 1990).
Wermeling et al., "Microneedles permit transdermal delivery of a skin-impermeant medication to humans," *Proc. Natl. Acad. Sci. USA*, 105(6):2058-2063 (Feb. 2008).
Williams et al., "Spironolactone versus placebo, bisoprolol, and doxazosin to determine the optimal treatment for drug-resistant hypertension (PATHWAY-2): a randomised, double-blind, crossover trial," *Lancet* 386(10008):2059-2068, (Nov. 2015).
Wittekindt et al., "Point mutations identify the glutamate binding pocket of the N-methyl-D-aspartate receptor as major site of conantokin-G inhibition," *Neuropharmacology*, 41(6):753-761 (Nov. 2001).
Wozakowska-Kaplon B., "Anp and B-type peptide: Twins or kins? A different predictive value in atrial fibrillation: Natriuretic peptides: Useful biomarkers in predicting the possibility of restoration and maintenance of sinus rhythm in patients with atrial fibrillation undergoing cardioversion?," *J. Cardiology*, 145(2):234-235 (2010).
Wu et al., "Processing of pro-atrial natriuretic peptide by corin in cardiac myocytes," *J. Biol. Chemistry*, 277(19):16900-16905 (Mar. 2002).
Yan et al., "Corin, a Mosaic Transmembrane Serine Protease Encoded by a Novel cDNA from Human Heart," *J Biol Chem.*, 274(21): 14926-14935 (May 21, 1999).
Yan et al., "Corin, a transmembrane cardiac serine protease, acts as a pro-atrial natriuretic peptide-converting enzyme," *Proc Natl Acad Sci USA.*, 97(15):8525-8529 (Jul. 18, 2000).
Zakeri et al., "Urinary C-type Natriuretic Peptide: A New Heart Failure Biomarker," *JACC Heart Failure*, 1(2):170-177 (Apr. 2013).
Zakeri et al., "Urinary C-Type Natriuretic Peptide: An Emerging Biomarker for Heart Failure and Renal Remodeling," *Clin. Chim. Acta*, 443:108-113 (Mar. 2015).
Zheng et al., "CRRL191: A Novel Bioengineered Peptide Activator of the Guanylyl Cyclase A Receptor that has More Potent and Long-Lasting Blood Pressure Lowering and Renal Enhancing Actions than Atrial Natriuretic Peptide," *JACC*, 81(8_Suppl.A):482 (Mar. 7, 2023).
Zhu et al., "Mesenchymal Stem Cells and Endothelial Progenitor Cells Decrease Renal Injury in Experimental Swine Renal Artery Stenosis Through Different Mechanisms," *Stem Cells*, 31(1):117-125 (Jan. 2013).
International Search Report and Written Opinion dated Jan. 17, 2025, in International Application No. PCT/US2024/045150, 29 pages.
International Search Report and Written Opinion dated Jul. 1, 2025, in International Application No. PCT/US2025/017647, 23 pages.

\* cited by examiner

Result7. (Y-var. PC): (RP MP t4w 5C,5)(RP MP t4w 5C,5)

Result7. (Y-var. PC): (RP MP t4w 5C,5)

Result7. PC: 5. Y-var, RP MP t4w 5C, (X-var=value): acetate=0.0000, His=0.0000, succinate=0.0000, Gly=0.0000, HP-b-CD=0.0000, sucr 93.773   94.805   95.837   96.869   97.901   98.933

*Response Surface*

Result7. PC: 5. Y-var, RP MP t4w 5C, (X-var=value): peptide=2.0000, His=0.0000, succinate, Gly=0.0000, HP-b-CD=0.0000,sucr 93.773   95.419   97.064   98.710   100.356   102.001

*Response Surface*

Result7. PC: 5. Y-var, RP MP t4w 5C, (X-var=value): peptide=2.0000, acetate=0.0000, succinate, Gly=0.0000, HP-b-CD=0.0000, 70.008   76.407   82.805   89.204   95.603   102.001

*Response Surface*

Result7. PC: 5. Y-var, RP MP t4w 5C, (X-var=value): peptide=2.0000, acetate=0.0000, His=0.0000, Gly=0.0000, HP-b-CD=0.0000

94.434   94.857   95.281   95.704   96.128   96.552

*Response Surface*

Result7. PC: 5. Y-var, RP MP t4w 5C, (X-var=value): peptide=2.0000, pH=5.0000, acetate=0.0000, His=0.0000, succinate=0.0000, 94.922   95.377   95.833   96.289   96.744   97.200

Result7. PC: 5. Y-var, RP MP t4w 5C, (X-var=value): peptide=2.0000, pH=5.0000, acetate=0.0000, His=0.0000, succinate=0.0000, Gly=0.0000

83.925   86.631   89.336   92.042   94.747   97.453

Result7. PC: 5. Y-var, RP MP t4w 5C, (X-var=value): peptide=2.0000, pH=5.0000, acetate=0.0000, His=0.0000, succinate=0.0000, Gly=0.0000

96.266  96.507  96.748  96.989  97.230  97.941

*Response Surface*

Result10. PC: 1. Y-var, RP MP t4w 5C, (X-var=value): acetate=0.0000, His=0.0000, Gly=0.0000, HP-b-CD=0.0000, sucrose=0.0000, 96.767  96.947  97.126  97.306  97.485  97.665

*Response Surface*

Result10. PC: 1. Y-var, RP MP t4w 5C, (X-var=value): peptide=2,0000, His=0.0000, Gly=0.0000, HP-b-CD=0.0000, sucrose=0.0000, 96.618   96.763   96.909   97.055   97.200   97.346

*Response Surface*

Result10. PC: 1. Y-var, RP MP t4w 5C, (X-var=value): peptide=2.0000, acetate=0.0000, Gly=0.0000, HP-b-CD=0.0000, sucrose=0.0000, 96.197   96.423   96.649   96.876   97.102   97.328

LB-409 R2 R3 RP..., PC:1. Y-var, RP MP t4w 5C, (X-var=value): peptide=2.0000, pH=6.0000, acetate=0.0000, His=0.0000, sucrose=0.0000

97.295  97.445  97.596  77.746  97.897  98.047

*Response Surface*

LB-409 R2 R3 RP..., PC:1. Y-var, RP MP t4w 5C, (X-var=value):
peptide=2.0000, pH=6.0000, acetate=0.0000, His=0.0000, Gly=0.0000

97.091  97.239  97.387  97.535  97.683  97.831

*Response Surface*

LB-409 R2 R3 RP..., PC:1. Y-var, RP MP t4w 5C, (X-var=value):
peptide=2.0000, His=0.0000, Gly=0.0000, HP-b-CD=0.0000, sucrose=250

SEQUENCE LISTING

```
Sequence total quantity: 1
SEQ ID NO: 1            moltype = AA  length = 40
FEATURE                 Location/Qualifiers
source                  1..40
                        mol_type = protein
                        organism = synthetic construct
SEQUENCE: 1
SLRRSSCFGG RMDRIGAQSG LGCNSFRYRI TAREDKQGWA                             40
```

FORMULATIONS OF MANP AND USES THEREOF

CROSS-REFERENCE TO RELATED APPLICATIONS

This application claims the benefit of U.S. Provisional Application No. 63/580,623, filed Sep. 5, 2023, and U.S. Provisional Application No. 63/588,186, filed Oct. 5, 2023, both of which are incorporated by reference in their entireties herein.

INCORPORATION OF SEQUENCE LISTING

A sequence listing contained in the file named "P35383WO00_SL.TXT" which is 1,996 bytes (measured in MS-Windows®) and created on Sep. 3, 2024, is filed electronically herewith and incorporated by reference in its entirety.

BACKGROUND

Natriuretic polypeptides are polypeptides that can cause natriuresis—increased sodium excretion in the urine. Natriuretic polypeptides can be produced by brain, heart, kidney, and/or vascular tissue. The natriuretic polypeptide family in humans includes the cardiac hormones atrial natriuretic peptide (ANP), B-type natriuretic peptide (BNP), C-type natriuretic peptide (CNP), and urodilatin (URO). Natriuretic polypeptides function via two well-characterized guanylyl cyclase receptors (NPR-A for ANP, BNP, and URO; and NPR-B for CNP) and the second messenger cyclic 3'5' guanosine monophosphate (cGMP) (Kuhn (2003) Circ. Res. 93:700-709; Tawaragi et al. (1991) Biochem. Biophys. Res. Commun. 175:645-651; and Komatsu et al. (1991) Endocrinol. 129:1104-1106). Extensive investigations have documented that ANP and BNP, via GC-A and cGMP, exert therapeutically relevant biological effects such as natriuresis, vasodilatation, suppression of the renin-angiotensin-aldosterone system (RAAS), inhibition of cardiac myocyte hypertrophy and apoptosis, stimulation of vascular regeneration, and inhibition of organ fibrosis.

As compared to ANP, mutant (or modified) atrial natriuretic peptide (MANP) is more potent at reducing blood pressure (BP), inducing natriuresis, and inhibiting aldosterone via pGC-A and its second messenger cGMP. International Patent Application No. PCT/US2017/060808 generally discloses analogues of MANP that exhibit pGC-A gain of function and can be used to treat cardiorenal and metabolic disease. International Patent Application No. PCT/US2019/060401 generally discloses materials and methods for treating hypertension (including resistant hypertension) with a combination of an M-atrial natriuretic peptide (MANP) and a diuretic agent (e.g., furosemide). There is a need for compositions and formulations of MANP that are stable for storage, transport, and administration to patients.

SUMMARY

The subject matter of the present disclosure is based in part on the surprising discovery that certain pharmaceutically-acceptable formulations of MANP comprising sucrose, polysorbate-20, and acetate, are stable for long-term storage and transport.

In an aspect, the present disclosure provides a composition comprising MANP, acetate, sucrose, and polysorbate 20. In an aspect, the concentration of MANP is about 2 mg/ml. In an aspect, the MANP consists essentially of SEQ ID NO: 1. In an aspect, the concentration of acetate is in the range of about 10 mM to about 40 mM. In an aspect, the concentration of acetate is about 10 mM. In an aspect, the concentration of sucrose is in the range of about 250 mM to about 275 mM. In an aspect, the concentration of sucrose is about 275 mM. In an aspect, the concentration of polysorbate 20 is about 0.02%. In an aspect, the pH is about 5.5. In an aspect, the osmolality is about 300-420 mOsm/kgH$_2$O. In an aspect, the osmolality is about 310-390 mOsm/kgH$_2$O.

In an aspect, the present disclosure provides a composition comprising MANP, acetate, mannitol, and polysorbate 20. In an aspect, the concentration of MANP is about 2 mg/ml. In an aspect, the MANP consists essentially of SEQ ID NO: 1. In an aspect, the concentration of acetate is in the range of about 10 mM to about 40 mM. In an aspect, the concentration of acetate is about 40 mM. the concentration of mannitol is in the range of about 250 mM to about 275 mM. In an aspect, the concentration of mannitol is about 250 mM. In an aspect, the concentration of polysorbate 20 is about 0.02%. In an aspect, the pH is about 5.5. In an aspect, the osmolality is about 300-420 mOsm/kgH$_2$O. In an aspect, the osmolality is about 310-390 mOsm/kgH$_2$O.

In an aspect, the present disclosure provides a composition for use in the treatment of hypertension, comprising MANP, acetate, sucrose, and polysorbate 20. In an aspect, the concentration of MANP is about 2 mg/ml. In an aspect, the MANP consists essentially of SEQ ID NO: 1. In an aspect, the concentration of acetate is in the range of about 10 mM to about 40 mM. In an aspect, the concentration of acetate is about 10 mM. In an aspect, the concentration of sucrose is in the range of about 250 mM to about 275 mM. In an aspect, the concentration of sucrose is about 275 mM. In an aspect, the concentration of polysorbate 20 is about 0.02%. In an aspect, the pH is about 5.5. In an aspect, the osmolality is about 300-420 mOsm/kgH$_2$O. In an aspect, the osmolality is about 310-390 mOsm/kgH$_2$O.

In an aspect, the present disclosure provides a composition for use in the treatment of hypertension, comprising MANP, acetate, mannitol, and polysorbate 20. In an aspect, the concentration of MANP is about 2 mg/ml. In an aspect, the MANP consists essentially of SEQ ID NO: 1. In an aspect, the concentration of acetate is in the range of about 10 mM to about 40 mM. In an aspect, the concentration of acetate is about 40 mM. In an aspect, the concentration of mannitol is in the range of about 250 mM to about 275 mM. In an aspect, the concentration of mannitol is about 250 mM. In an aspect, the concentration of polysorbate 20 is about 0.02%. In an aspect, the pH is about 5.5. In an aspect, the osmolality is about 300-420 mOsm/kgH$_2$O. In an aspect, the osmolality is about 310-390 mOsm/kgH$_2$O.

In an aspect, the present disclosure provides a pharmaceutical composition, comprising about 2 mg/ml MANP, about 10 mM acetate, about 275 mM sucrose, and about 0.02% polysorbate 20.

In an aspect, the present disclosure provides a pharmaceutical composition, comprising about 2 mg/ml MANP, about 40 mM acetate, about 250 mM mannitol, and about 0.02% polysorbate 20.

In an aspect, the present disclosure provides a pharmaceutical composition, comprising about 2 mg/ml MANP, about 10 mM acetate, about 275 mM sucrose, and about 0.02% polysorbate 20, wherein less than 0.5% of monomers aggregate after 24 months when stored at 2-8° C., as measured by the relative area of the main peak obtained via size exclusion chromatography.

In an aspect, the present disclosure provides a pharmaceutical composition, comprising about 2 mg/ml MANP, about 10 mM acetate, about 275 mM sucrose, and about 0.02% polysorbate 20, wherein the composition loses less than 1% purity after 6 months when stored at 5° C., as measured by the height of the main peak obtained via reversed phase HPLC. In an aspect, the composition loses less than 0.5% purity after 6 months when stored at 5° C., as measured by the height of the main peak obtained via reversed phase HPLC. In an aspect, the composition loses less than 0.2% purity after 6 months when stored at 5° C., as measured by the height of the main peak obtained via reversed phase HPLC.

In an aspect, the present disclosure provides a pharmaceutical composition, comprising about 2 mg/ml MANP, about 10 mM acetate, about 275 mM sucrose, and about 0.02% polysorbate 20, wherein the composition loses less than 10% purity after 12 months when stored at 5° C., as measured by the relative area of the main peak obtained via reversed phase HPLC. In an aspect, the composition loses less than 5% purity after 12 months when stored at 5° C., as measured by the relative area of the main peak obtained via reversed phase HPLC. In an aspect, the composition loses less than 3% purity after 12 months when stored at 5° C., as measured by the relative area of the main peak obtained via reversed phase HPLC.

In an aspect, the present disclosure provides a pharmaceutical composition, comprising about 2 mg/ml MANP, about 10 mM acetate, about 275 mM sucrose, and about 0.02% polysorbate 20, wherein the composition loses less than 10% purity after 24 months when stored at 5° C., as measured by the relative area of the main peak obtained via reversed phase HPLC. In an aspect, the composition loses less than 5% purity after 24 months when stored at 5° C., as measured by the relative area of the main peak obtained via reversed phase HPLC.

In an aspect, the present disclosure provides a pharmaceutical composition, comprising about 2 mg/ml MANP, about 10 mM acetate, about 275 mM sucrose, and about 0.02% polysorbate 20, wherein the composition loses less than 0.2% purity after 12 months when stored at 5° C., as measured by the relative area of the main peak obtained via size exclusion chromatography. In an aspect, the composition loses less than 0.18% purity after 12 months when stored at 5° C., as measured by the relative area of the main peak obtained via size exclusion chromatography.

In an aspect, the present disclosure provides a pharmaceutical composition, comprising about 2 mg/ml MANP, about 10 mM acetate, about 275 mM sucrose, and about 0.02% polysorbate 20, wherein the composition loses less than 0.5% purity after 24 months when stored at 5° C., as measured by the relative area of the main peak obtained via size exclusion chromatography. In an aspect, the composition loses less than 0.35% purity after 24 months when stored at 5° C., as measured by the relative area of the main peak obtained via size exclusion chromatography.

In an aspect, the present disclosure provides a composition comprising MANP, a buffer, a stabilizer/tonicity agent, and a non-ionic surfactant. In an aspect, the buffer is selected from the group consisting essentially of acetate, acetic acid, alanine, arginine, aspartic acid, bicarbonate, bicine, carbonate, citrate, citric acid, glycine, glycylglycine, glutamic acid, histidine, lysine, malic acid, potassium phosphate, sodium acetate, sodium citrate, sodium dihydrogen phosphate, disodium hydrogen phosphate, sodium phosphate, sodium succinate, succinic acid, sulphate, nitrate, maleic acid, fumaric acid, tartaric acid, aspartic acid, tricine, tris(hydroxymethyl)-aminomethane, and tromethamine. In an aspect, the buffer is acetate. In an aspect, the concentration of acetate is in the range of about 10 mM to 40 mM. In an aspect, the concentration of acetate is about 10 mM. In an aspect, the concentration of acetate is about 40 mM. In an aspect, the the stabilizer/tonicity agent is selected from the group consisting essentially of albumin, arginine, Brij 30, Brij 35, dextrose, dimethylsulfon, ethylenediaminetetraacetic acid, glycerol, glycerin, glycine, guanine, hydroxypropyl-b-cyclodextrin, lactose monohydrate, magnesium chloride, maltose, mannitol, methionine, 2-methylthioethanol, monothioglycerol, myo-inositol, potassium chloride, polaxamers, polyethylene glycols, polysorbate 20, polysorbate 80, polyvinyl alcohol, polyvinylpyrrolidone, propylene glycol, protamine sulfate, sodium chloride, sorbitol, sucrose, thioglycolic acid, trehalose, and Triton. In an aspect, the stabilizer/tonicity agent is sucrose. In an aspect, the concentration of sucrose is about 275 mM. In an aspect, the stabilizer/tonicity agent is mannitol. In an aspect, the concentration of mannitol is about 250 mM. In an aspect, the non-ionic surfactant is selected from the group consisting essentially of behenoyl polyoxylglycerides, polysorbate 20, polysorbate 40, docusate sodium, polysorbate 60, polysorbate 80, benzalkonium chloride, caprylocaproyl polyoxylglycerides, cetylpyridinium chloride, lauroyl polyoxylglycerides, linoleoyl polyoxylglycerides, octoxynol 9, oleoyl polyoxylglycerides, poloxamer, polyoxyl 10 oleyl ether, polyoxyl 15 hydroxystearate, nonoxynol 9, polyoxyl 20 cetostearyl ether, polyoxyl 40 stearate, pullulan, polyoxyl lauryl ether, polyoxyl stearyl ether, sodium lauryl sulfate, sorbitan monolaurate, sorbitan monooleate, polyoxyl stearate, sorbitan monopalmitate, sorbitan monostearate, stearoyl polyoxylglycerides, sorbitan sesquiolcate, sorbitan triolcate, and tyloxapol. In an aspect, the non-ionic surfactant is polysorbate 20. In an aspect, the concentration of polysorbate 20 is about 0.2%. In an aspect, the pH is about 5.5. In an aspect, the osmolality is about 300-420 mOsm/kgH$_2$O. In an aspect, the osmolality is about 310-390 mOsm/kgH$_2$O.

In an aspect, the present disclosure provides a vial containing a formulation comprising MANP, acetate, sucrose, and polysorbate 20. In an aspect, the concentration of MANP is about 2 mg/ml. In an aspect, the MANP consists essentially of SEQ ID NO: 1. In an aspect, the concentration of acetate is in the range of about 10 mM to about 40 mM. In an aspect, the concentration of acetate is about 10 mM. In an aspect, the concentration of sucrose is about 275 mM. In an aspect, the concentration of polysorbate 20 is about 0.02%. In an aspect, the pH is about 5.5. In an aspect, the osmolality is about 300-420 mOsm/kgH$_2$O. In an aspect, the osmolality is about 310-390 mOsm/kgH$_2$O.

In an aspect, the present disclosure provides a lyophilized powder made according to the steps of: (a) combining in a liquid solution: MANP, acetate, sucrose, and polysorbate 20; and (b) lyophilizing the combination of step (a). In an aspect, the concentration of MANP in the liquid composition is about 2 mg/ml. In an aspect, the MANP consists essentially of SEQ ID NO: 1. In an aspect, the concentration of acetate in the liquid composition is in the range of about 10 mM to about 40 mM. In an aspect, the concentration of acetate in the liquid composition is about 10 mM. In an aspect, the concentration of sucrose in the liquid composition is in the range of about 250 mM to about 275 mM. In an aspect, the concentration of sucrose in the liquid composition is about 275 mM. In an aspect, the concentration of polysorbate 20 in the liquid composition is about 0.02%. In an aspect, the pH of the liquid composition is about 5.5. In an aspect, the osmolality of the liquid composition is about 300-420 mOsm/kgH$_2$O. In an aspect, the osmolality of the liquid composition is about 310-390 mOsm/kgH$_2$O.

In an aspect, the present disclosure provides a lyophilized powder made according to the steps of: (a) combining in a liquid solution: MANP, acetate, mannitol, and polysorbate 20; and (b) lyophilizing the combination of step (a). In an aspect, the concentration of MANP in the liquid composition is about 2 mg/ml. In an aspect, the MANP consists essentially of SEQ ID NO: 1. In an aspect, the concentration of acetate in the liquid composition is in the range of about 10 mM to about 40 mM. In an aspect, the concentration of acetate in the liquid composition is about 40 mM. In an aspect, the concentration of mannitol in the liquid composition is in the range of about 250 mM to about 275 mM. In an aspect, the concentration of mannitol in the liquid composition is about 250 mM. In an aspect, the concentration of polysorbate 20 in the liquid composition is about 0.02%. In an aspect, the pH of the liquid composition is about 5.5. In an aspect, the osmolality of the liquid composition is about 300-420 mOsm/kgH$_2$O. In an aspect, the osmolality of the liquid composition is about 310-390 mOsm/kgH$_2$O.

In an aspect, the present disclosure provides a dry powder composition comprising MANP, acetate, sucrose, and polysorbate 20.

In an aspect, the present disclosure provides a powder made by spray drying, wherein the spray drying comprises the steps of: (a) providing a liquid comprising MANP, acetate, sucrose, and polysorbate 20; (b) spray-drying the liquid of step (a) with a spray-drying device.

In an aspect, the present disclosure provides a lyophilized powder made by freeze-drying, wherein the freeze-drying comprises the steps of: (a) providing a liquid comprising MANP, acetate, sucrose, and polysorbate 20; (b) freeze-drying the liquid of step (a) at a temperature for a length of time sufficient to transform the liquid formation into a solid state.

In an aspect, the present disclosure provides a lyophilized powder made by a method comprising the steps of: (a) providing a liquid comprising MANP, acetate, sucrose, and polysorbate 20; (b) lyophilizing the liquid of step (a).

In an aspect, the present disclosure provides a pre-filled syringe containing MANP, acetate, sucrose, and polysorbate 20. In an aspect, the concentration of MANP is about 2 mg/ml. In an aspect, the MANP consists essentially of SEQ ID NO: 1. In an aspect, the concentration of acetate is in the range of about 10 mM to about 40 mM. In an aspect, the concentration of acetate is about 10 mM. In an aspect, the concentration of sucrose is about 275 mM. In an aspect, the concentration of polysorbate 20 is about 0.02%. In an aspect, the pH is about 5.5. In an aspect, the osmolality is about 300-420 mOsm/kgH$_2$O. In an aspect, the osmolality is about 310-390 mOsm/kgH$_2$O.

BRIEF DESCRIPTION OF THE DRAWINGS

Aspects of the disclosure are herein described, by way of example only, with reference to the accompanying drawings. With specific reference now to the drawings in detail, it is stressed that the particulars shown are by way of example and are for purposes of illustrative discussion of aspects of the disclosure. In this regard, the description and the drawings, considered alone and together, make apparent to those skilled in the art how aspects of the disclosure may be practiced.

DETAILED DESCRIPTION

Figure 1:
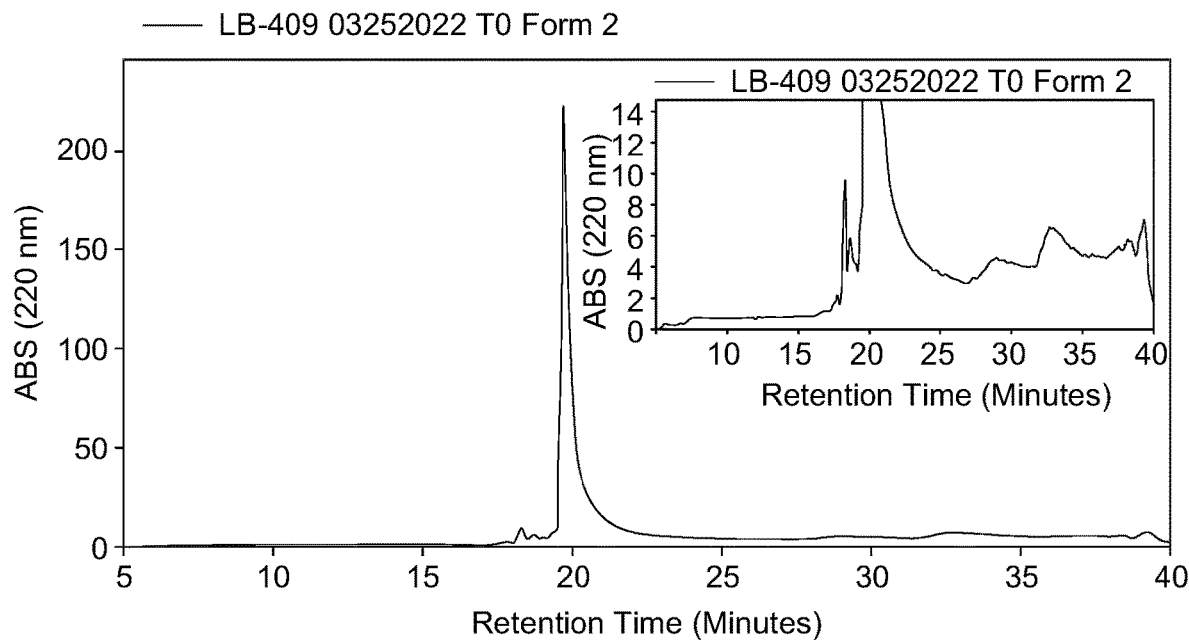
FIG. 1 depicts an exemplary reversed-phase HPLC chromatogram.

The present disclosure describes, and includes, pharmaceutically-acceptable formulations of MANP, or a pharmaceutically acceptable salt thereof, comprising sucrose, polysorbate-20, and acetate.

This description is not intended to be a detailed catalog of all the different ways in which the disclosure may be implemented, or all the features that may be added to the instant disclosure. For example, features illustrated with respect to one embodiment may be incorporated into other embodiment, and features illustrated with respect to a particular embodiment may be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. In other instances, well-known structures, interfaces, and processes have not been shown in detail in order not to unnecessarily obscure the disclosure. It is intended that no part of this specification be construed to effect a disavowal of any part of the full scope of the disclosure. Hence, the following descriptions are intended to illustrate some particular embodiments of the disclosure, and not to exhaustively specify all permutations, combinations or variations thereof.

Unless otherwise defined, all technical and scientific terms used herein have the same meaning as commonly understood by one of ordinary skill in the art to which this disclosure belongs. The terminology used in the description of the disclosure herein is for the purpose of describing particular aspects or embodiments only and is not intended to be limiting of the disclosure.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted.

The methods disclosed herein include and comprise one or more steps or actions for achieving the described method. The method steps and/or actions may be interchanged with one another without departing from the scope of the present disclosure. In other words, unless a specific order of steps or actions is required for proper operation of the embodiment, the order and/or use of specific steps and/or actions may be modified without departing from the scope of the present disclosure.

As used in the description of the disclosure and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The terms "about" and "approximately" as used herein when referring to a measurable value such as a length, a frequency, or a measurement value and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

As used herein, the term "exemplary" is used to mean serving as an example, instance, or illustration. Any embodiment or aspect described as "exemplary" is not necessarily to be construed as preferred or advantageous over other embodiments or aspects, nor is it meant to preclude equivalent structures and techniques known to those of ordinary skill in the art. Rather, use of the word exemplary is intended to present concepts in a concrete fashion, and the disclosed subject matter is not limited by such examples.

Compositions

In an aspect, the present disclosure provides for, and includes, compositions comprising MANP, acetate, sucrose, and polysorbate 20. In an aspect, the present disclosure provides for, and includes, compositions comprising MANP, acetate, mannitol, and polysorbate 20. In an aspect, the present disclosure provides for, and includes, compositions comprising MANP, a buffer, a stabilizer or tonicity agent, and a non-ionic surfactant.

In an aspect, the present disclosure provides compositions comprising MANP. As used herein, an "MANP" is an ANP-based peptide having an amino acid sequence that includes the 28 amino acid mature human ANP sequence with an additional 12 amino acid carboxy terminus. Without being bound by theory, MANP is a pGC-A/cGMP activator that can significantly lower blood pressure and vascular resistance. In an aspect, MANP comprises a peptide with the sequence set forth in SEQ ID NO:1 SLRRSSCFGGRMDRIGAQSGLGCNSFRYRITAREDKQGWA. In an aspect, an MANP can be a variant of the sequence set forth in SEQ ID NO: 1. In an aspect, an MANP can contain the amino acid sequence set forth in SEQ ID NO: 1, together with one or more amino acid additions, subtractions, or substitutions. In an aspect, an MANP can contain the amino acid sequence set forth in SEQ ID NO:1, together with one or more amino acid additions, subtractions, and substitutions. In an aspect, an MANP can contain the amino acid sequence set forth in SEQ ID NO:1, together with one, two, three, four, five, six, seven, eight, nine, or ten single amino acid residue additions, subtractions, or substitutions. In an aspect, an MANP can contain the amino acid sequence set forth in SEQ ID NO: 1, together with one, two, three, four, five, six, seven, eight, nine, or ten single amino acid residue additions, subtractions, and substitutions.

In an aspect, any amino acid residue set forth in SEQ ID NO: 1 can be subtracted, and any amino acid residue (e.g., any of the 20 conventional amino acid residues or any other type of amino acid such as ornithine or citrulline) can be added to the sequence set forth in SEQ ID NO: 1. In an aspect, an MANP can contain one or more chemical structures such as e-aminohexanoic acid; hydroxylated amino acids such as 3-hydroxyproline, 4-hydroxyproline, (5R)-5-hydroxy-L-lysine, allo-hydroxylysine, and 5-hydroxy-L-norvaline; and/or glycosylated amino acids such as amino acids containing monosaccharides (e.g., D-glucose, D-galactose, D-mannose, D-glucosamine, and D-galactosamine) or combinations of monosaccharides.

MANPs having one or more amino acid additions, subtractions, or substitutions relative to the representative MANP sequence set forth in SEQ ID NO: 1, also referred to herein as "variant" MANPs, can be generated using any suitable method. In an aspect, amino acid substitutions can be made by selecting substitutions that do not differ significantly in their effect on maintaining (a) the structure of the peptide backbone in the area of the substitution, (b) the charge or hydrophobicity of the molecule at the target site, or (c) the bulk of the side chain. For example, naturally occurring residues can be divided into groups based on side-chain properties: (1) hydrophobic amino acids (norleucine, methionine, alanine, valine, leucine, and isoleucine); (2) neutral hydrophilic amino acids (cysteine, serine, and threonine); (3) acidic amino acids (aspartic acid and glutamic acid); (4) basic amino acids (asparagine, glutamine, histidine, lysine, and arginine); (5) amino acids that influence chain orientation (glycine and proline); and (6) aromatic amino acids (tryptophan, tyrosine, and phenylalanine). Substitutions made within these groups can be considered conservative substitutions. Non-limiting examples of useful conservative substitutions can include, without limitation, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenylalanine, glycine for proline, threonine for serine, serine for threonine, tyrosine for tryptophan, phenylalanine for tyrosine, and/or leucine for valine.

In an aspect, an MANP can include one or more non-conservative substitutions. Non-conservative substitutions typically entail exchanging a member of one of the classes described above for a member of another class. Such production can be desirable to provide large quantities or alternative embodiments of such compounds. Whether an amino acid change results in a functional polypeptide can readily be determined by assaying the specific activity of the polypeptide variant using, for example, methods disclosed herein.

In an aspect, an MANP can have a length of, for example, 35 to 45 amino acid residues (e.g., 35 to 40, 40 to 45, 35 to 37, 36 to 38, 37 to 39, 38 to 40, 39 to 41, 40 to 42, 41 to 43, 42 to 44, or 43 to 45 amino acid residues).

In an aspect, the compositions comprise MANP at a concentration effective for treatment of disease. In an aspect, the compositions comprise MANP at a concentration of at about 0.1 mg/ml, about 0.2 mg/ml, about 0.3 mg/ml, about 0.4 mg/ml, about 0.5 mg/ml, about 0.6 mg/ml, about 0.7 mg/ml, about 0.8 mg/ml, about 0.9 mg/ml, about 1.0 mg/ml, about 2.0 mg/ml, about 3.0 mg/ml, about 4.0 mg/ml, about 5.0 mg/ml, about 6.0 mg/ml, about 7.0 mg/ml, about 8.0 mg/ml, about 9.0 mg/ml, or about 10.0 mg/ml. In an aspect, the compositions comprise MANP at a concentration of at least 0.1 mg/ml, at least 0.2 mg/ml, at least 0.3 mg/ml, at least 0.4 mg/ml, at least 0.5 mg/ml, at least 0.6 mg/ml, at least 0.7 mg/ml, at least 0.8 mg/ml, at least 0.9 mg/ml, at least 1.0 mg/ml, at least 2.0 mg/ml, at least 3.0 mg/ml, at least 4.0 mg/ml, at least 5.0 mg/ml, at least 6.0 mg/ml, at least 7.0 mg/ml, at least 8.0 mg/ml, at least 9.0 mg/ml, or at least 10.0 mg/ml. In an aspect, the compositions comprise MANP at a concentration of about 0.5 mg/ml to 5.0 mg/ml. In an aspect, the compositions comprise MANP at a concentration of about 0.75 mg/ml to 4.0 mg/ml. In an aspect, the compositions comprise MANP at a concentration of about 1.0 mg/ml to 3.0 mg/ml. In an aspect, the compositions comprise MANP at a concentration of about 2.0 mg/ml.

The present disclosure provides compositions comprising MANP in a suitable buffer. In an aspect, the buffer is selected from the group consisting of acetate, bicarbonate, carbonate, citrate, glycylglycine, histidine, glycine, glutamate, lysine, arginine, sodium dihydrogen phosphate, disodium hydrogen phosphate, sodium phosphate, tris(hydroxymethyl)-aminomethane, bicine, tricine, malic acid, succinate, sulphate, nitrate, maleic acid, fumaric acid, tartaric acid, aspartic acid or mixtures thereof. In an aspect, the buffer is citrate. In an aspect, the buffer is acetate. In an aspect, the buffer is Tris-HCl. In an aspect, the buffer is phosphate. In an aspect, the buffer is Histidine. In an aspect, the composition comprises MANP in an acetate buffer.

The buffer may be present in a concentration suitable for regulating the pH of the composition. In an aspect, the compositions comprise a buffer at a concentration of about 1 mM, about 2 mM, about 5 mM, about 10 mM, about 20 mM, about 30 mM, about 40 mM, about 50 mM, about 60 mM, about 70 mM, about 80 mM, about 90 mM, about 100 mM, about 150 mM, about 200 mM, about 250 mM, about 300 mM, about 350 mM, or about 500 mM. In an aspect, the compositions comprise a buffer at a concentration of at least 1 mM, at least 2 mM, at least 5 mM, at least 10 mM, at least 20 mM, at least 30 mM, at least 40 mM, at least 50 mM, at least 60 mM, at least 70 mM, at least 80 mM, at least 90 mM, at least 100 mM, at least 150 mM, at least 200 mM, at least 250 mM, at least 300 mM, at least 350 mM, or at least 500 mM. In an aspect, the compositions comprise a buffer at a concentration of about 1 mM to about 50 mM. In an aspect, the compositions comprise a buffer at a concentration of about 5 mM to about 40 mM. In an aspect, the compositions comprise a buffer at a concentration of about 10 mM to about 40 mM. In an aspect, the compositions comprise acetate at a concentration of about 10 mM. In an aspect, the compositions comprise acetate at a concentration of about 14 mM.

The pH of the composition is selected for stability of the MANP peptide. In an aspect, the pH of the composition is in the range of about 4.0 to about 9.0. In an aspect, the pH of the composition is in the range of about 5.0 to about 7.0. In an aspect, the pH of the composition is in the range of about 5.0 to about 7.0. In an aspect, the pH of the composition is in the range of about 5.0 to about 6.0. In an aspect, the pH of the composition is 5.0. In an aspect, the pH of the composition is about 5.5. In an aspect, the pH of the composition is about 6.0.

A tonicity agent may be present in a concentration suitable for regulating the stability of the composition. In an aspect, the composition comprises any known tonicity agent, including, but not limited to, propylene glycol, sorbitol, sucrose, glycine, mannitol, lactose monohydrate, arginine, dextrose, trehalose, sodium chloride, potassium chloride, glycerol, glycerin, myo-inositol and dimethylsulfon.

In an aspect, the composition comprises sucrose. In an aspect, the composition comprises sucrose at a concentration in the range of about 200 mM to about 300 mM. In an aspect, the composition comprises sucrose at a concentration in the range of about 250 mM to about 275 mM. In an aspect, the composition comprises sucrose at a concentration of about 275 mM. In an aspect, the composition comprises mannitol. In an aspect, the composition comprises mannitol at a concentration in the range of about 200 mM to about 300 mM. In an aspect, the composition comprises mannitol at a concentration in the range of about 250 mM to about 275 mM. In an aspect, the composition comprises mannitol at a concentration of about 250 mM.

A stabilizer comprising high molecular weight polymers may be present in a concentration suitable for regulating the stability of the composition. In an aspect, the composition comprises any known stabilizer, including but not limited to, hydroxypropyl-b-cyclodextrin, polyethylene glycol (e.g., PEG 3350), polysorbate 20 (Tween 20), polysorbate 80 (Tween 80), Polaxamer (Pluronic F68 and F127), polyvinyl alcohol (PVA), polyvinylpyrrolidone (PVP), carboxy-/hydroxycellulose or derivates thereof (e.g., HPC, HPC-SL, HPC-L and HPCM), Triton X-100, Brij 30, Brij 35, sulphur-containing substances as monothioglycerol, thioglycolic acid and 2-methylthiocthanol, and different salts (e.g. sodium chloride).

Additional stabilizing agents, e.g., those that further enhance the stability of therapeutically active MANP peptide, may be included. Examples of such stabilizers include, but are not limited to, methionine and EDTA, which protect against methionine oxidation, and nonionic surfactants, which protect against aggregation associated with freeze-thawing and mechanical shearing.

In an aspect, the composition comprises polysorbate 20. In an aspect, the composition comprises polysorbate 20 at a concentration in the range of about 0.005% to 0.5%. In an aspect, the composition comprises polysorbate 20 at a concentration in the range of about 0.01% to 0.1%. In an aspect, the composition comprises polysorbate 20 at a concentration in the range of about 0.01% to 0.02%. In an aspect, the composition comprises polysorbate 20 at a concentration of about 0.02%. In an aspect, the composition comprises polysorbate 80. In an aspect, the composition comprises polysorbate 80 at a concentration in the range of about 0.005% to 0.5%. In an aspect, the composition comprises polysorbate 80 at a concentration in the range of about 0.01% to 0.1%. In an aspect, the composition comprises polysorbate 80 at a concentration in the range of about 0.01% to 0.02%. In an aspect, the composition comprises polysorbate 80 at a concentration of about 0.02%. In an aspect, the composition comprises hydroxypropyl-b-cyclodextrin. In an aspect, the composition comprises hydroxypropyl-b-cyclodextrin at a concentration in the range of about 1 mM to 200 mM. In an aspect, the composition comprises hydroxypropyl-b-cyclodextrin at a concentration in the range of about 15 mM to 100 mM. In an aspect, the composition comprises hydroxypropyl-b-cyclodextrin at a concentration of about 15 mM. In an aspect, the composition comprises hydroxypropyl-b-cyclodextrin at a concentration of about 25 mM. In an aspect, the composition comprises hydroxypropyl-b-cyclodextrin at a concentration of about 50 mM. In an aspect, the composition comprises hydroxypropyl-b-cyclodextrin at a concentration of about 100 mM. In an aspect, the composition comprises methionine. In an aspect, the composition comprises methionine at a concentration in the range of about 1 mM to about 50 mM. In an aspect, the composition comprises methionine at a concentration in the range of about 5 mM to about 25 mM. In an aspect, the composition comprises methionine at a concentration in the range of about 10 mM to about 20 mM. In an aspect, the composition comprises methionine at a concentration of about 5 mM. In an aspect, the composition comprises methionine at a concentration of about 10 mM. In an aspect, the composition comprises methionine at a concentration of about 20 mM.

In an aspect, the osmolality of the composition is in the range of about 250 mOsm/kgH$_2$O to about 500 mOsm/kgH$_2$O. In an aspect, the osmolality of the composition is in the range of about 290 mOsm/kgH$_2$O to about 400 mOsm/kgH$_2$O. In an aspect, the osmolality of the composition is in the range of about 300 mOsm/kgH$_2$O to about 420 mOsm/kgH$_2$O. In an aspect, the osmolality of the composition is in the range of about 310 mOsm/kgH$_2$O to about 390 mOsm/kgH$_2$O.

As used herein, the term "surfactant" refers to any molecules or ions that are comprised of a water-soluble (hydrophilic) part, the head, and a fat-soluble (lipophilic) segment. Surfactants accumulate preferably at interfaces, which the hydrophilic part is orientated towards the water (hydrophilic phase) and the lipophilic part towards the oil- or hydrophobic phase (i.e. glass, air, oil etc.). The concentration at which surfactants begin to form micelles is known as the critical micelle concentration or CMC. Furthermore, surfactants lower the surface tension of a liquid. Surfactants are also known as amphipathic compounds. The term "detergent" is a synonym used for surfactants in general. Surfactants may be anionic (e.g., chenodeoxycholic acid, cholic acid, digitonin, digitoxigenin, N-Lauroylsarcosine, lithium dodecyl sulfate, sodium dodecyl sulfate, sodium hexanesulfonate, taurochenodeoxycholic acid, sodium dodecyl sulfate or sodium lauryl sulfate), cationic (e.g., alkyltrimethylammonium bromide, benzalkonium chloride, dimethyldioctadecylammonium bromide, dodecylethyldimethylammonium bromide, dodecyltrimethylammonium bromide, dodecyltrimethylammonium bromide, ethylhexadecyldimethylammonium bromide, hexadecyltrimethylammonium bromide, hexadecyltrimethylammonium bromide, polyoxyethylene (10)-N-tallow-1,3-diaminopropane, thonzonium bromide, and/or trimethyl(tetradecyl) ammonium bromide), or non-ionic (e.g., BigCHAP, bis(polyethylene glycol bis [imidazoyl carbonyl]), block copolymers as polyethyleneoxide/polypropyleneoxide block copolymers such as poloxamers, poloxamer 188 and poloxamer 407, Brij 35, Brij 56, Brij 72, Brij 76, Brij 92V, Brij 97, Brij 58P, Cremophor EL, decacthylene glycol monododecyl ether, N-decanoyl-N-methylglucamine, n-dodecanoyl-N-methylglucamide, alkylpolyglucosides, ethoxylated castor oil, heptaethylene glycol monodecyl ether, heptaethylene glycol monododecyl ether, heptaethylene glycol monotetradecyl ether, hexacthylene glycol monododecyl ether, hexacthylene glycol monohexadecyl ether, hexacthylene glycol monooctadecyl ether, hexacthylene glycol monotetradecyl ether, Igepal CA-630, Igepal CA-630, methyl-6-O—(N-heptylcarbamoyl)-beta-D-glucopyranoside, nonacthylene glycol monododecyl ether, N-nonanoyl-N-methylglucamine, N-nonanoyl-N-methylglucamine, octacthylene glycol monodecyl ether, octacthylene glycol monododecyl ether, octacthylene glycol monohexadecyl ether, octacthylene glycol monooctadecyl ether, octaethylene glycol monotetradecyl ether, octyl-β-D-glucopyranoside, pentaethylene glycol monodecyl ether, pentaethylene glycol monododecyl ether, pentaethylene glycol monohexadecyl ether, pentaethylene glycol monohexyl ether, pentaethylene glycol monooctadecyl ether, pentaethylene glycol monooctyl ether, polyethylene glycol diglycidyl ether, polyethylene glycol ether W-1, polyoxyethylene 10 tridecyl ether, polyoxyethylene 100 stearate, polyoxyethylene 20 isohexadecyl ether, polyoxyethylene 20 olcyl ether, polyoxyethylene 40 stearate, polyoxyethylene 50 stearate, polyoxyethylene 8 stearate, polyoxyethylene bis(imidazolyl carbonyl), Polyoxyethylene 25 propylene glycol stearate, saponin from Quillaja bark, Tergitol, tetradecyl-B-D-maltoside, tetraethylene glycol monodecyl ether, tetraethylene glycol monododecyl ether, tetraethylene glycol monotetradecyl ether, triethylene glycol monodecyl ether, triethylene glycol monododecyl ether, triethylene glycol monohexadecyl ether, triethylene glycol monooctyl ether, triethylene glycol monotetradecyl ether, Triton, TWEEN, Tyloxapol, sphingophospholipids (sphingomyelin), and sphingoglycolipids (ceramides, gangliosides), phospholipids, and n-Undecyl β-D-glucopyranoside.

In an aspect, pharmaceutically-acceptable formulations described herein are stable for long-term storage and transport. As used herein, "stability" may refer to "chemical stability" or "physical stability." As used herein, a substance has "chemical stability" if it is not particularly reactive in a particular environment and retains its useful properties during a defined period of expected usefulness. As used herein, a substance has "physical stability" if its original physical properties, including but not limited to appearance, palatability, uniformity, dissolution, and suspendability, are retained during a defined period of time. In an aspect, pharmaceutically-acceptable formulations described herein are chemically stable for long-term storage and transport. In an aspect, pharmaceutically-acceptable formulations described herein are physically stable for long-term storage and transport.

Compositions for Use in Treatment of Hypertension

In an aspect, the present disclosure provides for, and includes compositions for use in the treatment of hypertension comprising MANP, acetate, sucrose, and polysorbate 20. In an aspect, the present disclosure provides for, and includes, compositions for use in the treatment of hypertension comprising MANP, acetate, mannitol, and polysorbate 20.

As used herein, "treatment of a disease" means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

As used herein, an "effective amount" means a dosage which is sufficient to be effective for the treatment of the patient compared with no treatment or treatment with a placebo.

Compositions comprising MANP described herein may be administered to a patient in need of treatment for hypertension. Compositions described herein may be administered to a patient in need of such treatment at several sites, for example, at topical sites, (e.g., skin and mucosal sites), at sites which bypass absorption, (e.g., administration in an artery, in a vein, in the heart), and at sites which involve absorption, (e.g., administration in the skin, under the skin, in a muscle or in the abdomen).

Administration of compositions described herein may be through several routes of administration, for example, lingual, sublingual, buccal, in the mouth, oral, in the stomach and intestine, nasal, pulmonary, (e.g., through the bronchioles and alveoli or a combination thereof), epidermal, dermal, transdermal, vaginal, rectal, ocular, for examples through the conjunctiva, uretal, and parenteral to patients in need of such a treatment.

Compositions described herein may be administered in several dosage forms, including, but not limited to, solutions, suspensions, emulsions, microemulsions, multiple emulsion, foams, salves, pastes, plasters, ointments, tablets, coated tablets, rinses, capsules, for example, hard gelatin capsules and soft gelatin capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions (e.g., in situ gelling, in situ setting, in situ precipitating, in situ crystallization), infusion solution, and implants.

Compositions described herein may further be compounded in, or attached to, for example through covalent, hydrophobic and electrostatic interactions, a drug carrier, drug delivery system and advanced drug delivery system in order to further enhance stability of the compound of the present embodiment, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers (e.g., cellulose and derivatives), polysaccharides (e.g., dextran and derivatives), starch and derivatives, poly(vinyl alcohol), acrylate and methacrylate polymers, polylactic and polyglycolic acid and block co-polymers thereof, polyethylene glycols, carrier proteins (e.g., albumin), gels (e.g., thermogelling systems), block co-polymeric systems well known to those skilled in the art, micelles, liposomes, microspheres, nanoparticulates, liquid crystals and dispersions thereof, L2 phase and dispersions thereof, well known to those skilled in the art of phase behavior in lipid-water systems, polymeric micelles, multiple emulsions, self-emulsifying, self-micro emulsifying, cyclodextrins and derivatives thereof, and dendrimers.

Compositions described herein may also be formulated for solids, semisolids, powder and solutions for pulmonary administration, using, for example a metered dose inhaler, dry powder inhaler and a nebulizer, or other devices known to those skilled in the art.

Compositions described herein are also useful in the formulation of controlled, sustained, protracting, retarded, and slow release drug delivery systems. In an aspect, the compositions described herein are useful in formulation of parenteral controlled release and sustained release systems (both systems leading to a many-fold reduction in number of administrations), well known to those skilled in the art. In an aspect, the compositions described herein are controlled release and sustained release systems administered subcutaneous. Without limiting the scope of the disclosure, examples of useful controlled release system and compositions are hydrogels, oleaginous gels, liquid crystals, polymeric micelles, microspheres, nanoparticles. Methods to produce controlled release systems useful for compositions of the current disclosure include, but are not limited to, crystallization, condensation, co-crystallization, precipitation, co-precipitation, emulsification, dispersion, high pressure homogenization, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

In an aspect, parenteral administration is performed by subcutaneous, intramuscular, intraperitoneal or intravenous injection by means of a syringe, optionally a pen-like syringe. In an aspect, parenteral administration can be performed by means of an infusion pump. In an aspect, the compositions described herein may be a solution or suspension or a powder for the administration of MANP in the form of a nasal or pulmonal liquid or powder spray. In an aspect, the pharmaceutical compositions containing MANP can also be adapted to transdermal administration (e.g. by needle-free injection or from a patch, an iontophoretic patch, or transmucosal administration).

In an aspect, the compositions described herein can be formulated for administration via the pulmonary route in a vehicle, as a solution, suspension or dry powder using any of known types of devices suitable for pulmonary drug delivery. Examples of these include, but are not limited to, the three general types of aerosol-generating for pulmonary drug delivery, and may include jet or ultrasonic nebulizers, metered-dose inhalers, or dry powder inhalers (Cf. Yu J, Chien Y W. Pulmonary drug delivery: Physiologic and mechanistic aspects. Crit Rev Ther Drug Carr Sys 14 (4) (1997) 395-453).

In an aspect, the compositions described herein can be formulated in a dried form, either by freeze drying (e.g., lyophilization), spray drying, or air drying. In an aspect, the compositions described herein can be formulated in a dried form for storage. In an aspect, the compositions described herein can be formulated in a dried form for transport. In an aspect, the compositions described herein can be formulated in a dried form for increased stability.

Pharmaceutical Compositions

As used herein, "pharmaceutical composition" means a product comprising an active compound or a salt thereof together with pharmaceutical excipients such as buffer, preservative, and optionally a tonicity modifier and/or a stabilizer. Thus a pharmaceutical composition is also known in the art as a pharmaceutical formulation. In an aspect, the pharmaceutical formulation is a freeze-dried formulation, whereto the physician or the patient adds solvents and/or diluents prior to use. In an aspect, the pharmaceutical formulation is a dried formulation (e.g. freeze-dried or spray-dried) ready for use without any prior dissolution. In an aspect, the pharmaceutical formulation is a lyophilized formulation, whereto the physician or the patient adds solvents and/or diluents prior to use.

As used herein, "pharmaceutically-acceptable" means suited for normal pharmaceutical applications, i.e. giving rise to no adverse events in patients etc.

As used herein, "excipient" means the chemical compounds which are normally added to pharmaceutical compositions, e.g. buffers, tonicity agents, preservatives and the like. In an aspect, the term "excipient" broadly refers to any component other than the active therapeutic ingredient(s). The excipient may be an inert substance, an inactive substance, and/or a not medicinally active substance. The formulation of pharmaceutically active ingredients with various excipients is known in the art, see e.g. Remington: The Science and Practice of Pharmacy (e.g. 19th edition (1995), and any later editions). Non-limiting examples of excipients are: solvents, diluents, buffers, preservatives, tonicity regulating agents (e.g isotonic agents), chelating agents, stabilizers (e.g. oxidation inhibitors, aggregation inhibitors, surfactants, and/or protease inhibitors).

The present disclosure provides a pharmaceutical composition, comprising MANP, acetate, sucrose, and polysorbate 20. In an aspect, a pharmaceutical composition described herein comprises about 2 mg/ml MANP, about 10 mM acetate, about 275 mM sucrose, and about 0.02% polysorbate 20. In an aspect, a pharmaceutical composition described herein comprises about 2 mg/ml MANP, about 40 mM acetate, about 250 mM mannitol, and about 0.02% polysorbate 20.

The present disclosure also provides a pharmaceutical composition, comprising MANP, acetate, sucrose, and polysorbate 20 with little aggregation when stored for a long period. As used herein "aggregation" or "aggregate formation" describes a physical interaction between polypeptide molecules described here (e.g., MANP) that results in formation of oligomers, which may remain soluble or may produce large visible aggregates that precipitate from the solution. As used herein, "storage" or "stored" describes a liquid pharmaceutical composition or formulation described herein, that once prepared, is not immediately administered to a patient, but rather, is packaged for storage, either in a liquid form, in a frozen state, or in a dried form for later reconstitution into a liquid form or other form suitable for administration to a patient. Without being bound by theory, aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

In an aspect, pharmaceutical compositions described herein are stored at about 1-10° C., about 2-5° C., or about 3-5° C. In an aspect, the pharmaceutical compositions described herein are stored at about 10° C., about 9° C., about 8° C., about 7° C., about 6° C., about 5° C., about 4° C., about 3° C., about 2° C., or about 1° C.

In an aspect, the amount of polypeptide can be evaluated by UV spectroscopy. Without being bound by theory, polypeptides absorb in the UV region of the electromagnetic spectrum, with aromatic amino acids like tryptophan absorbing around 280 nm, disulfide bonds absorbing around 250-320 nm, and peptide bonds absorbing around 190 nm and 210-220 nm. In an aspect, the concentration of polypeptide can be determined by dividing the absorbance by the path length of the light through the sample and the extinction coefficient of the polypeptide. In an aspect, the amount of polypeptide (e.g., MANP described herein) can be determined by measuring the absorbance of UV through the polypeptide sample. In an aspect, the amount of polypeptide (e.g., MANP described herein) can be determined by measuring the absorbance of UV at 190-250 nm. In an aspect, the presence of monomer aggregation or the degree of aggregation can be evaluated by UV spectroscopy. Precipitation of aggregates reduces the amount of monomers in solution that can be detected through a decrease in polypeptide concentration.

In an aspect, the presence of monomer aggregation or the degree of aggregation can be evaluated by visual inspection. Without being bound by theory, formation of large aggregates that scatter light result in cloudy appearance, and in some cases, gel formation. In an aspect, monomer aggregation is evaluated by visual inspection.

In an aspect, the presence of monomer aggregation or the degree of aggregation can be evaluated by size exclusion chromatography. Size-exclusion chromatography (SEC) is a chromatographic method in which molecules in solution are separated by their size, molecular weight, or hydrodynamic volume. Without being bound by theory, an aqueous solution is used to transport the molecules of interest through a chromatographic column, that is packed with fine, porous beads typically made of dextran, agarose, or polyacrylamide polymers. As the solution travels down the column the molecules enter into the pores. Larger particles cannot enter into as many pores and as a result, elute faster from the column. Smaller molecules travel through more pores and elute slower from the column. The eluants are collected in constant volumes or fractions, and the collected fractions are examined by spectroscopic techniques to determine the concentration of the particles eluted. In an aspect, UV-vis spectroscopy is used to determine the concentration of polypeptides eluted. In an aspect, the UV absorption at 220 nm is used to determine the concentration of polypeptides eluted. In an aspect, multi-angle laser light scattering (MALS) is used to determine the concentration of polypeptides eluted. In an aspect, refractive index measurements are used to determine the concentration of polypeptides eluted. In an aspect, viscosity measurements are used to determine the concentration of polypeptides eluted.

The SEC elution profile of a sample provides information regarding the mass and conformational heterogeneity of the sample. The elution profile is a plot of the amount of sample eluted over time, with molecules of similar sizes eluting at about the same time. Without being bound by theory, the presence of peaks in the elution profile indicates molecules of different sizes, with the main peak usually comprising the monomers (when there is little to no aggregation), the higher molecular weight peaks usually comprising aggregates (e.g., dimers, trimers, and higher order aggregates), and the lower molecular weight peaks comprising degradation products. Without being bound by theory, the height of the peak indicates the concentration of polypeptide of a particular size in the eluant and the area under the peak indicates the total amount of polypeptide of a particular size. Accordingly, the relative area of a particular peak indicates the amount of polypeptide of a particular size. That is, the higher the relative area of the main peak, the higher the amount of monomer and the lower the amount of aggregation. For example, a loss of relative area of the main peak may indicate that the monomers aggregated, fell out of solution, or that there was a loss of purity.

In an aspect, a pharmaceutical composition described herein comprises about 2 mg/ml MANP, about 10 mM acetate, about 275 mM sucrose, and about 0.02% polysorbate 20, wherein less than 0.5% of monomers aggregate after 24 months when stored at 2-8° C., as measured by the relative area of the main peak obtained via size exclusion chromatography. In an aspect, a pharmaceutical composition described herein comprises about 2 mg/ml MANP, about 10 mM acetate, about 275 mM sucrose, and about 0.02% polysorbate 20, wherein the composition loses less than 0.2% purity after 12 months when stored at 5° C., as measured by the relative area of the main peak obtained via size exclusion chromatography. In an aspect, the composition loses less than 0.18% purity after 12 months when stored at 5° C., as measured by the relative area of the main peak obtained via size exclusion chromatography. In an aspect, a pharmaceutical composition described herein comprises about 2 mg/ml MANP, about 10 mM acetate, about 275 mM sucrose, and about 0.02% polysorbate 20, wherein the composition loses less than 0.5% purity after 24 months when stored at 5° C., as measured by the relative area of the main peak obtained via size exclusion chromatography. In an aspect, the composition loses less than 0.35% purity after 24 months when stored at 5° C., as measured by the relative area of a main peak obtained via size exclusion chromatography.

In an aspect, the chemical stability of a sample can be evaluated by high performance liquid chromatography (HPLC). High-performance liquid chromatography (HPLC) is a broad analytical chemistry technique used to separate compounds in a chemical mixture. These separations utilize the pressure-driven flow of a mobile phase through a column packed with a stationary phase. The mobile phase carries a liquid sample through the column to the detector, and compounds or analytes separate due to varying degrees of interaction with the stationary phase. In reversed-phase HPLC (RP-HPLC), the stationary phase is typically a chemically bonded inorganic oxide while the mobile phase is typically aqueous-organic solvent mixtures (e.g., mixtures of acetonitrile, water, and trifluoroacetic acid). In RP-HPLC, the sample passes through the column and different compound groups interact differently with the stationary phase, leading to different retention times depending on the chemical properties. Thus, separation takes place of different analytes or components in a sample. Without being bound by theory, the presence of peaks in the elution profile indicates molecules of different chemical compositions. For a sample with a single analyte, the main peak usually comprises the analyte (when there is little to no degradation) while the other peaks indicate different degradation products, the amount of which is impacted by temperature, analyte concentration and formulation composition. In an aspect, the relative height of the main peak indicates the amount of undegraded polypeptide (e.g., the MANP described herein) in the sample. For example, a loss of height of the main peak may indicate that a proportion of the polypeptides degraded, fell out of solution, or that there was a loss of purity. In an aspect, the relative area of the main peak indicates the amount of undegraded polypeptide (e.g., the MANP described herein) in the sample. That is, the higher the relative area of the main peak, the higher the amount of undegraded polypetide and the lower the amount of degradation products. For example, a loss of relative area of the main peak may indicate that a proportion of the polypeptides degraded, fell out of solution, or that there was a loss of purity.

In an aspect, a pharmaceutical composition described herein comprises about 2 mg/ml MANP, about 10 mM acetate, about 275 mM sucrose, and about 0.02% polysorbate 20, wherein the composition loses less than 1% purity after 6 months when stored at 5° C., as measured by a height of a main peak obtained via reversed phase HPLC. In an aspect, the composition loses less than 0.5% purity after 6 months when stored at 5° C., as measured by the height of the main peak in reversed phase HPLC. In an aspect, a pharmaceutical composition described herein comprises about 2 mg/ml MANP, about 10 mM acetate, about 275 mM sucrose, and about 0.02% polysorbate 20, wherein the composition loses less than 10% purity after 12 months when stored at 5° C., as measured by the relative area of a main peak obtained via reversed phase HPLC. In an aspect, the composition loses less than 5% purity after 12 months when stored at 5° C., as measured by the relative area of the main peak in reversed phase HPLC. In an aspect, the composition loses less than 3% purity after 12 months when stored at 5° C., as measured by the relative area of the main peak in reversed phase HPLC. In an aspect, a pharmaceutical composition described herein comprises about 2 mg/ml MANP, about 10 mM acetate, about 275 mM sucrose, and about 0.02% polysorbate 20, wherein the composition loses less than 10% purity after 24 months when stored at 5° C., as measured by the relative area of a main peak obtained via reversed phase HPLC. In an aspect, the composition loses less than 5% purity after 24 months when stored at 5° C., as measured by the relative area of the main peak in reversed phase HPLC.

Kits, Vials, and Pre-Filled Syringes

The present disclosure provides kits for use in treating hypertension in a patient in need of, comprising the compositions described herein. In an aspect, a kit for use in treating hypertension in a patient in need thereof, comprises a composition described herein, and an injection device for ejecting a dose of the composition. In an aspect, the injection device is a syringe. In an aspect, the injection device is a dose-limiting syringe. In an aspect, the injection device is a pen-like syringe. In an aspect, the injection device is a catheter. In an aspect, the injection device is a syringe with an auto-injector.

The present disclosure provides vials containing the compositions described herein. Vials made of materials that do not interact or degrade the compositions stored in them determine the long-term stability of the compositions. In an aspect, a vial is a glass container. In an aspect, a vial comprises a glass body and a cap. In an aspect, a vial is an ampule. In an aspect, the vial contains a formulation comprising MANP, acetate, mannitol, and polysorbate 20. In an aspect, the vial contains a formulation comprising MANP, acetate, sucrose, and polysorbate 20. In an aspect, the compositions described herein, stored in the vial, loses less than 1% purity after 6 months when stored at 5° C., as measured by the height of a main peak obtained via reversed phase HPLC. In an aspect, the compositions described herein, stored in the vial, has less than 0.5% of monomers aggregate after 24 months when stored at 2-8° C., as measured by the relative area of a main peak obtained via SEC. In an aspect, the compositions described herein, stored in the vial, loses less than 10% purity after 12 months when stored at 5° C., as measured by the relative area of a main peak obtained via RP-HPLC. In an aspect, the compositions described herein, stored in the vial, loses less than 10% purity after 24 months when stored at 5° C., as measured by the relative area of a main peak obtained via RP-HPLC. In an aspect, the compositions described herein, stored in a vial, lose less than 0.2% purity after 12 months when stored at 5° C., as measured by the relative area of a main peak obtained via SEC. In an aspect, the compositions described herein, stored in a vial, lose less than 0.5% purity after 24 months when stored at 5° C., as measured by the relative area of a main peak obtained via SEC.

The present disclosure also provides pre-filled syringes containing the compositions described herein. In an aspect, a pre-filled syringe is a syringe which is filled with drug prior to distribution to the end user who will administer the drug to the patient. In an aspect, the pre-filled syringe contains the compositions herein in a drug contain (e.g., a syringe body), an elastomeric plunger for expelling the drug, and either an attached hypodermic needle or else features to allow a needle to be attached by the user prior to administration of the drug so that the drug can be delivered directly from the syringe in which it is supplied through the needle into the patient. The user of the syringe will typically need to be trained in the skill of administering injections, and may be the patient themselves, a doctor, a nurse or other carer such as a family member. In an aspect, the compositions disclosed herein are present in the pre-filled syringe at a concentration of about 0.1 mg/ml, about 0.2 mg/ml, about 0.5 mg/ml, about 1 mg/ml, about 2 mg/ml, about 5 mg/ml, about 10 mg/ml, about 20 mg/ml, about 50 mg/ml, about 100 mg/ml, about 200 mg/ml, about 500 mg/ml. In an aspect, the pre-filled syringe may be useful for administering about 0.1 ml, about 0.2 ml, about 0.3 ml, about 0.4 ml, about 0.5 ml, about 0.6 ml, about 0.7 ml, about 0.8 ml, about 0.9 ml, about 1.0 ml, about 1.1 ml, about 1.2 ml, about 1.3 ml, about 1.4 ml, about 1.5 ml, about 1.6 ml, about 1.7 ml, about 1.8 ml, about 1.9 ml, about 2.0 ml, about 2.1 ml, about 2.2 ml, about 2.3 ml, about 2.4 ml, about 2.5 ml, about 2.6 ml, about 2.7 ml, about 2.8 ml, about 2.9 ml, about 3.0 ml, about 3.1 ml, about 3.2 ml, about 3.3 ml, about 3.4 ml, about 3.5 ml, about 3.6 ml, about 3.7 ml, about 3.8 ml, about 3.9 ml, about 4.0 ml, about 4.1 ml, about 4.2 ml, about 4.3 ml, about 4.4 ml, about 4.5 ml, about 4.6 ml, about 4.7 ml, about 4.8 ml, about 4.9 ml, about 5.0 ml, about 5.1 ml, about 5.2 ml, about 5.3 ml, about 5.4 ml, about 5.5 ml, about 5.6 ml, about 5.7 ml, about 5.8 ml, about 5.9 ml, about 6.0 ml, about 7.0 ml, about 8.0 ml, about 9.0 ml, about 10.0 ml, about 15 ml, about 20 ml, about 25 ml, about 30 ml, about 35 ml, about 40 ml, about 45 ml, about 50 ml, or about 100 ml, of the compositions described herein per patient per dose.

EXAMPLES

The present disclosure is illustrated by the following examples. The examples set out herein illustrate several aspects of the present disclosure but should not be construed as limiting the scope of the present disclosure in any manner.

Example 1: Formulation Development Studies

The primary purpose of this study is to develop a liquid formulation comprising MANP, that is stable for storage at 2-8° C. with a target concentration of about 2 mg/ml, a pH of 7.4, and osmolality of 290-310 mOsm/L.

The study uses the following equipment as shown in Table 1.

TABLE 1

Materials used in the study

| Study No. | Equipment | Manufacturer | Model | Serial Number |
|---|---|---|---|---|
| 1 | Sterile Filter, MillexGV, 0.22 µm PVDF, 4 mm | Millex | SLGV004SL | R9MA86772 |
|  | Vials, 1 mL, Fiolax Clear 27.00 × 13.75 | Schott | 1661079 | 6105408953 |
|  | Caps, S2-F451 D777-1 R B2-40 | West | 19560001 | 807034 |
| 2 | Sterile Filter, MillexGV, 0.22 µm PVDF, 4 mm | Millex | SLGV004SL | ROMB10278 |
|  | Vials, 1 mL, Fiolax Clear 27.00 × 13.75 | Schott | 6800384 | 6105408953 |

TABLE 1-continued

Materials used in the study

| Study No. | Equipment | Manufacturer | Model | Serial Number |
|---|---|---|---|---|
|  | Caps, S2-F451 D777-1 R B2-40 | West | 19560001 | 807034 |
| 3 | Sterile Filter, MillexGV, 0.22 µm PVDF, 4 mm | Millex | SLGV004SL | ROMB10278 |
|  | Vials, 1 mL, Fiolax Clear 27.00 × 13.75 | Schott | 1661079 | 6105408953 |
|  | Caps, S2-F451 D777-1 R B2-40 | West | 19560001 | 807034 |
| 4 | Sterile Filter, MillexGV, 0.22 µm PVDF, 4 mm | Millex | SLGVR33RS | RIAB86554 |
|  | Vials, 1 mL, Fiolax Clear 27.00 × 13.75 | Schott | 1661086 | 6105091515 |
|  | Caps, S2-F451 D777-1 R B2-40 | West | 19560001 | 807034 |

Method: UV Analysis

In order to prevent sample loss and the error due to preparing the UV sample, the concentration of each formulation is measured using the SoloVPE. The concentration of the sample is measured by adding 100 µL of material into a SoloVPE small UV disposable vessel. A new fibrette is installed and the sample absorbance is measured by the instrument, using an extinction coefficient of 1.58 mL*mg-1 cm-1, and correcting background scattering. The extinction coefficient is calculated from the primary amino acid sequence of the peptide. 1 After analysis, the sample is removed with a pipette from the disposable vessel. The disposable vessel and fibrette are both then disposed. This procedure is repeated for each sample.

Method: pH Analysis

After sample preparation, the pH is checked for each formulation and the measured pH of the sample is within +0.1 of the target pH. Before the start of analysis, the pH probe is calibrated with three pH standards ordered from Fisher. The pH of the formulation will be measured by inserting the pH probe into the sample and waiting until the measured value has stabilized, which can take up to 1 to 2 minutes. After the analysis the pH probe is washed with 18 M2 water for one minute and stored in the pH storage solution.

Method: Osmometry

The osmotic analysis is performed using Advanced Instruments Osmo 1. At the start of analysis, a reference standard at 290 mOsm is analyzed to ensure the instrument is working properly. After the reference standard has passed, the samples are then analyzed. 20 µL of material is removed and analyzed by Osmo 1. After analysis the chamber is cleared by using a chamber cleaner. This procedure is repeated for each sample.

Method: Size Exclusion Chromatography (SEC)

The SEC method is used to measure and trend changes in the physical stability of the peptide stability samples. Parameters for SEC analysis are described below:

Column: Sepax Zenix-C Sec-80,
    Manufacturer: Sepax,
    Specification: 7.8×300 mm,
    Part Number: 233080-7830,
    Mobile Phase: 50% Acetonitrile and 50% Water, 0.1% TFA,
    Sample Concentration (mg/mL): 2 mg/mL,
    Autosampler Temp: 5° C.±3° C.,
    Column Temp.: 25° C.° C.,
    Flow Rate: 0.8 mL/minute, Injection Vol: 7 µg (3.75 µL for 2 mg/mL),
UV Setting: 220 nm, and
Data Collection Time: 10 Hz.
Method: Reversed Phase Chromatography (RP)

The method is used to measure and trend changes in the chemical stability of the peptide. A number of reversed phase methods are used to study the chemical stability of the peptide. The Original method and C8 method are used for the first study. The Primary reversed phase method is used for all the studies after the first study. An exemplary chromatogram from the C8 method is shown in FIG. 1. The parameters for Original reversed phase methods are described as follows:

Column: Waters XBridge C18, 4.6×150 mm, 3.5 µm,
Manufacturer: Waters,
Part Number: 186003034,
Mobile Phase A: 0.2% Methanesulfonic Acid (MSA) in water,
Mobile Phase B: 100% Acetonitrile,
Sample Concentration (mg/mL): 2 mg/mL,
Autosampler Temp: 5.0±3.0° C.,
Column Temp.: 40° C.,
Flow Rate: 1.2 mL/minute,
Injection Vol: 5 µL, and
UV Setting: 215 nm.

The parameters for C8 reversed phase methods are described as follows:

Column: Aeris Widepore, 3.6 µm XB-C8, 250×2.1 mm,
Manufacturer: Phenomenex,
Part Number: 00G-4481-AN,
Mobile Phase A: Water, 0.1% TFA,
Mobile Phase B: Acetonitrile, 0.1% TFA,
Sample Concentration (mg/mL): 2.5 µg on column,
Autosampler Temp: 5±3° C.,
Column Temp.: 40° C.,
Flow Rate: 0.4 mL/minute,
Injection Vol: 2.5 µL, and
UV Setting: 220 nm.

The parameters for Primary reversed phase methods are described in Table 2 and as follows:

Column: XSelect CSH, C18, 3.5 µm,
Manufacturer: Waters,
Specification: 4.6×150 mm,
Part Number: 186005270,
Mobile Phase A: 15% Acetonitrile, 85% Water, 0.1% TFA,
Mobile Phase B: 30% Acetonitrile, 70% Water, 0.1% TFA,
Mobile Phase C: 80% Acetonitrile, 20% Water, 0.1% TFA,
Sample Concentration (mg/mL): 2 mg/mL injected neat,
Autosampler Temp: 8±3° C.,
Column Temp.: 40° C.° C.,
Flow Rate: 0.4 mL/minute,
Injection Vol: 1.25 µL,
UV Setting: 220 nm, and
Data Collection Time: 10 Hz.

TABLE 2

Primary Reversed Phase Mobile Phase Gradient

| Time (Min) | Flow Rate (mL/min) | Mobile Phase B (%) | Mobile Phase C (%) |
|---|---|---|---|
| 0.5 | 0.4 | 10 | 0 |
| 30.0 | 0.4 | 85 | 0 |
| 30.1 | 0.4 | 85 | 0 |
| 40.0 | 0.4 | 0 | 100 |
| 42.0 | 0.4 | 0 | 100 |
| 42.1 | 0.4 | 10 | 0 |
| 42.5 | 0.4 | 10 | 0 |
| 60 | 0.4 | 10 | 0 |

Method: General Sample Preparation, Sterile Filtering and Sample Filling

The 10 mg/mL peptide solution is prepared on the day of formulation, the 2× formulation buffer is prepared the day before. The 10 mg/mL peptide solution is prepared by weighing out the peptide into a sterile container and added Milli-Q water to reach the target peptide concentration. The volume of the 10 mg/mL peptide solution is calculated based on the target sample volume. The calculated volume of the peptide is then added to a new sterile container. The volume of the 2× buffer added to the peptide solution is half the volume of the sample target volume. The pH of the peptide and the 2× buffer is then checked with a pH probe, If the pH value is outside±0.1 pH units, the sample pH is adjusted with 0.1 M of NaCl. The sample is then QS to the target sample volume with Milli-Q water, followed by measuring the pH and peptide concentration again.

The samples are sterile filtered in a clean hood that is wiped down with 70% ethanol. Each formulation is loaded into a sterile syringe with sterile filter attached. The sample is then slowly pushed through filter into a sterile container. After the samples has been sterile filtered, they are loaded into the vials.

Method: Agitation Study

Depending on the study the samples are agitated over the course of 1 day at 25° C. For each temperature two different samples are prepared an agitation sample, which is a 0.5 mL fill into a 2 mL vial and the QS sample that placed next to the shaker plate as a control which is a 0.2 mL fill in a 2 mL vial. The agitation sample are placed in a sample box horizontal and shaker at 590 rpm (which was based on the orbital radius of the shaker). After 24 hours both the agitation sample and the control are analyzed.

Method: Freeze-Thaw Procedure

Formulated samples from Round 4 are frozen at −80° C. for 10 minutes and thawed at 5° C. for 15 minutes. A 2 mL vial is used for these studies, 0.25 mL of the bulk material is loaded in the containers and experiences 5 freeze thaw cycles. On the 5th freeze-thaw cycle the samples are placed at −80° C. overnight and thawed the next day at 5° C. After the sample experiences 5 freeze-thaw cycles they are analyzed.

Method: Multivariate Statistical Modeling Using Partial Least-Squares (PLS)

Partial least squares regression (PLS) is used to shed additional light on the effects of the various formulation parameters on stability for the stage 1 and 2 samples. For any large matrix of values, where there are a reasonable number of samples (together forming the so-called X-matrix), mathematical models can be constructed that explain the largest amount of variance in the dependent variable(s) of interest (the Y-matrix). The best single description of the relationship between the variation in the X-matrix and the endpoint (the Y matrix) is called the first principal component, PC1.

The next important (in terms of describing the variance in the Y-matrix) component is called the second principal component, PC2, and so on. Quite often, only one or two PCs are required to explain most of the variance in the Y-matrix. Each of these PCs contains some contribution from each of the variables in the X-matrix. If a variable within the X-matrix contributes heavily to the construction of a given PC, then it is ranked as being significant. In fact, regression coefficients can be calculated for each variable in the X-matrix for a given model, where a model is the composite of a certain number of PCs in order to provide an adequate description of the Y-matrix. In summary, PLS takes information from the X-matrix, calculates the desired number of PCs, and constructs a suitable model. The model that includes all of the samples is termed a calibration model. The overall coefficient of determination (r2) indicates the quality of the model. All PLS calculations were conducted using Unscrambler software (CAMO, Corvallis, OR). A PLS analysis done with a single variable in the Y-matrix is termed PLS1 analysis. Building a model that fits multiple variables in the Y-matrix is called PLS2 analysis.

A full cross validation is performed on all calibration models using standard techniques. Briefly, one sample is removed at a time, the data set is recalibrated, and a new model is constructed. This process is repeated until all the calibration samples are removed once and quantified as a validation model. Therefore, the first set, containing all samples is referred to as the calibration set and the one after cross-validation as the validation set. The jack-knife algorithm is used to determine statistical significance for any factor used in constructing the PLS models described above. Study 1 Result: Determine Optimal pH and Buffer Concentration for MANP by Visual Inspection, pH, and UV Study 1 is designed to examine the effect of different pH, buffer type, and different stabilizers/tonicity modifiers on the stability of MANP. The conditions tested are as follows:

TABLE 3

Study 1 Formulation Design

| Form. No. | MANP (mg/ml) | pH | Acetate (mM) | Histidine (mM) | Citrate (mM) | Phosphate (mM) | Tris (mM) | NaCl (mM) | Mannitol (mM) |
|---|---|---|---|---|---|---|---|---|---|
| 1 | 1 | 4.5 | 20 | 0 | 0 | 0 | 0 | 130 | 0 |
| 2 | 2 | 5.0 | 20 | 0 | 0 | 0 | 0 | 0 | 250 |
| 3 | 1 | 5.5 | 20 | 0 | 0 | 0 | 0 | 130 | 0 |
| 4 | 2 | 5.5 | 0 | 20 | 0 | 0 | 0 | 0 | 250 |
| 5 | 1 | 5.5 | 0 | 0 | 20 | 0 | 0 | 130 | 0 |
| 6 | 2 | 6.0 | 0 | 20 | 0 | 0 | 0 | 0 | 250 |
| 7 | 1 | 6.0 | 0 | 0 | 20 | 0 | 0 | 130 | 0 |
| 8 | 2 | 6.0 | 0 | 0 | 0 | 20 | 0 | 0 | 250 |
| 9 | 1 | 6.5 | 0 | 20 | 0 | 0 | 0 | 130 | 0 |
| 10 | 2 | 6.5 | 0 | 0 | 20 | 0 | 0 | 0 | 250 |
| 11 | 1 | 6.5 | 0 | 0 | 0 | 20 | 0 | 130 | 0 |
| 12 | 2 | 7.0 | 0 | 0 | 0 | 20 | 0 | 0 | 250 |
| 13 | 1 | 7.0 | 0 | 0 | 20 | 0 | 0 | 130 | 0 |
| 14 | 2 | 7.5 | 0 | 0 | 0 | 20 | 0 | 0 | 250 |
| 15 | 1 | 7.5 | 0 | 0 | 0 | 0 | 20 | 130 | 0 |
| 16 | 2 | 8.0 | 0 | 0 | 0 | 0 | 20 | 0 | 250 |

The stability samples are characterized by visual inspection, pH and UV. Over the course of Study 1 all the samples except for Formulations 2, 4 and 6 showed signs of physical instability (Tables 4 and 5). The signs of physical instability observed for the majority of the samples are a cloudy appearance and gel formation after T=0.

Figure 2:
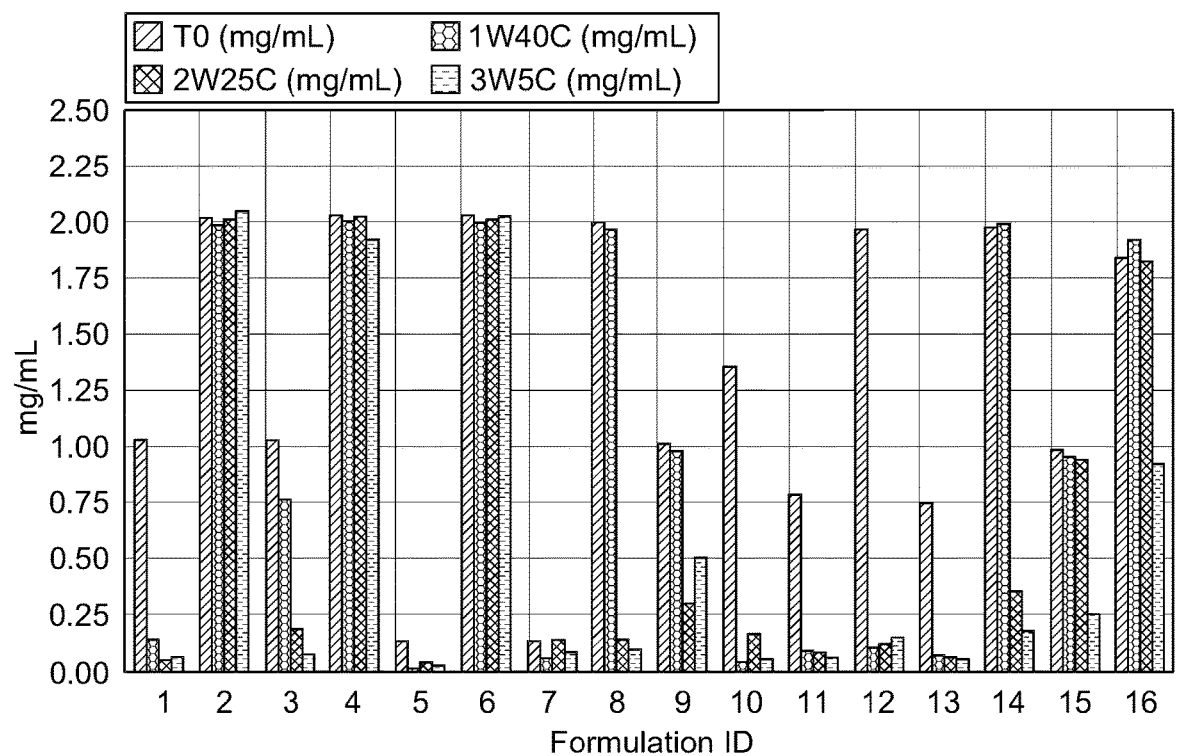
FIG. 2 depicts the peptide concentrations measured for each formulation evaluated in Study 1.
Figure 3:
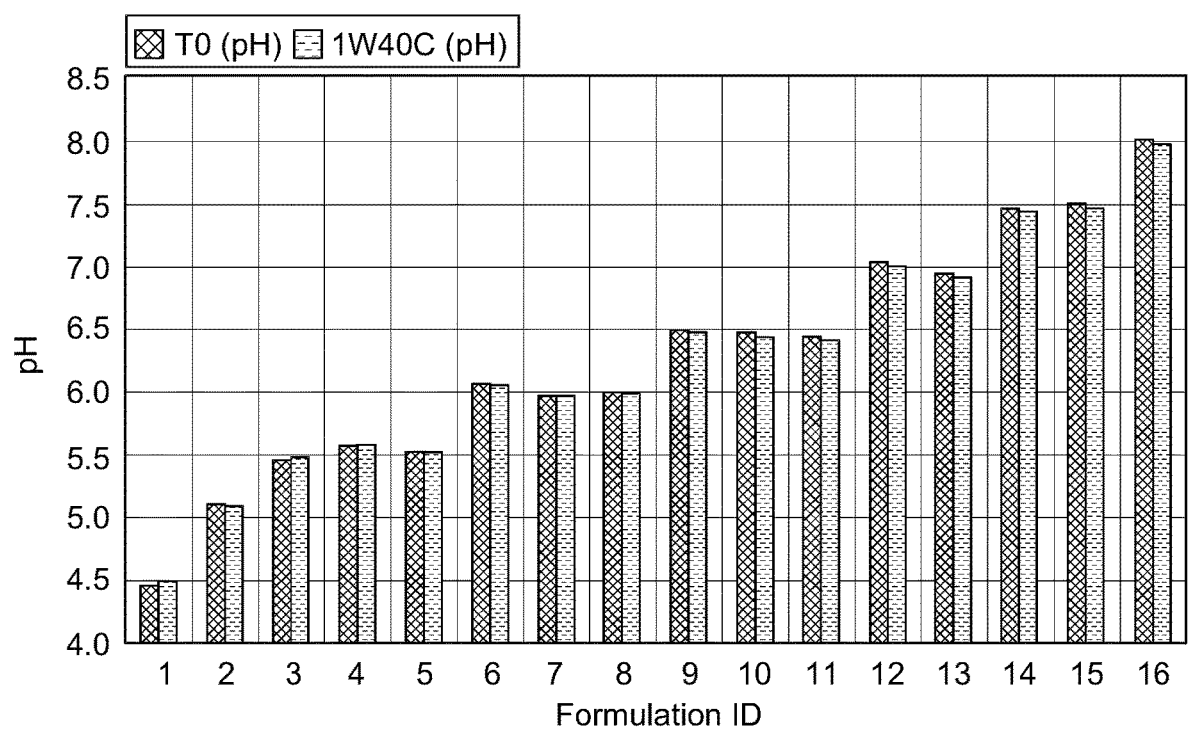
FIG. 3 depicts the pH measured for each formulation evaluated in Study 1.

Changes in peptide concentration for the samples mirror the observations by visual inspection (Table 6). For samples that show signs of physical instability, also showed large decreases in peptide concentration, as much 100% loss (FIG. 2). The change in the peptide concentration for Formulation 2,4 and 6 over the course study was less than 5% difference compared to T=0. The pH values for the stability samples were unchanged over the course of the entire study (FIG. 3).

TABLE 4

Study 1 visual characterization of stability samples at T = 0 and T = 1 week at 40° C.

| Form. No. | MANP (mg/ml) | pH | Observations at T = 0 | | | Observations at T = 1 week at 40° C. | | |
|---|---|---|---|---|---|---|---|---|
| | | | Color | Particle | Visual | Color | Particle | Visual |
| 1 | 1 | 4.5 | No | No | Clear | No | Yes | Clear |
| 2 | 2 | 5.0 | No | No | Clear | No | No | Clear |
| 3 | 1 | 5.5 | No | No | Clear | No | Yes | Clear |
| 4 | 2 | 5.5 | No | No | Clear | No | No | Clear |
| 5 | 1 | 5.5 | No | Yes | Clear | No | Yes | Cloudy |
| 6 | 2 | 6.0 | No | No | Clear | No | No | Clear |

TABLE 4-continued

Study 1 visual characterization of stability samples at
T = 0 and T = 1 week at 40° C.

| Form. No. | MANP (mg/ml) | pH | Observations at T = 0 | | | Observations at T = 1 week at 40° C. | | |
|---|---|---|---|---|---|---|---|---|
| | | | Color | Particle | Visual | Color | Particle | Visual |
| 7 | 1 | 6.0 | No | Yes | Clear | No | Yes | Clear |
| 8 | 2 | 6.0 | No | No | Clear | No | No | Clear |
| 9 | 1 | 6.5 | No | No | Clear | No | No | Clear |
| 10 | 2 | 6.5 | No | No | Clear | No | Yes | Cloudy |
| 11 | 1 | 6.5 | No | No | Clear | No | Gel | Cloudy |
| 12 | 2 | 7.0 | No | No | Clear | No | Yes | Clear |
| 13 | 1 | 7.0 | No | No | Clear | No | No | Cloudy |
| 14 | 2 | 7.5 | No | No | Clear | No | No | Clear |
| 15 | 1 | 7.5 | No | No | Clear | No | No | Clear |
| 16 | 2 | 8.0 | No | No | Clear | No | No | Clear |

TABLE 5

Study 1 visual characterization of stability samples at T = 2
weeks at 25° C. and T = 3 weeks at 5° C.

| Form. No. | MANP (mg/ml) | pH | Observations at T = 2 weeks at 25° | | | Observations at T = 3 weeks at 5° C. | | |
|---|---|---|---|---|---|---|---|---|
| | | | Color | Particle | Visual | Color | Particle | Visual |
| 1 | 1 | 4.5 | No | Yes | Clear | No | Yes | Chunky |
| 2 | 2 | 5.0 | No | No | Clear | No | No | Clear |
| 3 | 1 | 5.5 | No | Yes | Clear | No | Yes | Clear |
| 4 | 2 | 5.5 | No | No | Clear | No | No | Clear |
| 5 | 1 | 5.5 | No | Yes | Clear | No | Yes | Clear |
| 6 | 2 | 6.0 | No | No | Clear | No | No | Clear |
| 7 | 1 | 6.0 | No | Yes | Clear | No | No | Clear |
| 8 | 2 | 6.0 | No | Yes | Clear | No | Yes | Chunky |
| 9 | 1 | 6.5 | No | Yes | Clear | No | Yes | Clear |
| 10 | 2 | 6.5 | No | Yes | Clear | No | Yes | Cloudy |
| 11 | 1 | 6.5 | No | No | Gel | No | No | Chunky |
| 12 | 2 | 7.0 | No | Yes | Clear | No | Yes | Cloudy |
| 13 | 1 | 7.0 | No | Yes | Clear | No | Yes | Cloudy |
| 14 | 2 | 7.5 | No | Yes | Clear | No | No | Clear |
| 15 | 1 | 7.5 | No | No | Clear | No | Yes | Cloudy |
| 16 | 2 | 8.0 | No | Yes | Clear | No | Gel | Clear |

TABLE 6

Study 1 peptide concentration and pH for the stability samples

| Form. No. | MANP (mg/ml) | pH | pH | | Peptide Concentration (mg/mL) | | | |
|---|---|---|---|---|---|---|---|---|
| | | | T = 0 | T = 1 week 40° C. | T = 0 | T = 1 week 40° C. | T = 2 weeks 25° C. | T = 3 weeks 5° C. |
| 1 | 1 | 4.5 | 4.47 | 4.49 | 1.03 | 0.13 | 0.04 | 0.05 |
| 2 | 2 | 5.0 | 5.11 | 5.09 | 2.01 | 1.98 | 2.01 | 2.04 |
| 3 | 1 | 5.5 | 5.46 | 5.49 | 1.02 | 0.75 | 0.18 | 0.07 |
| 4 | 2 | 5.5 | 5.58 | 5.59 | 2.02 | 2.00 | 2.01 | 1.92 |
| 5 | 1 | 5.5 | 5.53 | 5.53 | 0.13 | 0.01 | 0.02 | 0.01 |
| 6 | 2 | 6.0 | 6.06 | 6.05 | 2.02 | 1.99 | 2.01 | 2.02 |
| 7 | 1 | 6.0 | 5.97 | 5.97 | 0.13 | 0.05 | 0.13 | 0.08 |
| 8 | 2 | 6.0 | 6.00 | 5.99 | 1.99 | 1.96 | 0.13 | 0.09 |
| 9 | 1 | 6.5 | 6.49 | 6.50 | 1.01 | 0.98 | 0.30 | 0.50 |
| 10 | 2 | 6.5 | 6.48 | 6.45 | 1.35 | 0.03 | 0.16 | 0.04 |
| 11 | 1 | 6.5 | 6.45 | 6.43 | 0.78 | 0.09 | 0.08 | 0.06 |
| 12 | 2 | 7.0 | 7.04 | 7.01 | 1.96 | 0.1 | 0.12 | 0.14 |
| 13 | 1 | 7.0 | 6.95 | 6.93 | 0.74 | 0.06 | 0.05 | 0.05 |
| 14 | 2 | 7.5 | 7.47 | 7.45 | 1.97 | 1.98 | 0.35 | 0.18 |
| 15 | 1 | 7.5 | 7.51 | 7.47 | 0.98 | 0.95 | 0.94 | 0.25 |
| 16 | 2 | 8.0 | 8.02 | 7.97 | 1.83 | 1.92 | 1.82 | 0.92 |

Figure 4:
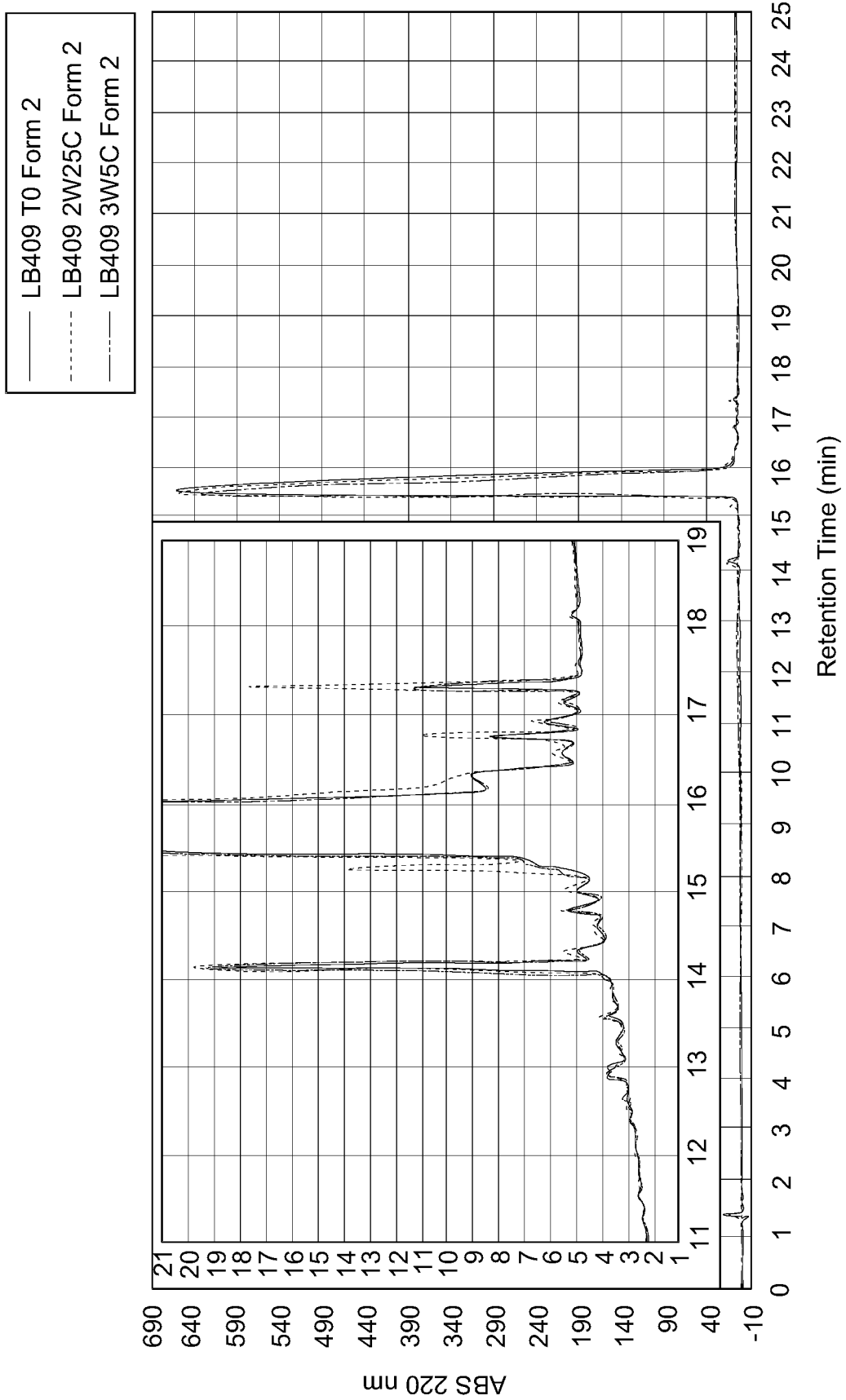
FIG. 4 depicts an exemplary C8 reversed-phase HPLC chromatogram for MANP.

Study 1 Result: Determine Optimal pH and Buffer Concentration for MANP by RP-HPLC The stability samples are characterized by Reversed Phase Chromatography. A typical chromatogram measured by the C8 reversed phase method is shown in FIG. 4, depicting that when the peptide is stressed at 25° C., a number of peaks before and after the main peak increase in intensity. Each peak represents a different degradation product, the amount of which is impacted by temperature, peptide concentration, and formulation composition.

Figure 5:
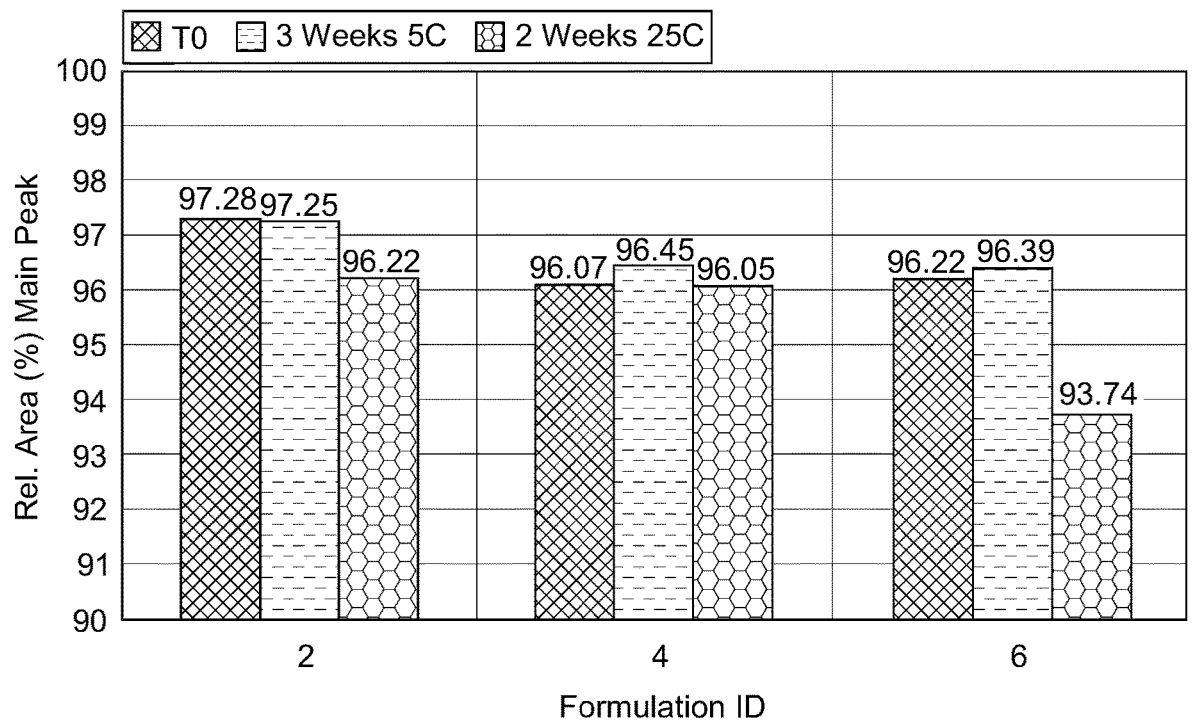
FIG. 5 depicts the relative areas of the main peak for select samples from Study 1 as measured by C8 RP-HPLC.

Only three formulations from Study 1 (Formulations 2, 4, and 6) are viable in terms of stability by RP-HPLC (Table 7). All of the other formulations show signs of physical instability (loss of concentration, precipitation, cloudiness, or gelation). These degraded samples are not analyzed further. The main peak for Formulation 1 starts with the highest T0 relative area (%) of 97.28 compared to Formulation 4 and Formulation 6 which are both around 96.4(%). When the samples are stored at 5° C. for 3 weeks, the change in the main peak is less than 0.1% for Formulation 1, and increased for Formulations 2 and 3 (FIG. 5). At 2 weeks, 25° C., all formulations lost some relative area (%) of the main peak, with Formulation 6 experiencing the greatest loss of 2.7% and Formulation 4 showing essentially no loss. The RP-HPLC data gathered in Study 1 indicates that the C8 method is sensitive to chemical changes, but further improvements are still required.

TABLE 7

Study 1 Reversed Phase data for Formulations 2, 4, and 6 stability samples

| Form. | Time (week) | Temp (° C.) | Retention Time (min) Main Peak | (mAU * min) Main Peak | Relative Area (%) Pre Peak 1 | Pre Peak 2 | Pre Peak 3 | Pre Peak 4 | Pre Peak 5 | Pre Peak 6 | Pre Peak 7 | Main Peak |
|---|---|---|---|---|---|---|---|---|---|---|---|---|
| 2 | 0 | 0  | 15.52 | 201.4 | 0.28 | 0.66 | 0.10 | 0.05 | 0.25 | 0.06 | 0.16 | 97.28 |
| 2 | 3 | 5  | 15.50 | 196.6 | 0.30 | 0.66 | 0.10 | 0.06 | 0.29 | 0.06 | 0.17 | 97.25 |
| 2 | 2 | 25 | 15.51 | 196.0 | 0.35 | 0.69 | 0.13 | 0.07 | 1.18 | 0.06 | 0.00 | 96.22 |
| 4 | 0 | 0  | 15.61 | 135.7 | 0.44 | 0.89 | 0.12 | 0.10 | 0.52 | 0.06 | 0.15 | 96.07 |
| 4 | 3 | 5  | 15.56 | 143.7 | 0.35 | 0.90 | 0.12 | 0.09 | 0.16 | 0.04 | 0.35 | 96.45 |
| 4 | 2 | 25 | 15.53 | 182.7 | 0.32 | 0.76 | 0.12 | 0.11 | 1.16 | 0.05 | 0.00 | 96.05 |
| 6 | 0 | 0  | 15.50 | 198.9 | 0.32 | 0.74 | 0.10 | 0.07 | 0.12 | 0.08 | 0.34 | 96.22 |
| 6 | 3 | 5  | 15.53 | 183.3 | 0.35 | 0.73 | 0.10 | 0.07 | 0.40 | 0.05 | 0.11 | 96.39 |
| 6 | 2 | 25 | 15.51 | 189.3 | 0.31 | 0.65 | 0.11 | 0.10 | 0.99 | 0.05 | 0.00 | 93.74 |

| Form. | Time (week) | Temp (° C.) | Main Peak | Relative Area (%) Post Peak 1 | Post Peak 2 | Post Peak 3 | Post Peak 4 | Post Peak 5 | Post Peak 6 | Post Peak 7 | Post Peak 8 |
|---|---|---|---|---|---|---|---|---|---|---|---|
| 2 | 0 | 0  | 97.28 | 0.48 | 0.00 | 0.09 | 0.20 | 0.11 | 0.06 | 0.16 | 0.06 |
| 2 | 3 | 5  | 97.25 | 0.47 | 0.00 | 0.09 | 0.21 | 0.11 | 0.06 | 0.17 | 0.00 |
| 2 | 2 | 25 | 96.22 | 0.48 | 0.00 | 0.12 | 0.34 | 0.13 | 0.06 | 0.00 | 0.17 |
| 4 | 0 | 0  | 96.07 | 0.26 | 0.40 | 0.11 | 0.38 | 0.12 | 0.06 | 0.15 | 0.17 |
| 4 | 3 | 5  | 96.45 | 0.27 | 0.38 | 0.09 | 0.37 | 0.10 | 0.04 | 0.35 | 0.01 |
| 4 | 2 | 25 | 96.05 | 0.15 | 0.42 | 0.11 | 0.50 | 0.13 | 0.05 | 0.00 | 0.07 |
| 6 | 0 | 0  | 96.22 | 0.40 | 0.54 | 0.11 | 0.39 | 0.15 | 0.08 | 0.34 | 0.22 |
| 6 | 3 | 5  | 96.39 | 0.43 | 0.57 | 0.09 | 0.38 | 0.13 | 0.05 | 0.11 | 0.04 |
| 6 | 2 | 25 | 93.74 | 3.07 | 0.11 | 0.60 | 0.00 | 0.14 | 0.05 | 0.00 | 0.08 |

Study 1 Result: Determine Optimal pH and Buffer Concentration for MANP by SEC

Figure 6:
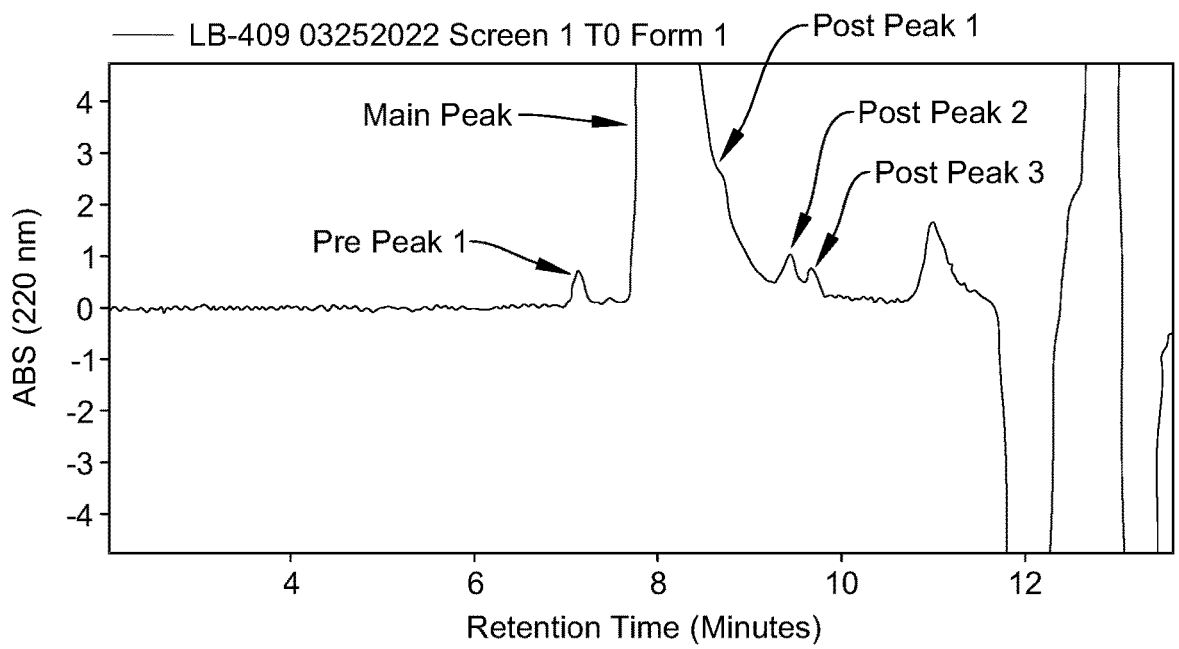
FIG. 6 depicts an exemplary size exclusion chromatography (SEC) chromatogram for MANP.
Figure 7:
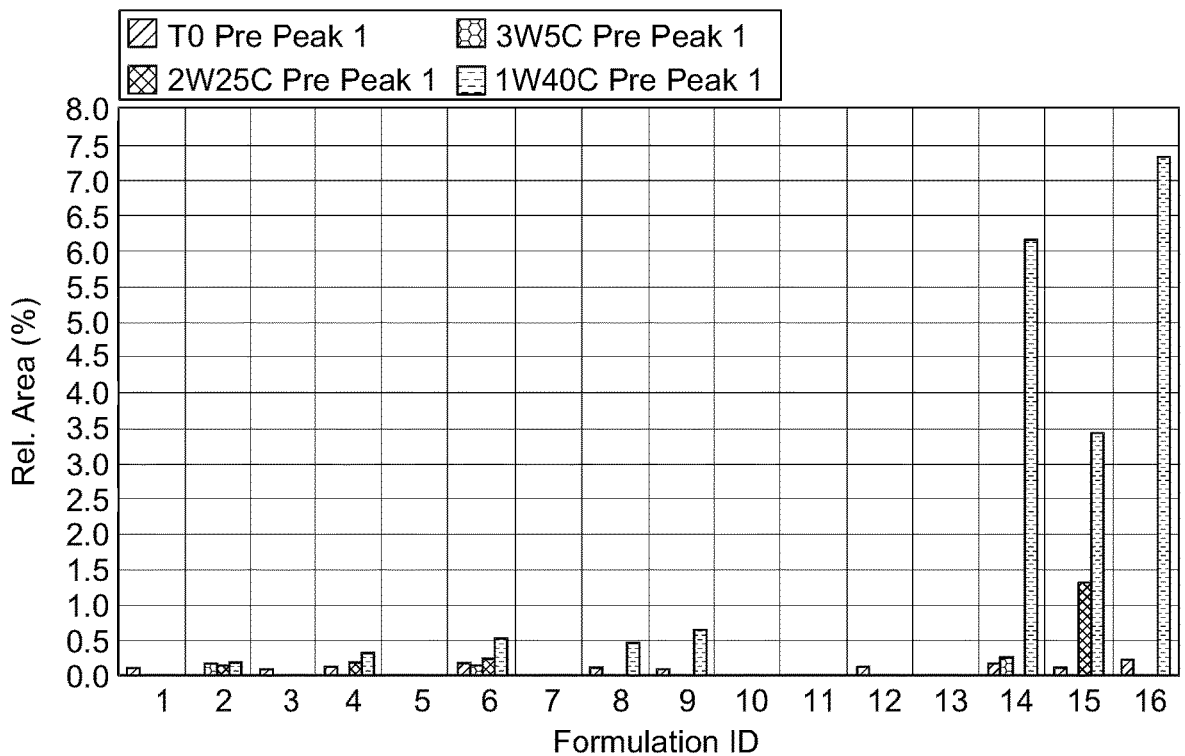
FIG. 7 depicts the relative areas of pre-peaks for samples from Study 1 as measured by SEC.
Figure 8:
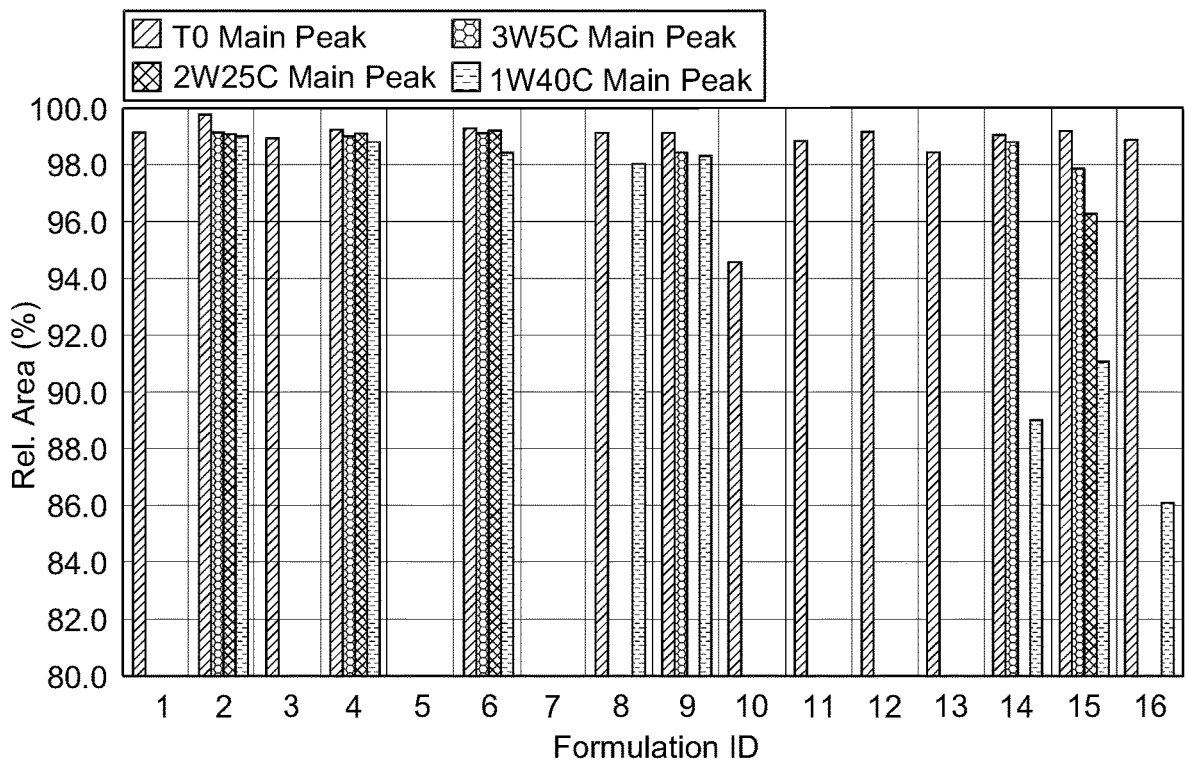
FIG. 8 depicts the relative areas of the main peak (monomer) for samples from Study 1 as measured by SEC.
Figure 9:
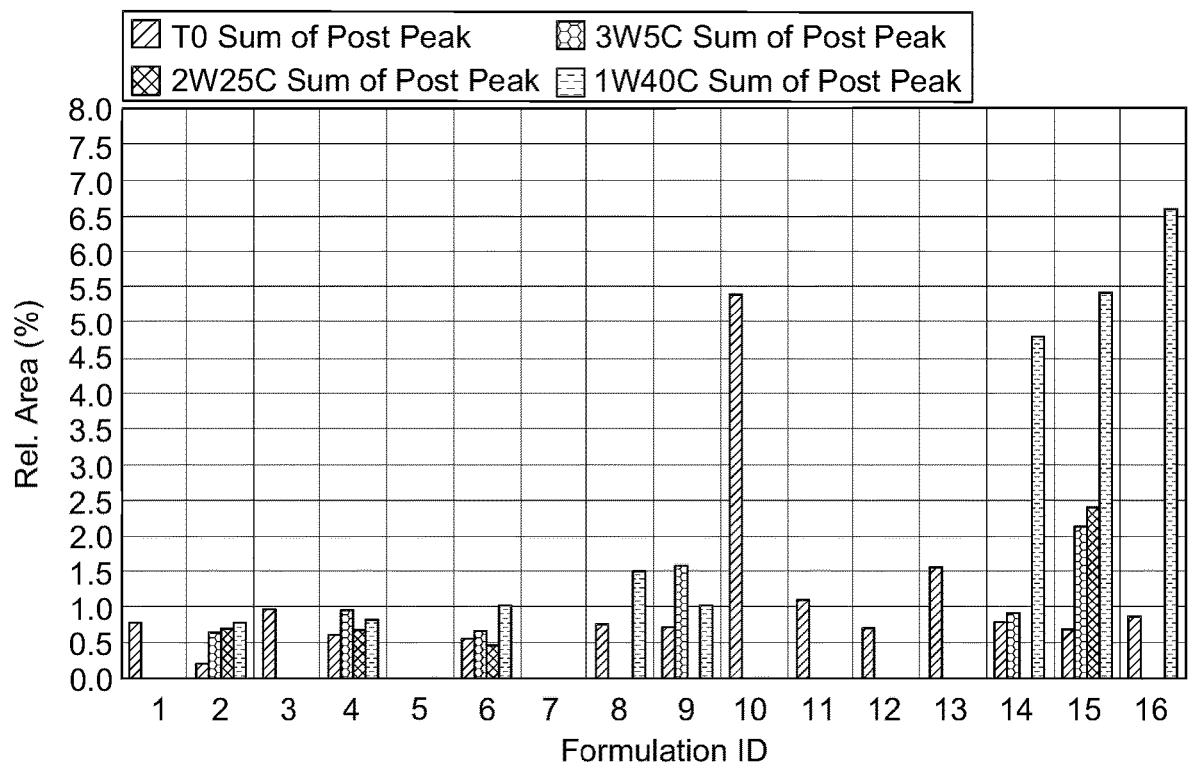
FIG. 9 depicts the relative areas of post-peaks for samples from Study 1 as measured by SEC.

Size exclusion chromatography (SEC) is used to monitor the changes in physical stability of the peptide, and also gives some chemical information. Peaks that elute before the main peak are high molecular weight (HMW) species, such as dimers or larger multimers. Peaks that elute after the main peak are lower molecular weight (LMW) species, such as peptide fragments caused by chemical degradation. An example of the peptide being analyzed by SEC is shown in FIG. 6.

The Study 1 samples are analyzed by SEC, with initial monomer (main peak) content around 98%, except for Formulation 10, which is closer to 95% (Tables 8-11). For the later time points, samples that exhibit ,acroscopic signs of physical instability are not analyzed, in part, to prevent fouling the SEC column. In stability samples at lower pH (between 4.5 to 6.5) the loss of the momomer is caused by an increase in HMW and LMW species around 1% (FIGS. 6-9). For stability samples at higher pH (between 7.5 to 8), the loss of the monomer is associated with larger increases in HMW and LMW species (around 10 to 14%). Formulations 2.4 and 6 are the best preforming formulations, with loss of the monomer bring less than 1%.

TABLE 8

Study 1 SEC results for the T = 0 stability samples

| Form. | Group Area (mAU * min) | Rel. Area (%) Pre Peak 1 | Rel. Area (%) Main Peak | Rel. Area (%) Post Peak 1 | Rel. Area (%) Post Peak 2 | Rel. Area (%) Post Peak 3 |
|---|---|---|---|---|---|---|
| 1 | 141.40 | 0.10 | 99.16 | 0.52 | 0.14 | 0.09 |
| 2 | 145.13 | 0.00 | 99.81 | 0.00 | 0.13 | 0.06 |
| 3 | 143.14 | 0.08 | 98.98 | 0.68 | 0.18 | 0.08 |
| 4 | 144.35 | 0.12 | 99.30 | 0.41 | 0.13 | 0.05 |
| 5 | n.a | n.a | n.a | n.a | n.a | n.a |
| 6 | 145.52 | 0.16 | 99.32 | 0.37 | 0.12 | 0.04 |
| 7 | n.a | n.a. | n.a | n.a | n.a | n.a |
| 8 | 140.49 | 0.12 | 99.13 | 0.54 | 0.15 | 0.06 |
| 9 | 139.50 | 0.09 | 99.21 | 0.52 | 0.13 | 0.06 |
| 10 | 10.06 | 0 | 94.60 | 2.98 | 1.48 | 0.94 |
| 11 | 76.89 | 0 | 98.91 | 0.69 | 0.27 | 0.14 |
| 12 | 138.41 | 0.12 | 99.17 | 0.48 | 0.15 | 0.08 |
| 13 | 77.47 | 0 | 98.46 | 1.16 | 0.26 | 0.12 |
| 14 | 139.77 | 0.17 | 99.04 | 0.58 | 0.13 | 0.08 |
| 15 | 133.45 | 0.12 | 99.21 | 0.47 | 0.14 | 0.06 |
| 16 | 116.82 | 0.23 | 98.92 | 0.58 | 0.20 | 0.08 |

TABLE 9

Study 1 SEC results for the T = 1 week 40° C. stability samples

| Form. | Group Area (mAU * min) | Rel. Area (%) Pre Peak 1 | Rel. Area (%) Main Peak | Rel. Area (%) Post Peak 1 | Rel. Area (%) Post Peak 2 | Rel. Area (%) Post Peak 3 |
|---|---|---|---|---|---|---|
| 1 | n.a | n.a | n.a | n.a | n.a | n.a |
| 2 | 141.28 | 0.18 | 99.04 | 0.62 | 0.11 | 0.04 |
| 3 | n.a | n.a | n.a | n.a | n.a | n.a |
| 4 | 143.58 | 0.32 | 98.86 | 0.63 | 0.13 | 0.05 |
| 5 | n.a | n.a | n.a | n.a | n.a | n.a |
| 6 | 142.37 | 0.53 | 98.46 | 0.79 | 0.16 | 0.06 |
| 7 | n.a | n.a. | n.a | n.a | n.a | n.a |
| 8 | 137.24 | 0.47 | 98.04 | 1.21 | 0.23 | 0.05 |
| 9 | 133.07 | 0.65 | 98.34 | 0.80 | 0.22 | 0 |
| 10 | n.a | n.a | n.a | n.a | n.a | n.a |
| 11 | n.a | n.a | n.a | n.a | n.a | n.a |
| 12 | n.a | n.a | n.a | n.a | n.a | n.a |
| 13 | n.a | n.a | n.a | n.a | n.a | n.a |
| 14 | 138.82 | 6.16 | 89.06 | 3.89 | 0.78 | 0.12 |
| 15 | 134.09 | 3.45 | 91.12 | 3.80 | 1.38 | 0.26 |
| 16 | 136.56 | 7.32 | 86.10 | 5.40 | 1.04 | 0.14 |

TABLE 10

Study 1 SEC results for the T = 2 weeks 25° C. stability samples

| Form. | Group Area (mAU * min) | Rel. Area (%) Pre Peak 1 | Rel. Area (%) Main Peak | Rel. Area (%) Post Peak 1 | Rel. Area (%) Post Peak 2 | Rel. Area (%) Post Peak 3 |
|---|---|---|---|---|---|---|
| 1 | n.a | n.a | n.a | n.a | n.a | n.a |
| 2 | 144.43 | 0.14 | 99.18 | 0.49 | 0.13 | 0.06 |
| 3 | n.a | n.a | n.a | n.a | n.a | n.a |
| 4 | 144.80 | 0.19 | 99.14 | 0.50 | 0.12 | 0.06 |
| 5 | n.a | n.a | n.a | n.a | n.a | n.a |
| 6 | 143.15 | 0.24 | 99.3 | 0.41 | 0.05 | 0 |
| 7 | n.a | n.a. | n.a | n.a | n.a | n.a |
| 8 | n.a | n.a. | n.a | n.a | n.a | n.a |
| 9 | n.a | n.a. | n.a | n.a | n.a | n.a |
| 10 | n.a | n.a | n.a | n.a | n.a | n.a |
| 11 | n.a | n.a | n.a | n.a | n.a | n.a |
| 12 | n.a | n.a | n.a | n.a | n.a | n.a |
| 13 | n.a | n.a | n.a | n.a | n.a | n.a |
| 14 | n.a | n.a. | n.a | n.a | n.a | n.a |
| 15 | 130.24 | 1.32 | 96.27 | 1.49 | 0.75 | 0.16 |
| 16 | n.a | n.a. | n.a | n.a | n.a | n.a |

TABLE 11

Study 1 SEC results for the T = 3 weeks 5° C. stability samples

| Form. | Group Area (mAU * min) | Rel. Area (%) Pre Peak 1 | Rel. Area (%) Main Peak | Rel. Area (%) Post Peak 1 | Rel. Area (%) Post Peak 2 | Rel. Area (%) Post Peak 3 |
|---|---|---|---|---|---|---|
| 1 | n.a | n.a | n.a | n.a | n.a | n.a |
| 2 | 144.55 | 0.16 | 99.21 | 0.44 | 0.13 | 0.06 |
| 3 | n.a | n.a | n.a | n.a | n.a | n.a |
| 4 | 136.85 | 0 | 99.06 | 0.61 | 0.22 | 0.11 |
| 5 | n.a | n.a | n.a | n.a | n.a | n.a |
| 6 | 143.99 | 0.14 | 99.21 | 0.46 | 0.13 | 0.06 |
| 7 | n.a | n.a. | n.a | n.a | n.a | n.a |
| 8 | n.a | n.a | n.a | n.a | n.a | n.a |
| 9 | 43.48 | 0 | 98.44 | 1.04 | 0.36 | 0.16 |
| 10 | n.a | n.a | n.a | n.a | n.a | n.a |
| 11 | n.a | n.a | n.a | n.a | n.a | n.a |
| 12 | n.a | n.a | n.a | n.a | n.a | n.a |
| 13 | n.a | n.a | n.a | n.a | n.a | n.a |
| 14 | 116.59 | 0.27 | 98.83 | 0.67 | 0.15 | 0.08 |
| 15 | 21.99 | 0 | 97.87 | 1.21 | 0.69 | 0.23 |
| 16 | n.a | n.a | n.a | n.a | n.a | n.a |

These results show that greater instability occurs above pH 6.5. Use of citrate buffer leads to precipitation and decreased peptide solubility. Mannitol is found to be more favorable for maintaining solubility than NaCl. The SEC results, in large part, mirror the solubility conclusions, with a preferred pH range of 5 to 6 or so.

Study 2 Result: Determine Optimal pH and Buffer Concentration for MANP by Visual Inspection, Peptide Concentrations, and pH Based on the results of Study 1, Study 2 focuses on a slightly acidic pH range using buffers like acetate and histidine (His), and includes nonelectrolytes as tonicity modifiers. The formulations tested are as follows in Table 12.

TABLE 12

Study 2 Formulation Design

| Form. | MANP (ml/ml) | pH | Acetate (mM) | Histidine (mM) | Succinate (mM) | Mannitol (mM) | Glycine (mM) | Sucrose (mM) | ArgHCl (mM) | HP-β-CD (mM) |
|---|---|---|---|---|---|---|---|---|---|---|
| 1 | 1 | 4.5 | 20 | 0 | 0 | 250 | 0 | 0 | 0 | 0 |
| 2 | 2 | 5 | 20 | 0 | 0 | 250 | 0 | 0 | 0 | 0 |
| 3 | 1 | 5.5 | 20 | 0 | 0 | 0 | 0 | 250 | 0 | 0 |
| 4 | 2 | 5.5 | 0 | 20 | 0 | 250 | 0 | 0 | 0 | 0 |
| 5 | 1 | 5.5 | 0 | 0 | 0 | 0 | 0 | 200 | 50 | 0 |
| 6 | 2 | 6 | 0 | 20 | 0 | 250 | 0 | 0 | 0 | 0 |
| 7 | 2 | 5 | 0 | 0 | 20 | 200 | 0 | 0 | 50 | 0 |
| 8 | 2 | 5.5 | 0 | 40 | 0 | 0 | 250 | 0 | 0 | 0 |
| 9 | 2 | 5.5 | 0 | 0 | 20 | 200 | 0 | 0 | 0 | 50 |
| 10 | 1 | 5.5 | 20 | 0 | 0 | 125 | 125 | 0 | 0 | 0 |
| 11 | 2 | 5.5 | 40 | 0 | 0 | 0 | 0 | 250 | 0 | 0 |
| 12 | 1 | 5 | 10 | 0 | 0 | 0 | 200 | 0 | 0 | 50 |
| 13 | 1 | 6 | 0 | 0 | 40 | 0 | 0 | 200 | 25 | 0 |
| 14 | 2 | 4.5 | 40 | 0 | 0 | 0 | 0 | 250 | 0 | 25 |
| 15 | 2 | 5 | 0 | 40 | 0 | 0 | 125 | 125 | 0 | 0 |
| 16 | 2 | 5 | 0 | 0 | 20 | 200 | 0 | 0 | 75 | 0 |

Figure 10:
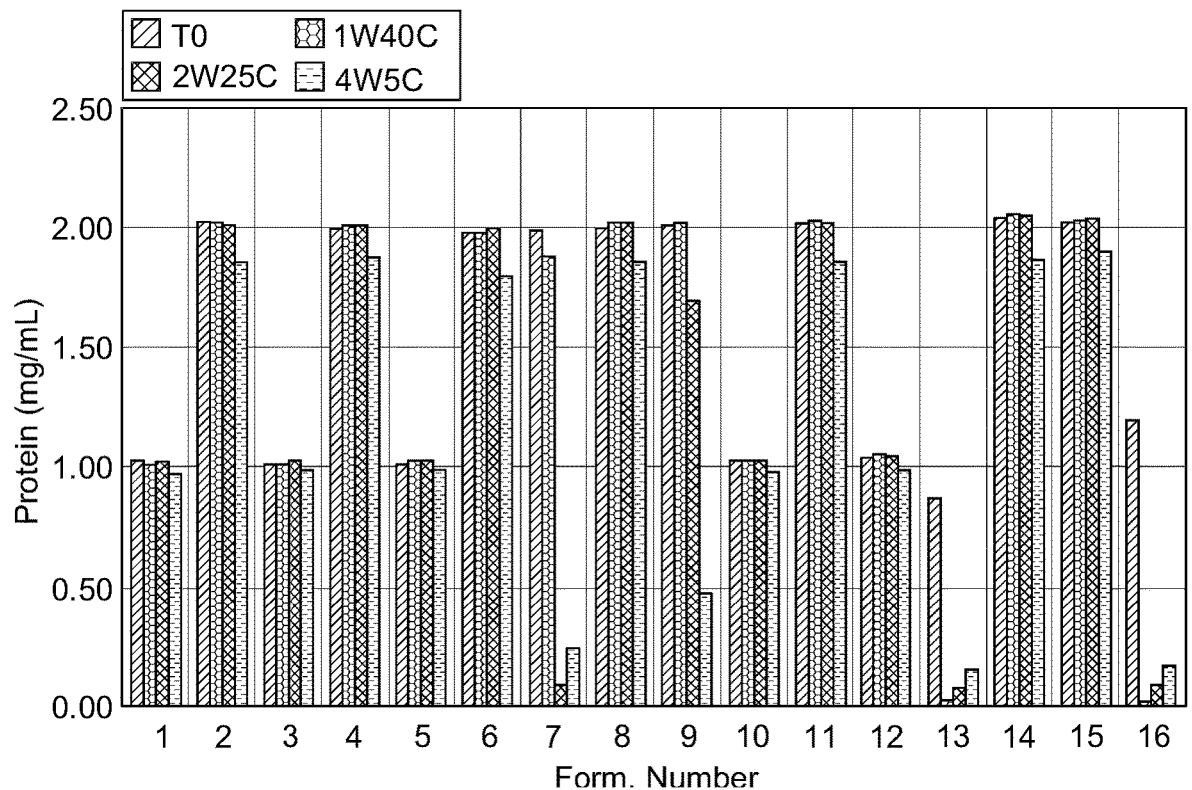
FIG. 10 depicts the peptide concentrations measured for each formulation evaluated in Study 2.
Figure 11:
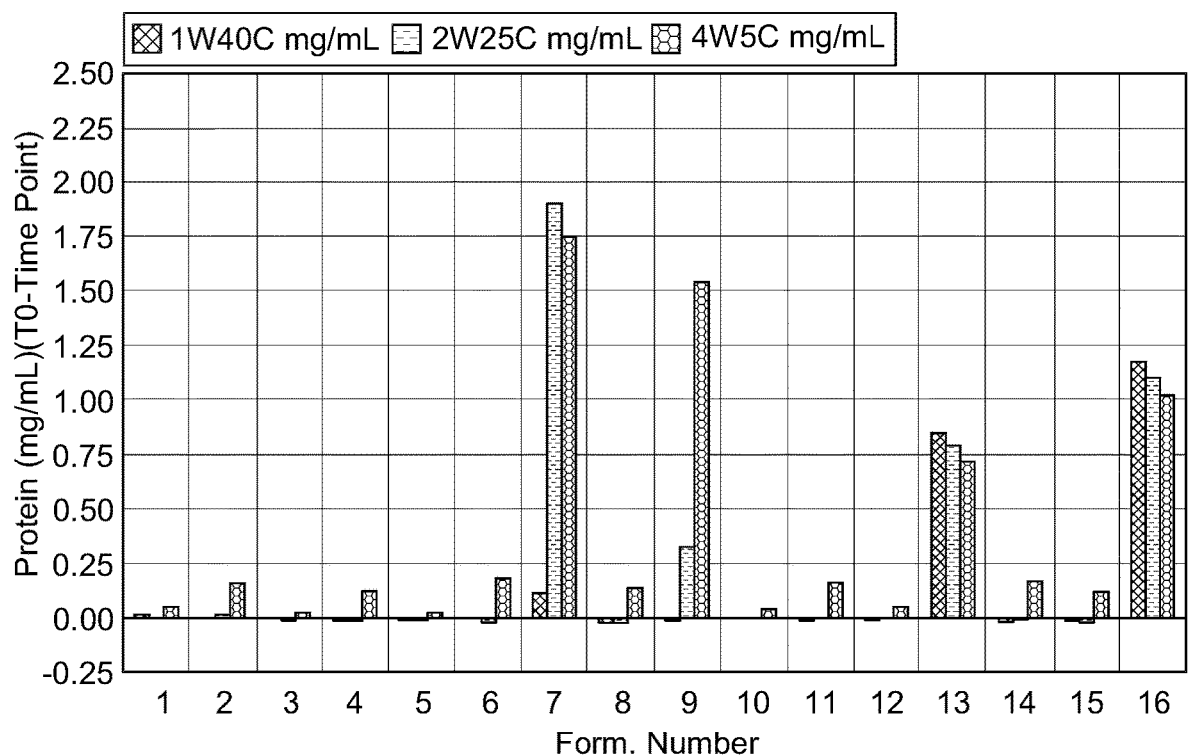
FIG. 11 depicts the peptide concentration difference for each formulation evaluated in Study 2, compared to T=0.
Figure 12:
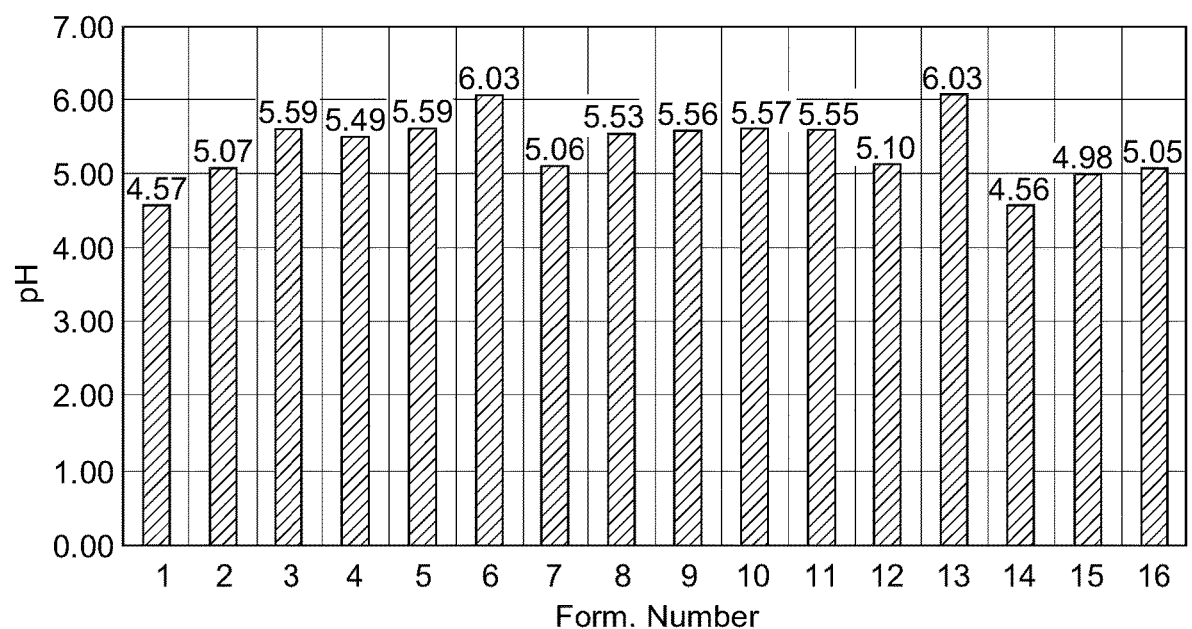
FIG. 12 depicts the pH values for each formulation evaluated in Study 2, compared to T=0.

Visual inspection of the Study 2 samples finds that they remain clear throughout the course of the four-week time course (Table 13). A few of the formulations display marked losses (up to 92%) of peptide concentration, such as Formulations 7, 9, 13, and 16 (Table 14). Many of these compositions contained ArgHCl. The actual peptide concentrations are plotted in FIG. 10. The relative losses in peptide concentration are plotted in FIG. 11. The actual initial pH values are shown in FIG. 12.

TABLE 13

Study 2 visual characterization of stability samples at T = 0 to T = 4 weeks at 5° C.

| Form. No. | MANP (mg/ml) | pH | Observations at T = 0 | | | Observations at T = 1 week at 40° C. | | |
|---|---|---|---|---|---|---|---|---|
| | | | Color | Particle | Visual | Color | Particle | Visual |
| 1 | 1 | 4.5 | No | No | Clear | No | No | Clear |
| 2 | 2 | 5 | No | No | Clear | No | No | Clear |
| 3 | 1 | 5.5 | No | No | Clear | No | No | Clear |
| 4 | 2 | 5.5 | No | No | Clear | No | No | Clear |
| 5 | 1 | 5.5 | No | No | Clear | No | No | Clear |
| 6 | 2 | 6 | No | No | Clear | No | No | Clear |
| 7* | 2 | 5 | No | No | Clear | No | No | Clear |
| 8 | 2 | 5.5 | No | No | Clear | No | No | Clear |
| 9* | 2 | 5.5 | No | No | Clear | No | No | Clear |
| 10 | 1 | 5.5 | No | No | Clear | No | No | Clear |
| 11 | 2 | 5.5 | No | No | Clear | No | No | Clear |
| 12 | 1 | 5 | No | No | Clear | No | No | Clear |
| 13* | 1 | 6 | No | No | Clear | No | Yes | Clear |
| 14 | 2 | 4.5 | No | No | Clear | No | No | Clear |
| 15 | 2 | 5 | No | No | Clear | No | No | Clear |
| 16* | 2 | 5 | No | No | Clear | No | Yes | Clear |

| Form. No. | MANP (mg/ml) | pH | Observations at T = 2 weeks at 25° C. | | | Observations at T = 4 weeks at 5° C. | | |
|---|---|---|---|---|---|---|---|---|
| | | | Color | Particle | Visual | Color | Particle | Visual |
| 1 | 1 | 4.5 | No | No | Clear | No | No | Clear |
| 2 | 2 | 5 | No | No | Clear | No | No | Clear |
| 3 | 1 | 5.5 | No | No | Clear | No | No | Clear |
| 4 | 2 | 5.5 | No | No | Clear | No | No | Clear |
| 5 | 1 | 5.5 | No | No | Clear | No | No | Clear |
| 6 | 2 | 6 | No | No | Clear | No | No | Clear |
| 7* | 2 | 5 | No | Yes | Clear | No | Yes | Clear |
| 8 | 2 | 5.5 | No | No | Clear | No | No | Clear |
| 9* | 2 | 5.5 | No | Yes | Clear | No | Yes | Clear |
| 10 | 1 | 5.5 | No | No | Clear | No | No | Clear |
| 11 | 2 | 5.5 | No | No | Clear | No | No | Clear |
| 12 | 1 | 5 | No | No | Clear | No | No | Clear |
| 13* | 1 | 6 | No | Yes | Clear | No | Yes | Clear |
| 14 | 2 | 4.5 | No | No | Clear | No | No | Clear |
| 15 | 2 | 5 | No | No | Clear | No | No | Clear |
| 16* | 2 | 5 | No | Yes | Clear | No | Yes | Clear |

TABLE 14

Study 2 peptide concentration and pH for the stability samples

| | | | | Peptide Concentration (mg/mL) | | | |
|---|---|---|---|---|---|---|---|
| Form. No. | MANP (mg/ml) | pH | T = 0 pH | T = 0 | T = 1 week 40° C. | T = 2 weeks 25° C. | T = 4 weeks 5° C. |
| 1 | 1 | 4.5 | 4.57 | 1.02 | 1.01 | 1.02 | 0.97 |
| 2 | 2 | 5 | 5.07 | 2.02 | 2.02 | 2.01 | 1.86 |
| 3 | 1 | 5.5 | 5.59 | 1.01 | 1.01 | 1.02 | 0.99 |
| 4 | 2 | 5.5 | 5.49 | 2.00 | 2.01 | 2.01 | 1.88 |
| 5 | 1 | 5.5 | 5.59 | 1.01 | 1.02 | 1.02 | 0.99 |
| 6 | 2 | 6 | 6.03 | 1.98 | 1.98 | 2.00 | 1.8 |
| 7 | 2 | 5 | 5.06 | 1.99 | 1.88 | 0.09 | 0.24 |
| 8 | 2 | 5.5 | 5.53 | 2.00 | 2.02 | 2.02 | 1.86 |
| 9 | 2 | 5.5 | 5.56 | 2.01 | 2.02 | 1.69 | 0.47 |
| 10 | 1 | 5.5 | 5.57 | 1.02 | 1.02 | 1.02 | 0.98 |
| 11 | 2 | 5.5 | 5.55 | 2.02 | 2.03 | 2.02 | 1.86 |
| 12 | 1 | 5 | 5.1 | 1.04 | 1.05 | 1.04 | 0.99 |
| 13 | 1 | 6 | 6.03 | 0.87 | 0.02 | 0.08 | 0.15 |
| 14 | 2 | 4.5 | 4.56 | 2.04 | 2.06 | 2.05 | 1.87 |
| 15 | 2 | 5 | 4.98 | 2.02 | 2.03 | 2.04 | 1.9 |
| 16 | 2 | 5 | 5.05 | 1.19 | 0.02 | 0.09 | 0.17 |

Figure 13:
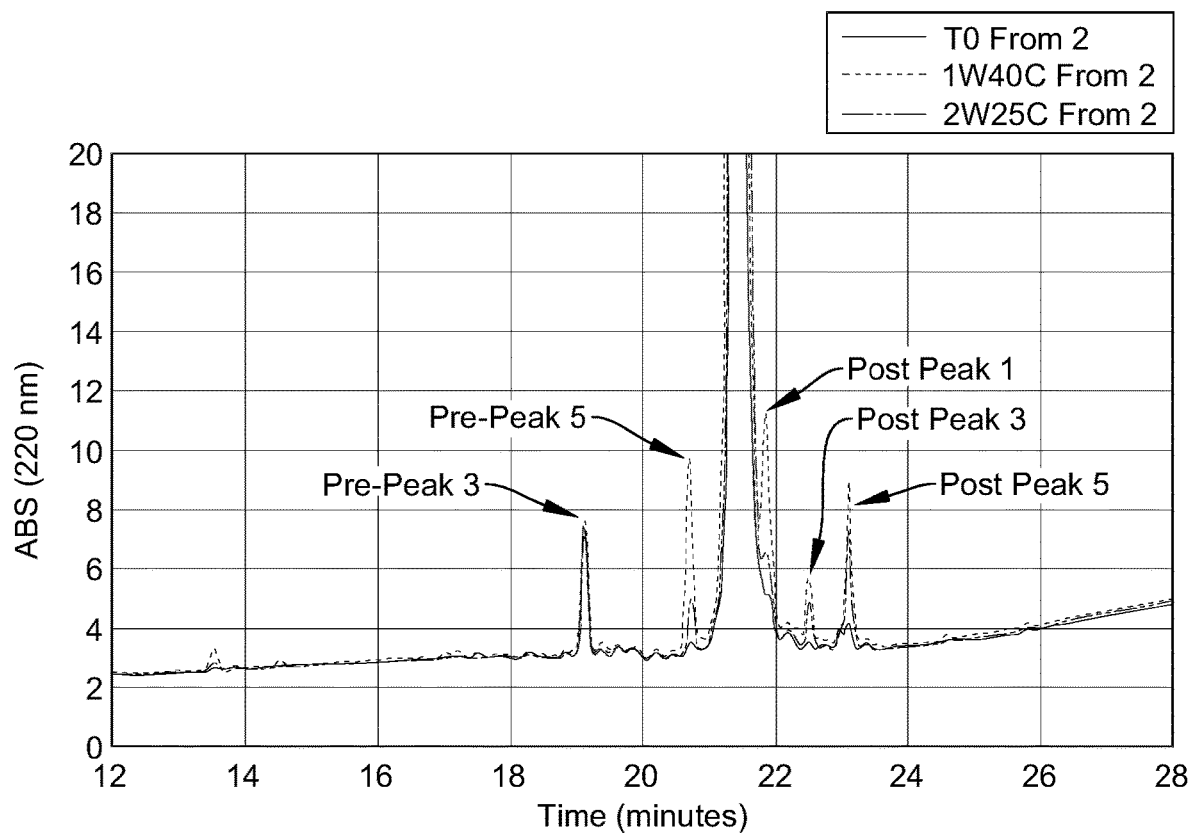
FIG. 13 depicts an exemplary reversed-phase HPLC chromatogram from Study 2 using the Primary reverse phase method showing the peak numbering scheme.

Study 2 Result: Determine Optimal pH and Buffer Concentration for MANP by RP-HPLC The stability samples are characterized by Reversed Phase Chromatography using the Primary reverse phase method described in the Methods section above. An example of the RP-HPLC chromatograms using this method for a Study 2 sample is provided in FIG. 13. The RP-HPLC results for all of the time points in Study 2 are tabulated in Tables 15-18.

Figure 14A:
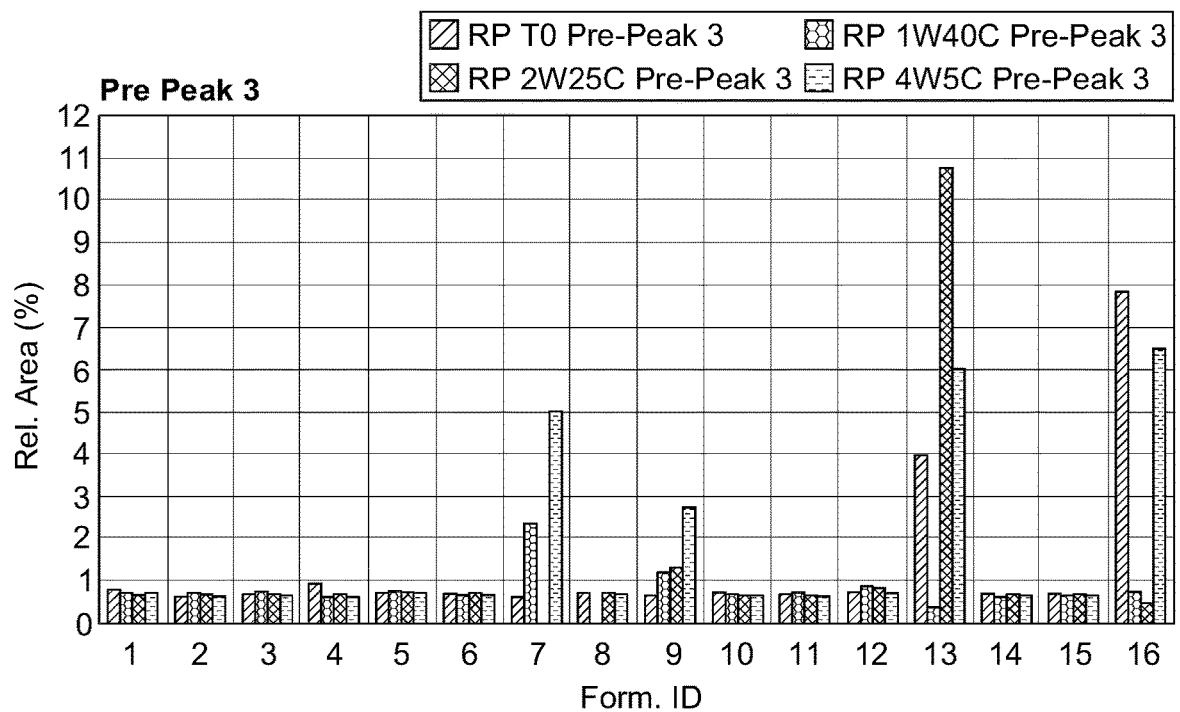
FIG. 14A depicts the relative areas of pre-peak 3 for samples from Study 2 as measured by RP-HPLC.
Figure 14B:
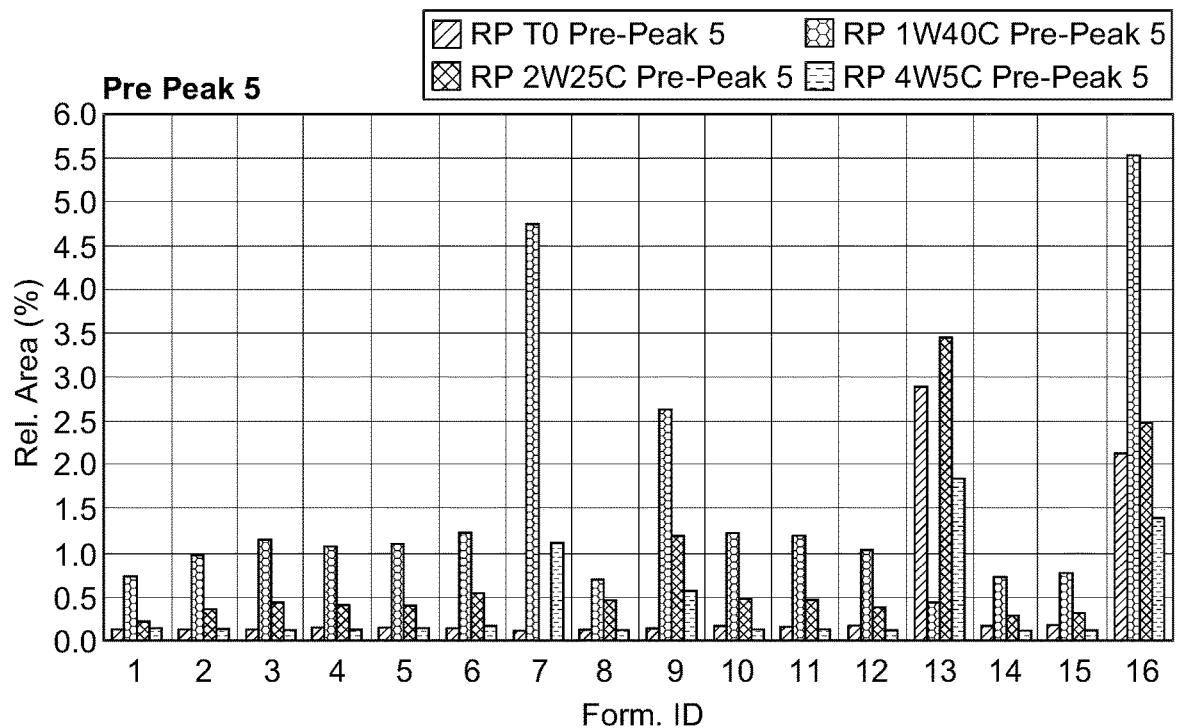
FIG. 14B depicts the relative areas of pre-peak 5 for samples from Study 2 as measured by RP-HPLC.
Figure 14C:
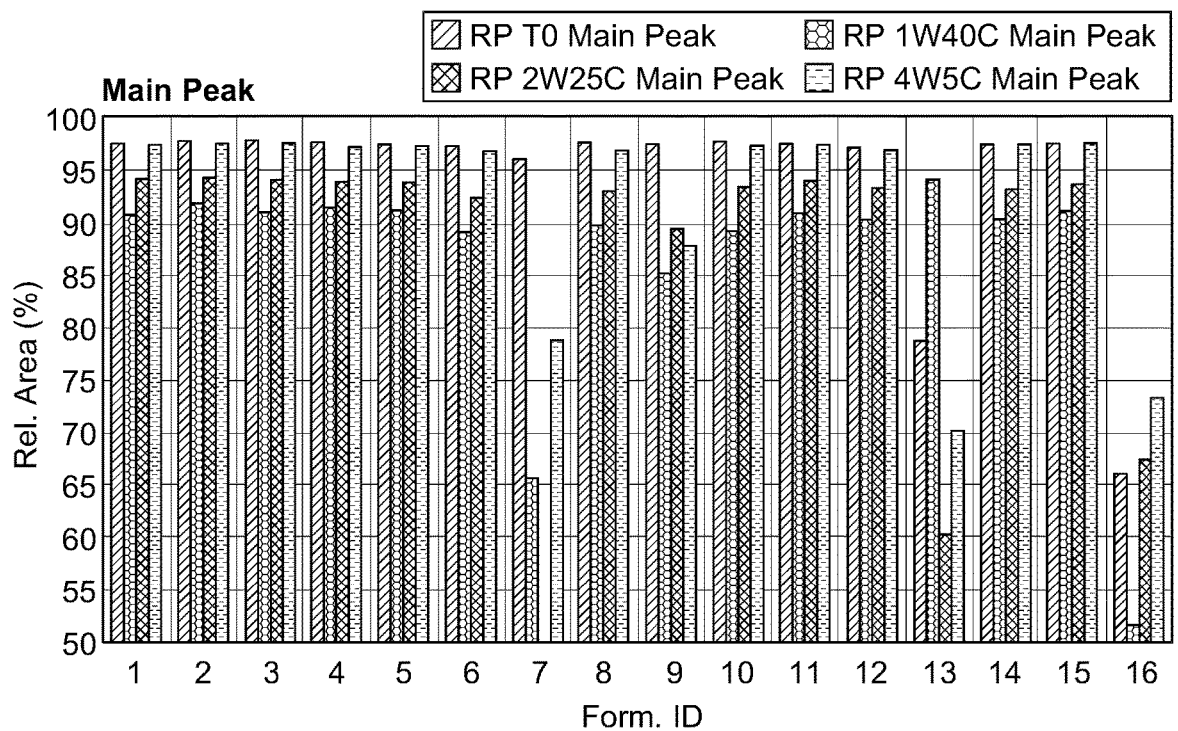
FIG. 14C depicts the relative areas of main peak for samples from Study 2 as measured by RP-HPLC.

Those formulations showing losses of peptide content also exhibit marked increases in pre-peaks 3 and 5 (FIGS. 14A and 14B), as well as loss of main peak intensity (FIG. 14C).

Figure 15:
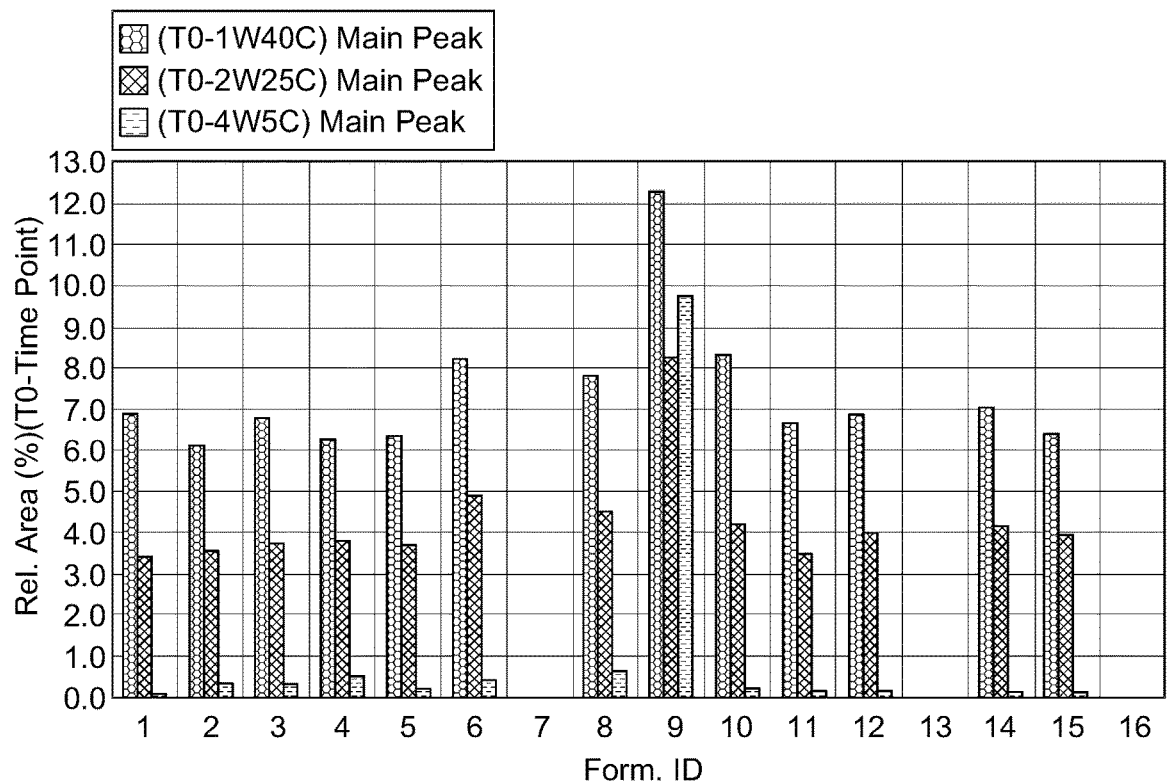
FIG. 15 depicts the changes in RP-HPLC main peak relative area for each formulation evaluated in Study 2, compared to T=0.
Figure 16:
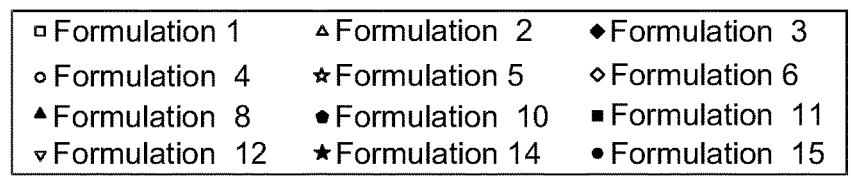
FIG. 16 depicts the estimated loss of RP-HPLC main peak extrapolated to 12 months when Study 2 samples are stored at 5° C.
Figure 16:
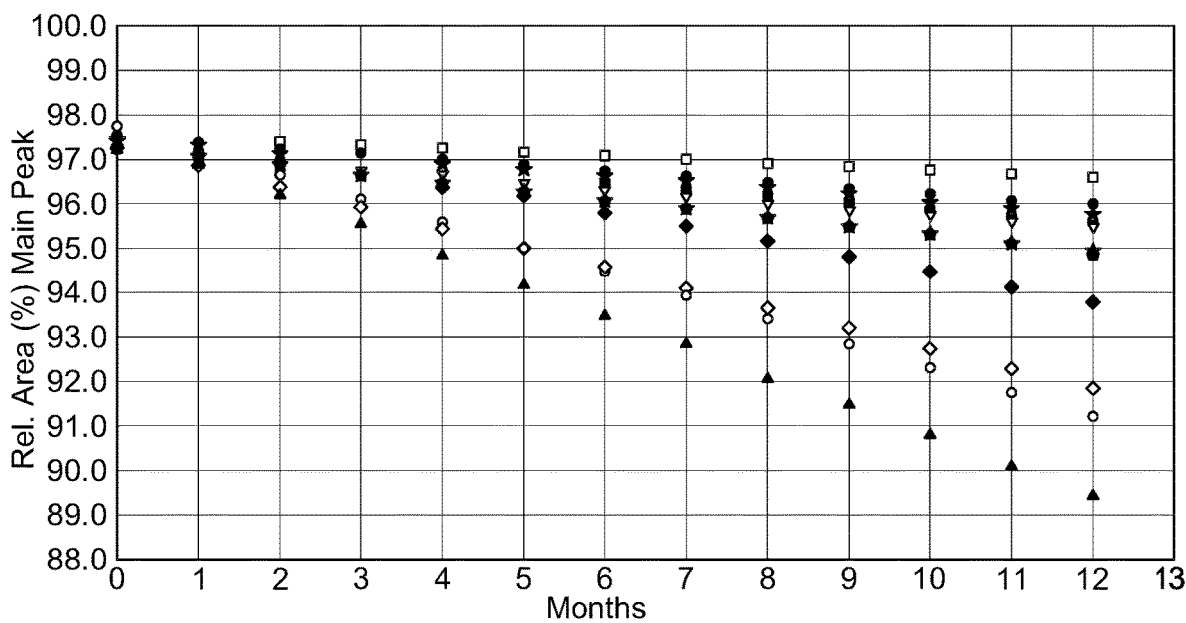
Figure 17A:
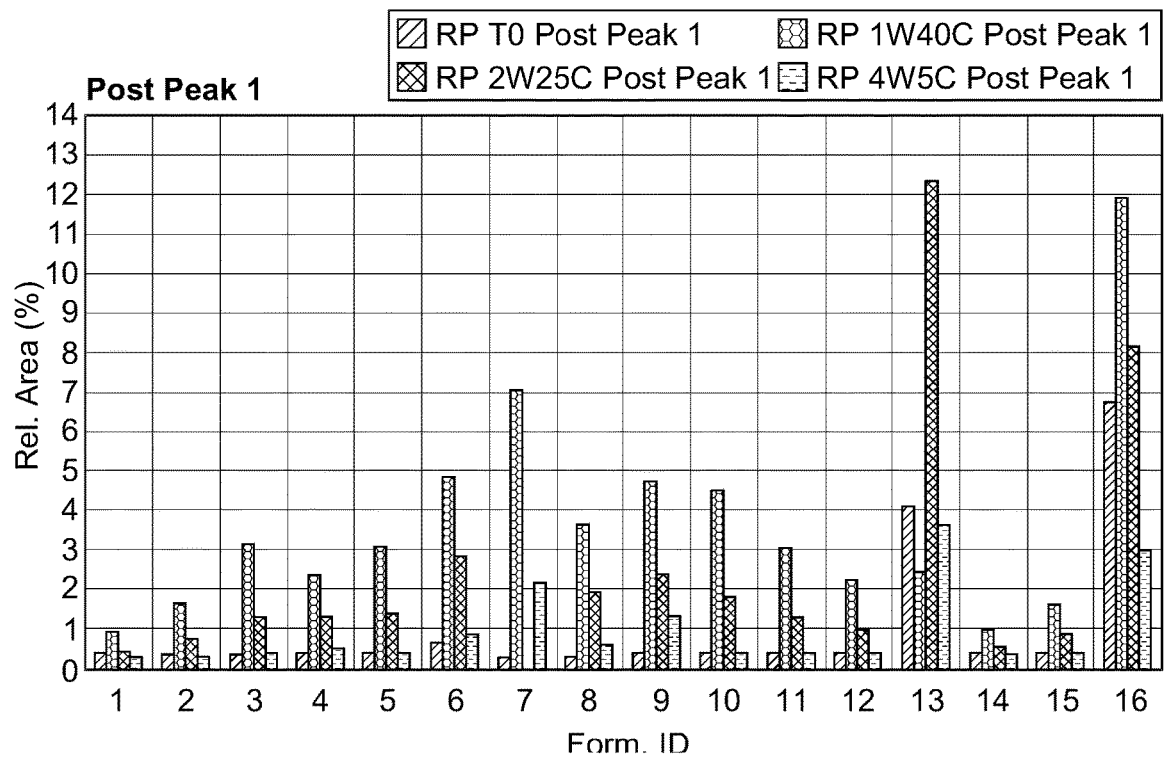
FIG. 17A depicts the relative areas of post-peak 1 for samples from Study 2 as measured by RP-HPLC.
Figure 17B:
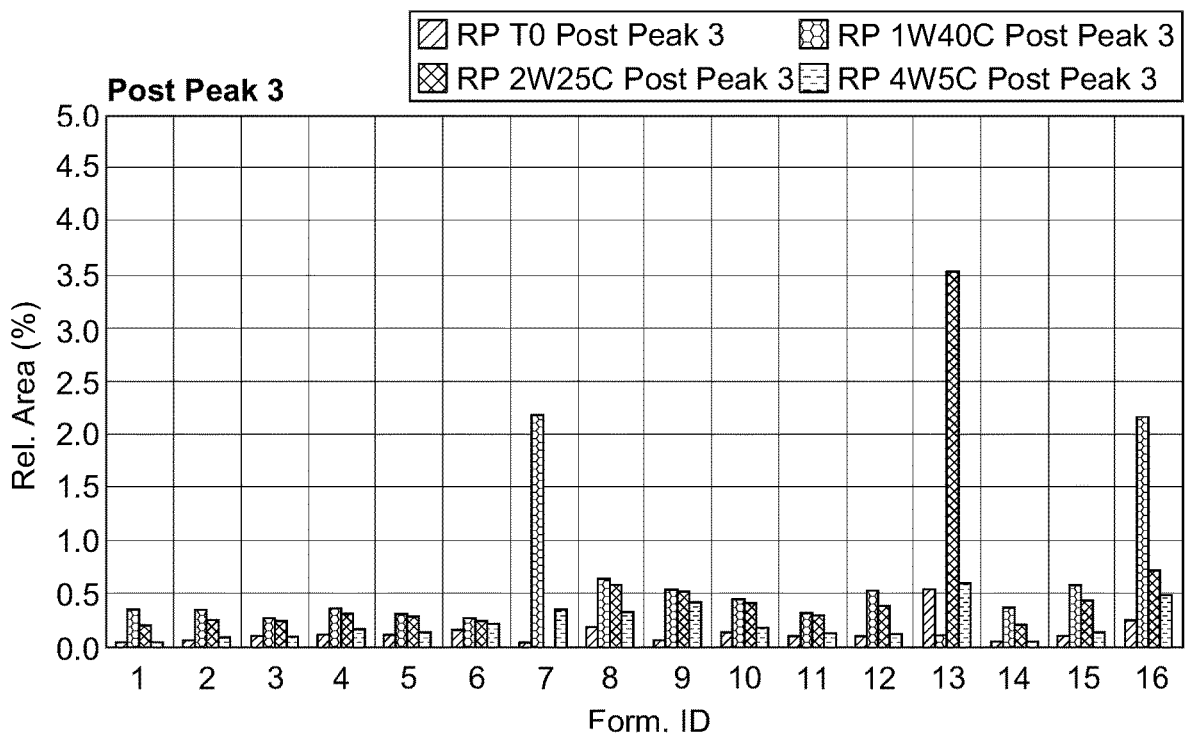
FIG. 17B depicts the relative areas of post-peak 3 for samples from Study 2 as measured by RP-HPLC.
Figure 17C:
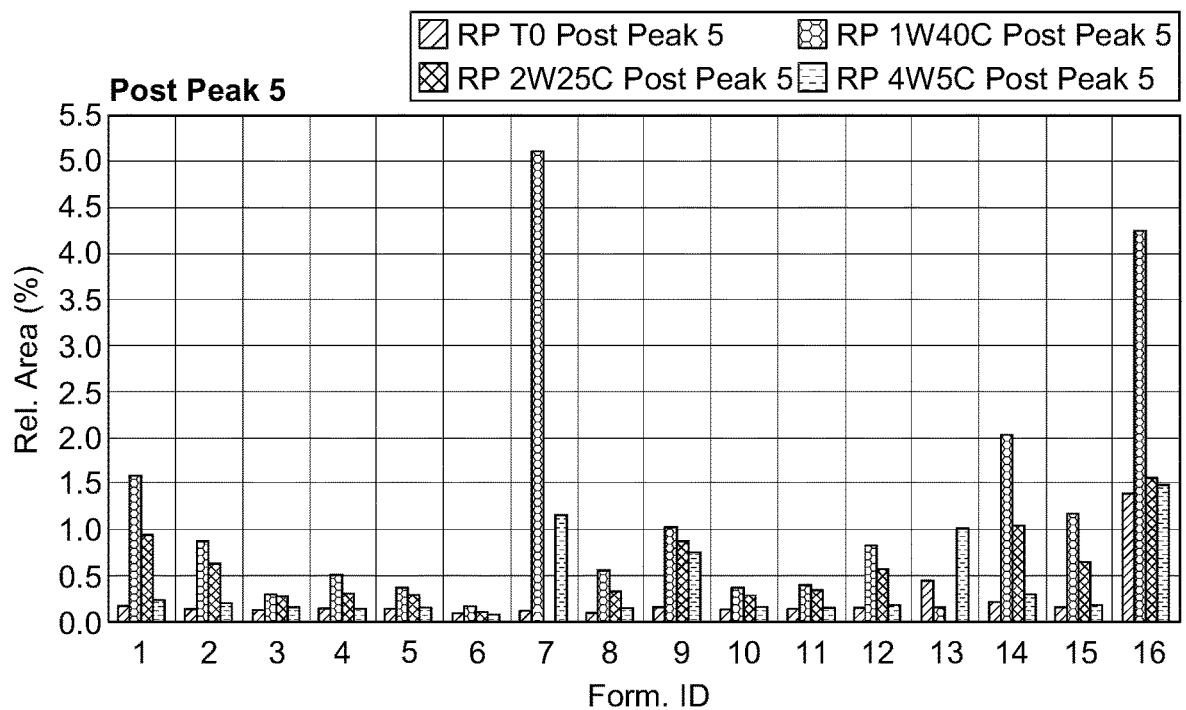
FIG. 17C depicts the relative areas of post-peak 5 for samples from Study 2 as measured by RP-HPLC.
Figure 18:
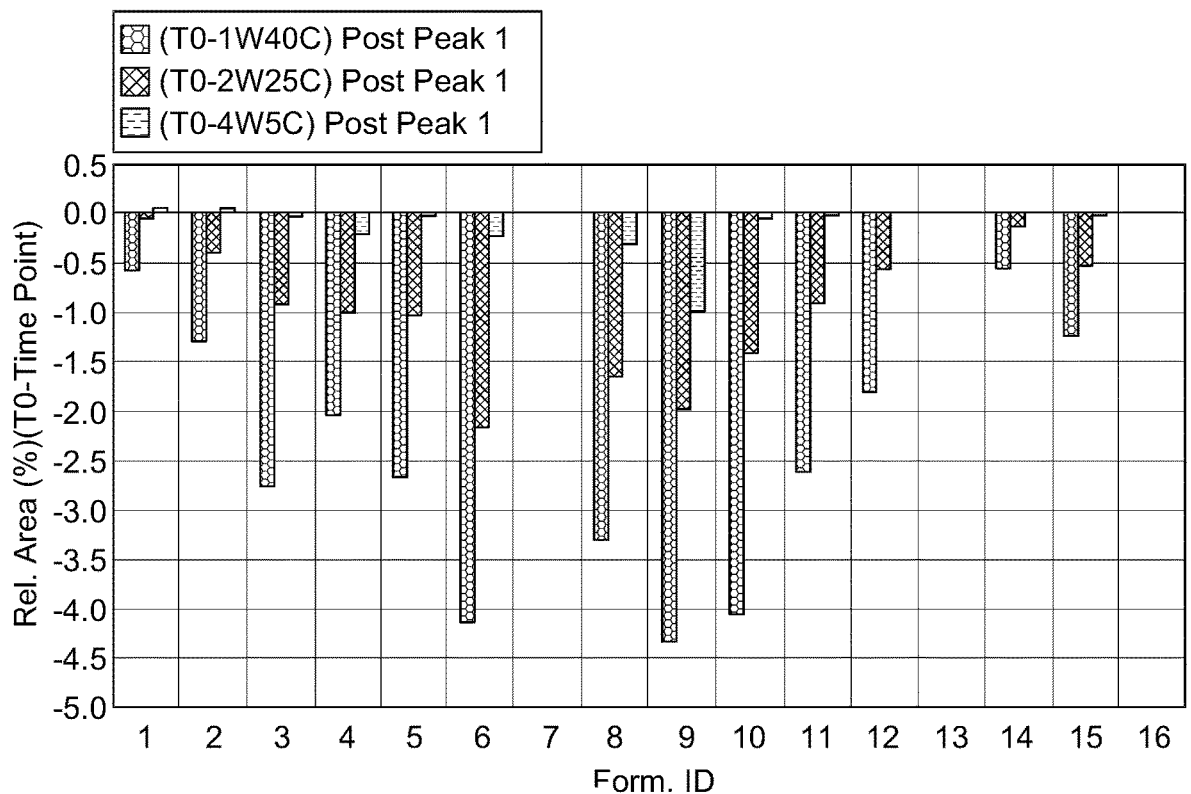
FIG. 18 depicts the changes in RP-HPLC post-peak 1 relative area for each formulation evaluated in Study 2, compared to T=0.

Changes in the relative areas of two of the pre-peaks as well as the RP-HPLC main peak are shown in FIGS. 14A-C, showing only small differences for most MANP formulations, except for Formulations 7, 9, 13, and 16. Loss of the main peak is sizable at elevated temperatures, but fairly small for samples stored at 5° C. (FIG. 15). A linear extrapolation of the main peak purity by RP-HPLC indicates that a number of the formulations from Study 3 would retain more than 95% main peak relative intensity after one year at 5° C. (FIG. 16). Of the least stable formulations (7, 13, and 16), there are pronounced increases in the post-peaks as well (FIGS. 17A-C). The relative changes in post-peak 1 are graphed in FIG. 18.

TABLE 15

Study 2 Reversed Phase data for T = 0 stability samples
Study 2 T = 0

| Form. | Temp (° C.) | Group Area (mAU * min) | Relative Area (%) | | | | | | | |
|---|---|---|---|---|---|---|---|---|---|---|
| | | | Pre Peak 1 | Pre Peak 2 | Pre Peak 3 | Pre Peak 4 | Pre Peak 5 | Pre Peak 6 | Main Peak | Post Peak A |
| 1 | n.a | 89.61 | 0.00 | 0.27 | 0.74 | 0.34 | 0.12 | n.a | 97.55 | n.a |
| 2 | n.a | 89.64 | 0.01 | 0.20 | 0.63 | 0.25 | 0.12 | n.a | 97.82 | n.a |
| 3 | n.a | 89.64 | 0.00 | 0.16 | 0.66 | 0.25 | 0.12 | n.a | 97.83 | n.a |
| 4 | n.a | 93.59 | 0.00 | 0.24 | 0.93 | n.a | 0.15 | n.a | 97.72 | n.a |
| 5 | n.a | 88.86 | 0.00 | 0.26 | 0.69 | 0.36 | 0.15 | n.a | 97.53 | n.a |
| 6 | n.a | 87.49 | 0.01 | 0.38 | 0.66 | 0.26 | 0.14 | n.a | 97.25 | n.a |
| 7 | n.a | 102.28 | 0.00 | 0.34 | 0.63 | 0.36 | 0.09 | n.a | 95.96 | n.a |
| 8 | n.a | 83.86 | 0.00 | 0.35 | 0.70 | 0.33 | 0.11 | n.a | 97.56 | n.a |
| 9 | n.a | 88.62 | 0.19 | 0.23 | 0.66 | 0.27 | 0.13 | n.a | 97.50 | n.a |
| 10 | n.a | 92.82 | 0.00 | 0.44 | 0.69 | 0.39 | 0.17 | n.a | 97.62 | n.a |
| 11 | n.a | 93.54 | 0.00 | 0.27 | 0.64 | 0.32 | 0.15 | n.a | 97.55 | n.a |
| 12 | n.a | 95.99 | 0.15 | 0.38 | 0.71 | 0.36 | 0.16 | n.a | 97.15 | n.a |
| 13 | n.a | 7.17 | 0.02 | 1.92 | 3.94 | 4.20 | 2.88 | n.a | 78.84 | n.a |
| 14 | n.a | 94.62 | 0.06 | 0.20 | 0.66 | 0.35 | 0.16 | n.a | 97.39 | n.a |
| 15 | n.a | 86.71 | 0.00 | 0.24 | 0.66 | 0.35 | 0.17 | n.a | 97.52 | n.a |
| 16 | n.a | 4.32 | n.a | 2.28 | 7.82 | 2.35 | 2.12 | 5.14 | 66.19 | 3.10 |

| Form. | Temp (° C.) | Group Area (mAU * min) | Relative Area (%) | | | | | | | |
|---|---|---|---|---|---|---|---|---|---|---|
| | | | Post Peak 1 | Post Peak 2 | Post Peak 3 | Post Peak 4 | Post Peak 5 | Post Peak 6 | Post Peak 7 | Post Peak 8 |
| 1 | n.a | 89.61 | 0.38 | 0.20 | 0.04 | 0.14 | 0.16 | 0.03 | 0.02 | 0.01 |
| 2 | n.a | 89.64 | 0.38 | 0.19 | 0.06 | 0.14 | 0.13 | 0.04 | 0.02 | 0.01 |
| 3 | n.a | 89.64 | 0.40 | 0.17 | 0.08 | 0.14 | 0.11 | 0.03 | 0.04 | 0.01 |
| 4 | n.a | 93.59 | 0.34 | 0.18 | 0.11 | 0.15 | 0.11 | 0.05 | 0.01 | 0.01 |
| 5 | n.a | 88.86 | 0.42 | 0.19 | 0.10 | 0.15 | 0.11 | 0.04 | n.a | 0.01 |
| 6 | n.a | 87.49 | 0.69 | 0.18 | 0.16 | 0.14 | 0.06 | 0.04 | 0.01 | 0.02 |
| 7 | n.a | 102.28 | 0.31 | 0.16 | 0.03 | 0.13 | 0.09 | 0.03 | 0.01 | 0.01 |
| 8 | n.a | 83.86 | 0.33 | 0.15 | 0.19 | 0.12 | 0.10 | 0.03 | 0.01 | 0.01 |
| 9 | n.a | 88.62 | 0.39 | 0.19 | 0.07 | 0.16 | 0.14 | 0.03 | 0.02 | n.a |
| 10 | n.a | 92.82 | 0.42 | 0.20 | 0.14 | 0.15 | 0.11 | 0.03 | 0.02 | 0.01 |
| 11 | n.a | 93.54 | 0.41 | 0.20 | 0.09 | 0.15 | 0.13 | 0.04 | 0.02 | 0.01 |
| 12 | n.a | 95.99 | 0.42 | 0.22 | 0.09 | 0.16 | 0.14 | 0.04 | 0.00 | 0.01 |
| 13 | n.a | 7.17 | 4.10 | 1.59 | 0.54 | 0.41 | 0.45 | 0.23 | 0.71 | 0.16 |
| 14 | n.a | 94.62 | 0.42 | 0.22 | 0.05 | 0.17 | 0.21 | 0.04 | 0.03 | 0.02 |
| 15 | n.a | 86.71 | 0.39 | 0.21 | 0.10 | 0.13 | 0.15 | 0.04 | 0.02 | 0.02 |
| 16 | n.a | 4.32 | 6.75 | 2.21 | 0.24 | 0.04 | 1.40 | 0.04 | n.a | 0.27 |

TABLE 16

Study 2 Reversed Phase data for T = 1 week 40° C. stability samples
Study 2 T = 1 week 40° C.

| Form. | Temp (° C.) | Group Area (mAU * min) | Relative Area (%) | | | | | | | |
|---|---|---|---|---|---|---|---|---|---|---|
| | | | Pre Peak 1 | Pre Peak 2 | Pre Peak 3 | Pre Peak 4 | Pre Peak 5 | Pre Peak 6 | Main Peak | Post Peak A |
| 1 | 40 | 89.51 | 0.10 | 0.51 | 0.70 | 0.42 | 0.71 | n.a | 90.65 | 3.55 |
| 2 | 40 | 85.22 | 0.15 | 0.37 | 0.68 | 0.36 | 0.98 | n.a | 91.71 | 2.42 |
| 3 | 40 | 88.89 | 0.28 | 0.30 | 0.72 | 0.35 | 1.14 | n.a | 91.06 | 1.77 |
| 4 | 40 | 87.54 | 0.18 | 0.30 | 0.59 | 0.31 | 1.07 | n.a | 91.45 | 2.18 |
| 5 | 40 | 89.45 | 0.16 | 0.33 | 0.70 | 0.36 | 1.09 | n.a | 91.16 | 1.73 |

TABLE 16-continued

Study 2 Reversed Phase data for T = 1 week 40° C. stability samples
Study 2 T = 1 week 40° C.

| | | | | | | | | | | |
|---|---|---|---|---|---|---|---|---|---|---|
| 6 | 40 | 90.64 | 0.20 | 0.35 | 0.65 | 0.44 | 1.23 | n.a | 89.02 | 1.83 |
| 7 | 40 | 12.71 | 0.83 | 2.11 | 2.36 | 1.76 | 4.76 | 2.18 | 65.71 | 4.44 |
| 8 | 40 | 89.49 | 0.17 | 0.43 | n.a | 0.42 | 0.69 | 1.09 | 89.75 | 1.93 |
| 9 | 40 | 43.27 | 0.51 | 0.50 | 1.20 | 0.73 | 2.62 | n.a | 85.21 | 2.10 |
| 10 | 40 | 90.98 | 0.28 | 0.31 | 0.66 | 0.41 | 1.23 | n.a | 89.29 | 1.78 |
| 11 | 40 | 92.13 | 0.24 | 0.30 | 0.70 | 0.35 | 1.20 | n.a | 90.92 | 1.87 |
| 12 | 40 | 91.84 | 0.33 | 0.31 | 0.84 | 0.39 | 1.04 | n.a | 90.28 | 2.51 |
| 13 | 40 | 51.81 | 0.18 | 0.35 | 0.36 | 0.53 | 0.43 | n.a | 94.11 | n.a |
| 14 | 40 | 95.28 | 0.13 | 0.44 | 0.65 | 0.31 | 0.70 | n.a | 90.36 | 3.52 |
| 15 | 40 | 90.82 | 0.12 | 0.27 | 0.63 | 0.33 | 0.77 | n.a | 91.10 | 2.75 |
| 16 | 40 | 3.26 | 1.15 | 4.06 | 0.73 | 4.42 | 5.54 | 5.83 | 51.61 | 4.49 |

| Form. | Temp (° C.) | Group Area (mAU * min) | Relative Area (%) | | | | | | | |
|---|---|---|---|---|---|---|---|---|---|---|
| | | | Post Peak 1 | Post Peak 2 | Post Peak 3 | Post Peak 4 | Post Peak 5 | Post Peak 6 | Post Peak 7 | Post Peak 8 |
| 1 | 40 | 89.51 | 0.96 | 0.26 | 0.35 | 0.09 | 1.58 | 0.08 | 0.02 | 0.02 |
| 2 | 40 | 85.22 | 1.66 | 0.29 | 0.34 | 0.08 | 0.86 | 0.06 | 0.02 | 0.02 |
| 3 | 40 | 88.89 | 3.15 | 0.38 | 0.26 | 0.19 | 0.30 | 0.04 | 0.04 | 0.02 |
| 4 | 40 | 87.54 | 2.38 | 0.43 | 0.35 | 0.17 | 0.50 | 0.05 | 0.02 | 0.02 |
| 5 | 40 | 89.45 | 3.09 | 0.48 | 0.30 | 0.18 | 0.34 | 0.05 | 0.01 | 0.02 |
| 6 | 40 | 90.64 | 4.82 | 0.70 | 0.26 | 0.18 | 0.14 | 0.05 | 0.02 | 0.11 |
| 7 | 40 | 12.71 | 7.05 | 1.17 | 2.18 | 0.02 | 5.10 | 0.15 | 0.06 | 0.12 |
| 8 | 40 | 89.49 | 3.63 | 0.44 | 0.64 | 0.15 | 0.55 | 0.06 | 0.01 | 0.04 |
| 9 | 40 | 43.27 | 4.73 | 0.70 | 0.52 | n.a | 1.02 | 0.07 | 0.05 | 0.05 |
| 10 | 40 | 90.98 | 4.48 | 0.56 | 0.44 | 0.17 | 0.36 | n.a | 0.02 | 0.02 |
| 11 | 40 | 92.13 | 3.03 | 0.42 | 0.31 | 0.20 | 0.39 | 0.05 | 0.03 | 0.02 |
| 12 | 40 | 91.84 | 2.22 | 0.39 | 0.52 | 0.21 | 0.82 | 0.11 | 0.01 | 0.02 |
| 13 | 40 | 51.81 | 2.46 | 0.63 | 0.11 | 0.38 | 0.16 | 0.19 | 0.01 | 0.09 |
| 14 | 40 | 95.28 | 0.98 | 0.28 | 0.37 | 0.06 | 2.03 | 0.15 | 0.02 | 0.02 |
| 15 | 40 | 90.82 | 1.62 | 0.37 | 0.59 | 0.15 | 1.18 | 0.08 | 0.01 | 0.02 |
| 16 | 40 | 3.26 | 11.90 | 2.88 | 2.16 | 0.44 | 4.26 | 0.11 | n.a | 0.42 |

TABLE 17

Study 2 Reversed Phase data for T = 2 week 25° C. stability samples
Study 2 T = 2 week 25° C.

| Form. | Temp (° C.) | Group Area (mAU * min) | Relative Area (%) | | | | | | | |
|---|---|---|---|---|---|---|---|---|---|---|
| | | | Pre Peak 1 | Pre Peak 2 | Pre Peak 3 | Pre Peak 4 | Pre Peak 5 | Pre Peak 6 | Main Peak | Post Peak A |
| 1 | 25 | 92.52 | 0.09 | 0.2 | 0.69 | 0.26 | 0.21 | n.a. | 94.15 | 2.48 |
| 2 | 25 | 88.74 | 0.06 | 0.29 | 0.67 | 0.31 | 0.34 | n.a. | 94.26 | 2.04 |
| 3 | 25 | 90.32 | 0.06 | 0.26 | 0.67 | 0.31 | 0.44 | n.a. | 94.1 | 1.9 |
| 4 | 25 | 94.92 | 0.06 | 0.34 | 0.65 | 0.29 | 0.41 | n.a. | 93.94 | 1.87 |
| 5 | 25 | 90.98 | 0.07 | 0.42 | 0.7 | 0.34 | 0.4 | n.a. | 93.82 | 1.73 |
| 6 | 25 | 86.56 | 0.06 | 0.56 | 0.66 | 0.37 | 0.53 | n.a. | 92.35 | 1.63 |
| 7 | 25 | 0.00 | n.a. | n.a. | n.a. | n.a. | n.a. | n.a. | n.a. | n.a. |
| 8 | 25 | 87.43 | 0.09 | 0.24 | 0.68 | 0.37 | 0.45 | n.a. | 93.06 | 1.79 |
| 9 | 25 | 36.15 | 0.37 | 0.48 | 1.34 | 0.75 | 1.19 | n.a. | 89.26 | 2.14 |
| 10 | 25 | 90.25 | 0.08 | 0.34 | 0.65 | 0.28 | 0.47 | n.a. | 93.39 | 1.73 |
| 11 | 25 | 91.23 | 0.05 | 0.19 | 0.65 | 0.32 | 0.46 | n.a. | 94.06 | 1.83 |
| 12 | 25 | 93.72 | 0.21 | 0.44 | 0.83 | 0.44 | 0.38 | n.a. | 93.15 | 2.08 |
| 13 | 25 | 2.47 | 0.49 | 0.54 | 10.77 | 1.57 | 3.45 | 5.75 | 60.26 | n.a. |
| 14 | 25 | 96.18 | 0.09 | 0.43 | 0.68 | 0.43 | 0.29 | n.a. | 93.22 | 2.54 |
| 15 | 25 | 94.32 | 0.05 | 0.32 | 0.67 | 0.42 | 0.32 | n.a. | 93.55 | 2.14 |
| 16 | 25 | 1.60 | n.a. | 4.67 | 0.44 | n.a. | 2.5 | 7.00 | 67.35 | 3.64 |

| Form. | Temp (° C.) | Group Area (mAU * min) | Relative Area (%) | | | | | | | |
|---|---|---|---|---|---|---|---|---|---|---|
| | | | Post Peak 1 | Post Peak 2 | Post Peak 3 | Post Peak 4 | Post Peak 5 | Post Peak 6 | Post Peak 7 | Post Peak 8 |
| 1 | 25 | 92.52 | 0.43 | 0.21 | 0.2 | 0.07 | 0.93 | 0.05 | 0.01 | 0.02 |
| 2 | 25 | 88.74 | 0.78 | 0.21 | 0.25 | 0.07 | 0.63 | 0.05 | 0.02 | 0.02 |
| 3 | 25 | 90.32 | 1.32 | 0.23 | 0.24 | 0.14 | 0.27 | 0.04 | 0 | 0.02 |
| 4 | 25 | 94.92 | 1.34 | 0.25 | 0.31 | 0.14 | 0.32 | 0.05 | 0.02 | 0.02 |

TABLE 17-continued

Study 2 Reversed Phase data for T = 2 week 25° C. stability samples
Study 2 T = 2 week 25° C.

| | | | | | | | | | | |
|---|---|---|---|---|---|---|---|---|---|---|
| 5 | 25 | 90.98 | 1.45 | 0.28 | 0.28 | 0.15 | 0.28 | 0.05 | 0.02 | 0.02 |
| 6 | 25 | 86.56 | 2.86 | 0.39 | 0.24 | 0.15 | 0.1 | 0.04 | 0.01 | 0.05 |
| 7 | 25 | 0.00 | n.a. | n.a. | n.a. | n.a. | n.a. | n.a. | n.a. | n.a. |
| 8 | 25 | 87.43 | 1.98 | 0.26 | 0.58 | 0.11 | 0.33 | 0.05 | 0.01 | 0.01 |
| 9 | 25 | 36.15 | 2.38 | 0.49 | 0.5 | 0.1 | 0.88 | 0.04 | 0.04 | 0.05 |
| 10 | 25 | 90.25 | 1.83 | 0.28 | 0.42 | 0.17 | 0.29 | 0.05 | 0.01 | 0.02 |
| 11 | 25 | 91.23 | 1.32 | 0.26 | 0.28 | 0.16 | 0.35 | 0.05 | 0.02 | 0.02 |
| 12 | 25 | 93.72 | 0.98 | 0.27 | 0.38 | 0.17 | 0.58 | 0.05 | 0.01 | 0.02 |
| 13 | 25 | 2.47 | 12.35 | n.a. | 3.54 | n.a. | n.a. | n.a. | 0.73 | 0.54 |
| 14 | 25 | 96.18 | 0.55 | 0.24 | 0.21 | 0.17 | 1.05 | 0.06 | 0.02 | 0.02 |
| 15 | 25 | 94.32 | 0.91 | 0.24 | 0.44 | 0.16 | 0.65 | 0.05 | 0.04 | 0.02 |
| 16 | 25 | 1.60 | 8.17 | 3.09 | 0.71 | 0.16 | 1.56 | n.a. | n.a. | 0.70 |

TABLE 18

Study 2 Reversed Phase data for T = 4 week 5° C. stability samples
Study 2 T = 4 week 5° C.

| | | | Relative Area (%) | | | | | | | |
|---|---|---|---|---|---|---|---|---|---|---|
| Form. | Temp (° C.) | Area (mAU * min) | Pre Peak 1 | Pre Peak 2 | Pre Peak 3 | Pre Peak 4 | Pre Peak 5 | Pre Peak 6 | Main Peak | Post Peak A |
| 1 | 5 | 93.29 | 0.00 | 0.29 | 0.71 | 0.32 | 0.14 | 0.00 | 97.47 | 0.00 |
| 2 | 5 | 94.88 | 0.00 | 0.23 | 0.65 | 0.25 | 0.12 | 0.15 | 97.49 | 0.00 |
| 3 | 5 | 93.53 | 0.01 | 0.19 | 0.64 | 0.23 | 0.12 | 0.17 | 97.50 | 0.00 |
| 4 | 5 | 94.18 | 0.01 | 0.26 | 0.63 | 0.25 | 0.13 | 0.21 | 97.19 | 0.00 |
| 5 | 5 | 93.62 | 0.00 | 0.21 | 0.68 | 0.27 | 0.13 | 0.20 | 97.31 | 0.00 |
| 6 | 5 | 93.77 | 0.00 | 0.23 | 0.64 | 0.26 | 0.16 | 0.22 | 96.81 | 0.00 |
| 7 | 5 | 9.21 | 0.02 | 1.91 | 4.99 | 2.58 | 1.12 | 3.26 | 78.74 | 1.56 |
| 8 | 5 | 93.93 | 0.00 | 0.26 | 0.67 | 0.28 | 0.11 | 0.19 | 96.90 | 0.00 |
| 9 | 5 | 17.93 | 0.00 | 1.34 | 2.73 | 0.77 | 0.56 | 1.88 | 87.75 | 0.96 |
| 10 | 5 | 93.25 | 0.01 | 0.15 | 0.65 | 0.24 | 0.11 | 0.17 | 97.43 | 0.00 |
| 11 | 5 | 95.78 | 0.01 | 0.25 | 0.63 | 0.23 | 0.12 | 0.19 | 97.38 | 0.00 |
| 12 | 5 | 94.2 | 0.18 | 0.24 | 0.71 | 0.29 | 0.12 | 0.21 | 97.01 | 0.00 |
| 13 | 5 | 4.50 | 0.00 | 2.02 | 6.03 | 2.62 | 1.84 | 5.27 | 70.21 | 2.79 |
| 14 | 5 | 94.29 | 0.06 | 0.20 | 0.65 | 0.27 | 0.11 | 0.21 | 97.26 | 0.00 |
| 15 | 5 | 93.62 | 0.00 | 0.23 | 0.64 | 0.26 | 0.11 | 0.20 | 97.39 | 0.00 |
| 16 | 5 | 6.05 | 0.07 | 0.65 | 6.51 | 2.75 | 1.40 | 4.47 | 73.41 | 2.22 |
| Form. | Temp (° C.) | Area (mAU * min) | Post Peak 1 | Post Peak 2 | Post Peak 3 | Post Peak 4 | Post Peak 5 | Post Peak 6 | Post Peak 7 | Post Peak 8 |
| 1 | 5 | 93.29 | 0.33 | 0.20 | 0.06 | 0.18 | 0.23 | 0.05 | 0.01 | 0.01 |
| 2 | 5 | 94.88 | 0.35 | 0.20 | 0.09 | 0.19 | 0.20 | 0.06 | 0.02 | 0.01 |
| 3 | 5 | 93.53 | 0.42 | 0.21 | 0.11 | 0.17 | 0.15 | 0.05 | 0.02 | 0.02 |
| 4 | 5 | 94.18 | 0.55 | 0.21 | 0.17 | 0.18 | 0.14 | 0.05 | 0.02 | 0.01 |
| 5 | 5 | 93.62 | 0.43 | 0.22 | 0.14 | 0.18 | 0.15 | 0.05 | 0.01 | 0.02 |
| 6 | 5 | 93.77 | 0.91 | 0.22 | 0.21 | 0.16 | 0.07 | 0.06 | 0.01 | 0.02 |
| 7 | 5 | 9.21 | 2.22 | 1.47 | 0.35 | 0.27 | 1.14 | 0.21 | 0.00 | 0.15 |
| 8 | 5 | 93.93 | 0.65 | 0.21 | 0.32 | 0.16 | 0.14 | 0.05 | 0.02 | 0.01 |
| 9 | 5 | 17.93 | 1.37 | 0.93 | 0.41 | 0.30 | 0.75 | 0.10 | 0.06 | 0.09 |
| 10 | 5 | 93.25 | 0.46 | 0.20 | 0.18 | 0.17 | 0.16 | 0.05 | 0.01 | 0.02 |
| 11 | 5 | 95.78 | 0.43 | 0.20 | 0.12 | 0.15 | 0.15 | 0.05 | 0.06 | 0.01 |
| 12 | 5 | 94.2 | 0.41 | 0.23 | 0.11 | 0.21 | 0.20 | 0.06 | 0.02 | 0.02 |
| 13 | 5 | 4.50 | 3.61 | 2.51 | 0.61 | 0.68 | 1.00 | 0.45 | 0.00 | 0.36 |
| 14 | 5 | 94.29 | 0.41 | 0.20 | 0.05 | 0.18 | 0.29 | 0.05 | 0.02 | 0.02 |
| 15 | 5 | 93.62 | 0.40 | 0.20 | 0.15 | 0.16 | 0.18 | 0.05 | 0.03 | 0.01 |
| 16 | 5 | 6.05 | 3.01 | 2.20 | 0.50 | 0.48 | 1.50 | 0.00 | 0.61 | 0.20 |

Study 2 Result: Determine Optimal pH and Buffer Concentration for MANP by SEC

Figure 19A:
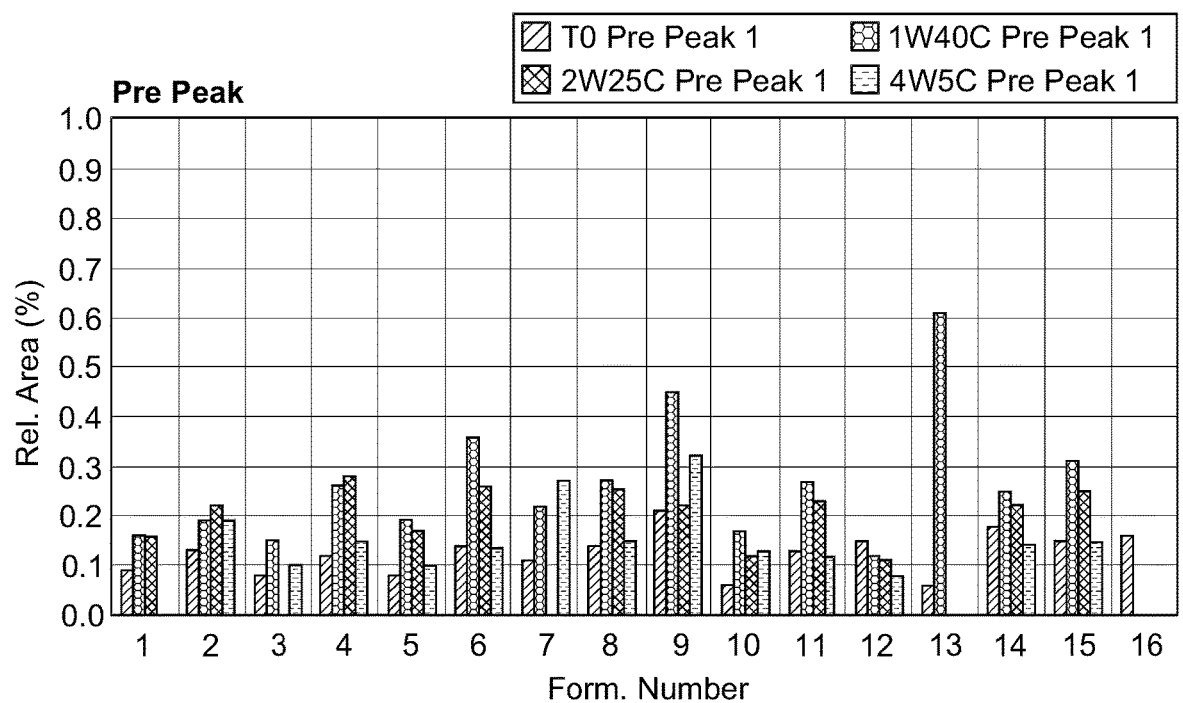
FIG. 19A depicts the relative areas of the pre-peak 1 for samples from Study 2, as measured by SEC.
Figure 19B:
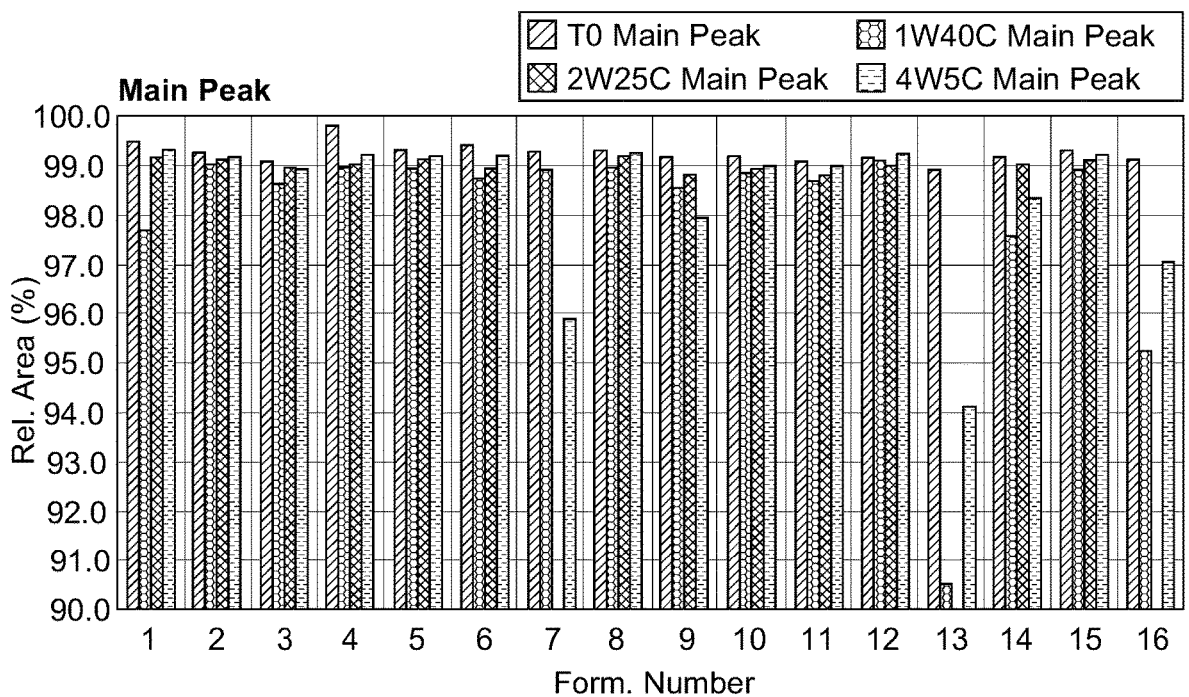
FIG. 19B depicts the relative areas of the main peak for samples from Study 2, as measured by SEC.
Figure 19C:
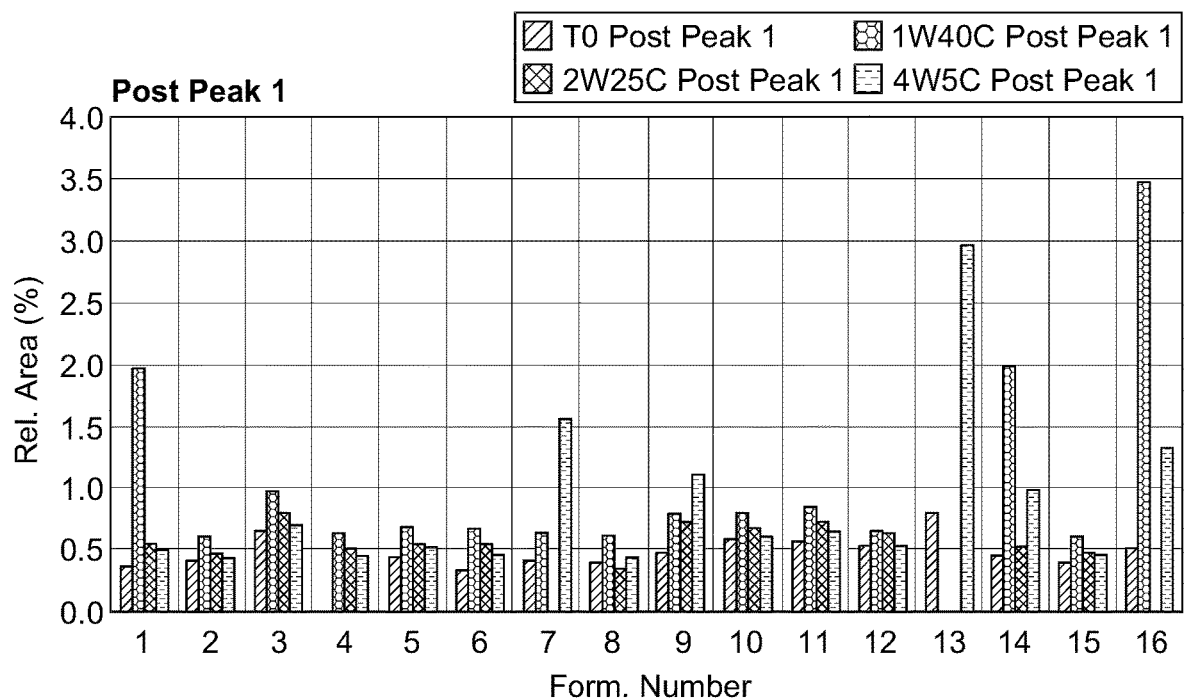
FIG. 19C depicts the relative areas of the post-peak 1 for samples from Study 2, as measured by SEC.
Figure 20A:
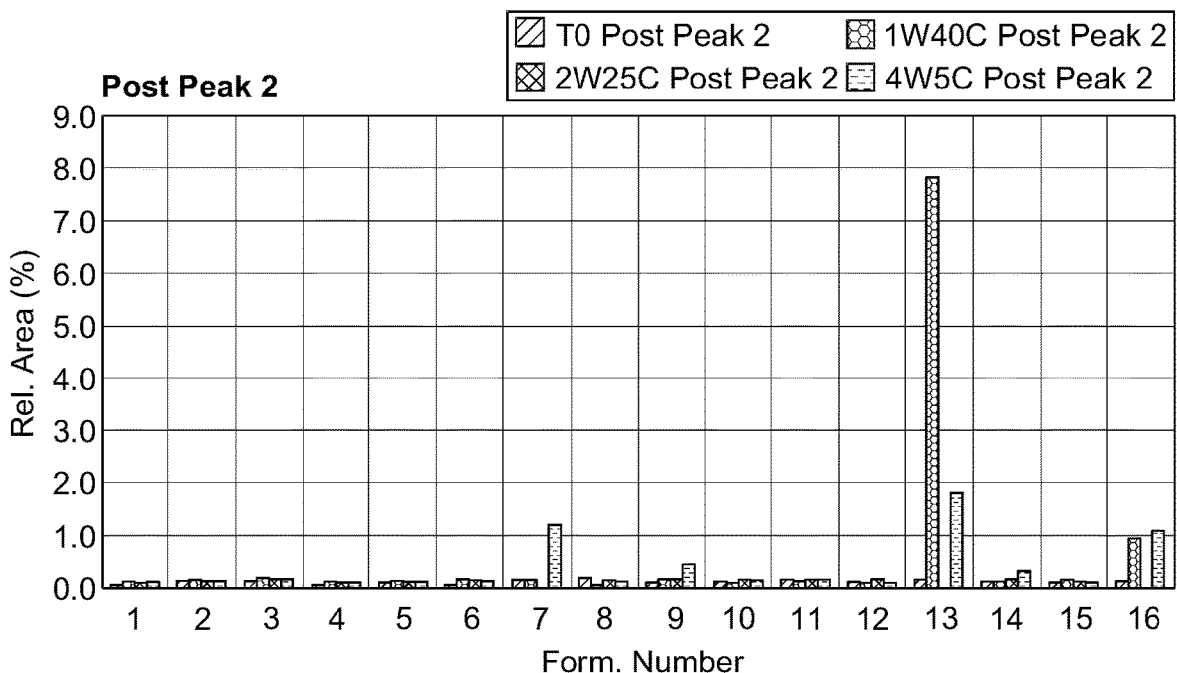
FIG. 20A depicts the relative areas of the post-peak 2 for samples from Study 2, as measured by SEC.
Figure 20B:
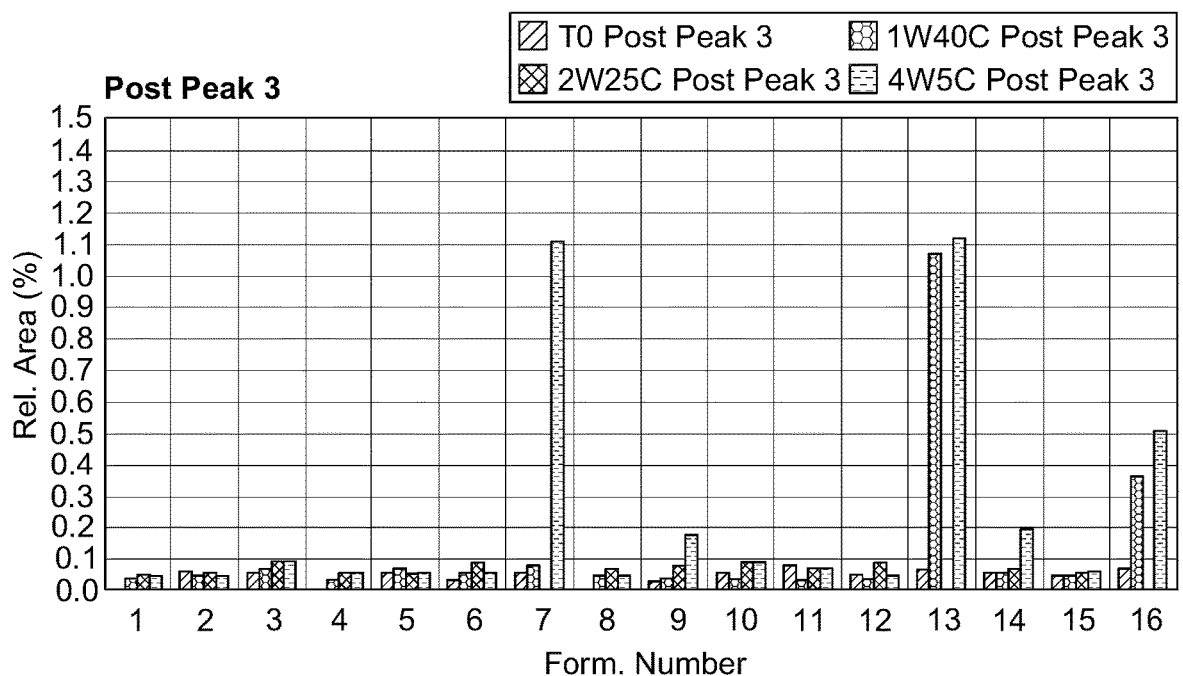
FIG. 20B depicts the relative areas of the post-peak 3 for samples from Study 2, as measured by SEC.
Figure 21:
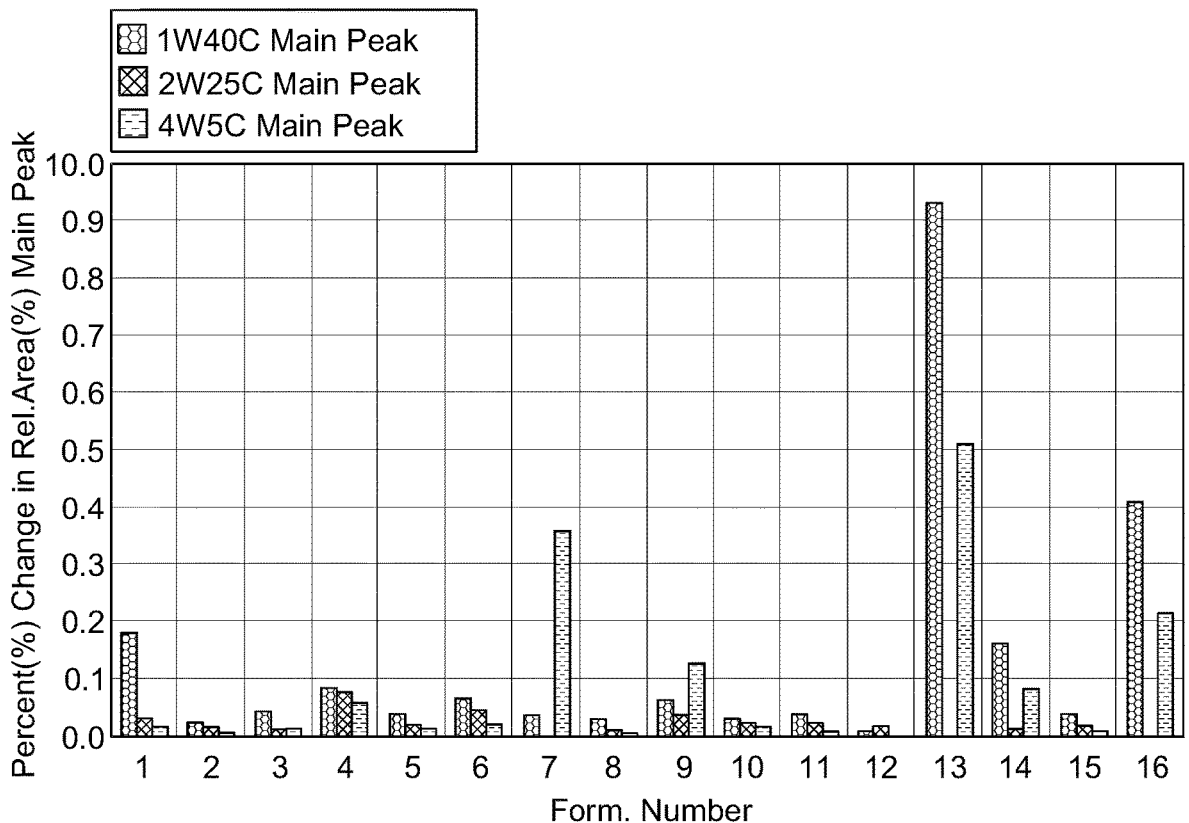
FIG. 21 depicts the changes in the relative area of the SEC main peak (monomer) for samples from Study 2.

The stability samples from Study 2 are also analyzed using SEC, as summarized in Tables 19-22. The largest losses of monomer appear to occur with Formulations 7, 13, and 16 (FIG. 19B), with concomitant increases in post-peak 1 (FIG. 19C). Increases in the other post-peaks are also observed (FIGS. 20A-B), indicating that these samples are degrading, to some extent, by fragmentation or proteolysis. As a result, the monomer content decreases to a greater extent in these samples, although some losses are seen in most formulations (FIG. 21). However, many of the formulations exhibit loss of monomer that is <0.5% at 5° C. over the course of four weeks.

TABLE 19

Study 2 SEC results for the T = 0 stability samples

| Form. | Group Area (mAU * min) | Rel. Area (%) Pre Peak 1 | Rel. Area (%) Main Peak T0 | Rel. Area (%) Post Peak 1 | Rel. Area (%) Post Peak 2 | Rel. Area (%) Post Peak 3 |
|---|---|---|---|---|---|---|
| 1 | 142.39 | 0.09 | 99.49 | 0.37 | 0.05 | 0 |
| 2 | 144.16 | 0.13 | 99.28 | 0.41 | 0.12 | 0.06 |
| 3 | 142.37 | 0.08 | 99.08 | 0.64 | 0.13 | 0.06 |
| 4 | 143.07 | 0.12 | 99.82 | 0 | 0.05 | 0 |
| 5 | 143.59 | 0.08 | 99.33 | 0.44 | 0.1 | 0.06 |
| 6 | 142.79 | 0.14 | 99.43 | 0.33 | 0.06 | 0.04 |
| 7 | 141.88 | 0.11 | 99.29 | 0.41 | 0.13 | 0.06 |
| 8 | 141.78 | 0.14 | 99.3 | 0.39 | 0.17 | 0 |
| 9 | 141.85 | 0.21 | 99.19 | 0.47 | 0.1 | 0.03 |
| 10 | 143.23 | 0.06 | 99.2 | 0.58 | 0.11 | 0.06 |
| 11 | 142.4 | 0.13 | 99.08 | 0.56 | 0.14 | 0.08 |
| 12 | 145.6 | 0.15 | 99.18 | 0.53 | 0.09 | 0.05 |
| 13 | 96.34 | 0.06 | 98.92 | 0.79 | 0.16 | 0.07 |
| 14 | 145.4 | 0.18 | 99.18 | 0.45 | 0.12 | 0.06 |
| 15 | 144.05 | 0.15 | 99.32 | 0.39 | 0.09 | 0.05 |
| 16 | 83.34 | 0.16 | 99.13 | 0.51 | 0.13 | 0.07 |

TABLE 20

Study 2 SEC results for the T = 1 week 40° C. stability samples

| Form. | Group Area (mAU * min) | Rel. Area (%) Pre Peak 1 | Rel. Area (%) Main Peak | Rel. Area (%) Post Peak 1 | Rel. Area (%) Post Peak 2 | Rel. Area (%) Post Peak 3 |
|---|---|---|---|---|---|---|
| 1 | 142.26 | 0.16 | 97.73 | 1.96 | 0.11 | 0.04 |
| 2 | 139.49 | 0.19 | 99.06 | 0.59 | 0.12 | 0.05 |
| 3 | 139.93 | 0.15 | 98.65 | 0.96 | 0.17 | 0.07 |
| 4 | 142.17 | 0.26 | 98.99 | 0.62 | 0.09 | 0.04 |
| 5 | 143.40 | 0.19 | 98.95 | 0.68 | 0.12 | 0.07 |
| 6 | 140.94 | 0.36 | 98.77 | 0.67 | 0.15 | 0.06 |
| 7 | 120.91 | 0.22 | 98.94 | 0.63 | 0.13 | 0.08 |
| 8 | 142.47 | 0.27 | 98.99 | 0.61 | 0.08 | 0.05 |
| 9 | 140.00 | 0.45 | 98.57 | 0.79 | 0.15 | 0.04 |
| 10 | 142.48 | 0.17 | 98.89 | 0.79 | 0.10 | 0.04 |
| 11 | 142.05 | 0.27 | 98.71 | 0.84 | 0.13 | 0.04 |
| 12 | 143.27 | 0.12 | 99.10 | 0.64 | 0.10 | 0.04 |
| 13 | 102.53 | 0.61 | 90.51 | 0.00 | 7.81 | 1.07 |
| 14 | 146.08 | 0.25 | 97.60 | 1.98 | 0.11 | 0.06 |
| 15 | 144.17 | 0.31 | 98.94 | 0.59 | 0.12 | 0.05 |
| 16 | 10.00 | 0.00 | 95.24 | 3.47 | 0.94 | 0.36 |

TABLE 21

Study 2 SEC results for the T = 2 weeks 25° C. stability samples

| Form. | Group Area (mAU * min) | Rel. Area (%) Pre Peak 1 | Rel. Area (%) Main Peak | Rel. Area (%) Post Peak 1 | Rel. Area (%) Post Peak 2 | Rel. Area (%) Post Peak 3 |
|---|---|---|---|---|---|---|
| 1 | 144.09 | 0.16 | 99.16 | 0.54 | 0.1 | 0.05 |
| 2 | 145.81 | 0.22 | 99.14 | 0.46 | 0.12 | 0.06 |
| 3 | 142.81 | 0 | 98.96 | 0.8 | 0.15 | 0.1 |
| 4 | 145.14 | 0.28 | 99.05 | 0.5 | 0.11 | 0.06 |
| 5 | 143.75 | 0.17 | 99.13 | 0.54 | 0.11 | 0.05 |
| 6 | 144.81 | 0.26 | 98.98 | 0.54 | 0.13 | 0.09 |
| 7 | n.a | n.a | n.a | n.a | n.a | n.a |
| 8 | 143.7 | 0.25 | 99.21 | 0.34 | 0.13 | 0.07 |
| 9 | 115.01 | 0.22 | 98.83 | 0.72 | 0.16 | 0.08 |
| 10 | 144.7 | 0.12 | 98.97 | 0.67 | 0.15 | 0.09 |
| 11 | 144.05 | 0.23 | 98.84 | 0.71 | 0.15 | 0.07 |
| 12 | 144.37 | 0.11 | 99.02 | 0.63 | 0.15 | 0.09 |
| 13 | n.a | n.a | n.a | n.a | n.a | n.a |
| 14 | 145.72 | 0.22 | 99.05 | 0.52 | 0.14 | 0.07 |
| 15 | 143.48 | 0.25 | 99.13 | 0.46 | 0.1 | 0.06 |
| 16 | n.a | n.a | n.a | n.a | n.a | n.a |

TABLE 22

Study 2 SEC results for the T = 4 weeks 5° C. stability samples

| Form. | Group Area (mAU * min) | Rel. Area (%) Pre Peak 1 | Rel. Area (%) Main Peak | Rel. Area (%) Post Peak 1 | Rel. Area (%) Post Peak 2 | Rel. Area (%) Post Peak 3 |
|---|---|---|---|---|---|---|
| 1 | 144.50 | n.a. | 99.32 | 0.50 | 0.12 | 0.05 |
| 2 | 145.32 | 0.19 | 99.21 | 0.43 | 0.13 | 0.05 |
| 3 | 144.12 | 0.10 | 98.95 | 0.70 | 0.15 | 0.10 |
| 4 | 147.09 | 0.15 | 99.24 | 0.44 | 0.11 | 0.06 |
| 5 | 144.45 | 0.10 | 99.21 | 0.52 | 0.11 | 0.06 |
| 6 | 144.24 | 0.14 | 99.23 | 0.45 | 0.12 | 0.06 |
| 7 | 15.08 | 0.27 | 95.87 | 1.55 | 1.20 | 1.11 |
| 8 | 143.20 | 0.15 | 99.25 | 0.43 | 0.11 | 0.05 |
| 9 | 30.01 | 0.32 | 97.96 | 1.10 | 0.44 | 0.18 |
| 10 | 145.71 | 0.13 | 99.03 | 0.61 | 0.14 | 0.09 |
| 11 | 146.53 | 0.12 | 99.01 | 0.64 | 0.16 | 0.07 |
| 12 | 145.22 | 0.08 | 99.26 | 0.52 | 0.10 | 0.05 |
| 13 | 7.60 | 0.00 | 94.12 | 2.96 | 1.80 | 1.12 |
| 14 | 146.56 | 0.14 | 98.36 | 0.98 | 0.32 | 0.20 |
| 15 | 145.11 | 0.15 | 99.24 | 0.45 | 0.10 | 0.06 |
| 16 | 10.07 | n.a. | 97.06 | 1.32 | 1.1 | 0.51 |

Study 3 Result: Refine Optimal pH and Buffer Concentration for MANP by Visual Inspection. Peptide Concentrations, and pH A third study is initiated to refine the optimal pH and buffer conditions for MANP. In addition, the study examines combinations of sucrose, mannitol, HP-b-CD, and Gly as potential 5 stabilizers. The twelve formulations evaluated in Study 3 are shown in Table 23.

TABLE 23

Study 3 Formulation Design

| Form. | MANP (ml/ml) | pH | Acetate (mM) | Histidine (mM) | Glycine (mM) | HP-β-CD (mM) | Sucrose (mM) | Mannitol (mM) |
|---|---|---|---|---|---|---|---|---|
| 1 | 1 | 4.5 | 40 | 0 | 0 | 50 | 200 | 0 |
| 2 | 1 | 4.5 | 20 | 0 | 200 | 50 | 0 | 0 |
| 3 | 1 | 4.5 | 20 | 0 | 0 | 0 | 275 | 0 |
| 4 | 1 | 5 | 40 | 0 | 275 | 0 | 0 | 0 |
| 5 | 1 | 5 | 0 | 40 | 275 | 0 | 0 | 0 |
| 6 | 1 | 5 | 0 | 20 | 0 | 100 | 150 | 0 |
| 7 | 1 | 4.5 | 10 | 0 | 100 | 0 | 0 | 150 |
| 8 | 1 | 5.5 | 0 | 40 | 150 | 100 | 0 | 0 |
| 9 | 1 | 5.5 | 0 | 20 | 0 | 50 | 0 | 200 |

TABLE 23-continued

Study 3 Formulation Design

| Form. | MANP (ml/ml) | pH | Acetate (mM) | Histidine (mM) | Glycine (mM) | HP-β-CD (mM) | Sucrose (mM) | Mannitol (mM) |
|---|---|---|---|---|---|---|---|---|
| 10 | 1 | 5 | 0 | 40 | 0 | 25 | 200 | 0 |
| 11 | 2 | 4.5 | 20 | 0 | 0 | 0 | 0 | 275 |
| 12 | 2 | 5 | 0 | 20 | 0 | 100 | 150 | 0 |

Note:
T0 and T = 4 weeks 5° C. reversed phase data was collected in triplicate and were not compared to T = 2 weeks 5° C.

Figure 22:
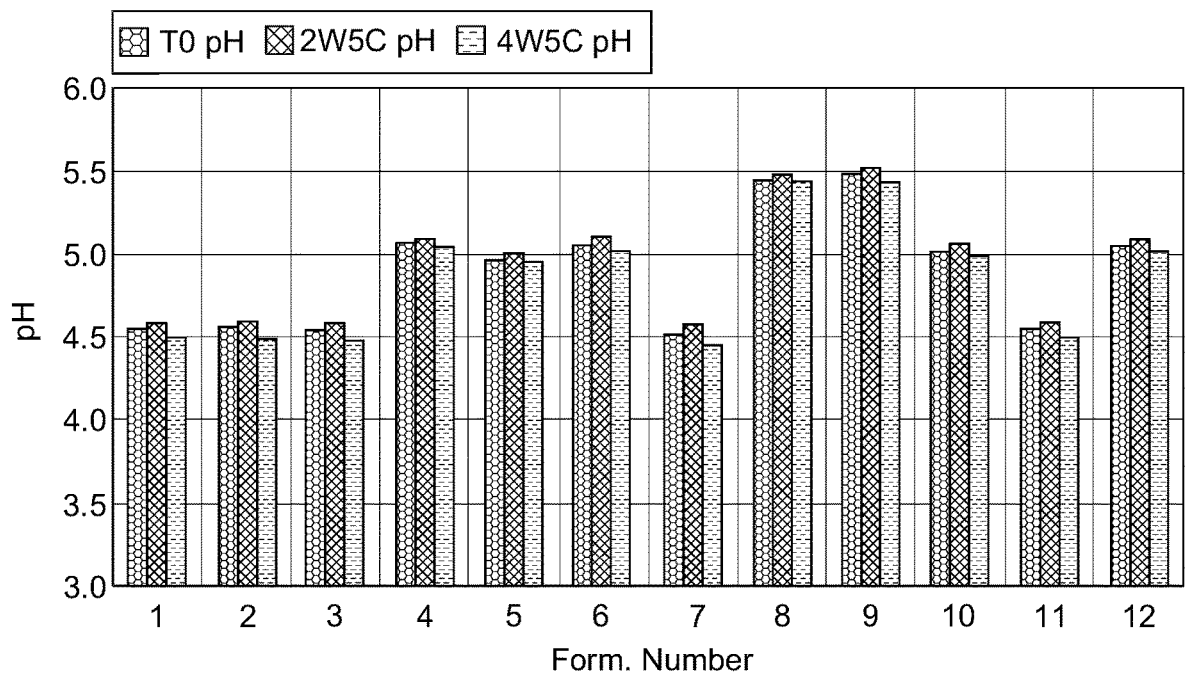
FIG. 22 depicts the pH values measured for each formulation evaluated in Study 3.
Figure 23:
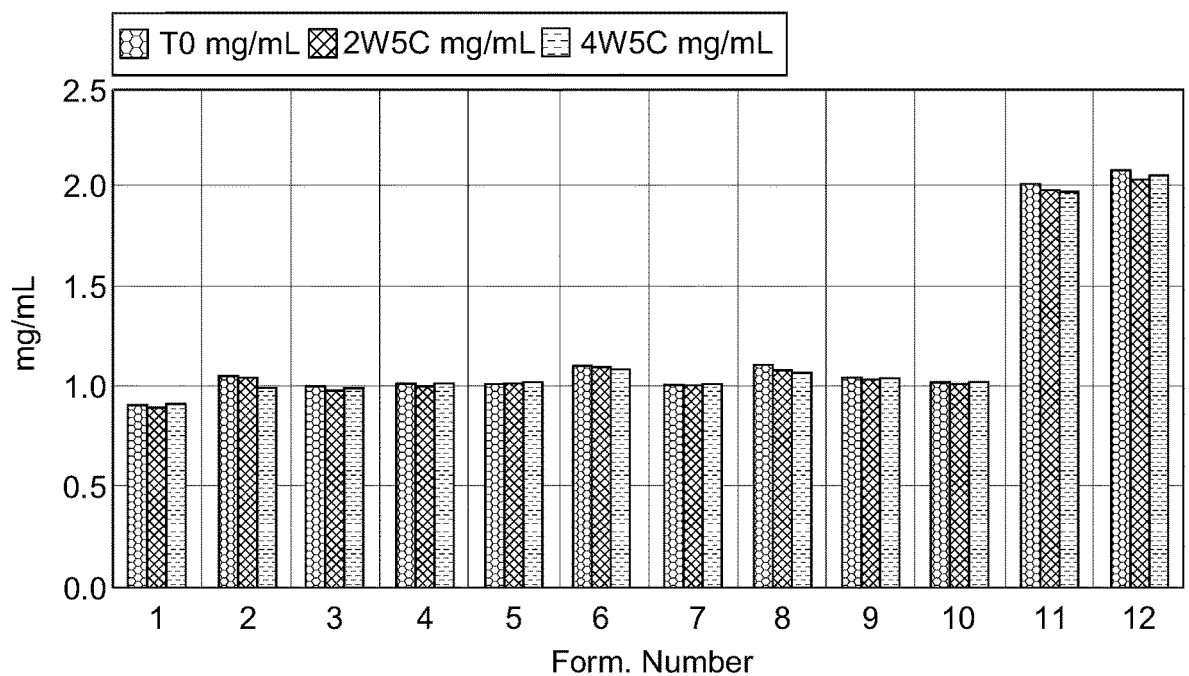
FIG. 23 depicts the measured peptide concentration for each formulation evaluated in Study 3.

As with Study 2, the visual inspection of these stability samples shows no evidence of particle formation, precipitation or discoloration (Table 24). The measured pH values at each time point are summarized in Table 25 and FIG. 22. The values are very close to the target values and do not vary appreciably across the course of the study. Likewise, the peptide concentrations are near the target values and do not vary across the study (Table 26, FIG. 23), indicating that the pH range chosen for this study provide suitable physical stability.

TABLE 24

Study 3 visual characterization of stability samples at T = 0, T = 2 weeks at 5° C., and T = 4 weeks at 5° C.

| Form. | MANP (mg/ml) | pH | Observations at T = 0 | | | Observations at T = 2 week at 5° C. | | | Observations at T = 4 week at 5° C. | | |
|---|---|---|---|---|---|---|---|---|---|---|---|
| | | | Color | Particle | Visual | Color | Particle | Visual | Color | Particle | Visual |
| 1 | 1 | 4.5 | No | No | Clear | No | No | Clear | No | No | Clear |
| 2 | 1 | 4.5 | No | No | Clear | No | No | Clear | No | No | Clear |
| 3 | 1 | 4.5 | No | No | Clear | No | No | Clear | No | No | Clear |
| 4 | 1 | 5 | No | No | Clear | No | No | Clear | No | No | Clear |
| 5 | 1 | 5 | No | No | Clear | No | No | Clear | No | No | Clear |
| 6 | 1 | 5 | No | No | Clear | No | No | Clear | No | No | Clear |
| 7 | 1 | 4.5 | No | No | Clear | No | No | Clear | No | No | Clear |
| 8 | 1 | 5.5 | No | No | Clear | No | No | Clear | No | No | Clear |
| 9 | 1 | 5.5 | No | No | Clear | No | No | Clear | No | No | Clear |
| 10 | 1 | 5 | No | No | Clear | No | No | Clear | No | No | Clear |
| 11 | 2 | 4.5 | No | No | Clear | No | No | Clear | No | No | Clear |
| 12 | 2 | 5 | No | No | Clear | No | No | Clear | No | No | Clear |

TABLE 25

Study 3 pH for the stability samples

| Form. No. | MANP (mg/ml) | pH | pH T = 0 | T = 2 weeks 5° C. | T = 4 weeks |
|---|---|---|---|---|---|
| 1 | 1 | 4.5 | 4.55 | 4.58 | 4.49 |
| 2 | 1 | 4.5 | 4.57 | 4.59 | 4.48 |
| 3 | 1 | 4.5 | 4.54 | 4.58 | 4.47 |
| 4 | 1 | 5 | 5.07 | 5.09 | 5.05 |
| 5 | 1 | 5 | 4.96 | 5.01 | 4.96 |
| 6 | 1 | 5 | 5.05 | 5.1 | 5.02 |
| 7 | 1 | 4.5 | 4.51 | 4.57 | 4.45 |
| 8 | 1 | 5.5 | 5.45 | 5.48 | 5.44 |
| 9 | 1 | 5.5 | 5.48 | 5.52 | 5.44 |
| 10 | 1 | 5 | 5.02 | 5.06 | 4.99 |
| 11 | 2 | 4.5 | 4.55 | 4.59 | 4.5 |
| 12 | 2 | 5 | 5.05 | 5.09 | 5.02 |

TABLE 26

Study 3 peptide concentration for the stability samples

| Form. No. | MANP (mg/ml) | pH | Peptide Concentration (mg/mL) | | |
|---|---|---|---|---|---|
| | | | T = 0 | T = 2 week 5° C. | T = 4 weeks 5° C. |
| 1 | 1 | 4.5 | 0.91 | 0.89 | 0.91 |
| 2 | 1 | 4.5 | 1.05 | 1.04 | 0.99 |
| 3 | 1 | 4.5 | 1 | 0.98 | 0.99 |
| 4 | 1 | 5 | 1.01 | 1 | 1.01 |
| 5 | 1 | 5 | 1.01 | 1.01 | 1.02 |
| 6 | 1 | 5 | 1.1 | 1.09 | 1.09 |
| 7 | 1 | 4.5 | 1 | 1 | 1 |
| 8 | 1 | 5.5 | 1.11 | 1.08 | 1.07 |
| 9 | 1 | 5.5 | 1.04 | 1.03 | 1.04 |
| 10 | 1 | 5 | 1.02 | 1.01 | 1.02 |
| 11 | 2 | 4.5 | 2.01 | 1.99 | 1.98 |
| 12 | 2 | 5 | 2.08 | 2.03 | 2.05 |

Study 3 Result: Refine Optimal pH and Buffer Concentration for MANP by RP-HPLC

Figure 24:
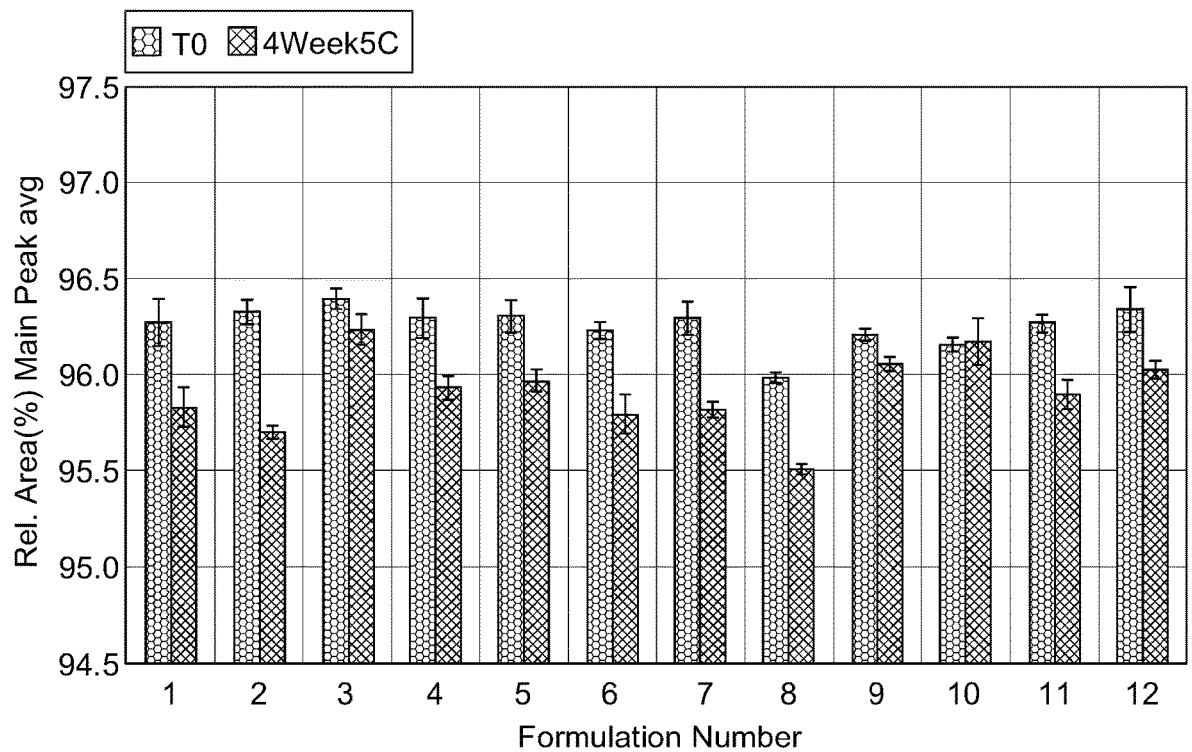
FIG. 24 depicts the relative areas of the main peak for samples from Study 3, as measured by RP-HPLC with UV detection.
Figure 25:
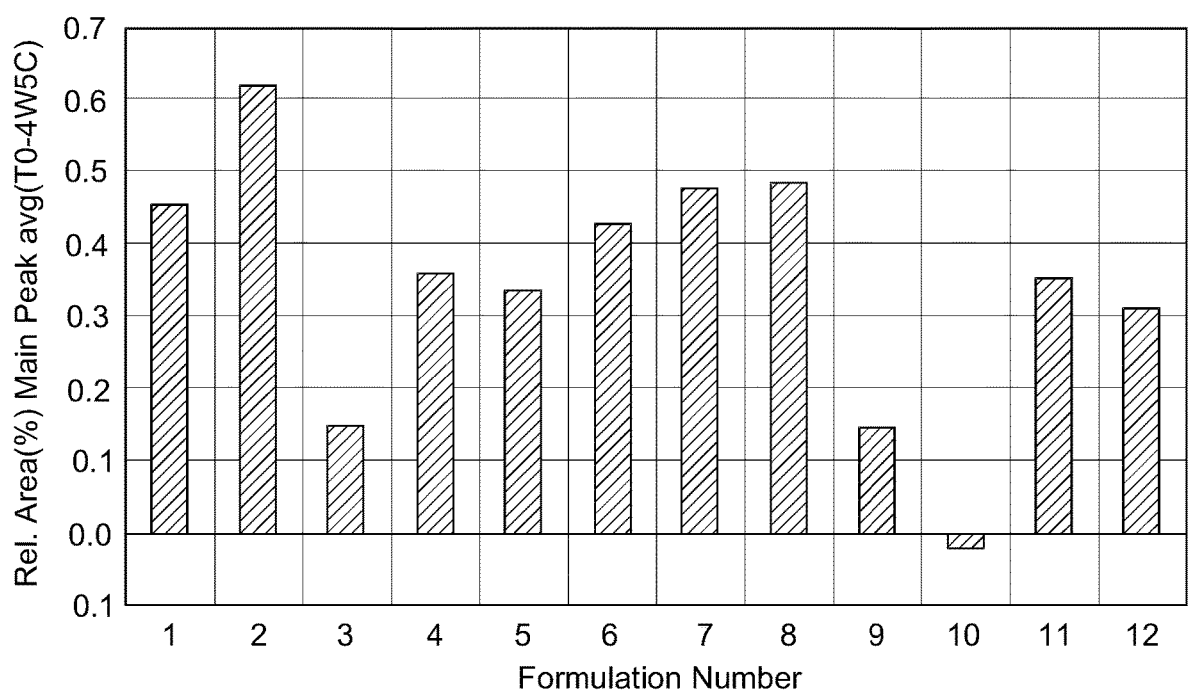
FIG. 25 depicts the differences main peak relative area (between T=0 and T=4 weeks at 5° C.) for each formulation evaluated in Study 3, as measured by RP-HPLC with UV detection.

Using the primary RP-HPLC method, the stability of Study 3 formulations is monitored for up to four weeks 5° C. The results from RP-HPLC analysis as measured by UV are summarized in Tables 27 and 28. Over the course of four weeks at 5° C., the loss of chemical purity by RP-HPLC is fairly small (<0.5%) (Table 29). Formulations 3, 9, and 10 showed the smallest losses of purity upon storage. These differences are shown graphically in FIG. 24 and FIG. 25.

Figure 26:
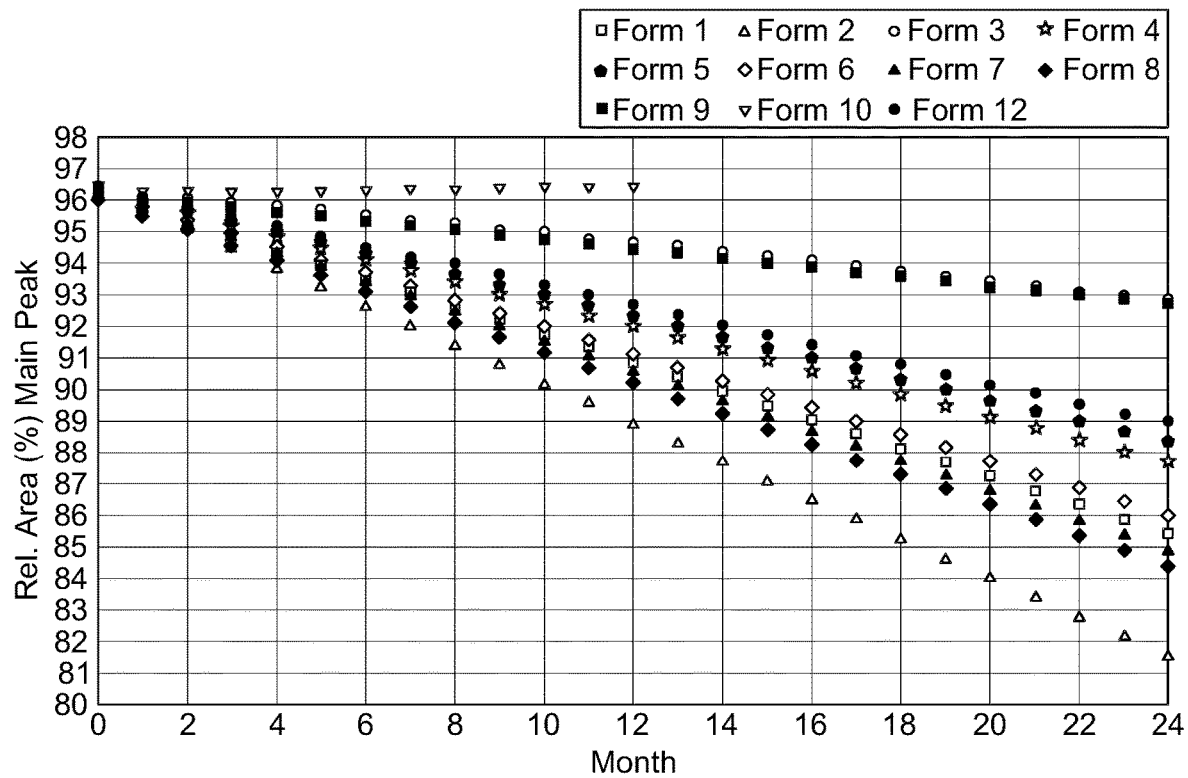
FIG. 26 depicts the extrapolated losses of main peak relative area (between T=0 and T=4 weeks at 5° C.) for each formulation evaluated in Study 3, as measured by RP-HPLC with UV detection.

The extrapolated losses of main peak relative areas for Study 3 samples using RP-HPLC with UV detection is shown in FIG. 26.

TABLE 27

Study 3 Reversed Phase data for T = 0 and T = 4 weeks 5° C. stability samples (Formulations 1-6) by UV

| Form. | Time (Weeks) | Temp (° C.) | Group Area (mAU * min) | Pre Peak 1 | Pre Peak 2 | Pre Peak 3 | Pre Peak 4 | Pre Peak 5 | Pre Peak 6 | Main Peak |
|---|---|---|---|---|---|---|---|---|---|---|
| 1 | 0 | n.a | 66.87 | 0.05 | n.a. | 0.80 | 0.29 | 0.14 | 0.37 | 96.37 |
| 1 | 0 | n.a | 66.25 | 0.05 | 0.03 | 0.76 | 0.31 | 0.15 | 0.39 | 96.15 |
| 1 | 0 | n.a | 66.15 | 0.05 | 0.04 | 0.80 | 0.30 | 0.13 | 0.38 | 96.31 |
| 1 | 4 | 5 | 66.08 | 0.04 | 0.03 | 0.90 | 0.31 | 0.16 | 0.38 | 95.82 |
| 1 | 4 | 5 | 66.30 | 0.03 | 0.04 | 0.93 | 0.36 | 0.15 | 0.39 | 95.73 |
| 1 | 4 | 5 | 66.41 | 0.04 | 0.03 | 0.93 | 0.33 | 0.16 | 0.36 | 95.92 |
| 2 | 0 | n.a | 66.38 | 0.06 | 0.03 | 0.88 | 0.31 | 0.12 | 0.37 | 96.4 |
| 2 | 0 | n.a | 66.47 | 0.06 | 0.03 | 0.89 | 0.32 | 0.12 | 0.37 | 96.28 |
| 2 | 0 | n.a | 66.25 | 0.06 | 0.03 | 0.89 | 0.29 | 0.13 | 0.38 | 96.28 |
| 2 | 4 | 5 | 67.25 | 0.04 | 0.03 | 100 | 0.42 | 0.17 | 0.38 | 95.67 |
| 2 | 4 | 5 | 67.29 | 0.05 | 0.02 | 1.01 | 0.43 | 0.16 | 0.37 | 95.71 |
| 2 | 4 | 5 | 66.97 | 0.05 | 0.02 | 1.00 | 0.37 | 0.14 | 0.37 | 95.73 |
| 3 | 0 | n.a | 65.23 | 0.04 | 0.02 | 0.82 | 0.28 | 0.15 | 0.35 | 96.35 |
| 3 | 0 | n.a | 65.40 | 0.05 | 0.04 | 0.85 | 0.27 | 0.12 | 0.36 | 96.36 |
| 3 | 0 | n.a | 64.92 | 0.05 | 0.04 | 0.84 | 0.25 | 0.14 | 0.36 | 96.44 |
| 3 | 4 | 5 | 66.42 | 0.03 | 0.02 | 0.82 | 0.26 | 0.12 | 0.35 | 96.31 |
| 3 | 4 | 5 | 66.58 | 0.06 | 0.03 | 0.85 | 0.27 | 0.13 | 0.36 | 96.24 |
| 3 | 4 | 5 | 65.61 | 0.03 | 0.04 | 0.86 | 0.29 | 0.14 | 0.37 | 96.15 |
| 4 | 0 | n.a | 64.11 | 0.06 | 0.03 | 0.92 | 0.30 | 0.15 | 0.37 | 96.21 |
| 4 | 0 | n.a | 63.50 | 0.05 | 0.03 | 0.92 | 0.26 | 0.12 | 0.34 | 96.41 |
| 4 | 0 | n.a | 64.21 | 0.06 | 0.03 | 0.92 | 0.27 | 0.14 | 0.37 | 96.26 |
| 4 | 4 | 5 | 65.55 | 0.05 | 0.92 | 0.02 | 0.32 | 0.15 | 0.36 | 95.89 |
| 4 | 4 | 5 | 65.79 | 0.05 | 0.02 | 0.93 | 0.34 | 0.16 | 0.34 | 96.00 |
| 4 | 4 | 5 | 64.87 | 0.05 | 0.02 | 0.92 | 0.31 | 0.16 | 0.36 | 95.91 |
| 5 | 0 | n.a | 63.65 | 0.05 | 0.02 | 0.91 | 0.28 | 0.13 | 0.35 | 96.27 |
| 5 | 0 | n.a | 63.15 | 0.05 | 0.02 | 0.91 | 0.29 | 0.13 | 0.35 | 96.39 |
| 5 | 0 | n.a | 63.14 | 0.06 | 0.01 | 0.90 | 0.32 | 0.16 | 0.37 | 96.24 |
| 5 | 4 | 5 | 64.33 | 0.06 | 0.03 | 0.92 | 0.34 | 0.14 | 0.35 | 95.93 |
| 5 | 4 | 5 | 64.58 | 0.05 | 0.02 | 0.92 | 0.32 | 0.15 | 0.35 | 95.94 |
| 5 | 4 | 5 | 64.45 | 0.06 | 0.02 | 0.92 | 0.33 | 0.15 | 0.34 | 96.03 |
| 6 | 0 | n.a | 67.73 | 0.05 | 0.03 | 0.95 | 0.30 | 0.12 | 0.36 | 96.21 |
| 6 | 0 | n.a | 67.49 | 0.06 | 0.02 | 0.95 | 0.28 | 0.15 | 0.40 | 96.19 |
| 6 | 0 | n.a | 67.34 | 0.06 | 0.02 | 0.95 | 0.30 | 0.14 | 0.36 | 96.26 |
| 6 | 4 | 5 | 67.02 | 0.05 | 0.02 | 1.05 | 0.33 | 0.15 | 0.36 | 95.91 |
| 6 | 4 | 5 | 66.96 | 0.06 | 0.02 | 1.07 | 0.38 | 0.16 | 0.38 | 95.72 |
| 6 | 4 | 5 | 66.60 | 0.06 | 0.02 | 1.06 | 0.38 | 0.18 | 0.36 | 95.75 |

| Form. | Time (Weeks) | Temp (° C.) | Group Area (mAU * min) | Post Peak 1 | Post Peak 2 | Post Peak 3 | Post Peak 4 | Post Peak 5 | Post Peak 6 | Post Peak 7 | Post Peak 8 |
|---|---|---|---|---|---|---|---|---|---|---|---|
| 1 | 0 | n.a | 66.87 | 0.89 | 0.49 | 0.2 | 0.22 | 0.16 | 0.03 | n.a. | n.a. |
| 1 | 0 | n.a | 66.25 | 0.9 | 0.54 | 0.21 | 0.28 | 0.17 | 0.04 | n.a. | n.a. |
| 1 | 0 | n.a | 66.15 | 0.88 | 0.51 | 0.2 | 0.22 | 0.16 | 0.03 | n.a. | n.a. |
| 1 | 4 | 5 | 66.08 | 1.01 | 0.54 | 0.23 | 0.25 | 0.28 | 0.04 | n.a. | n.a. |
| 1 | 4 | 5 | 66.30 | 1.01 | 0.52 | 0.25 | 0.26 | 0.27 | 0.04 | n.a. | n.a. |
| 1 | 4 | 5 | 66.41 | 1 | 0.51 | 0.21 | 0.23 | 0.25 | 0.03 | n.a. | n.a. |
| 2 | 0 | n.a | 66.38 | 0.86 | 0.47 | 0.17 | 0.15 | 0.15 | 0.03 | n.a. | n.a. |
| 2 | 0 | n.a | 66.47 | 0.88 | 0.49 | 0.19 | 0.18 | 0.15 | 0.03 | n.a. | n.a. |
| 2 | 0 | n.a | 66.25 | 0.91 | 0.48 | 0.2 | 0.17 | 0.15 | 0.03 | n.a. | n.a. |
| 2 | 4 | 5 | 67.25 | 1.02 | 0.52 | 0.24 | 0.22 | 0.25 | 0.04 | n.a. | n.a. |
| 2 | 4 | 5 | 67.29 | 0.99 | 0.52 | 0.23 | 0.21 | 0.25 | 0.03 | n.a. | n.a. |
| 2 | 4 | 5 | 66.97 | 1.03 | 0.55 | 0.22 | 0.23 | 0.26 | 0.04 | n.a. | n.a. |
| 3 | 0 | n.a | 65.23 | 0.89 | 0.49 | 0.21 | 0.21 | 0.16 | 0.04 | n.a. | n.a. |
| 3 | 0 | n.a | 65.40 | 0.89 | 0.53 | 0.19 | 0.18 | 0.14 | 0.02 | n.a. | n.a. |
| 3 | 0 | n.a | 64.92 | 0.87 | 0.5 | 0.19 | 0.16 | 0.15 | 0.03 | n.a. | n.a. |
| 3 | 4 | 5 | 66.42 | 0.98 | 0.48 | 0.18 | 0.18 | 0.23 | 0.03 | n.a. | n.a. |
| 3 | 4 | 5 | 66.58 | 0.98 | 0.48 | 0.18 | 0.16 | 0.23 | 0.04 | n.a. | n.a. |
| 3 | 4 | 5 | 65.61 | 1.01 | 0.5 | 0.18 | 0.18 | 0.22 | 0.03 | n.a. | n.a. |
| 4 | 0 | n.a | 64.11 | 0.89 | 0.51 | 0.19 | 0.21 | 0.13 | 0.03 | n.a. | n.a. |
| 4 | 0 | n.a | 63.50 | 0.89 | 0.47 | 0.17 | 0.18 | 0.13 | 0.02 | n.a. | n.a. |
| 4 | 0 | n.a | 64.21 | 0.9 | 0.51 | 0.19 | 0.2 | 0.13 | 0.02 | n.a. | n.a. |
| 4 | 4 | 5 | 65.55 | 0.98 | 0.51 | 0.23 | 0.3 | 0.22 | 0.04 | n.a. | n.a. |

TABLE 27-continued

Study 3 Reversed Phase data for T = 0 and T = 4 weeks 5° C. stability samples
(Formulations 1-6) by UV

| 4 | 4 | 5 | 65.79 | 0.94 | 0.5 | 0.21 | 0.26 | 0.21 | 0.03 | n.a. | n.a. |
| 4 | 4 | 5 | 64.87 | 1 | 0.51 | 0.21 | 0.29 | 0.22 | 0.04 | n.a. | n.a. |
| 5 | 0 | n.a | 63.65 | 0.9 | 0.47 | 0.21 | 0.23 | 0.13 | 0.03 | n.a. | n.a. |
| 5 | 0 | n.a | 63.15 | 0.87 | 0.47 | 0.17 | 0.21 | 0.12 | 0.02 | n.a. | n.a. |
| 5 | 0 | n.a | 63.14 | 0.9 | 0.49 | 0.19 | 0.22 | 0.13 | 0.02 | n.a. | n.a. |
| 5 | 4 | 5 | 64.33 | 0.97 | 0.53 | 0.21 | 0.31 | 0.18 | 0.04 | n.a. | n.a. |
| 5 | 4 | 5 | 64.58 | 0.98 | 0.5 | 0.21 | 0.33 | 0.18 | 0.03 | n.a. | n.a. |
| 5 | 4 | 5 | 64.45 | 0.93 | 0.51 | 0.21 | 0.29 | 0.18 | 0.04 | n.a. | n.a. |
| 6 | 0 | n.a | 67.73 | 0.87 | 0.5 | 0.21 | 0.21 | 0.13 | 0.04 | n.a. | n.a. |
| 6 | 0 | n.a | 67.49 | 0.87 | 0.52 | 0.21 | 0.19 | 0.12 | 0.03 | n.a. | n.a. |
| 6 | 0 | n.a | 67.34 | 0.85 | 0.5 | 0.2 | 0.19 | 0.13 | 0.04 | n.a. | n.a. |
| 6 | 4 | 5 | 67.02 | 0.93 | 0.52 | 0.23 | 0.22 | 0.18 | 0.03 | n.a. | n.a. |
| 6 | 4 | 5 | 66.96 | 0.95 | 0.54 | 0.23 | 0.26 | 0.2 | 0.05 | n.a. | n.a. |
| 6 | 4 | 5 | 66.60 | 0.96 | 0.55 | 0.23 | 0.24 | 0.19 | 0.04 | n.a. | n.a. |

TABLE 28

Study 3 Reversed Phase data for T = 0 and T = 4 weeks 5° C. stability samples
(Formulations 7-12) byUV

| Form. | Time (Weeks) | Temp (° C.) | Group Area (mAU * min) | Relative Area (%) | | | | | | Main Peak |
|---|---|---|---|---|---|---|---|---|---|---|
| | | | | Pre Peak 1 | Pre Peak 2 | Pre Peak 3 | Pre Peak 4 | Pre Peak 5 | Pre Peak 6 | |
| 7 | 0 | n.a | 65.85 | 0.07 | 0.04 | 0.96 | 0.32 | 0.12 | 0.32 | 96.31 |
| 7 | 0 | n.a | 65.5 | 0.07 | 0.04 | 0.97 | 0.3 | 0.13 | 0.33 | 96.21 |
| 7 | 0 | n.a | 64.79 | 0.07 | 0.04 | 0.97 | 0.27 | 0.12 | 0.32 | 96.36 |
| 7 | 4 | 5 | 66.01 | 0.07 | 0.05 | 1.04 | 0.42 | 0.13 | 0.33 | 95.78 |
| 7 | 4 | 5 | 66 | 0.08 | 0.04 | 1.05 | 0.43 | 0.13 | 0.29 | 95.83 |
| 7 | 4 | 5 | 65.99 | 0.07 | 0.04 | 1.04 | 0.39 | 0.13 | 0.3 | 95.84 |
| 8 | 0 | n.a | 66.57 | 0.06 | 0.03 | 0.96 | 0.36 | 0.15 | 0.36 | 96 |
| 8 | 0 | n.a | 67.08 | 0.06 | 0.02 | 0.96 | 0.36 | 0.15 | 0.37 | 95.99 |
| 8 | 0 | n.a | 67.1 | 0.06 | 0.02 | 0.96 | 0.34 | 0.18 | 0.39 | 95.96 |
| 8 | 4 | 5 | 65.79 | 0.07 | 0.02 | 1.07 | 0.47 | 0.17 | 0.37 | 95.52 |
| 8 | 4 | 5 | 65.87 | 0.06 | 0.02 | 1.07 | 0.5 | 0.19 | 0.37 | 95.47 |
| 8 | 4 | 5 | 65.85 | 0.06 | 0.02 | 1.07 | 0.48 | 0.18 | 0.38 | 95.51 |
| 9 | 0 | n.a | 66.81 | 0.06 | 0.02 | 0.86 | 0.27 | 0.17 | 0.38 | 96.18 |
| 9 | 0 | n.a | 67.1 | 0.06 | 0.03 | 0.88 | 0.29 | 0.14 | 0.36 | 96.22 |
| 9 | 0 | n.a | 66.56 | 0.07 | 0.03 | 0.88 | 0.29 | 0.16 | 0.38 | 96.22 |
| 9 | 4 | 5 | 67.97 | 0.06 | 0.02 | 0.9 | 0.31 | 0.17 | 0.36 | 96.04 |
| 9 | 4 | 5 | 67.24 | 0.05 | 0.02 | 0.89 | 0.29 | 0.19 | 0.36 | 96.09 |
| 9 | 4 | 5 | 67.88 | 0.05 | 0.03 | 0.92 | 0.35 | 0.18 | 0.37 | 96.05 |
| 10 | 0 | n.a | 66.98 | n.a. | 0.03 | 0.88 | 0.31 | 0.3 | 0.37 | 96.13 |
| 10 | 0 | n.a | 67.11 | n.a. | 0.03 | 0.9 | 0.33 | 0.29 | 0.35 | 96.16 |
| 10 | 0 | n.a | 67.13 | n.a. | 0.04 | 0.9 | 0.29 | 0.28 | 0.36 | 96.16 |
| 10 | 4 | 5 | 67.76 | n.a. | 0.03 | 0.89 | 0.33 | 0.16 | 0.35 | 96.1 |
| 10 | 4 | 5 | 67.21 | n.a. | 0.03 | 0.89 | 0.3 | 0.13 | 0.34 | 96.3 |
| 10 | 4 | 5 | 67.6 | n.a. | 0.04 | 0.9 | 0.33 | 0.17 | 0.36 | 96.11 |
| 11 | 0 | n.a | 66.36 | 0.04 | 0.04 | 0.87 | 0.33 | 0.13 | 0.34 | 96.22 |
| 11 | 0 | n.a | 66.31 | 0.08 | 0.04 | 0.84 | 0.26 | 0.14 | 0.34 | 96.28 |
| 11 | 0 | n.a | 65.58 | 0.04 | 0.04 | 0.88 | 0.33 | 0.12 | 0.32 | 96.27 |
| 11 | 4 | 5 | 67.64 | 0.11 | 0.11 | 0.87 | 0.34 | 0.14 | 0.33 | 95.83 |
| 11 | 4 | 5 | 66.92 | 0.05 | 0.11 | 0.88 | 0.37 | 0.15 | 0.31 | 95.99 |
| 11 | 4 | 5 | 66.2 | 0.09 | 0.04 | 0.86 | 0.32 | 0.15 | 0.34 | 95.89 |
| 12 | 0 | n.a | 67.3 | 0.05 | 0.03 | 0.87 | 0.24 | 0.13 | 0.37 | 96.45 |
| 12 | 0 | n.a | 67.28 | 0.08 | 0.03 | 0.86 | 0.26 | 0.15 | 0.38 | 96.22 |
| 12 | 0 | n.a | 66.63 | 0.05 | 0.03 | 0.88 | 0.25 | 0.12 | 0.37 | 96.34 |
| 12 | 4 | 5 | 67.75 | 0.09 | 0.02 | 0.89 | 0.26 | 0.14 | 0.38 | 96.04 |
| 12 | 4 | 5 | 68.73 | 0.09 | 0.02 | 0.89 | 0.3 | 0.15 | 0.38 | 95.98 |
| 12 | 4 | 5 | 67.88 | 0.06 | 0.02 | 0.89 | 0.31 | 0.16 | 0.38 | 96.06 |

TABLE 28-continued

Study 3 Reversed Phase data for T = 0 and T = 4 weeks 5° C. stability samples
(Formulations 7-12) by UV

| | | | Group | Relative Area (%) | | | | | | | |
|---|---|---|---|---|---|---|---|---|---|---|---|
| Form. | Time (Weeks) | Temp (° C.) | Area (mAU * min) | Post Peak 1 | Post Peak 2 | Post Peak 3 | Post Peak 4 | Post Peak 5 | Post Peak 6 | Post Peak 7 | Post Peak 8 |
| 7 | 0 | n.a | 65.85 | 0.92 | 0.46 | 0.17 | 0.14 | 0.13 | 0.02 | n.a. | n.a. |
| 7 | 0 | n.a | 65.5 | 0.92 | 0.49 | 0.19 | 0.16 | 0.15 | 0.03 | n.a. | n.a. |
| 7 | 0 | n.a | 64.79 | 0.92 | 0.47 | 0.17 | 0.14 | 0.14 | 0.02 | n.a. | n.a. |
| 7 | 4 | 5 | 66.01 | 1.03 | 0.5 | 0.19 | 0.2 | 0.23 | 0.02 | n.a. | n.a. |
| 7 | 4 | 5 | 66 | 1.04 | 0.46 | 0.18 | 0.19 | 0.24 | 0.04 | n.a. | n.a. |
| 7 | 4 | 5 | 65.99 | 1.04 | 0.48 | 0.2 | 0.19 | 0.24 | 0.04 | n.a. | n.a. |
| 8 | 0 | n.a | 66.57 | 0.86 | 0.55 | 0.22 | 0.28 | 0.13 | 0.05 | n.a. | n.a. |
| 8 | 0 | n.a | 67.08 | 0.86 | 0.53 | 0.23 | n.a. | 0.29 | 0.13 | 0.05 | n.a. |
| 8 | 0 | n.a | 67.1 | 0.86 | 0.55 | 0.24 | 0.28 | 0.12 | 0.04 | n.a. | n.a. |
| 8 | 4 | 5 | 65.79 | 0.9 | 0.61 | 0.24 | 0.35 | n.a. | 0.16 | 0.04 | n.a. |
| 8 | 4 | 5 | 65.87 | 0.92 | 0.61 | 0.23 | 0.34 | 0.16 | 0.04 | n.a. | n.a. |
| 8 | 4 | 5 | 65.85 | 0.88 | 0.62 | 0.24 | 0.35 | 0.16 | 0.05 | n.a. | n.a. |
| 9 | 0 | n.a | 66.81 | 0.86 | 0.54 | 0.22 | 0.28 | 0.12 | 0.04 | n.a. | n.a. |
| 9 | 0 | n.a | 67.1 | 0.87 | 0.51 | 0.22 | 0.27 | 0.11 | 0.04 | n.a. | n.a. |
| 9 | 0 | n.a | 66.56 | 0.86 | 0.5 | 0.2 | 0.26 | 0.11 | 0.04 | n.a. | n.a. |
| 9 | 4 | 5 | 67.97 | 0.9 | 0.56 | 0.22 | 0.3 | 0.13 | 0.04 | n.a. | n.a. |
| 9 | 4 | 5 | 67.24 | 0.89 | 0.55 | 0.21 | 0.29 | 0.13 | 0.04 | n.a. | n.a. |
| 9 | 4 | 5 | 67.88 | 0.88 | 0.54 | 0.21 | 0.27 | 0.12 | 0.03 | n.a. | n.a. |
| 10 | 0 | n.a | 66.98 | 0.92 | 0.5 | 0.21 | 0.22 | 0.12 | 0.02 | n.a. | n.a. |
| 10 | 0 | n.a | 67.11 | 0.88 | 0.49 | 0.2 | n.a. | 0.21 | 0.13 | 0.03 | n.a. |
| 10 | 0 | n.a | 67.13 | 0.9 | 0.49 | 0.2 | 0.22 | 0.13 | 0.03 | n.a. | n.a. |
| 10 | 4 | 5 | 67.76 | 0.96 | 0.52 | 0.21 | 0.25 | 0.17 | 0.03 | n.a. | n.a. |
| 10 | 4 | 5 | 67.21 | 0.96 | 0.46 | 0.17 | 0.23 | 0.16 | 0.03 | n.a. | n.a. |
| 10 | 4 | 5 | 67.6 | 0.94 | 0.52 | 0.2 | 0.23 | 0.18 | 0.04 | n.a. | n.a. |
| 11 | 0 | n.a | 66.36 | 0.96 | 0.49 | 0.18 | 0.2 | 0.17 | 0.04 | n.a. | n.a. |
| 11 | 0 | n.a | 66.31 | 0.95 | 0.49 | 0.19 | 0.18 | 0.17 | 0.04 | n.a. | n.a. |
| 11 | 0 | n.a | 65.58 | 0.95 | 0.47 | 0.17 | 0.19 | 0.17 | 0.04 | n.a. | n.a. |
| 11 | 4 | 5 | 67.64 | 1.07 | 0.5 | 0.21 | 0.21 | 0.25 | 0.04 | n.a. | n.a. |
| 11 | 4 | 5 | 66.92 | 1.04 | 0.47 | 0.19 | 0.16 | 0.25 | 0.04 | n.a. | n.a. |
| 11 | 4 | 5 | 66.2 | 1.05 | 0.52 | 0.21 | 0.21 | 0.25 | 0.05 | n.a. | n.a. |
| 12 | 0 | n.a | 67.3 | 0.86 | 0.49 | 0.18 | 0.16 | 0.12 | 0.05 | n.a. | n.a. |
| 12 | 0 | n.a | 67.28 | 0.86 | 0.52 | 0.23 | 0.23 | 0.12 | 0.05 | n.a. | n.a. |
| 12 | 0 | n.a | 66.63 | 0.86 | 0.5 | 0.21 | 0.21 | 0.12 | 0.05 | n.a. | n.a. |
| 12 | 4 | 5 | 67.75 | 0.92 | 0.54 | 0.22 | 0.23 | 0.17 | 0.06 | n.a. | n.a. |
| 12 | 4 | 5 | 68.73 | 0.92 | 0.52 | 0.22 | 0.24 | 0.18 | 0.06 | 0.01 | n.a. |
| 12 | 4 | 5 | 67.88 | 0.93 | 0.53 | 0.21 | 0.24 | 0.17 | 0.05 | n.a. | n.a. |

TABLE 29

Study 3 Reversed Phase Main peak purities by UV
(averages and standard deviations)

| Form. | Time (weeks) | Temp (° C.) | RP Main Peak (average) | RP Main Peak (st. dev.) | Difference between Main Peak T = 0 and T = 4 weeks 5° C. |
|---|---|---|---|---|---|
| 1 | 0 | 0 | 96.28 | 0.11 | |
| 2 | 0 | 0 | 96.32 | 0.07 | |
| 3 | 0 | 0 | 96.38 | 0.05 | |
| 4 | 0 | 0 | 96.29 | 0.1 | |
| 5 | 0 | 0 | 96.3 | 0.08 | |
| 6 | 0 | 0 | 96.22 | 0.04 | |
| 7 | 0 | 0 | 96.29 | 0.08 | |
| 8 | 0 | 0 | 95.98 | 0.02 | |
| 9 | 0 | 0 | 96.21 | 0.02 | |
| 10 | 0 | 0 | 96.15 | 0.02 | |
| 11 | 0 | 0 | 96.26 | 0.03 | |
| 12 | 0 | 0 | 96.34 | 0.12 | |
| 1 | 4 | 5 | 95.82 | 0.1 | 0.45 |
| 2 | 4 | 5 | 95.7 | 0.03 | 0.62 |
| 3 | 4 | 5 | 96.23 | 0.08 | 0.15 |
| 4 | 4 | 5 | 95.93 | 0.06 | 0.36 |
| 5 | 4 | 5 | 95.97 | 0.06 | 0.33 |
| 6 | 4 | 5 | 95.79 | 0.1 | 0.43 |
| 7 | 4 | 5 | 95.82 | 0.03 | 0.48 |
| 8 | 4 | 5 | 95.5 | 0.03 | 0.48 |
| 9 | 4 | 5 | 96.06 | 0.03 | 0.15 |
| 10 | 4 | 5 | 96.17 | 0.11 | −0.02 |
| 11 | 4 | 5 | 95.9 | 0.08 | 0.35 |
| 12 | 4 | 5 | 96.03 | 0.04 | 0.31 |

The RP-HPLC measurements discussed above are made with UV detection. The RP-HPLC method is also run using fluorescence detection in an effort to provide greater selectivity for peptide over other non-proteinaceous material. A summary of the RP-HPLC results using fluorescence detection is provided in Tables 30 and 31. A comparison of the initial main peak purities and those after storage at 5° C. are shown in Table 32. In general, the trends seen with UV detection are similar to those observed when using RP-HPLC with fluorescence detection. Losses are <0.5% and the rank ordering of the best formulations is the same.

TABLE 30

Study 3 Reversed Phase data for T = 0 and T = 4 weeks 5° C. stability samples by Fluorescence (Formulations 1-6)

| Form. | Time (Weeks) | Temp (° C.) | Group Area (mAU * min) | Relative Area (%) | | | | | | |
|---|---|---|---|---|---|---|---|---|---|---|
| | | | | Pre Peak 1 | Pre Peak 2 | Pre Peak 3 | Pre Peak 4 | Pre Peak 5 | Pre Peak 6 | Main Peak |
| 1 | 0 | n.a | 3884226 | 0.07 | n.a. | 0.72 | 0.10 | 0.09 | 0.29 | 97.47 |
| 1 | 0 | n.a | 3839474 | 0.08 | n.a. | 0.72 | 0.10 | 0.10 | 0.29 | 97.46 |
| 1 | 0 | n.a | 3851069 | 0.07 | n.a. | 0.72 | 0.08 | 0.09 | 0.28 | 97.52 |
| 1 | 4 | 5 | 3839738 | 0.05 | n.a. | 0.87 | 0.08 | 0.09 | 0.28 | 97.35 |
| 1 | 4 | 5 | 3842238 | 0.05 | n.a. | 0.88 | 0.08 | 0.09 | 0.28 | 97.32 |
| 1 | 4 | 5 | 3858041 | 0.07 | n.a. | 0.88 | 0.08 | 0.10 | 0.28 | 97.27 |
| 2 | 0 | n.a | 3865758 | 0.08 | n.a. | 0.84 | 0.10 | 0.10 | 0.28 | 97.46 |
| 2 | 0 | n.a | 3856409 | 0.08 | n.a. | 0.85 | 0.09 | 0.10 | 0.26 | 97.57 |
| 2 | 0 | n.a | 3848934 | 0.07 | n.a. | 0.84 | 0.08 | 0.09 | 0.25 | 97.52 |
| 2 | 4 | 5 | 3883874 | 0.05 | n.a. | 0.96 | 0.09 | 0.08 | 0.29 | 97.31 |
| 2 | 4 | 5 | 3900452 | 0.06 | n.a. | 1.08 | n.a. | 0.09 | 0.32 | 97.24 |
| 2 | 4 | 5 | 3879846 | 0.06 | n.a. | 0.99 | 0.11 | 0.10 | 0.25 | 97.30 |
| 3 | 0 | n.a | 3782297 | 0.05 | n.a. | 0.78 | n.a. | 0.15 | 0.27 | 97.73 |
| 3 | 0 | n.a | 3793028 | 0.06 | n.a. | 0.79 | 0.17 | n.a. | 0.24 | 97.68 |
| 3 | 0 | n.a | 3778492 | 0.05 | n.a. | 0.79 | 0.08 | 0.08 | 0.26 | 97.62 |
| 3 | 4 | 5 | 3869226 | 0.05 | n.a. | 0.79 | 0.07 | 0.07 | 0.25 | 97.6 |
| 3 | 4 | 5 | 3875886 | 0.04 | n.a. | 0.80 | 0.08 | 0.08 | 0.3 | 97.51 |
| 3 | 4 | 5 | 3808153 | 0.04 | n.a. | 0.82 | 0.09 | 0.08 | 0.24 | 97.56 |
| 4 | 0 | n.a | 3716387 | 0.06 | n.a. | 0.89 | 0.10 | 0.09 | 0.26 | 97.52 |
| 4 | 0 | n.a | 3679296 | 0.07 | n.a. | 0.88 | 0.09 | 0.08 | 0.27 | 97.48 |
| 4 | 0 | n.a | 3729358 | 0.07 | n.a. | 0.90 | 0.12 | 0.10 | 0.3 | 97.38 |
| 4 | 4 | 5 | 3789340 | 0.09 | n.a. | 0.89 | 0.18 | n.a. | 0.26 | 97.37 |
| 4 | 4 | 5 | 3812742 | 0.08 | n.a. | 0.89 | 0.08 | 0.09 | 0.22 | 97.50 |
| 4 | 4 | 5 | 3754728 | 0.08 | n.a. | 1.11 | n.a. | n.a. | 0.32 | 97.27 |
| 5 | 0 | n.a | 3687263 | 0.08 | n.a. | 0.87 | 0.08 | 0.08 | 0.29 | 97.51 |
| 5 | 0 | n.a | 3662400 | 0.09 | n.a. | 0.87 | 0.08 | 0.09 | 0.24 | 97.57 |
| 5 | 0 | n.a | 3656062 | 0.07 | n.a. | 0.89 | 0.1 | 0.11 | 0.24 | 97.51 |
| 5 | 4 | 5 | 3727410 | 0.07 | n.a. | 0.88 | 0.1 | 0.10 | 0.26 | 97.34 |
| 5 | 4 | 5 | 3736986 | 0.08 | n.a. | 0.89 | 0.1 | 0.10 | 0.27 | 97.30 |
| 5 | 4 | 5 | 3731604 | 0.07 | n.a. | 0.9 | 0.12 | 0.11 | 0.27 | 97.31 |
| 6 | 0 | n.a | 3928269 | 0.07 | n.a. | 0.91 | 0.1 | 0.09 | 0.29 | 97.39 |
| 6 | 0 | n.a | 3904708 | 0.06 | n.a. | 0.90 | 0.09 | 0.10 | 0.29 | 97.42 |
| 6 | 0 | n.a | 3908659 | 0.07 | n.a. | 0.92 | 0.12 | 0.09 | 0.22 | 97.43 |
| 6 | 4 | 5 | 3884715 | 0.05 | 0.01 | 1.03 | 0.13 | 0.11 | 0.26 | 97.16 |
| 6 | 4 | 5 | 3871088 | 0.08 | 0.01 | 1.01 | 0.10 | 0.10 | 0.28 | 97.18 |
| 6 | 4 | 5 | 3856166 | 0.08 | 0.04 | 1.04 | 0.14 | 0.10 | 0.30 | 97.02 |

| Form. | Time (Weeks) | Temp (° C.) | Group Area (mAU * min) | Relative Area (%) | | | | | | | |
|---|---|---|---|---|---|---|---|---|---|---|---|
| | | | | Post Peak 1 | Post Peak 2 | Post Peak 3 | Post Peak 4 | Post Peak 5 | Post Peak 6 | Post Peak 7 | Post Peak 8 |
| 1 | 0 | n.a | 3884226 | n.a. | 0.53 | 0.2 | 0.26 | 0.17 | 0.1 | n.a. | n.a. |
| 1 | 0 | n.a | 3839474 | n.a. | 0.52 | 0.21 | 0.24 | 0.18 | 0.11 | n.a. | n.a. |
| 1 | 0 | n.a | 3851069 | n.a. | 0.52 | 0.2 | 0.24 | 0.18 | 0.1 | n.a. | n.a. |
| 1 | 4 | 5 | 3839738 | n.a. | 0.54 | 0.18 | 0.23 | 0.26 | 0.03 | 0.04 | n.a. |
| 1 | 4 | 5 | 3842238 | n.a | 0.54 | 0.19 | 0.23 | 0.26 | 0.03 | 0.04 | n.a. |
| 1 | 4 | 5 | 3858041 | n.a. | 0.54 | 0.19 | 0.25 | 0.27 | 0.04 | 0.04 | n.a. |
| 2 | 0 | n.a | 3865758 | n.a. | 0.54 | 0.19 | 0.2 | 0.16 | 0.05 | n.a. | n.a. |
| 2 | 0 | n.a | 3856409 | n.a. | 0.51 | 0.18 | 0.18 | 0.16 | 0.03 | n.a. | n.a. |
| 2 | 0 | n.a | 3848934 | n.a. | 0.53 | 0.19 | 0.2 | 0.16 | 0.05 | n.a. | n.a. |
| 2 | 4 | 5 | 3883874 | n.a. | 0.53 | 0.19 | 0.2 | 0.26 | 0.04 | n.a. | n.a. |
| 2 | 4 | 5 | 3900452 | n.a. | 0.53 | 0.19 | 0.2 | 0.26 | 0.04 | n.a. | n.a. |
| 2 | 4 | 5 | 3879846 | n.a. | 0.54 | 0.18 | 0.19 | 0.26 | 0.04 | n.a. | n.a. |
| 3 | 0 | n.a | 3782297 | n.a. | 0.49 | 0.19 | 0.18 | 0.14 | 0.03 | n.a. | n.a. |
| 3 | 0 | n.a | 3793028 | n.a. | 0.5 | 0.18 | 0.19 | 0.15 | 0.04 | n.a. | n.a. |
| 3 | 0 | n.a | 3778492 | n.a. | 0.51 | 0.19 | 0.19 | 0.16 | 0.05 | n.a. | n.a. |
| 3 | 4 | 5 | 3869226 | n.a. | 0.52 | 0.2 | 0.19 | 0.24 | 0.04 | n.a. | n.a. |
| 3 | 4 | 5 | 3875886 | n.a. | 0.52 | 0.19 | 0.2 | 0.24 | 0.04 | n.a. | n.a. |
| 3 | 4 | 5 | 3808153 | n.a. | 0.51 | 0.19 | 0.19 | 0.24 | 0.04 | n.a. | n.a. |
| 4 | 0 | n.a | 3716387 | n.a. | 0.5 | 0.18 | 0.23 | 0.14 | 0.04 | n.a. | n.a. |
| 4 | 0 | n.a | 3679296 | n.a. | 0.52 | 0.18 | 0.23 | 0.14 | 0.04 | n.a. | n.a. |
| 4 | 0 | n.a | 3729358 | n.a. | 0.51 | 0.2 | 0.22 | 0.15 | 0.04 | n.a. | n.a. |
| 4 | 4 | 5 | 3789340 | n.a. | 0.52 | 0.19 | 0.25 | 0.21 | 0.04 | n.a. | n.a. |
| 4 | 4 | 5 | 3812742 | n.a. | 0.5 | 0.18 | 0.24 | 0.2 | 0.03 | n.a. | n.a. |
| 4 | 4 | 5 | 3754728 | n.a. | 0.52 | 0.18 | 0.26 | 0.22 | 0.05 | n.a. | n.a. |
| 5 | 0 | n.a | 3687263 | n.a. | 0.51 | 0.18 | 0.23 | 0.14 | 0.04 | n.a. | n.a. |
| 5 | 0 | n.a | 3662400 | n.a. | 0.5 | 0.18 | n.a. | 0.39 | n.a. | n.a. | n.a. |
| 5 | 0 | n.a | 3656062 | n.a. | 0.5 | 0.18 | 0.23 | 0.13 | 0.03 | n.a. | n.a. |
| 5 | 4 | 5 | 3727410 | n.a. | 0.52 | 0.19 | 0.3 | 0.19 | 0.05 | n.a. | n.a. |

TABLE 30-continued

Study 3 Reversed Phase data for T = 0 and T = 4 weeks 5° C. stability samples by Fluorescence (Formulations 1-6)

| | | | | | | | | | | |
|---|---|---|---|---|---|---|---|---|---|---|
| 5 | 4 | 5 | 3736986 | n.a. | 0.53 | 0.19 | 0.3 | 0.2 | 0.05 | n.a. | n.a. |
| 5 | 4 | 5 | 3731604 | n.a. | 0.52 | 0.19 | 0.3 | 0.18 | 0.04 | n.a. | n.a. |
| 6 | 0 | n.a | 3928269 | n.a. | 0.52 | 0.21 | 0.22 | 0.14 | 0.05 | n.a. | n.a. |
| 6 | 0 | n.a | 3904708 | n.a. | 0.53 | 0.19 | 0.23 | 0.13 | 0.05 | n.a. | n.a. |
| 6 | 0 | n.a | 3908659 | n.a. | 0.52 | 0.2 | 0.23 | 0.14 | 0.06 | n.a. | n.a. |
| 6 | 4 | 5 | 3884715 | n.a. | 0.53 | 0.22 | 0.25 | 0.21 | 0.05 | n.a. | n.a. |
| 6 | 4 | 5 | 3871088 | n.a. | 0.53 | 0.21 | 0.24 | 0.2 | 0.06 | n.a. | n.a. |
| 6 | 4 | 5 | 3856166 | n.a. | 0.55 | 0.22 | 0.25 | 0.2 | 0.06 | n.a. | n.a. |

TABLE 31

Study 3 Reversed Phase data for T = 0 and T = 4 weeks 5° C. stability samples by fluorescence (Formulations 7-12)

| | | | Group Area | Relative Area (%) | | | | | | |
|---|---|---|---|---|---|---|---|---|---|---|
| Form. | Time (Weeks) | Temp (° C.) | (mAU * min) | Pre Peak 1 | Pre Peak 2 | Pre Peak 3 | Pre Peak 4 | Pre Peak 5 | Pre Peak 6 | Main Peak |
| 7 | 0 | n.a | 3810144 | 0.07 | n.a | 0.91 | 0.09 | 0.08 | 0.25 | 97.54 |
| 7 | 0 | n.a | 3788215 | 0.06 | n.a. | 0.92 | 0.08 | 0.08 | 0.26 | 97.54 |
| 7 | 0 | n.a | 3757021 | 0.07 | n.a. | 0.93 | 0.1 | 0.08 | 0.26 | 97.5 |
| 7 | 4 | 5 | 3816004 | 0.09 | n.a. | 0.99 | 0.11 | 0.1 | 0.21 | 97.3 |
| 7 | 4 | 5 | 3821086 | 0.08 | n.a. | 0.98 | 0.1 | 0.09 | 0.25 | 97.31 |
| 7 | 4 | 5 | 3819894 | 0.09 | n.a. | 0.99 | 0.12 | 0.1 | 0.23 | 97.29 |
| 8 | 0 | n.a. | 3856379 | 0.07 | n.a. | 0.91 | 0.09 | 0.08 | 0.31 | 97.34 |
| 8 | 0 | n.a. | 3884040 | 0.06 | n.a. | 0.93 | 0.12 | 0.1 | 0.29 | 97.31 |
| 8 | 0 | n.a. | 3882168 | 0.06 | n.a. | 0.92 | 0.1 | 0.09 | 0.28 | 97.36 |
| 8 | 4 | 5 | 3808470 | 0.06 | 0.02 | 1.04 | 0.13 | 0.13 | 0.23 | 96.96 |
| 8 | 4 | 5 | 3806669 | 0.06 | 0.03 | 1.05 | 0.15 | 0.13 | 0.21 | 96.94 |
| 8 | 4 | 5 | 3806957 | 0.07 | 0.04 | 1.06 | 0.15 | 0.15 | 0.21 | 96.91 |
| 9 | 0 | n.a. | 3861333 | 0.08 | n.a. | 0.84 | 0.11 | 0.09 | 0.31 | 97.43 |
| 9 | 0 | n.a. | 3878517 | 0.08 | n.a. | 0.84 | 0.1 | 0.1 | 0.22 | 97.5 |
| 9 | 0 | n.a. | 3850061 | 0.08 | n.a. | 0.82 | 0.08 | 0.08 | 0.21 | 97.55 |
| 9 | 4 | 5 | 3931894 | n.a. | 0.02 | 0.87 | 0.13 | 0.13 | 0.27 | 97.27 |
| 9 | 4 | 5 | 3891097 | 0.07 | n.a. | 0.86 | 0.11 | 0.12 | 0.27 | 97.26 |
| 9 | 4 | 5 | 3926952 | 0.08 | n.a. | 0.85 | 0.08 | 0.12 | 0.27 | 97.32 |
| 10 | 0 | n.a. | 3881305 | 0.08 | n.a. | 0.85 | 0.11 | 0.26 | 0.27 | 97.31 |
| 10 | 0 | n.a. | 3894723 | 0.08 | n.a. | 0.85 | 0.11 | 0.26 | 0.32 | 97.25 |
| 10 | 0 | n.a. | 3887086 | 0.09 | n.a. | 0.85 | 0.1 | 0.25 | 0.3 | 97.33 |
| 10 | 4 | 5 | 3926320 | 0.08 | n.a. | 0.85 | 0.11 | 0.1 | 0.25 | 97.42 |
| 10 | 4 | 5 | 3898984 | 0.08 | n.a. | 0.85 | 0.11 | 0.11 | 0.17 | 97.46 |
| 10 | 4 | 5 | 3911548 | 0.08 | n.a. | 0.86 | 0.11 | 0.1 | 0.25 | 97.43 |
| 11 | 0 | n.a. | 3837247 | 0.07 | 0.03 | 0.81 | 0.11 | 0.09 | 0.3 | 97.47 |
| 11 | 0 | n.a. | 3836853 | 0.06 | 0.03 | 0.81 | 0.11 | 0.09 | 0.29 | 97.49 |
| 11 | 0 | n.a. | 3795451 | 0.06 | 0.04 | 0.83 | 0.13 | 0.1 | 0.3 | 97.4 |
| 11 | 4 | 5 | 3898130 | 0.06 | 0.04 | 0.83 | 0.12 | 0.1 | 0.24 | 97.4 |
| 11 | 4 | 5 | 3865153 | 0.09 | 0.05 | 0.83 | 0.13 | 0.1 | 0.28 | 97.3 |
| 11 | 4 | 5 | 3822333 | 0.09 | 0.07 | 0.84 | 0.14 | 0.1 | 0.26 | 97.28 |
| 12 | 0 | n.a. | 3902683 | 0.09 | n.a. | 0.81 | 0.09 | 0.09 | 0.2 | 97.65 |
| 12 | 0 | n.a. | 3889096 | 0.09 | n.a. | 0.83 | 0.1 | 0.1 | 0.19 | 97.59 |
| 12 | 0 | n.a. | 3862319 | 0.07 | n.a. | 0.81 | 0.1 | 0.1 | 0.23 | 97.57 |
| 12 | 4 | 5 | 3921165 | 0.06 | 0.02 | 0.85 | 0.1 | 0.1 | 0.21 | 97.48 |
| 12 | 4 | 5 | 3969631 | 0.07 | 0.02 | 0.85 | 0.1 | 0.1 | 0.21 | 97.49 |
| 12 | 4 | 5 | 3922001 | 0.08 | 0.02 | 0.85 | 0.1 | 0.1 | 0.22 | 97.46 |

| | | | Group Area | Relative Area (%) | | | | | | |
|---|---|---|---|---|---|---|---|---|---|---|
| Form. | Time (Weeks) | Temp (° C.) | (mAU * min) | Post Peak 1 | Post Peak 2 | Post Peak 3 | Post Peak 4 | Post Peak 5 | Post Peak 6 | Post Peak 7 | Post Peak 8 |
| 7 | 0 | n.a | 3810144 | n.a. | 0.52 | 0.18 | 0.18 | 0.16 | 0.03 | n.a. | n.a. |
| 7 | 0 | n.a | 3788215 | n.a. | 0.5 | 0.19 | 0.18 | 0.15 | 0.03 | n.a. | n.a. |
| 7 | 0 | n.a | 3757021 | n.a. | 0.51 | 0.19 | 0.17 | 0.16 | 0.03 | n.a. | n.a. |
| 7 | 4 | 5 | 3816004 | n.a. | 0.52 | 0.18 | 0.2 | 0.24 | 0.04 | n.a. | n.a. |
| 7 | 4 | 5 | 3821086 | n.a. | 0.52 | 0.18 | 0.19 | 0.25 | 0.04 | n.a. | n.a. |
| 7 | 4 | 5 | 3819894 | n.a. | 0.52 | 0.18 | 0.2 | 0.24 | 0.04 | n.a. | n.a. |
| 8 | 0 | n.a. | 3856379 | n.a. | 0.54 | 0.2 | 0.28 | 0.13 | 0.05 | n.a. | n.a. |
| 8 | 0 | n.a. | 3884040 | n.a. | 0.54 | 0.2 | 0.29 | 0.13 | 0.04 | n.a. | n.a. |
| 8 | 0 | n.a. | 3882168 | n.a. | 0.55 | 0.19 | 0.27 | n.a. | 0.13 | 0.04 | n.a. |
| 8 | 4 | 5 | 3808470 | n.a. | 0.61 | 0.22 | 0.37 | 0.17 | 0.05 | n.a. | n.a. |
| 8 | 4 | 5 | 3806669 | n.a. | 0.62 | 0.23 | 0.35 | 0.18 | 0.05 | n.a. | n.a. |

TABLE 31-continued

Study 3 Reversed Phase data for T = 0 and T = 4 weeks 5° C. stability samples by fluorescence (Formulations 7-12)

| 8  | 4 | 5   | 3806957 | n.a. | 0.61 | 0.23 | 0.36 | 0.18 | 0.05 | n.a. | n.a. |
|----|---|-----|---------|------|------|------|------|------|------|------|------|
| 9  | 0 | n.a | 3861333 | n.a. | 0.51 | 0.2  | 0.27 | 0.11 | n.a. | 0.04 | n.a. |
| 9  | 0 | n.a | 3878517 | n.a. | 0.53 | 0.19 | 0.27 | 0.12 | 0.05 | n.a. | n.a. |
| 9  | 0 | n.a | 3850061 | n.a. | 0.53 | 0.19 | 0.28 | 0.12 | 0.05 | n.a. | n.a. |
| 9  | 4 | 5   | 3931894 | n.a. | 0.57 | 0.22 | 0.32 | 0.14 | 0.05 | n.a. | n.a. |
| 9  | 4 | 5   | 3891097 | n.a. | 0.57 | 0.22 | 0.32 | 0.14 | 0.05 | n.a. | n.a. |
| 9  | 4 | 5   | 3926952 | n.a. | 0.56 | 0.22 | 0.32 | 0.14 | 0.05 | n.a. | n.a. |
| 10 | 0 | n.a | 3881305 | n.a. | 0.5  | 0.2  | 0.23 | 0.14 | 0.04 | n.a. | n.a. |
| 10 | 0 | n.a | 3894723 | n.a. | 0.52 | 0.19 | 0.23 | 0.14 | 0.04 | n.a. | n.a. |
| 10 | 0 | n.a | 3887086 | n.a. | 0.51 | 0.19 | 0.22 | 0.14 | 0.03 | n.a. | n.a. |
| 10 | 4 | 5   | 3926320 | n.a. | 0.51 | 0.2  | 0.26 | 0.18 | 0.04 | n.a. | n.a. |
| 10 | 4 | 5   | 3898984 | n.a. | 0.52 | 0.2  | 0.27 | 0.19 | 0.04 | n.a. | n.a. |
| 10 | 4 | 5   | 3911548 | n.a. | 0.51 | 0.2  | 0.26 | 0.18 | 0.04 | n.a. | n.a. |
| 11 | 0 | n.a | 3837247 | n.a. | 0.52 | 0.19 | 0.19 | 0.18 | 0.04 | n.a. | n.a. |
| 11 | 0 | n.a | 3836853 | n.a. | 0.51 | 0.19 | 0.19 | 0.17 | 0.05 | n.a. | n.a. |
| 11 | 0 | n.a | 3795451 | n.a. | 0.52 | 0.2  | 0.2  | 0.17 | 0.05 | n.a. | n.a. |
| 11 | 4 | 5   | 3898130 | n.a. | 0.52 | 0.19 | 0.2  | 0.25 | 0.05 | n.a. | n.a  |
| 11 | 4 | 5   | 3865153 | n.a. | 0.53 | 0.19 | 0.2  | 0.26 | 0.05 | n.a. | n.a. |
| 11 | 4 | 5   | 3822333 | n.a. | 0.54 | 0.18 | 0.2  | 0.25 | 0.05 | n.a. | n.a. |
| 12 | 0 | n.a | 3902683 | n.a. | 0.51 | 0.19 | 0.2  | 0.12 | 0.04 | n.a. | n.a. |
| 12 | 0 | n.a | 3889096 | n.a. | 0.54 | 0.19 | 0.2  | 0.12 | 0.04 | n.a. | n.a  |
| 12 | 0 | n.a | 3862319 | n.a. | 0.51 | 0.21 | 0.22 | 0.13 | 0.05 | n.a. | n.a. |
| 12 | 4 | 5   | 3921165 | n.a. | 0.51 | 0.21 | 0.23 | 0.18 | 0.04 | n.a. | n.a. |
| 12 | 4 | 5   | 3969631 | n.a. | 0.52 | 0.2  | 0.22 | 0.18 | 0.04 | n.a. | n.a. |
| 12 | 4 | 5   | 3922001 | n.a. | 0.53 | 0.19 | 0.23 | 0.17 | 0.04 | n.a. | n.a. |

TABLE 32

Study 3 Reversed Phase Main peak purities by fluorescence (averages and standard deviations)

| Form. | Time (weeks) | Temp (° C.) | RP Main Peak (average) | RP Main Peak (st. dev.) | Difference between Main Peak T = 0 and T = 4 weeks 5° C. |
|-------|--------------|-------------|------------------------|-------------------------|----------------------------------------------------------|
| 1  | 0 | 0 | 97.48 | 0.03 |       |
| 2  | 0 | 0 | 97.52 | 0.06 |       |
| 3  | 0 | 0 | 97.68 | 0.06 |       |
| 4  | 0 | 0 | 97.46 | 0.07 |       |
| 5  | 0 | 0 | 97.53 | 0.03 |       |
| 6  | 0 | 0 | 97.41 | 0.02 |       |
| 7  | 0 | 0 | 97.53 | 0.02 |       |
| 8  | 0 | 0 | 97.34 | 0.03 |       |
| 9  | 0 | 0 | 97.49 | 0.06 |       |
| 10 | 0 | 0 | 97.3  | 0.04 |       |
| 11 | 0 | 0 | 97.45 | 0.05 |       |
| 12 | 0 | 0 | 97.6  | 0.04 |       |
| 1  | 4 | 5 | 97.31 | 0.04 | 0.17  |
| 2  | 4 | 5 | 97.28 | 0.04 | 0.23  |
| 3  | 4 | 5 | 97.56 | 0.05 | 0.12  |
| 4  | 4 | 5 | 97.38 | 0.12 | 0.08  |
| 5  | 4 | 5 | 97.32 | 0.02 | 0.21  |
| 6  | 4 | 5 | 97.12 | 0.09 | 0.29  |
| 7  | 4 | 5 | 97.3  | 0.01 | 0.23  |
| 8  | 4 | 5 | 96.94 | 0.03 | 0.4   |
| 9  | 4 | 5 | 97.28 | 0.03 | 0.21  |
| 10 | 4 | 5 | 97.44 | 0.02 | −0.14 |
| 11 | 4 | 5 | 97.33 | 0.06 | 0.13  |
| 12 | 4 | 5 | 97.48 | 0.02 | 0.13  |

Figure 27:
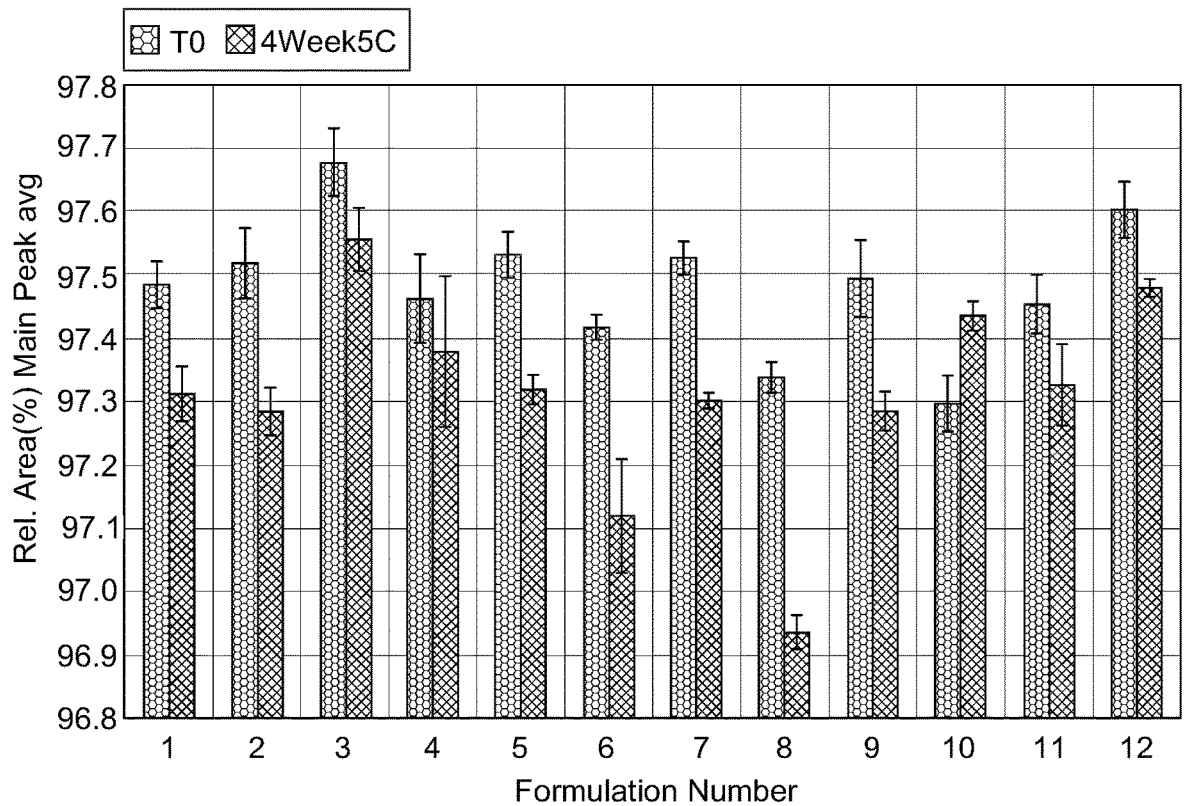
FIG. 27 depicts the relative areas of the main peak for samples from Study 3, as measured by RP-HPLC with fluorescence detection.
Figure 28:
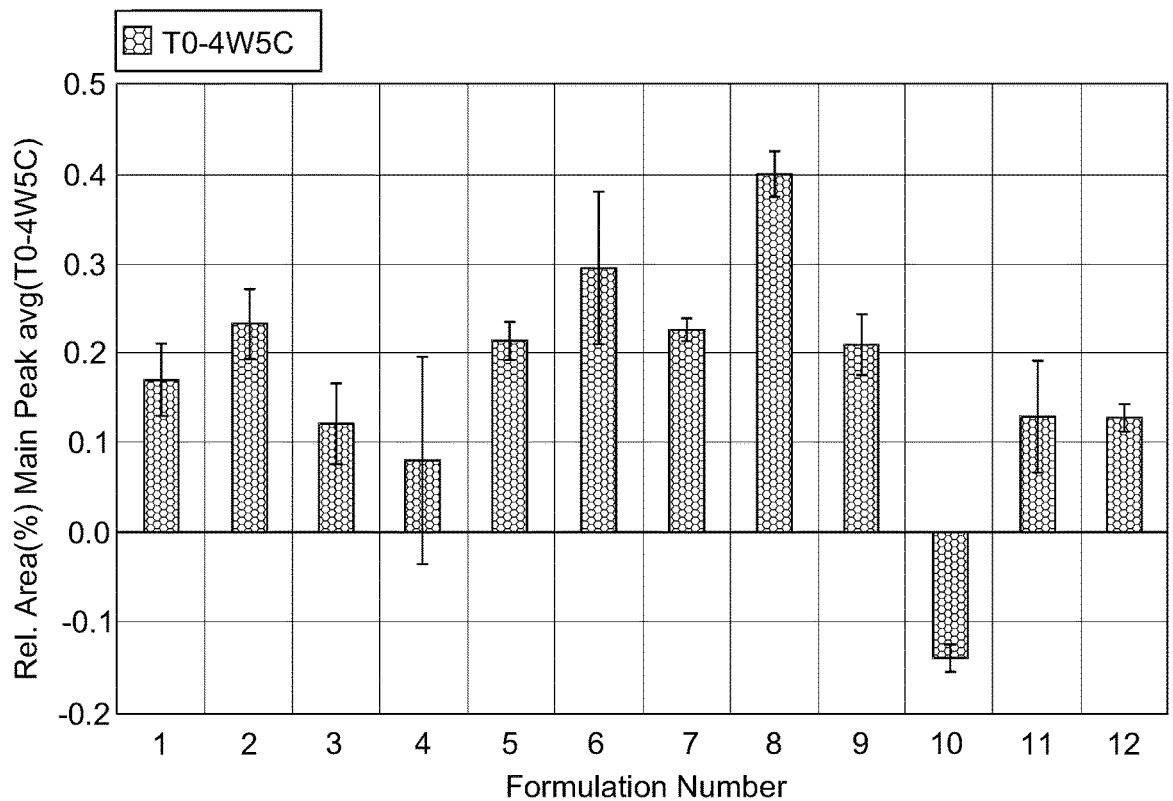
FIG. 28 depicts the differences main peak relative area (between T=0 and T=4 weeks at 5° C.) for each formulation evaluated in Study 3, as measured by RP-HPLC with fluorescence detection.
Figure 29:
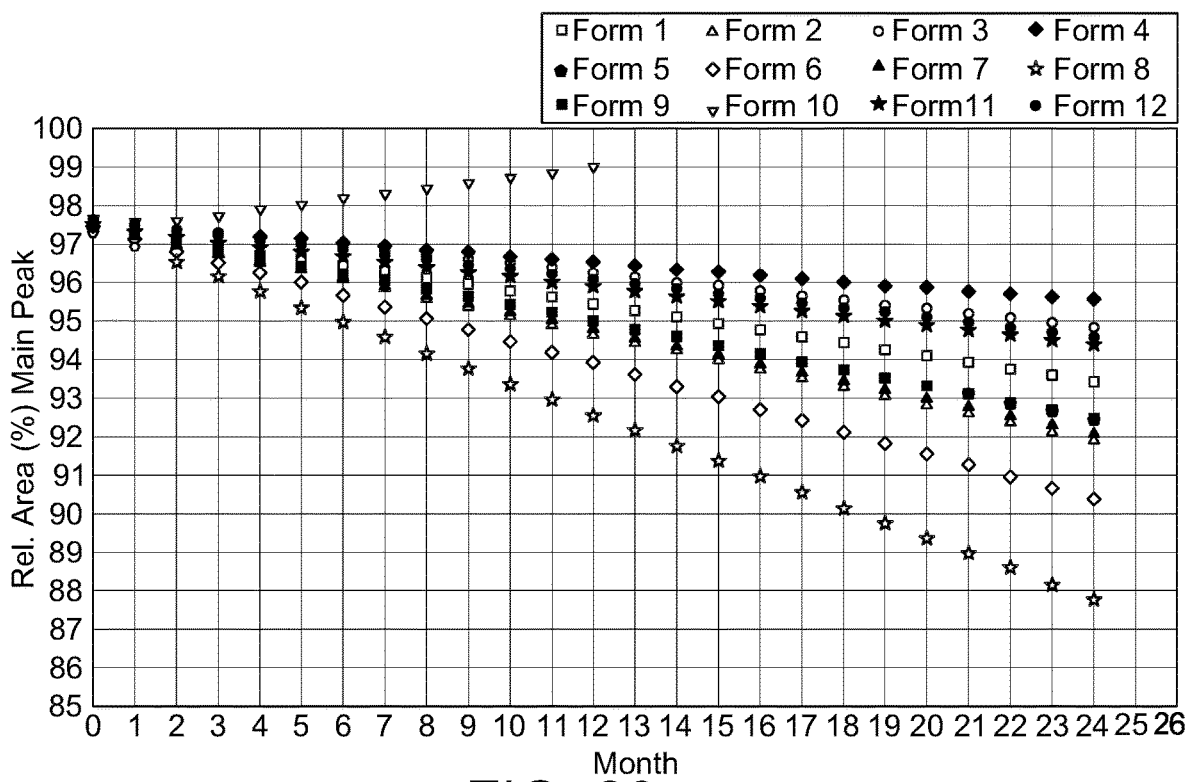
FIG. 29 depicts the extrapolated losses of main peak relative area (between T=0 and T=4 weeks at 5° C.) for each formulation evaluated in Study 3, as measured by RP-HPLC with fluorescence detection.

The relative areas of the RP-HPLC main peaks remains near 97% even after storage at 5° C. for four weeks (FIG. 27 and FIG. 28). When extrapolated to 24 months, most of the main peak purities remains above 93% (FIG. 29).

Study 3 Result: Refine Optimal pH and Buffer Concentration for MANP by SEC

Figure 30:
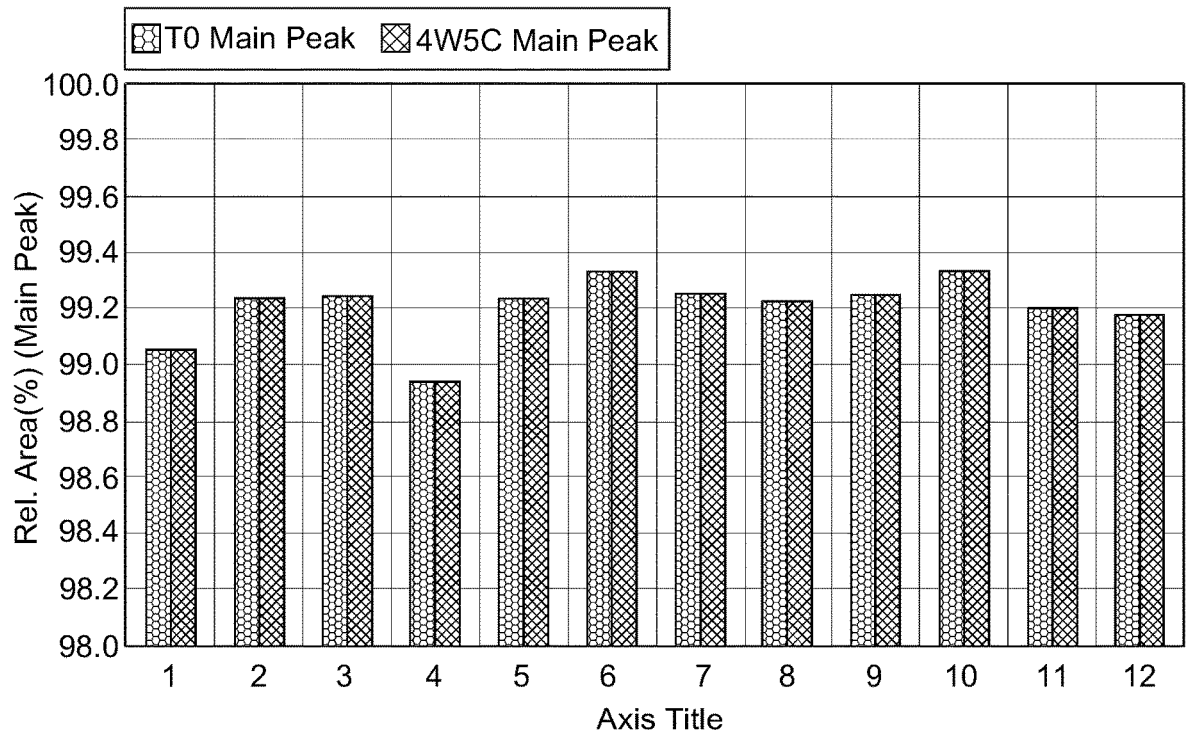
FIG. 30 depicts the relative areas of the main peak for T=0 and T=4 weeks at 5° C. samples from Study 3, as measured by SEC.

The same stability samples in Study 3 are analyzed using SEC. There is virtually no change in monomer content over the course of four weeks of storage at 5 C (Table 33, FIG. 30). There is almost no measurable loss of peptide due to aggregate formation as determined by SEC. The primary degradation pathways appear to be chemical in nature, so subsequent focus is on the chemical stability of MANP, as determined using RP-HPLC.

TABLE 33

Study 3 SEC data for T = 0 and T = 4 weeks 5° C. stability samples

| Form. | Time (Weeks) | Temp (° C.) | Group Area (mAU * min) | Rel. Area (%) Pre Peak 1 | Rel. Area (%) Pre Peak 2 | Rel. Area (%) Pre Shoulder | Rel. Area (%) Main Peak | Rel. Area (%) Post Peak 1 | Rel. Area (%) Post Peak 2 | Rel. Area (%) Post Peak 3 |
|-------|--------------|-------------|------------------------|--------------------------|--------------------------|-----------------------------|-------------------------|---------------------------|---------------------------|---------------------------|
| 1 | 0 | 0 | 101.31 | 0.00 | 0.06 | 0.08 | 99.09 | 0.63 | 0.1  | 0.04 |
| 2 | 0 | 0 | 101.74 | 0.00 | 0.06 | 0.08 | 99.23 | 0.51 | 0.08 | 0.04 |

TABLE 33-continued

Study 3 SEC data for T = 0 and T = 4 weeks 5° C. stability samples

| Form. | Time (Weeks) | Temp (° C.) | Group Area (mAU * min) | Rel. Area (%) Pre Peak 1 | Rel. Area (%) Pre Peak 2 | Rel. Area (%) Pre Shoulder | Rel. Area (%) Main Peak | Rel. Area (%) Post Peak 1 | Rel. Area (%) Post Peak 2 | Rel. Area (%) Post Peak 3 |
|---|---|---|---|---|---|---|---|---|---|---|
| 3 | 0 | 0 | 99.45 | 0.00 | 0.07 | 0.00 | 99.24 | 0.51 | 0.12 | 0.06 |
| 4 | 0 | 0 | 98.84 | 0.00 | 0.08 | 0.00 | 98.97 | 0.71 | 0.14 | 0.11 |
| 5 | 0 | 0 | 98.94 | 0.00 | 0.07 | 0.00 | 99.34 | 0.45 | 0.07 | 0.06 |
| 6 | 0 | 0 | 102.77 | 0.00 | 0.06 | 0.14 | 99.31 | 0.42 | 0.04 | 0.02 |
| 7 | 0 | 0 | 99.63 | 0.00 | 0.08 | 0.00 | 99.24 | 0.52 | 0.11 | 0.06 |
| 8 | 0 | 0 | 103.4 | 0.01 | 0.10 | 0.17 | 99.2 | 0.45 | 0.05 | 0.02 |
| 9 | 0 | 0 | 102.56 | 0.00 | 0.05 | 0.09 | 99.26 | 0.46 | 0.08 | 0.05 |
| 10 | 0 | 0 | 102.12 | 0.00 | 0.07 | 0.06 | 99.3 | 0.46 | 0.07 | 0.04 |
| 11 | 0 | 0 | 101.54 | 0.00 | 0.14 | 0.00 | 99.26 | 0.43 | 0.12 | 0.05 |
| 12 | 0 | 0 | 102.8 | 0.00 | 0.11 | 0.15 | 99.21 | 0.40 | 0.08 | 0.04 |
| 1 | 4 | 5 | 97.70 | 0.00 | 0.06 | 0.08 | 99.06 | 0.65 | 0.10 | 0.05 |
| 2 | 4 | 5 | 102.26 | 0.00 | 0.04 | 0.08 | 99.24 | 0.52 | 0.07 | 0.04 |
| 3 | 4 | 5 | 101.26 | 0.02 | 0.07 | 0.00 | 99.24 | 0.51 | 0.12 | 0.06 |
| 4 | 4 | 5 | 100.91 | 0.00 | 0.08 | 0.00 | 98.94 | 0.72 | 0.14 | 0.11 |
| 5 | 4 | 5 | 101.46 | 0.00 | 0.08 | 0.01 | 99.23 | 0.49 | 0.09 | 0.1 |
| 6 | 4 | 5 | 102.43 | 0.00 | 0.04 | 0.15 | 99.33 | 0.42 | 0.04 | 0.02 |
| 7 | 4 | 5 | 101.83 | 0.00 | 0.08 | 0.00 | 99.25 | 0.51 | 0.1 | 0.06 |
| 8 | 4 | 5 | 100.49 | 0.00 | 0.07 | 0.18 | 99.22 | 0.45 | 0.05 | 0.03 |
| 9 | 4 | 5 | 102.82 | 0.00 | 0.06 | 0.10 | 99.25 | 0.46 | 0.09 | 0.05 |
| 10 | 4 | 5 | 103.00 | 0.00 | 0.06 | 0.05 | 99.33 | 0.45 | 0.07 | 0.04 |
| 11 | 4 | 5 | 101.55 | 0.02 | 0.17 | 0.00 | 99.2 | 0.45 | 0.12 | 0.05 |
| 12 | 4 | 5 | 104.051 | n.a. | 0.13 | 0.16 | 99.18 | 0.41 | 0.08 | 0.03 |

Figure 31:
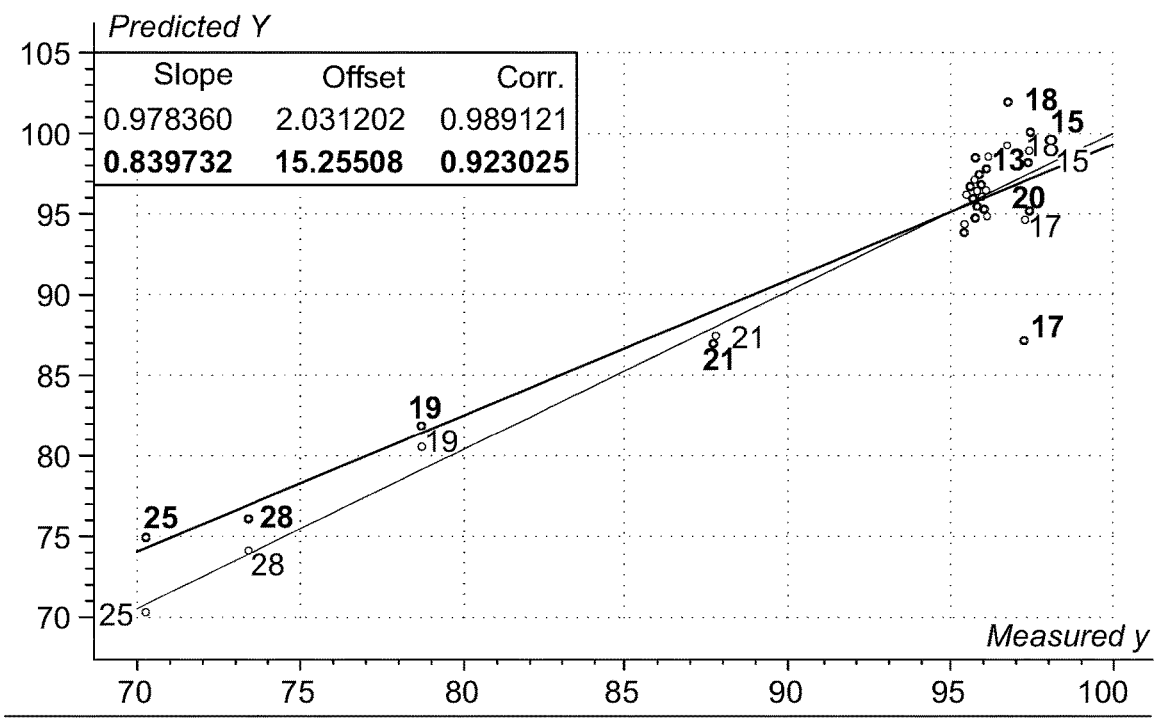
FIG. 31 depicts the predicted vs. measured values for the PLS model using RP-HPLC main peak purity of Study 2 and Study 3 samples after 4 weeks at 5° C. as the endpoint.
Figure 32:
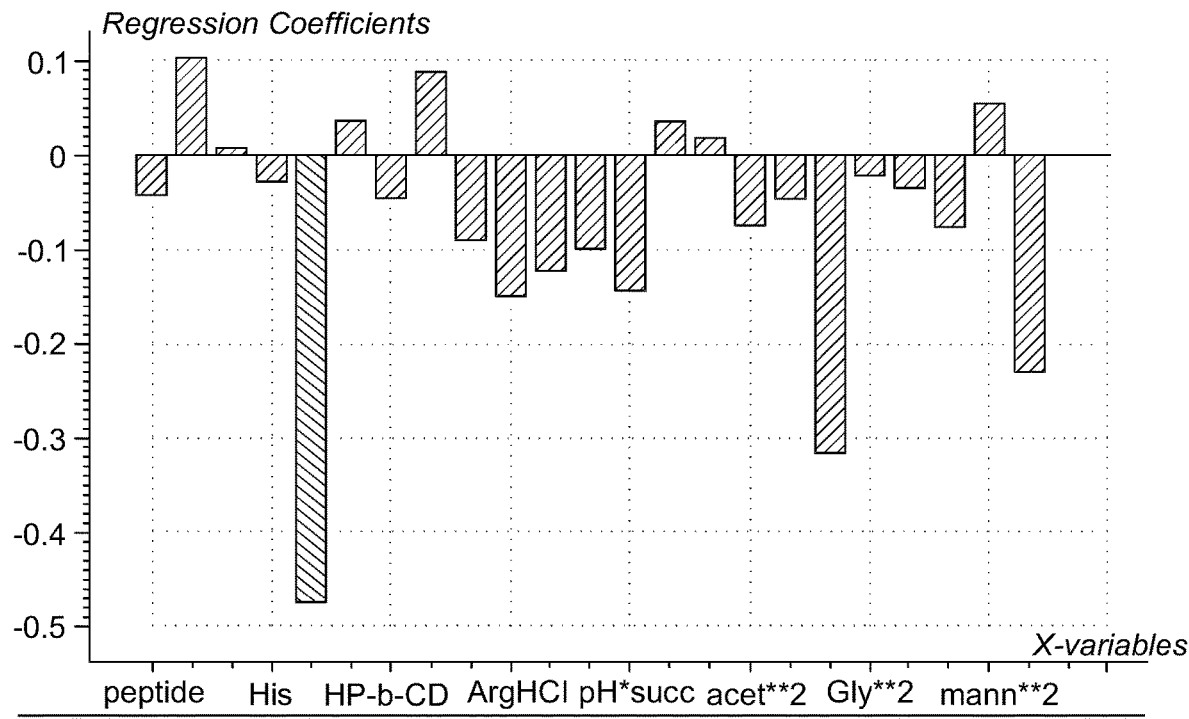
FIG. 32 depicts the regression coefficients for the PLS model using RP-HPLC main peak purity of Study 2 and Study 3 samples after 4 weeks at 5° C. as the endpoint.

As Studies 2 and 3 appear to provide a number of promising formulations, further mathematical analyses of the data are performed. Using a PLS approach, various models are constructed, as shown below. The first PLS model uses the main peak purity (relative area) after four weeks at 5° C. as the endpoint, drawing on results from both Studies 2 and 3 (28 total formulations). None of the formulations are determined to be outliers, with succinate calculated to be a significant factor. The predicted vs. measured values are shown in FIG. 31. Both the calibration and validation sets exhibit very high r-values (>0.92), indicating a PLS model of quite high quality. The regression coefficients are provided in FIG. 32, where the value of succinate is large and negative. A negative regression coefficient indicates that lower concentrations will yield higher levels of RPHPLC purity. In other words, succinate is deemed to be a significant destabilizer in this model.

Figure 33:
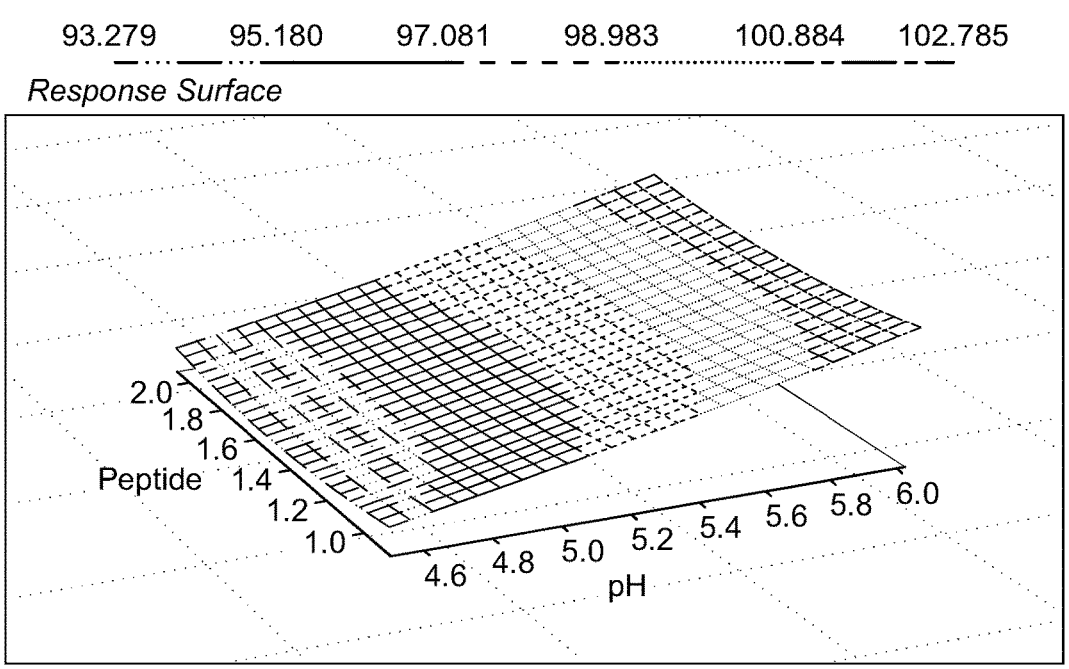
FIG. 33 depicts the effect of pH and peptide concentration according to the PLS model using RP-HPLC main peak purity of Study 2 and Study 3 samples after 4 weeks at 5° C. as the endpoint.

A response surface for the effect of pH and peptide concentration is shown in FIG. 33. Across the pH range used in these studies, the model predicts that there will be better chemical stability at higher pH values (say, near 6.0) compared to lower pH values near 4.5 to 5.0. The effect of peptide concentration is small, but the model indicates that stability at 2 mg/ml is comparable to that at lower peptide concentrations.

Figure 34:
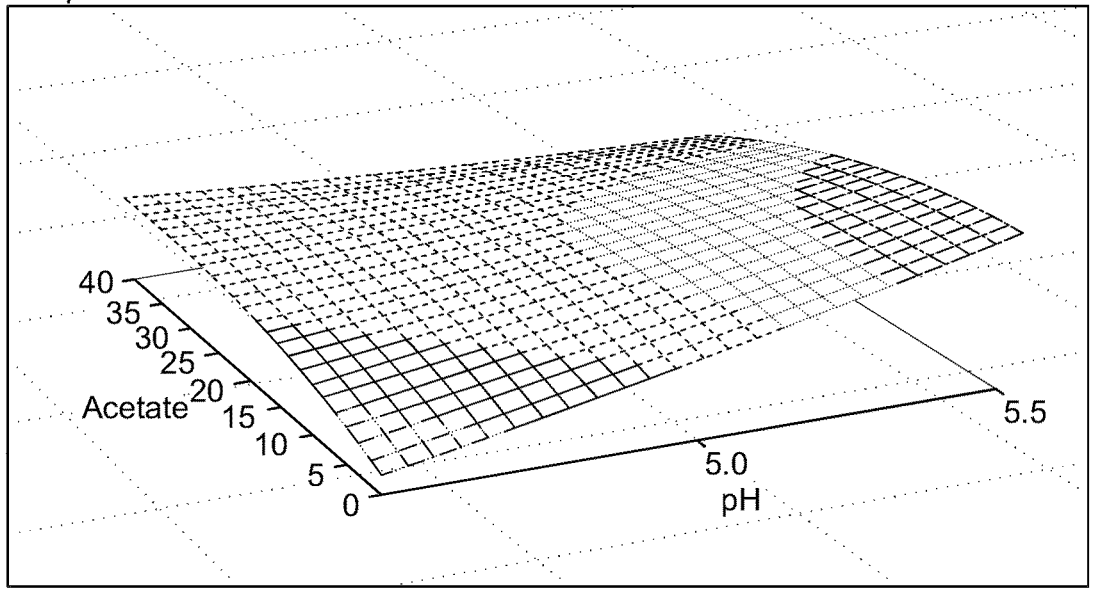
FIG. 34 depicts the effect of pH and acetate according to the PLS model using RP-HPLC main peak purity of Study 2 and Study 3 samples after 4 weeks at 5° C. as the endpoint. The peptide concentration was fixed at 2 mg/ml.
Figure 35:
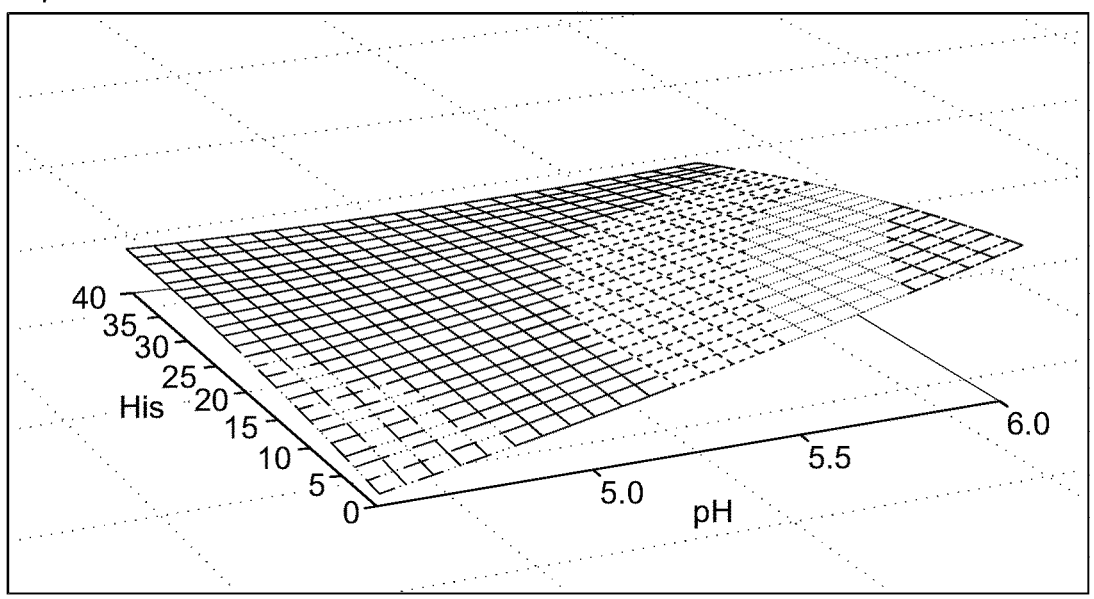
FIG. 35 depicts the effect of pH and Histidine according to the PLS model using RP-HPLC main peak purity of Study 2 and Study 3 samples after 4 weeks at 5° C. as the endpoint. The peptide concentration was fixed at 2 mg/ml.
Figure 36:
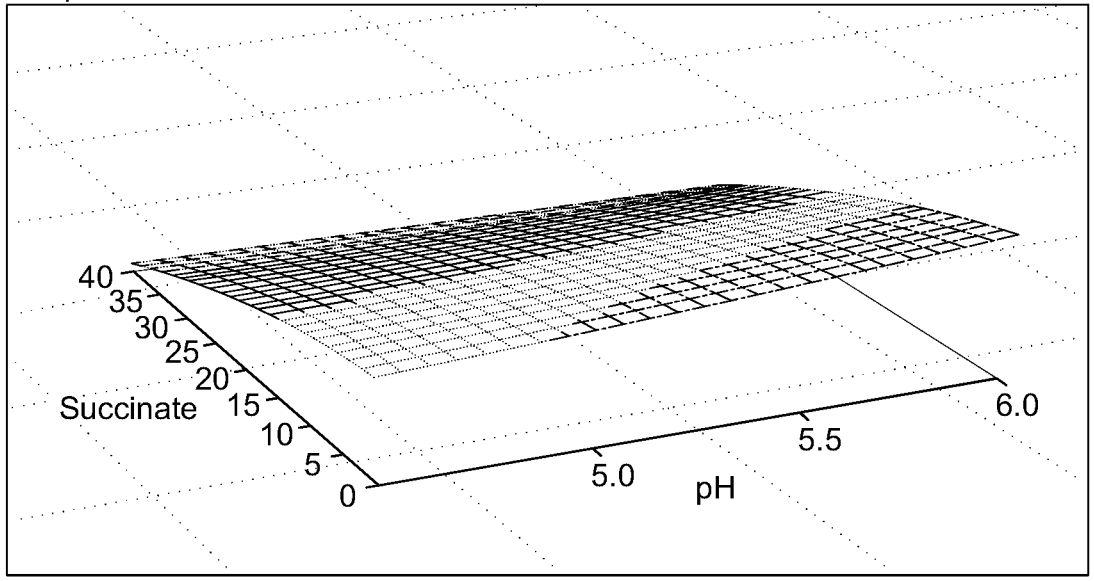
FIG. 36 depicts the effect of pH and succinate according to the PLS model using RP-HPLC main peak purity of Study 2 and Study 3 samples after 4 weeks at 5° C. as the endpoint. The peptide concentration was fixed at 2 mg/ml.

That response surface is generated in the absence of any buffer. If one examines the effect of pH in the presence of acetate (FIG. 34), the response is fairly complex. Note that these are quadratic models, which allows for non-linear responses as a function of concentration. In addition, pH buffer interactions terms are specifically included. As a result, the effect of acetate as a function of pH can and does vary. At lower pH values, acetate is predicted to be stabilizing, but has little, if any, benefit at higher pH values, where stability is greater. The trends for His buffer are similar to that for acetate (FIG. 35), but the magnitudes of the effects are smaller. The one buffer that is clearly and significantly detrimental is succinate (FIG. 36).

Figure 37:
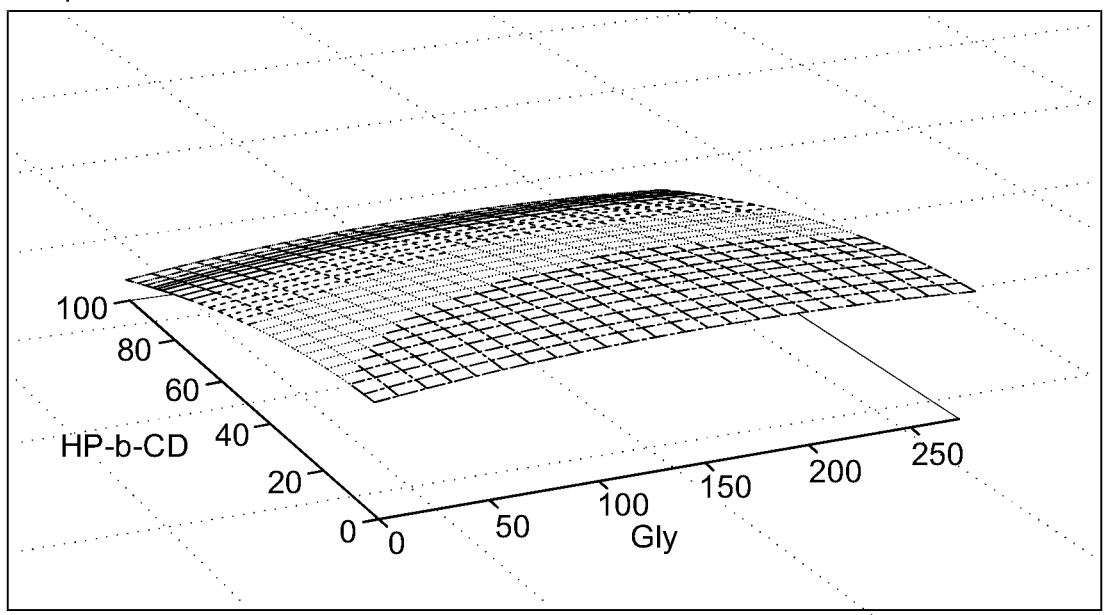
FIG. 37 depicts the effect of Glycine and HP-b-CD according to the PLS model using RP-HPLC main peak purity of Study 2 samples after 4 weeks at 5° C. as the endpoint. The peptide concentration was fixed at 2 mg/ml and the pH at 5.0.
Figure 38:
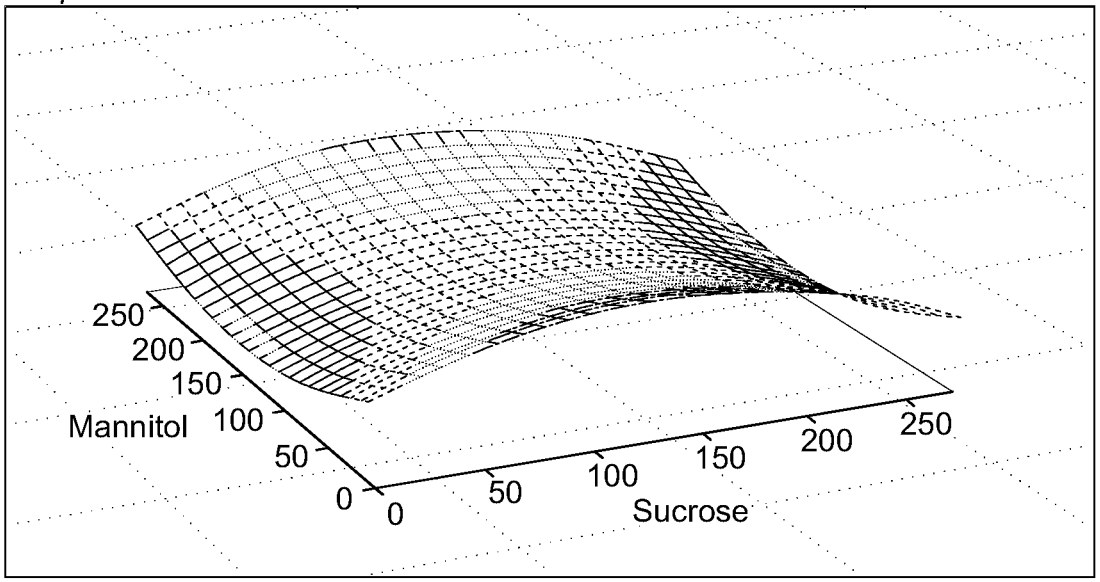
FIG. 38 depicts the effect of mannitol and sucrose according to the PLS model using RP-HPLC main peak purity of Study 2 samples after 4 weeks at 5° C. as the endpoint. The peptide concentration was fixed at 2 mg/ml and the pH at 5.0.
Figure 39:
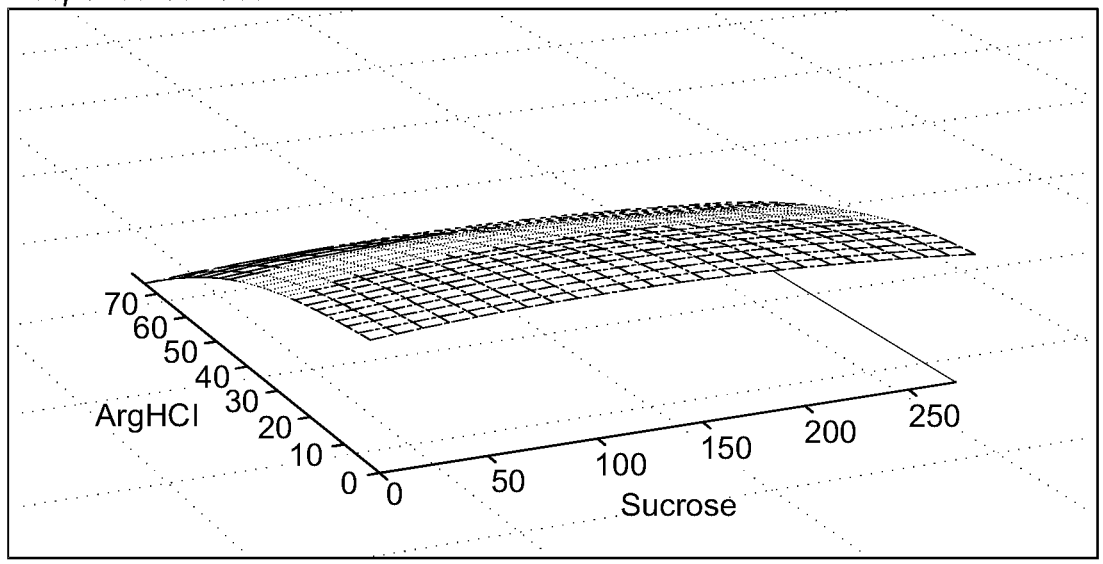
FIG. 39 depicts the effect of ArgHCl and sucrose according to the PLS model using RP-HPLC main peak purity of Study 2 samples after 4 weeks at 5° C. as the endpoint. The peptide concentration was fixed at 2 mg/ml and the pH at 5.0.

The model indicates that HP-b-CD trends towards lower stability, while the impact of Gly is almost zero (FIG. 37). The effects of mannitol and sucrose are predicted to be non-linear (FIG. 38), with maximal stability from sucrose being achieved near 100-200 mM. By comparison, the effect of ArgHCl is much greater, trending towards lower stability (FIG. 39). Given the clearly negative effects of ArgHCl and succinate, a new model is constructed where those formulations were removed, in order to identify the factors/excipients that were most favorable for stability.

Figure 40:
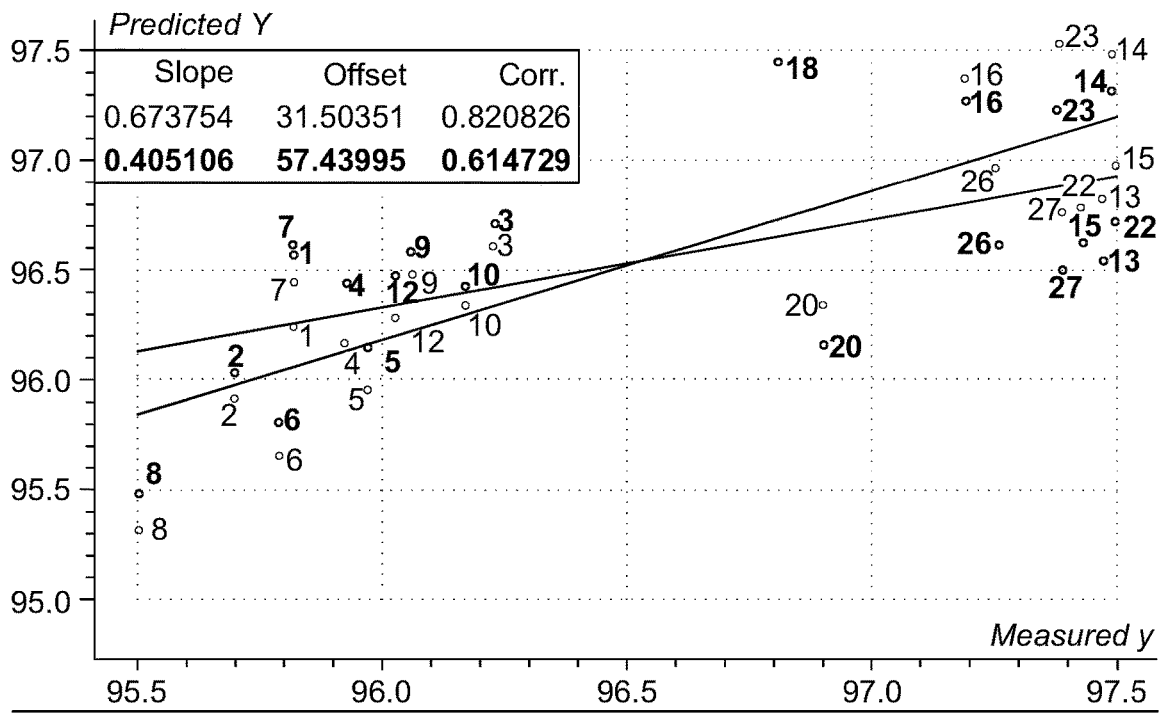
FIG. 40 depicts the predicted vs. measured values for the second PLS model using RP-HPLC main peak purity of Study 2 and Study 3 samples after 4 weeks at 5° C. as the endpoint.
Figure 41:
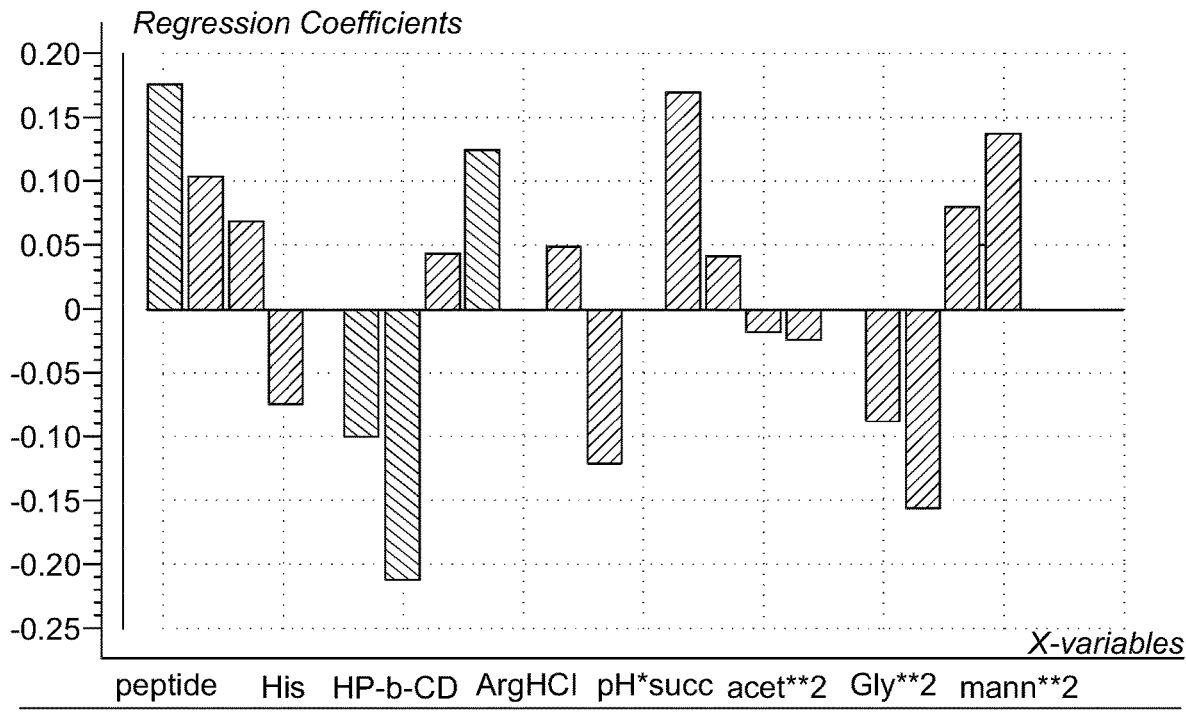
FIG. 41 depicts the regression coefficients for the second PLS model using RP-HPLC main peak purity of Study 2 and Study 3 samples after 4 weeks at 5° C. as the endpoint.

The next PLS model uses the same endpoint as the previous model (main peak purity by RP-HPLC after four weeks at 5° C.), but with formulations containing succinate and ArgHCl excluded from consideration. Two of the remaining formulations (Study 3, F11 and Study 2, F12) are determined to be outliers. In this new model, a number of factors (peptide concentration, Gly, HP-b-CD, and mannitol) are found to be significant. The predicted vs. measured values from the model are shown in FIG. 40. The model is somewhat noisier than the previous model, partly due to the smaller number of formulations included. The regression coefficients are summarized in a bar graph (FIG. 41). Significant factors are shown in blue hatched bars.

Figure 42:
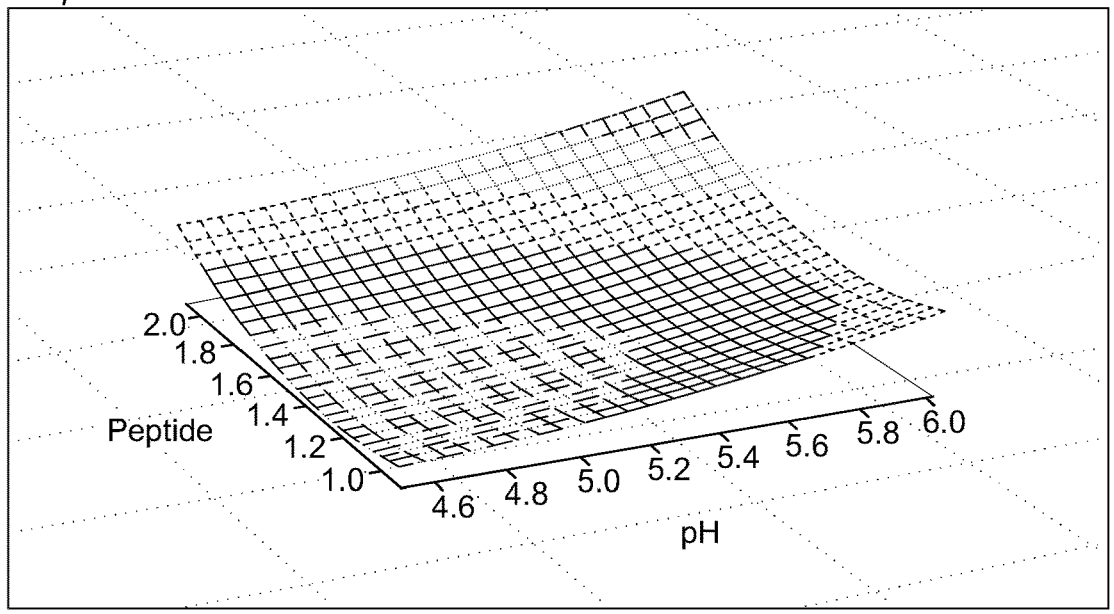
FIG. 42 depicts the effect of pH and peptide concentration according to the second PLS model using RP-HPLC main peak purity of Study 2 and Study 3 samples after 4 weeks at 5° C. as the endpoint.
Figure 43:
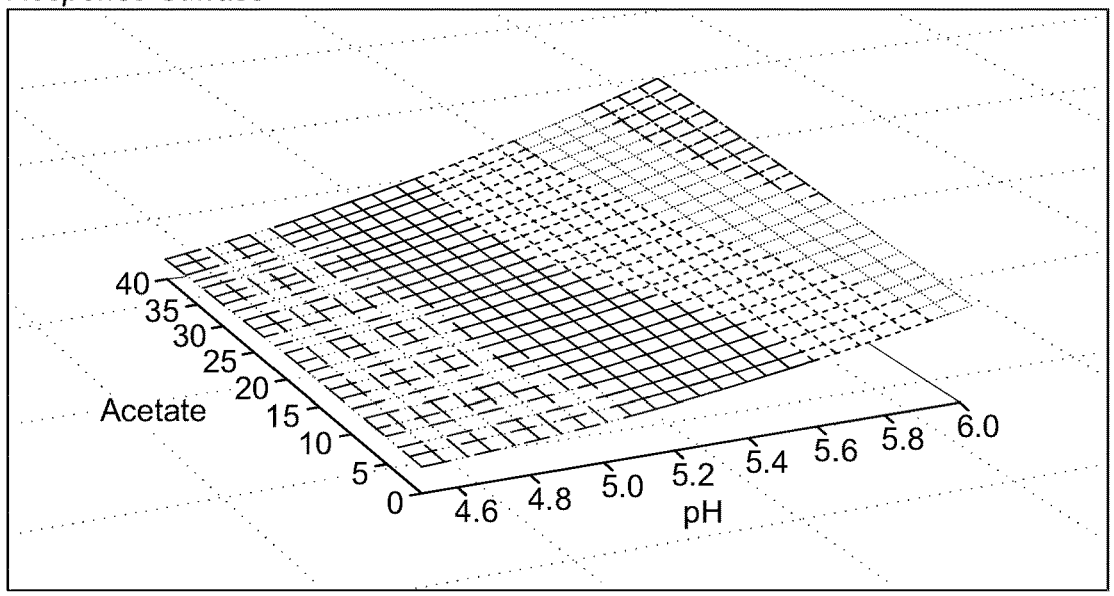
FIG. 43 depicts the effect of pH and acetate according to the second PLS model using RP-HPLC main peak purity of Study 2 and Study 3 samples after 4 weeks at 5° C. as the endpoint. The peptide concentration was fixed at 2 mg/ml.
Figure 44:
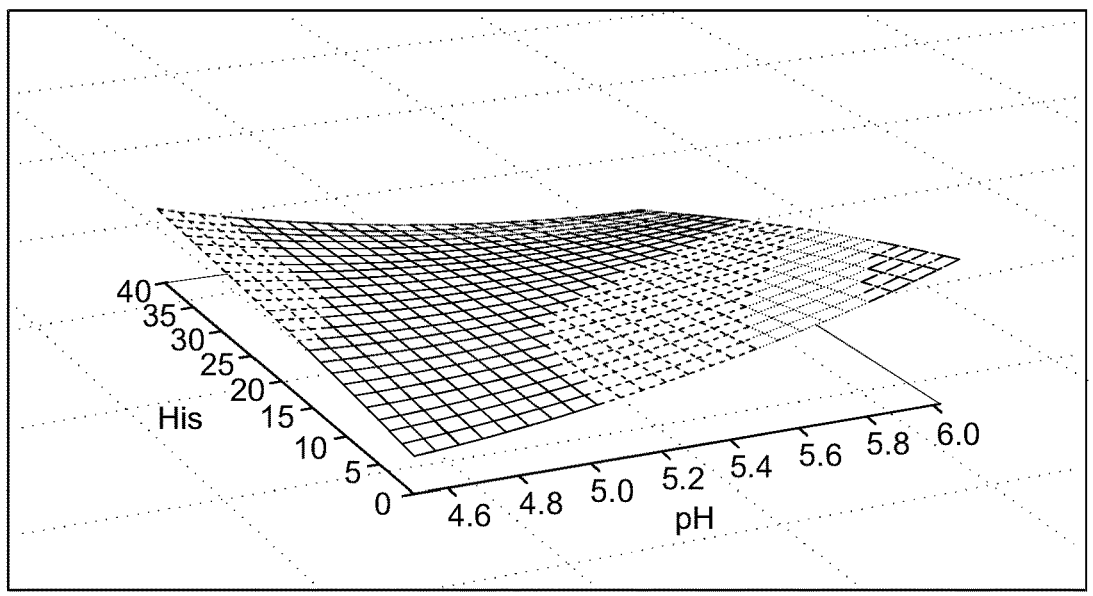
FIG. 44 depicts the effect of pH and Histidine according to the second PLS model using RP-HPLC main peak purity of Study 2 and Study 3 samples after 4 weeks at 5° C. as the endpoint. The peptide concentration was fixed at 2 mg/ml.

The effect of pH and peptide concentration from this second PLS model is shown in FIG. 42. The model indicates that a somewhat higher pH is beneficial, at least in the absence of a buffer. Meanwhile, greater stability is seen at higher peptide concentrations. For this reason, future studies tended to focus on formulations at 2 mg/ml. If the peptide concentration is fixed at 2 mg/ml, the effect of acetate and pH can be examined (FIG. 43). At the upper part of the pH range (approaching pH 6.0), acetate is predicted to be help stabilize MANP. On the contrary, the model indicates that His would be detrimental under the same conditions (FIG. 44). Thus, acetate appears to be preferred based on this analysis.

Figure 45:
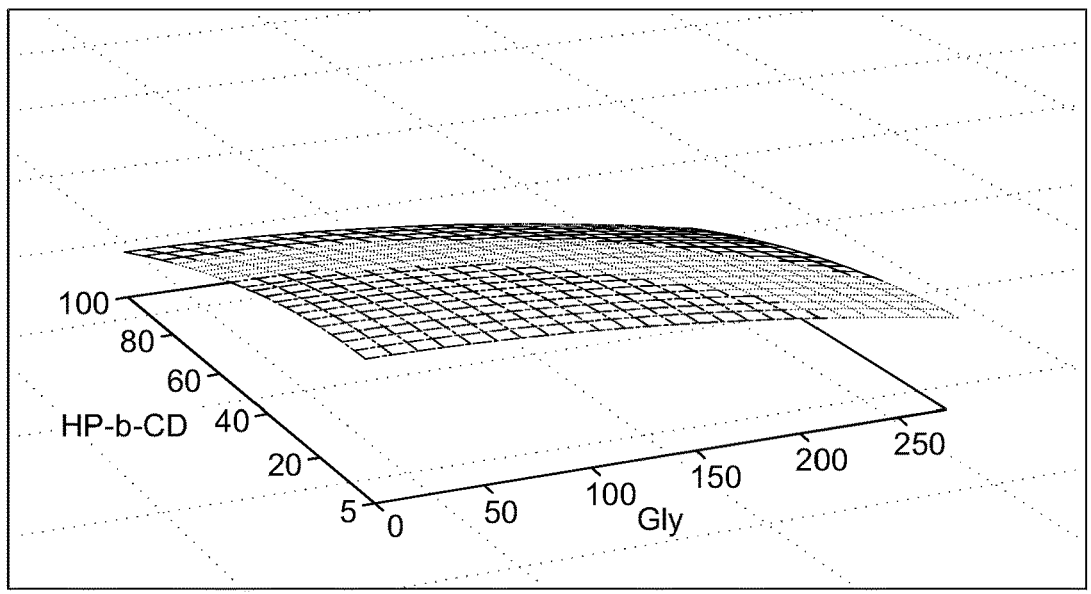
FIG. 45 depicts the effect of Glycine and HP-b-CD according to the second PLS model using RP-HPLC main peak purity of Study 2 samples after 4 weeks at 5° C. as the endpoint. The peptide concentration was fixed at 2 mg/ml and the pH at 6.0.
Figure 46:
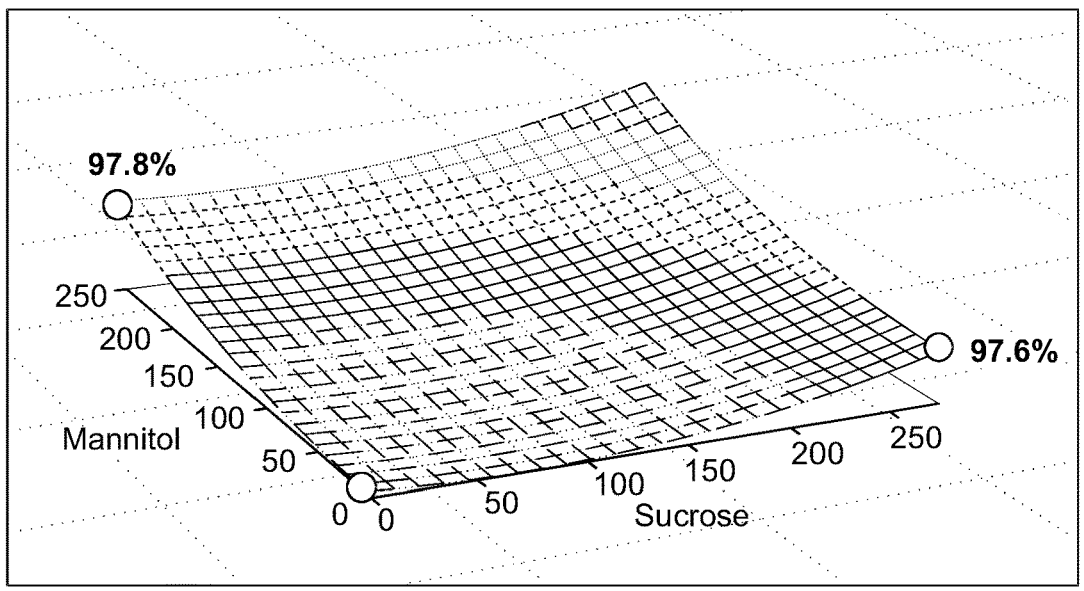
FIG. 46 depicts the effect of mannitol and sucrose according to the second PLS model using RP-HPLC main peak purity of Study 2 samples after 4 weeks at 5° C. as the endpoint. The peptide concentration was fixed at 2 mg/ml and the pH at 6.0.
Figure 47:
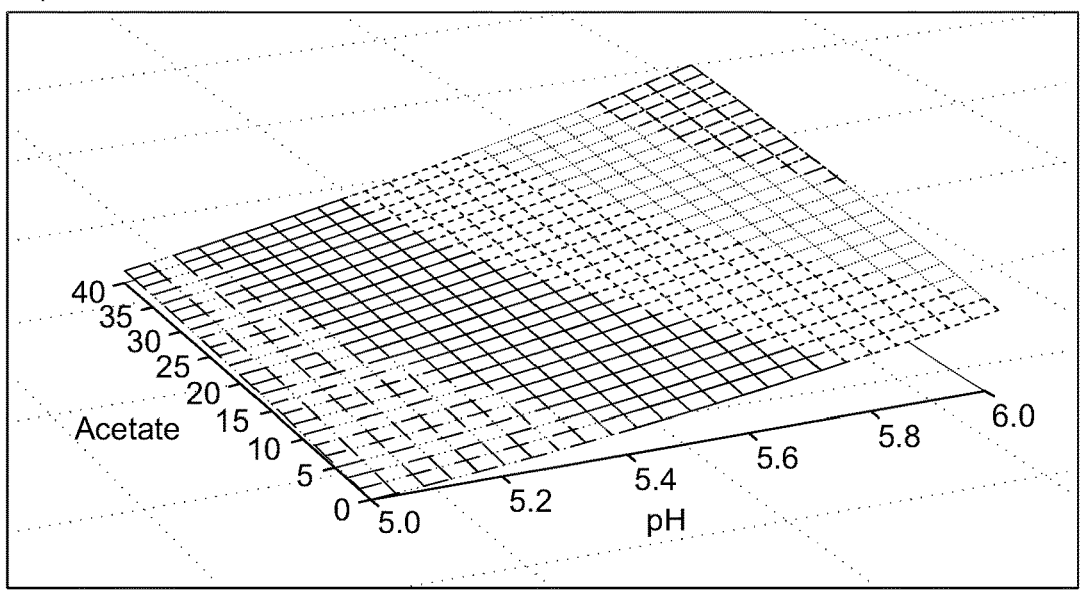
FIG. 47 depicts the effect of pH and acetate according to the second PLS model using RP-HPLC main peak purity of Study 2 and Study 3 samples after 4 weeks at 5° C. as the endpoint. The peptide concentration was fixed at 2 mg/ml and sucrose at 250 mM.

The model predicts that both HP-b-CD and Gly will reduce chemical stability upon storage (FIG. 45). Conversely, mannitol and sucrose are both shown to provide some degree of stabilization (FIG. 46). In order to provide some degree of quantitation to the model prediction, the chemical purity in the absence of the excipients is shown to be 97.3% (as noted by the circle in the lower left-hand corner). In the presence of 250 mM sucrose, the purity upon storage rises to 97.6%. However, addition of mannitol appears to be slightly more helpful, increasing the storage stability to 97.8% at the same concentration. Given that mannitol and sucrose appear to be stabilizing to some degree, the effect of acetate and pH are replotted where 250 mM sucrose was included (FIG. 47). The response surface indicates that even in the presence of a stabilizer like sucrose, acetate will improve the stability, if used at pH 6.0 and at maximal concentration (40 mM).

Study 3 Result: Refine Optimal pH and Buffer Concentration for MANP by RP-HPLC

Figure 48:
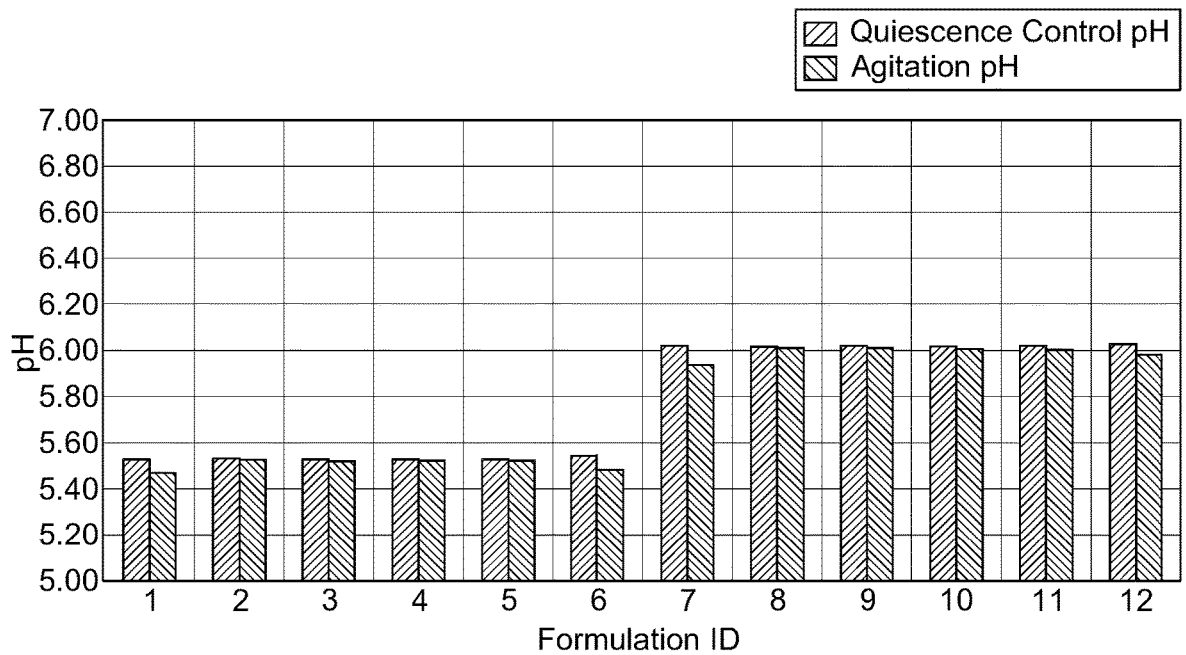
FIG. 48 depicts the pH values for Study 4 samples with and without agitation.
Figure 49:
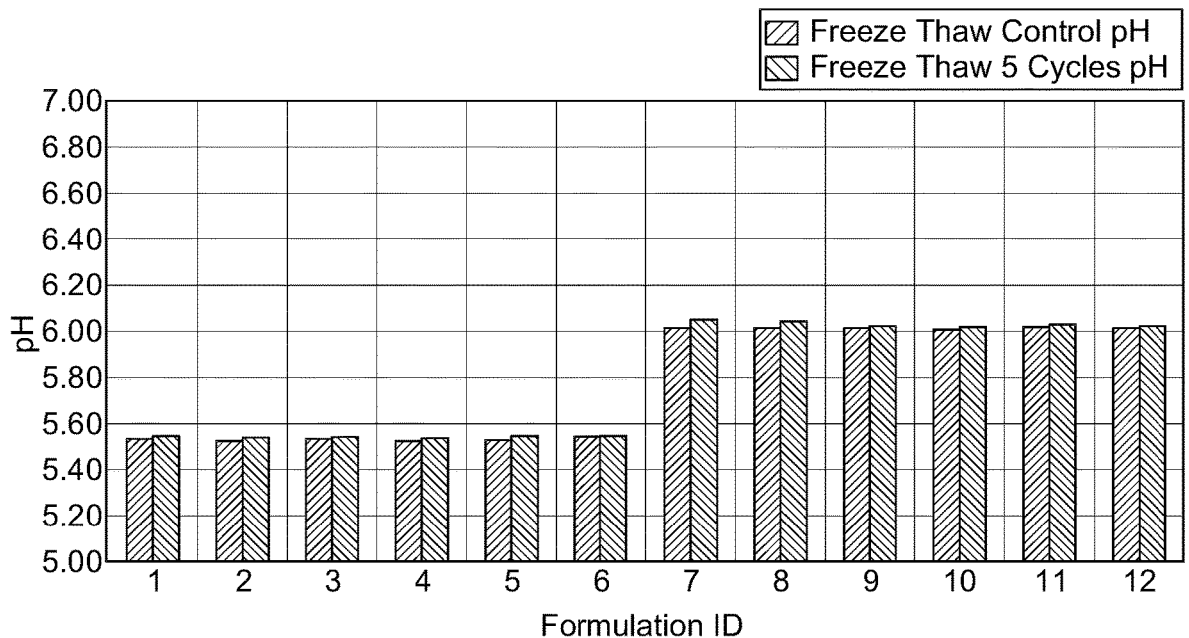
FIG. 49 depicts the pH values for Study 4 samples with and without freeze-thaw stress.
Figure 50:
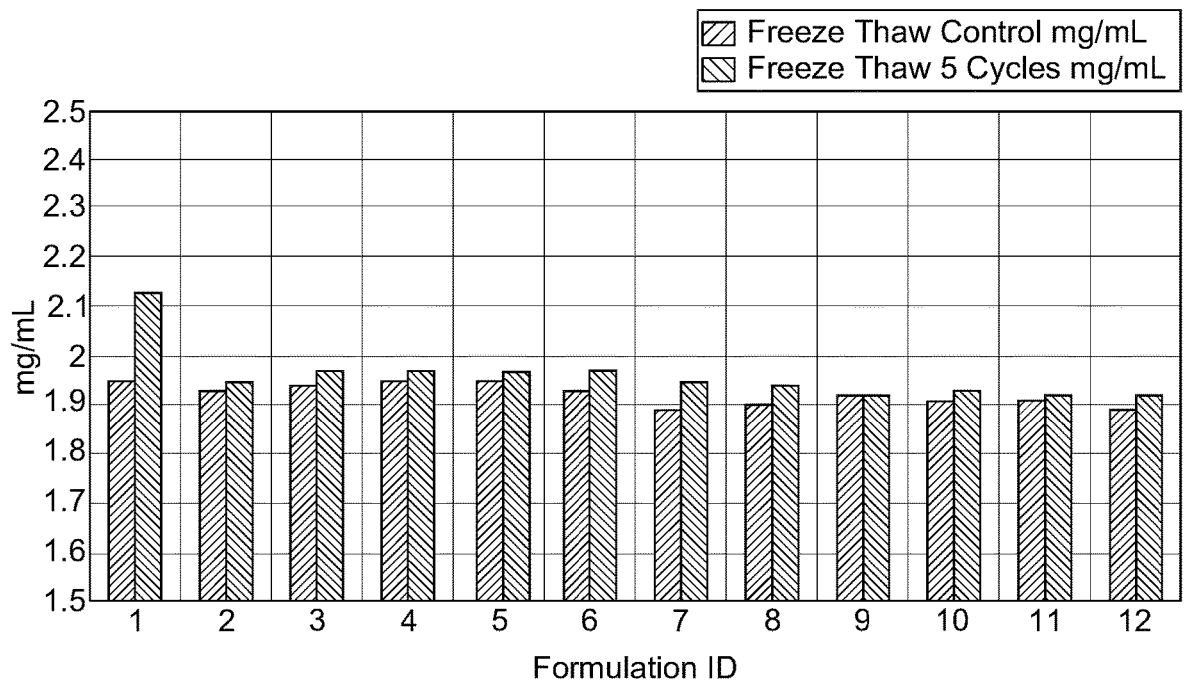
FIG. 50 depicts the peptide concentrations for Study 4 samples with and without agitation.
Figure 51:
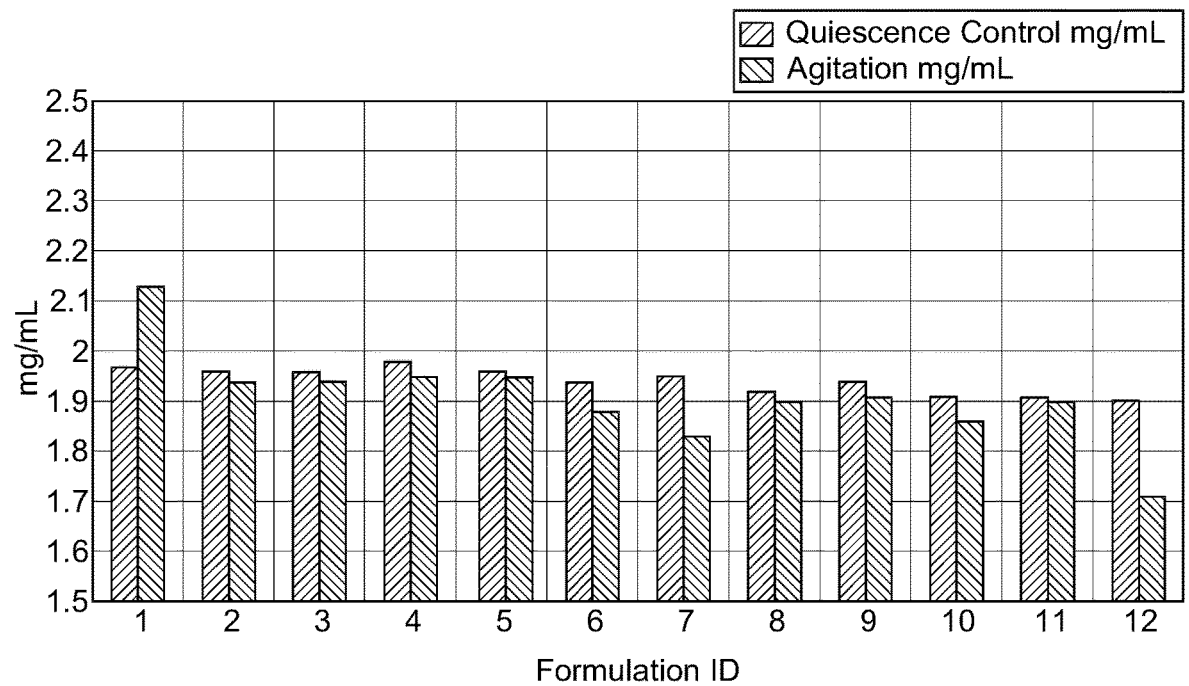
FIG. 51 depicts the peptide concentrations for Study 4 samples with and without freeze-thaw stress.

The fourth study examined the impact of surfactants on the stability of MANP using two different, optimized base formulations (40 mM acetate, 270 mM sucrose, pH 5.5 and pH 6.0). The design for Study 4 is shown in Table 4.

the samples remain clear, even after stress. The pH values of the samples remain virtually unchanged, even with agitation or repeated freeze-thaw (F/T) cycling (Table 36, FIG. 48 and FIG. 49). The peptide concentrations are also unaffected by these two stresses (Table 37, FIG. 50 and FIG. 51).

TABLE 35

Study 4 visual characterization of the stability samples for freeze-thaw and agitation

| | Freeze Thaw Control | | | Freeze Thaw 5 cycles | | | Quiescence Control | | | Agitation | | |
|---|---|---|---|---|---|---|---|---|---|---|---|---|
| Form. | Color | Particle | Visual | Color | Particle | Visual | Color | Particle | Visual | Color | Particle | Visual |
| 1 | No | No | Clear | No | No | Clear | No | No | Clear | No | No | Clear |
| 2 | No | No | Clear | No | No | Clear | No | No | Clear | No | No | Clear |
| 3 | No | No | Clear | No | No | Clear | No | No | Clear | No | No | Clear |
| 4 | No | No | Clear | No | No | Clear | No | No | Clear | No | No | Clear |
| 5 | No | No | Clear | No | No | Clear | No | No | Clear | No | No | Clear |
| 6 | No | No | Clear | No | No | Clear | No | No | Clear | No | No | Clear |
| 7 | No | No | Clear | No | No | Clear | No | No | Clear | No | No | Clear |
| 8 | No | No | Clear | No | No | Clear | No | No | Clear | No | No | Clear |
| 9 | No | No | Clear | No | No | Clear | No | No | Clear | No | No | Clear |
| 10 | No | No | Clear | No | No | Clear | No | No | Clear | No | No | Clear |
| 11 | No | No | Clear | No | No | Clear | No | No | Clear | No | No | Clear |
| 12 | No | No | Clear | No | No | Clear | No | No | Clear | No | No | Clear |

TABLE 34

Study 4 Formulation Design

| Form. | pH | Na Acetate (mM) | Sucrose (mM) | PS20 (%) | PS80 (%) | HP-β-CD (mM) |
|---|---|---|---|---|---|---|
| 1 | 5.5 | 40 | 270 | 0 | 0 | 0 |
| 2 | 5.5 | 40 | 270 | 0.01 | 0 | 0 |
| 3 | 5.5 | 40 | 270 | 0.02 | 0 | 0 |
| 4 | 5.5 | 40 | 270 | 0 | 0.01 | 0 |
| 5 | 5.5 | 40 | 270 | 0 | 0.02 | 0 |
| 6 | 5.5 | 40 | 270 | 0 | 0 | 15 |
| 7 | 6.0 | 40 | 270 | 0 | 0 | 0 |
| 8 | 6.0 | 40 | 270 | 0.01 | 0 | 0 |
| 9 | 6.0 | 40 | 270 | 0.02 | 0 | 0 |
| 10 | 6.0 | 40 | 270 | 0 | 0.01 | 0 |
| 11 | 6.0 | 40 | 270 | 0 | 0.02 | 0 |
| 12 | 6.0 | 40 | 270 | 0 | 0 | 15 |

Study 4 Result: Determine Surfactant and Base Formulation for MANP by Visual Inspection, Peptide Concentrations, and pH Visual inspection of the samples shows no evidence of particles or haziness except for certain samples after agitation (Table 35). This includes the two samples with no surfactant added (1 and 7) and the pH 5.5 formulation that contained HP-b-CD instead of surfactant. Otherwise, all of

TABLE 36

Study 4 pH for Agitation and Freeze Thaw Samples

| Form. | pH | Quiescence Control pH | Agitation pH | Freeze Thaw Control pH | Freeze Thaw 5 Cycles pH |
|---|---|---|---|---|---|
| 1 | 5.5 | 5.52 | 5.46 | 5.53 | 5.54 |
| 2 | 5.5 | 5.53 | 5.52 | 5.52 | 5.54 |
| 3 | 5.5 | 5.53 | 5.52 | 5.53 | 5.54 |
| 4 | 5.5 | 5.53 | 5.52 | 5.52 | 5.53 |
| 5 | 5.5 | 5.52 | 5.52 | 5.52 | 5.54 |
| 6 | 5.5 | 5.54 | 5.48 | 5.54 | 5.54 |
| 7 | 6.0 | 6.02 | 5.93 | 6.01 | 6.05 |
| 8 | 6.0 | 6.02 | 6.01 | 6.01 | 6.04 |
| 9 | 6.0 | 6.02 | 6.01 | 6.01 | 6.02 |
| 10 | 6.0 | 6.02 | 6.00 | 6.00 | 6.01 |
| 11 | 6.0 | 6.02 | 6.00 | 6.02 | 6.03 |
| 12 | 6.0 | 6.03 | 5.98 | 6.01 | 6.02 |

TABLE 37

Study 4 peptide concentration for Agitation and Freeze Thaw Samples

| Form. | pH | Quiescence Control (mg/mL) | Agitation (mg/mL) | Freeze Thaw Control (mg/mL) | Freeze Thaw 5 Cycles (mg/mL) |
|---|---|---|---|---|---|
| 1 | 5.5 | 1.97 | 2.13 | 1.95 | 2.13 |
| 2 | 5.5 | 1.96 | 1.94 | 1.93 | 1.95 |
| 3 | 5.5 | 1.96 | 1.94 | 1.94 | 1.97 |
| 4 | 5.5 | 1.98 | 1.95 | 1.95 | 1.97 |
| 5 | 5.5 | 1.96 | 1.95 | 1.95 | 1.97 |
| 6 | 5.5 | 1.94 | 1.88 | 1.93 | 1.97 |
| 7 | 6.0 | 1.95 | 1.83 | 1.89 | 1.95 |
| 8 | 6.0 | 1.92 | 1.9 | 1.9 | 1.94 |
| 9 | 6.0 | 1.94 | 1.91 | 1.92 | 1.92 |
| 10 | 6.0 | 1.91 | 1.86 | 1.91 | 1.93 |
| 11 | 6.0 | 1.91 | 1.9 | 1.91 | 1.92 |
| 12 | 6.0 | 1.9 | 1.71 | 1.89 | 1.92 |

Figure 52:
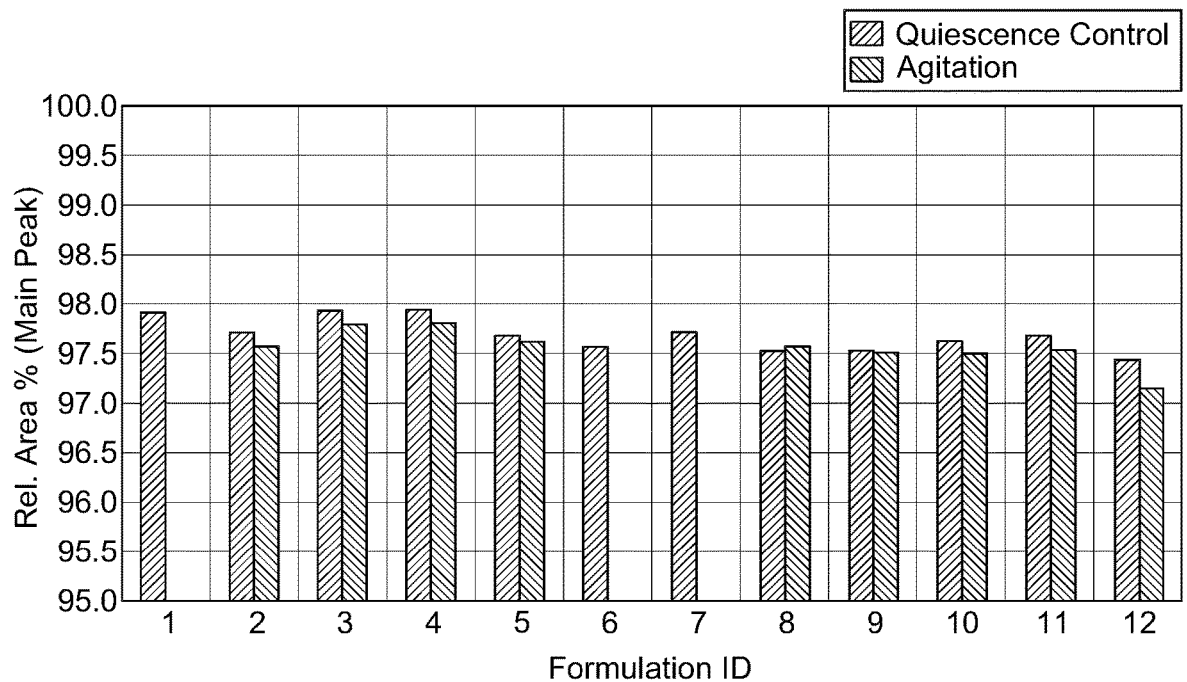
FIG. 52 depicts the main peak purity for Study 4 samples with and without agitation, as measured by RP-HPLC.
Figure 53:
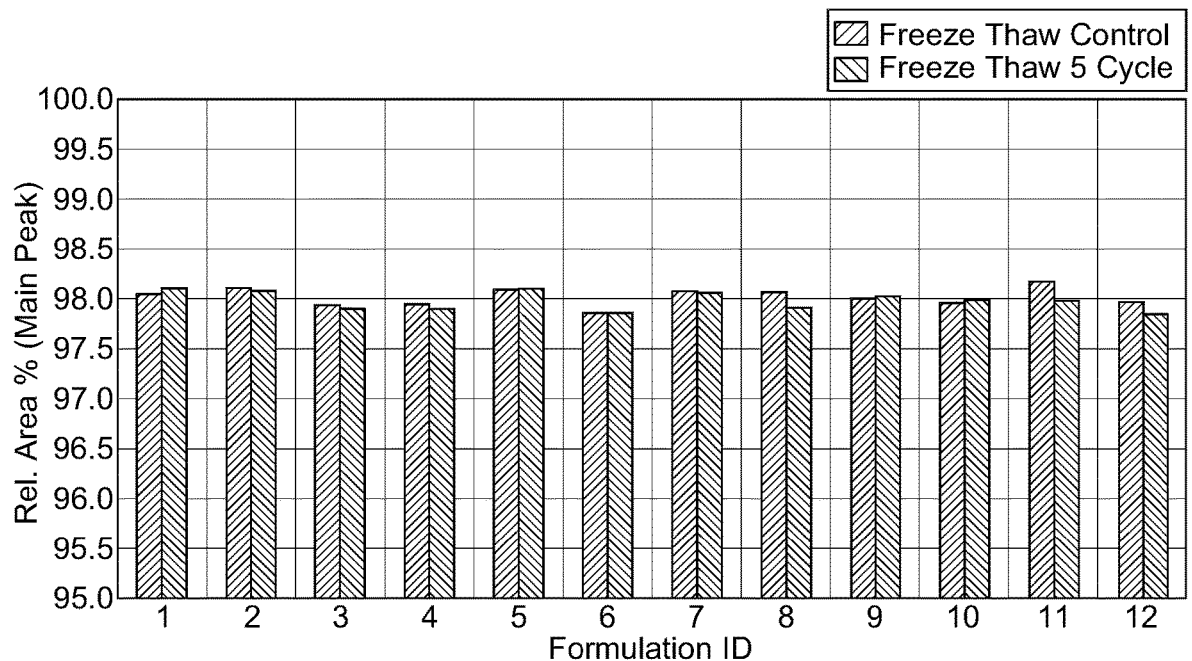
FIG. 53 depicts the main peak purity for Study 4 samples with and without freeze-thaw stress, as measured by RP-HPLC.
Figure 54:
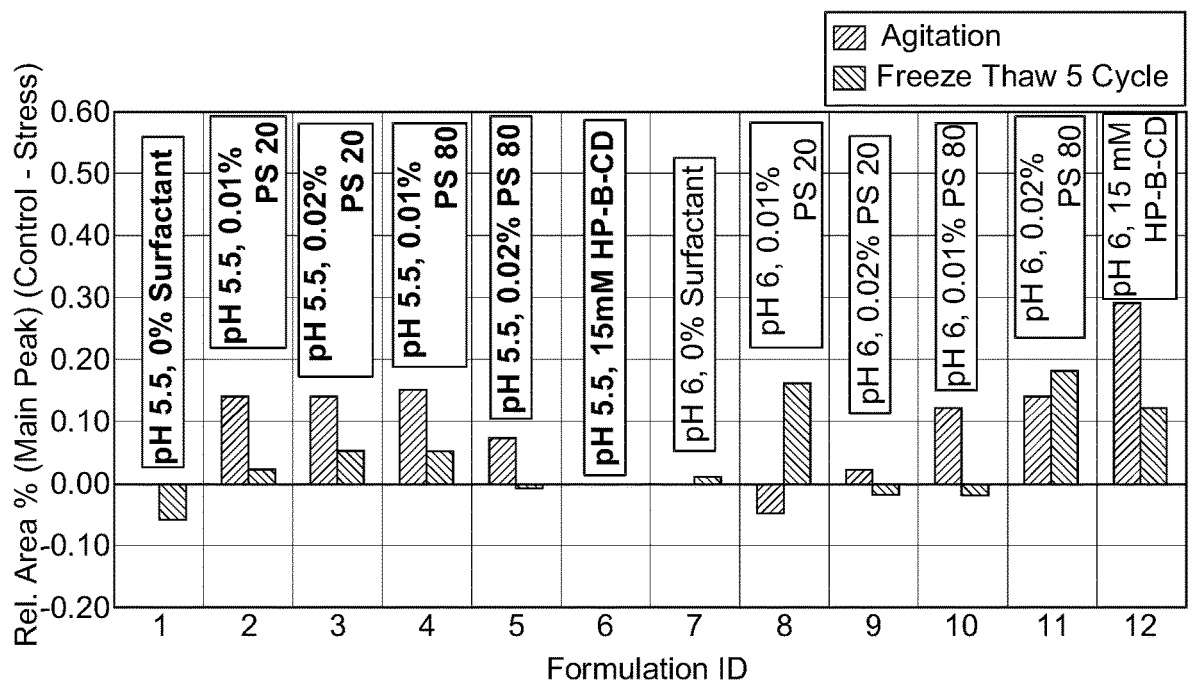
FIG. 54 depicts the change in main peak purity for Study 4 samples for freeze-thaw stress and agitation stress (T=0-Stressed), as measured by RP-HPLC.

Study 4 Result: Determine Surfactant and Base Formulation for MANP by Reverse Phase Chromatography The RP-HPLC Primary method is employed to assess the impact of F/T and agitation on MANP formulations in Study 4. The results are listed in Tables 38 and 39. Some small losses in purity are seen for agitation samples (FIG. 52), but little, if any, loss is seen for samples exposed to F/T cycling (FIG. 53). A graph of the loss of relative main peak area by RP-HPLC indicates there is little differentiation between formulations based on surfactant composition (FIG. 54), which could be expected when assessing chemical stability under a short-term interfacial stress.

TABLE 38

Study 4 Reversed Phase data for Agitation samples

| | | Relative Area (%) | | | | | | |
|---|---|---|---|---|---|---|---|---|
| Form. | Type | Pre Peak 1 | Pre Peak 2 | Pre Peak 3 | Pre Peak 4 | Pre Peak 5 | Pre Peak 6 | Main Peak |
| 1 | Quiescence | 0.03 | 0.04 | 0.40 | 0.18 | 0.15 | 0.06 | 97.91 |
| 2 | Quiescence | 0.03 | 0.05 | 0.42 | 0.21 | 0.18 | 0.08 | 97.71 |
| 3 | Quiescence | 0.03 | 0.06 | 0.36 | 0.17 | 0.16 | 0.07 | 97.93 |
| 4 | Quiescence | 0.03 | 0.05 | 0.39 | 0.15 | 0.15 | 0.06 | 97.94 |
| 5 | Quiescence | 0.03 | 0.06 | 0.37 | 0.16 | 0.17 | 0.08 | 97.68 |
| 6 | Quiescence | 0.03 | 0.07 | 0.52 | 0.23 | 0.19 | 0.10 | 97.57 |
| 7 | Quiescence | 0.02 | 0.06 | 0.36 | 0.17 | 0.24 | 0.07 | 97.71 |
| 8 | Quiescence | 0.02 | 0.08 | 0.39 | 0.20 | 0.24 | 0.08 | 97.52 |
| 9 | Quiescence | 0.02 | 0.06 | 0.40 | 0.25 | 0.25 | 0.08 | 97.52 |
| 10 | Quiescence | 0.01 | 0.09 | 0.40 | 0.17 | 0.23 | 0.08 | 97.61 |
| 11 | Quiescence | 0.02 | 0.06 | 0.40 | 0.16 | 0.23 | 0.08 | 97.67 |
| 12 | Quiescence | 0.02 | 0.05 | 0.48 | 0.26 | 0.25 | 0.09 | 97.43 |
| 1 | Agitation | n.a | n.a | n.a | n.a | n.a | n.a | n.a |
| 2 | Agitation | 0.02 | 0.07 | 0.43 | 0.25 | 0.19 | 0.09 | 97.57 |
| 3 | Agitation | 0.02 | 0.09 | 0.37 | 0.20 | 0.17 | 0.07 | 97.79 |
| 4 | Agitation | 0.02 | 0.05 | 0.37 | 0.17 | 0.17 | 0.08 | 97.79 |
| 5 | Agitation | 0.02 | 0.07 | 0.42 | 0.22 | 0.17 | 0.09 | 97.61 |
| 6 | Agitation | n.a | n.a | n.a | n.a | n.a | n.a | n.a |
| 7 | Agitation | n.a | n.a | n.a | n.a | n.a | n.a | n.a |
| 8 | Agitation | 0.02 | 0.06 | 0.42 | 0.20 | 0.24 | 0.07 | 97.57 |
| 9 | Agitation | 0.02 | 0.06 | 0.41 | 0.20 | 0.25 | 0.07 | 97.50 |
| 10 | Agitation | 0.02 | 0.04 | 0.39 | 0.24 | 0.27 | 0.09 | 97.49 |
| 11 | Agitation | 0.02 | 0.03 | 0.38 | 0.18 | 0.25 | 0.10 | 97.53 |
| 12 | Agitation | 0.02 | 0.08 | 0.58 | 0.25 | 0.31 | 0.11 | 97.14 |

| | | Relative Area (%) | | | | | | |
|---|---|---|---|---|---|---|---|---|
| Form. | Type | Main Peak | Post Peak 1 | Post Peak 2 | Post Peak 3 | Post Peak 4 | Post Peak 5 | Post Peak 6 | Post Peak 7 |
| 1 | Quiescence | 97.91 | n.a. | 0.37 | 0.17 | 0.33 | 0.18 | 0.04 | 0.15 |
| 2 | Quiescence | 97.71 | n.a. | 0.41 | 0.19 | 0.35 | 0.18 | 0.04 | 0.15 |
| 3 | Quiescence | 97.93 | n.a. | 0.37 | 0.16 | 0.33 | 0.18 | 0.05 | 0.14 |
| 4 | Quiescence | 97.94 | n.a. | 0.37 | 0.17 | 0.32 | 0.19 | 0.04 | 0.15 |
| 5 | Quiescence | 97.68 | n.a. | 0.41 | 0.20 | 0.42 | 0.19 | 0.05 | 0.17 |
| 6 | Quiescence | 97.57 | n.a. | 0.40 | 0.19 | 0.38 | 0.19 | 0.04 | 0.10 |
| 7 | Quiescence | 97.71 | n.a. | 0.57 | 0.12 | 0.40 | 0.11 | 0.04 | 0.12 |
| 8 | Quiescence | 97.52 | n.a. | 0.60 | 0.14 | 0.42 | 0.11 | 0.04 | 0.16 |
| 9 | Quiescence | 97.52 | n.a. | 0.58 | 0.13 | 0.43 | 0.11 | 0.05 | 0.12 |
| 10 | Quiescence | 97.61 | n.a. | 0.60 | 0.12 | 0.37 | 0.11 | 0.04 | 0.16 |
| 11 | Quiescence | 97.67 | n.a. | 0.59 | 0.12 | 0.38 | 0.10 | 0.04 | 0.17 |
| 12 | Quiescence | 97.43 | n.a. | 0.59 | 0.12 | 0.42 | 0.12 | 0.05 | 0.12 |
| 1 | Agitation | n.a | n.a | n.a | n.a | n.a | n.a | n.a | n.a |
| 2 | Agitation | 97.57 | n.a. | 0.41 | 0.19 | 0.39 | 0.20 | 0.05 | 0.15 |
| 3 | Agitation | 97.79 | n.a. | 0.37 | 0.17 | 0.34 | 0.19 | 0.04 | 0.17 |
| 4 | Agitation | 97.79 | n.a. | 0.41 | 0.18 | 0.35 | 0.2 | 0.05 | 0.14 |
| 5 | Agitation | 97.61 | n.a. | 0.41 | 0.19 | 0.39 | 0.20 | 0.05 | 0.16 |
| 6 | Agitation | n.a | n.a | n.a | n.a | n.a | n.a | n.a | n.a |
| 7 | Agitation | n.a | n.a | n.a | n.a | n.a | n.a | n.a | n.a |
| 8 | Agitation | 97.57 | n.a. | 0.58 | 0.12 | 0.39 | 0.12 | 0.05 | 0.16 |
| 9 | Agitation | 97.5 | n.a. | 0.61 | 0.12 | 0.41 | 0.12 | 0.05 | 0.17 |
| 10 | Agitation | 97.49 | n.a. | 0.59 | 0.13 | 0.43 | 0.12 | 0.04 | 0.16 |
| 11 | Agitation | 97.53 | n.a. | 0.61 | 0.14 | 0.43 | 0.12 | 0.06 | 0.15 |
| 12 | Agitation | 97.14 | n.a. | 0.61 | 0.15 | 0.44 | 0.12 | 0.04 | 0.15 |

TABLE 39

Study 4 Reversed Phase data for Freeze Thaw samples

| | | Relative Area (%) | | | | | | |
|---|---|---|---|---|---|---|---|---|
| Form. | Type | Pre Peak 1 | Pre Peak 2 | Pre Peak 3 | Pre Peak 4 | Pre Peak 5 | Pre Peak 6 | Main Peak |
| 1 | Control | 0.04 | 0.04 | 0.45 | 0.14 | 0.09 | 0.07 | 98.08 |
| 2 | Control | 0.03 | 0.02 | 0.4 | 0.17 | 0.13 | 0.09 | 98.13 |

TABLE 39-continued

| | | | | | | | | |
|---|---|---|---|---|---|---|---|---|
| 3 | Control | 0.03 | 0.03 | 0.4 | 0.18 | 0.12 | 0.08 | 97.97 |
| 4 | Control | 0.03 | 0.06 | 0.43 | 0.2 | 0.12 | 0.08 | 97.98 |
| 5 | Control | 0.02 | 0.04 | 0.41 | 0.19 | 0.12 | 0.08 | 98.12 |
| 6 | Control | 0.03 | 0.07 | 0.46 | 0.19 | 0.13 | 0.09 | 97.89 |
| 7 | Control | 0.02 | 0.04 | 0.36 | 0.17 | 0.14 | 0.08 | 98.11 |
| 8 | Control | 0.03 | 0.04 | 0.4 | 0.14 | 0.11 | 0.07 | 98.1 |
| 9 | Control | 0.02 | 0.04 | 0.41 | 0.15 | 0.13 | 0.09 | 98.04 |
| 10 | Control | 0.02 | 0.03 | 0.39 | 0.22 | 0.13 | 0.08 | 98 |
| 11 | Control | 0.02 | 0.06 | 0.39 | 0.11 | 0.13 | 0.08 | 98.2 |
| 12 | Control | 0.02 | 0.06 | 0.43 | 0.17 | 0.13 | 0.08 | 98 |
| 1 | 5 Cycles | 0.03 | 0.03 | 0.41 | 0.18 | 0.12 | 0.07 | 98.14 |
| 2 | 5 Cycles | 0.03 | 0.05 | 0.38 | 0.15 | 0.11 | 0.08 | 98.11 |
| 3 | 5 Cycles | 0.02 | 0.1 | 0.42 | 0.21 | 0.14 | 0.09 | 97.92 |
| 4 | 5 Cycles | 0.03 | 0.04 | 0.36 | 0.25 | 0.16 | 0.1 | 97.93 |
| 5 | 5 Cycles | 0.02 | 0.04 | 0.37 | 0.12 | 0.12 | 0.08 | 98.13 |
| 6 | 5 Cycles | 0.02 | 0.04 | 0.44 | 0.23 | 0.14 | 0.1 | 97.89 |
| 7 | 5 Cycles | 0.02 | 0.07 | 0.38 | 0.15 | 0.11 | 0.08 | 98.1 |
| 8 | 5 Cycles | 0.03 | 0.08 | 0.43 | 0.2 | 0.13 | 0.07 | 97.94 |
| 9 | 5 Cycles | 0.04 | 0.06 | 0.36 | 0.13 | 0.13 | 0.08 | 98.06 |
| 10 | 5 Cycles | 0.03 | 0.05 | 0.39 | 0.19 | 0.14 | 0.09 | 98.02 |
| 11 | 5 Cycles | 0.03 | 0.05 | 0.38 | 0.14 | 0.14 | 0.09 | 98.02 |
| 12 | 5 Cycles | 0.04 | 0.07 | 0.43 | 0.21 | 0.15 | 0.1 | 97.88 |

Study 4 Reversed Phase data for Agitation samples

| | | Relative Area (%) | | | | | | |
|---|---|---|---|---|---|---|---|---|
| Form. | Type | Main Peak | Post Peak 1 | Post Peak 2 | Post Peak 3 | Post Peak 4 | Post Peak 5 | Post Peak 6 | Post Peak 7 |
| 1 | Control | 98.08 | n.a. | 0.35 | 0.26 | 0.27 | 0.12 | 0.05 | 0.06 |
| 2 | Control | 98.13 | n.a. | 0.36 | 0.25 | 0.24 | 0.11 | 0.05 | 0.03 |
| 3 | Control | 97.97 | n.a. | 0.36 | 0.27 | 0.29 | 0.12 | 0.09 | 0.05 |
| 4 | Control | 97.98 | n.a. | 0.36 | 0.25 | 0.28 | 0.12 | 0.05 | 0.04 |
| 5 | Control | 98.12 | n.a. | 0.34 | 0.25 | 0.23 | 0.11 | 0.04 | 0.04 |
| 6 | Control | 97.89 | n.a. | 0.36 | 0.25 | 0.29 | 0.12 | 0.05 | 0.07 |
| 7 | Control | 98.11 | n.a | 0.36 | 0.21 | 0.27 | 0.1 | 0.05 | 0.09 |
| 8 | Control | 98.1 | n.a. | 0.35 | 0.21 | 0.3 | 0.11 | 0.05 | 0.09 |
| 9 | Control | 98.04 | n.a. | 0.37 | 0.23 | 0.3 | 0.09 | 0.04 | 0.09 |
| 10 | Control | 98 | n.a. | 0.36 | 0.22 | 0.31 | 0.1 | 0.05 | 0.09 |
| 11 | Control | 98.2 | n.a. | 0.35 | 0.2 | 0.26 | 0.09 | 0.04 | 0.08 |
| 12 | Control | 98 | n.a. | 0.37 | 0.21 | 0.32 | 0.09 | 0.05 | 0.07 |
| 1 | 5 Cycles | 98.14 | n.a. | 0.35 | 0.26 | 0.27 | 0.12 | 0.05 | 0.06 |
| 2 | 5 Cycles | 98.11 | n.a. | 0.36 | 0.25 | 0.24 | 0.11 | 0.05 | 0.03 |
| 3 | 5 Cycles | 97.92 | n.a | 0.36 | 0.27 | 0.29 | 0.12 | 0.09 | 0.05 |
| 4 | 5 Cycles | 97.93 | n.a. | 0.36 | 0.25 | 0.28 | 0.12 | 0.05 | 0.04 |
| 5 | 5 Cycles | 98.13 | n.a. | 0.34 | 0.25 | 0.23 | 0.11 | 0.04 | 0.04 |
| 6 | 5 Cycles | 97.89 | n.a. | 0.36 | 0.25 | 0.29 | 0.12 | 0.05 | 0.07 |
| 7 | 5 Cycles | 98.1 | n.a. | 0.36 | 0.21 | 0.27 | 0.1 | 0.05 | 0.09 |
| 8 | 5 Cycles | 97.94 | n.a. | 0.35 | 0.21 | 0.3 | 0.11 | 0.05 | 0.09 |
| 9 | 5 Cycles | 98.06 | n.a. | 0.37 | 0.23 | 0.3 | 0.09 | 0.04 | 0.09 |
| 10 | 5 Cycles | 98.02 | n.a. | 0.36 | 0.22 | 0.31 | 0.1 | 0.05 | 0.09 |
| 11 | 5 Cycles | 98.02 | n.a. | 0.35 | 0.2 | 0.26 | 0.09 | 0.04 | 0.08 |
| 12 | 5 Cycles | 97.88 | n.a. | 0.37 | 0.21 | 0.32 | 0.09 | 0.05 | 0.07 |

Study 4 Result: Determine Surfactant and Base Formulation for MANP by SEC

Figure 55:
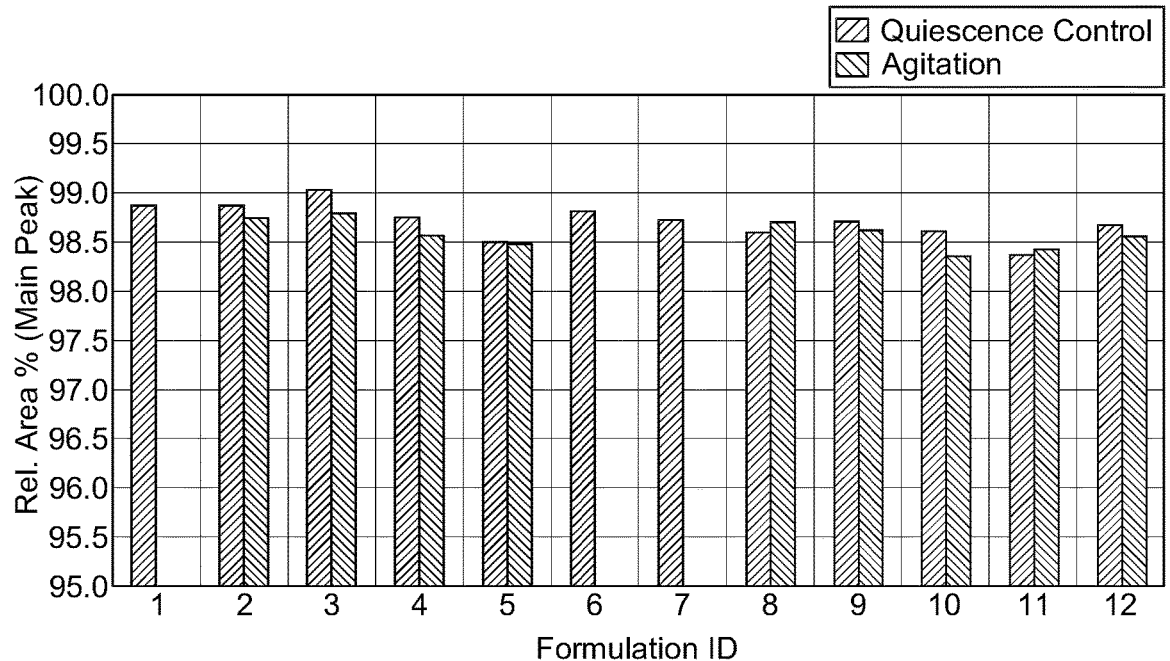
FIG. 55 depicts the monomer content for Study 4 samples with and without agitation stress, as measured by SEC.
Figure 56:
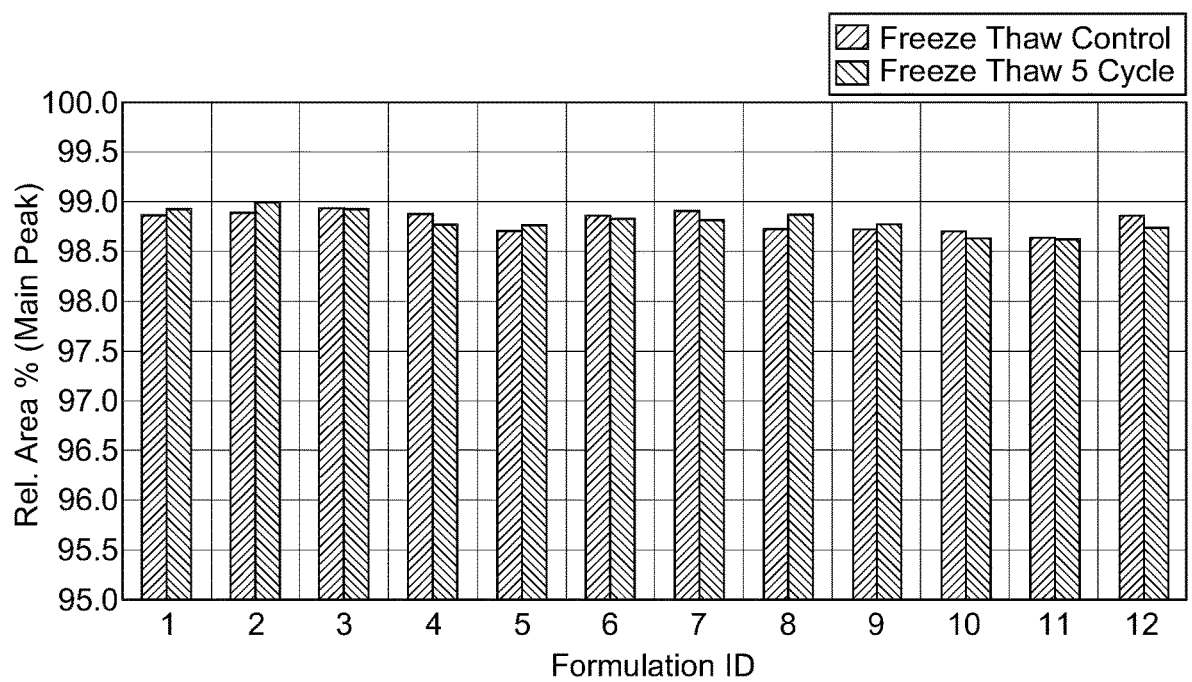
FIG. 56 depicts the monomer content for Study 4 samples with and without freeze-thaw stress, as measured by SEC.
Figure 57:
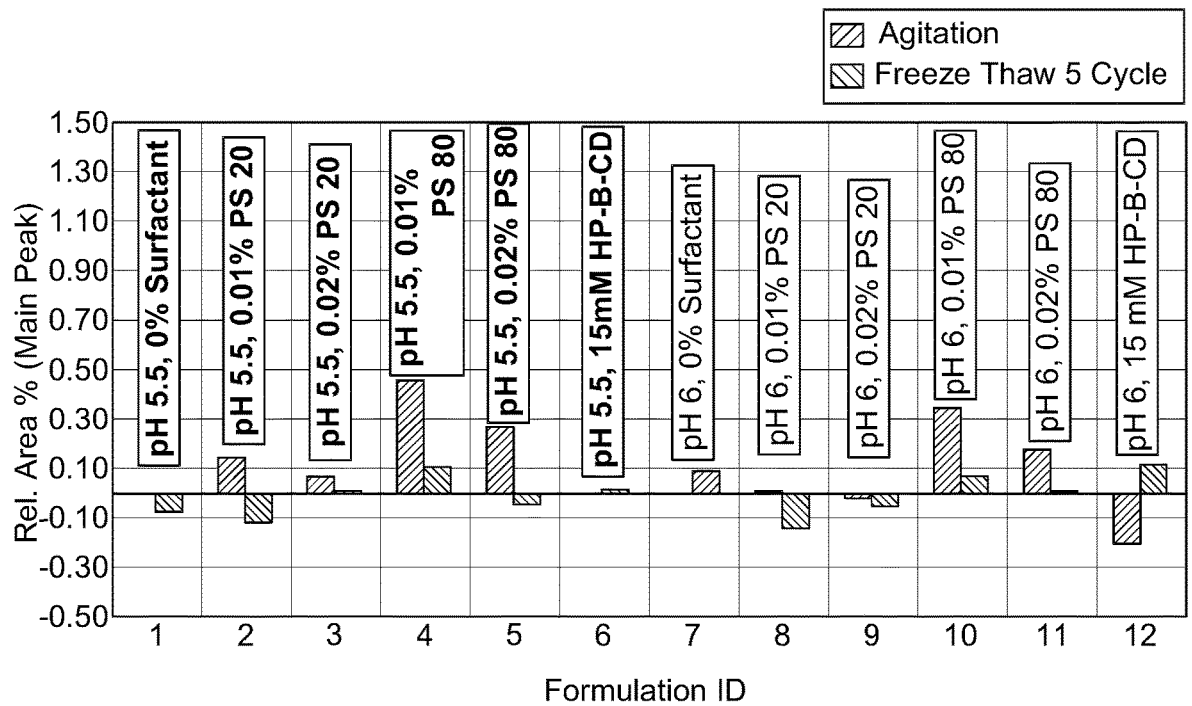
FIG. 57 depicts the change in main peak (monomer) for Study 4 samples undergoing agitation stress and freeze-thaw stress (T=0-Stressed), as measured by SEC.

These same Study 4 samples are tested using SEC as well in order to determine if any aggregation occurs upon interfacial stress. The SEC results are found in Tables 40 and 41. Agitation samples that display cloudiness are not analyzed. For the remaining agitation samples, there are some small changes in monomer content (FIG. 55), as there are for samples exposed to F/T cycling (FIG. 56). A graph of the loss of monomer before and after stress for Study 4 samples is shown in FIG. 57. Overall, PS 20 appears to perform slightly better than PS 80. Moreover, the lowest concentration of PS 20 seems to be able to provide suitable stability. In addition, stability seems to be slightly improved at pH 6.0 over pH 5.5.

TABLE 40

SEC results for Study 4 samples with (AG) and without (QS) agitation stress

| Form. | Type | Rel. Area (%) Pre-Peak 1 | Rel. Area (%) Main Peak | Rel. Area (%) Post-Peak 1 |
|---|---|---|---|---|
| 1 | Quiescence | 0.17 | 98.88 | 0.96 |
| 2 | Quiescence | 0.17 | 98.86 | 0.98 |
| 3 | Quiescence | 0.14 | 99.02 | 0.84 |
| 4 | Quiescence | 0.15 | 98.74 | 1.11 |
| 5 | Quiescence | 0.18 | 98.49 | 1.33 |
| 6 | Quiescence | 0.16 | 98.81 | 1.03 |
| 7 | Quiescence | 0.23 | 98.71 | 1.06 |
| 8 | Quiescence | 0.24 | 98.59 | 1.17 |
| 9 | Quiescence | 0.27 | 98.70 | 1.03 |
| 10 | Quiescence | 0.23 | 98.6 | 1.17 |
| 11 | Quiescence | 0.21 | 98.36 | 1.43 |
| 12 | Quiescence | 0.23 | 98.67 | 1.1 |
| 1 | Agitation | n.a | n.a | n.a |
| 2 | Agitation | 0.16 | 98.73 | 1.11 |

TABLE 40-continued

SEC results for Study 4 samples with (AG) and without (QS) agitation stress

| Form. | Type | Rel. Area (%) Pre-Peak 1 | Rel. Area (%) Main Peak | Rel. Area (%) Post-Peak 1 |
|---|---|---|---|---|
| 3 | Agitation | 0.17 | 98.79 | 1.04 |
| 4 | Agitation | 0.19 | 98.56 | 1.26 |
| 5 | Agitation | 0.15 | 98.47 | 1.38 |
| 6 | Agitation | n.a | n.a | n.a |
| 7 | Agitation | n.a | n.a | n.a |
| 8 | Agitation | 0.25 | 98.70 | 1.04 |
| 9 | Agitation | 0.28 | 98.61 | 1.11 |
| 10 | Agitation | 0.26 | 98.35 | 1.39 |
| 11 | Agitation | 0.20 | 98.42 | 1.39 |
| 12 | Agitation | 0.26 | 98.56 | 1.18 |

TABLE 41

SEC results for Study 4 samples with (AG) and without (QS) agitation stress

| Form. | Type | Rel. Area (%) Pre-Peak 1 | Rel. Area (%) Main Peak | Rel. Area (%) Post-Peak 1 |
|---|---|---|---|---|
| 1 | Control | 0.11 | 98.86 | 1.03 |
| 2 | Control | 0.09 | 98.89 | 1.02 |
| 3 | Control | 0.14 | 98.94 | 0.92 |
| 4 | Control | 0.09 | 98.88 | 1.03 |
| 5 | Control | 0.1 | 98.72 | 1.18 |
| 6 | Control | 0.11 | 98.86 | 1.04 |
| 7 | Control | 0.15 | 98.91 | 0.95 |
| 8 | Control | 0.18 | 98.73 | 1.09 |
| 9 | Control | 0.21 | 98.72 | 1.07 |
| 10 | Control | 0.15 | 98.71 | 1.14 |
| 11 | Control | 0.13 | 98.64 | 1.24 |
| 12 | Control | 0.15 | 98.86 | 0.99 |
| 1 | 5 Cycles | 0.1 | 98.93 | 0.97 |
| 2 | 5 Cycles | 0.07 | 99 | 0.93 |
| 3 | 5 Cycles | 0.1 | 98.93 | 0.97 |
| 4 | 5 Cycles | 0.12 | 98.77 | 1.11 |
| 5 | 5 Cycles | 0.08 | 98.76 | 1.16 |
| 6 | 5 Cycles | 0.1 | 98.84 | 1.06 |
| 7 | 5 Cycles | 0.15 | 98.82 | 1.04 |
| 8 | 5 Cycles | 0.15 | 98.87 | 0.98 |
| 9 | 5 Cycles | 0.16 | 98.77 | 1.06 |
| 10 | 5 Cycles | 0.22 | 98.64 | 1.14 |
| 11 | 5 Cycles | 0.1 | 98.63 | 1.26 |
| 12 | 5 Cycles | 0.15 | 98.74 | 1.11 |

Study 5: Effect of Methionine Oxidation on MANP Stability

One final study is performed to finalize the MANP formulation. As there is some proclivity for Met oxidation of MANP, four select formulations are prepared, as listed in Table 42. This study would help determine whether addition of some amount of free Met might help reduce oxidation of the peptide.

TABLE 42

Study 5 Methionine Formulation Design

| Form. | pH | Na Acetate (mM) | Sucrose (mM) | Methionine (mM) |
|---|---|---|---|---|
| 1 | 5.5 | 40 | 270 | 0 |
| 2 | 5.5 | 40 | 270 | 5 |
| 3 | 5.5 | 40 | 270 | 10 |
| 4 | 5.5 | 40 | 270 | 20 |

Figure 58:
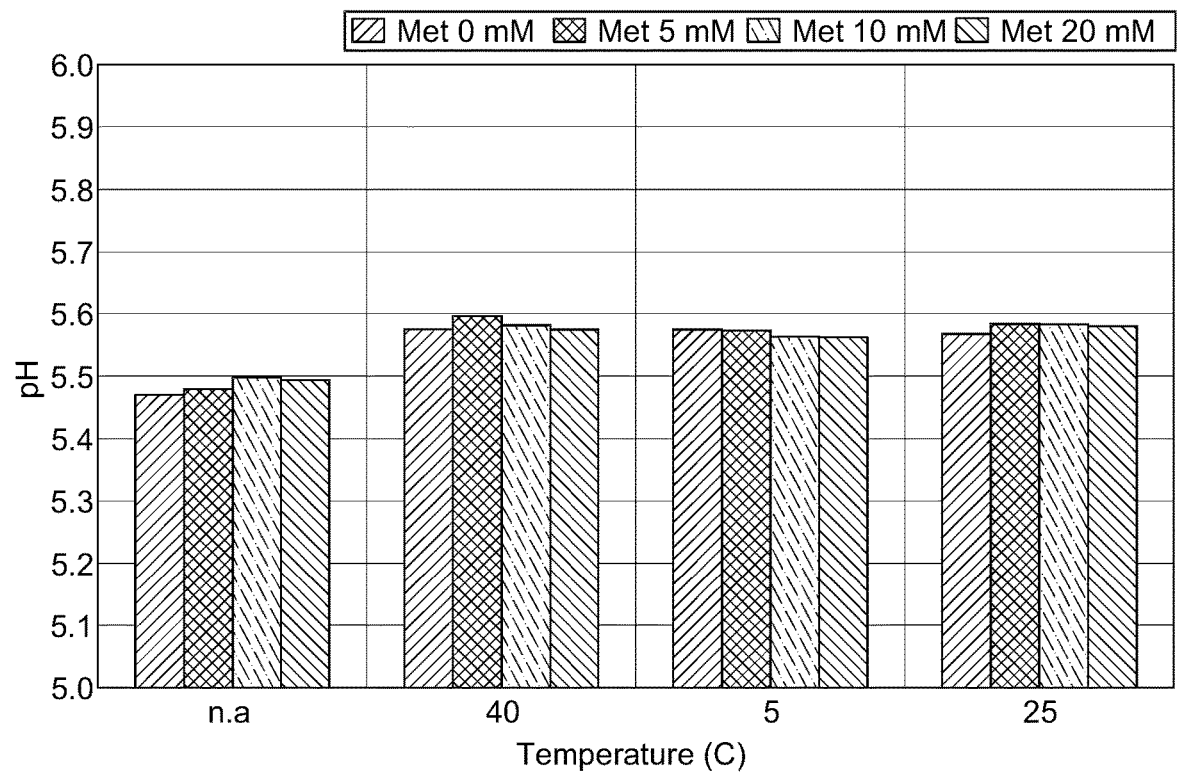
FIG. 58 depicts the peptide concentrations for Study 5 samples.
Figure 59:
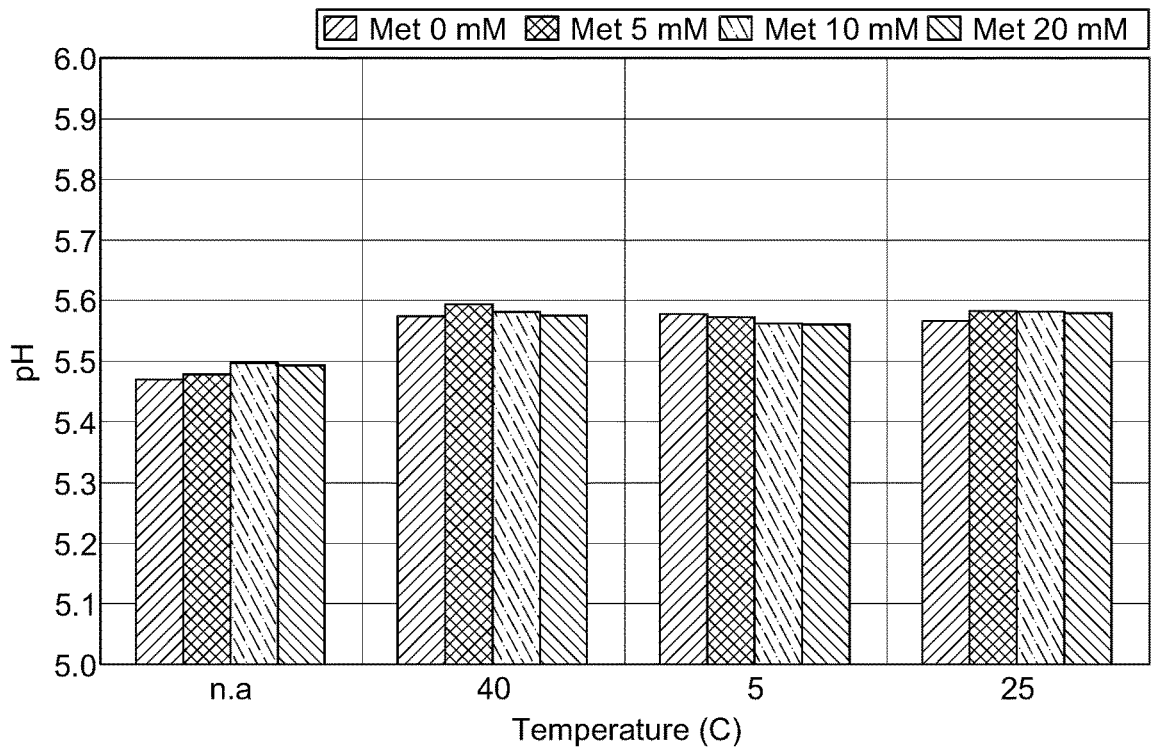
FIG. 59 depicts the pH values for the Study 5 samples.

Study 5 Result: Determine Methionine Oxidation of MANP by Visual Characterization, Peptide Concentrations and pH Each sample is evaluated by visual inspection (Table 46). All samples remain clear and colorless over the course of Study 5. The pH values and peptide concentrations do not change appreciably over the course of the study (Table 47). Graphs of the peptide concentrations (FIG. 58) and pH values (FIG. 59) for each of the stored samples illustrates how little these values varied over the course of the storage stability study.

TABLE 43

Study 5 visual characterization, pH, osmolality, and peptide concentration of the stability samples for MET samples

| Form. | pH | Time (weeks) | Temp (° C.) | Visual | Color | Particle | Osmolality (mOsm/kg H20) | Peptide Concentration (mg/mL) | pH |
|---|---|---|---|---|---|---|---|---|---|
| 1 | 0 | 0 | n.a | Clear | No Color | No Particle | 398 | 2.05 | 5.47 |
| 2 | 5 | 0 | n.a | Clear | No Color | No Particle | 405 | 2.03 | 5.48 |
| 3 | 10 | 0 | n.a | Clear | No Color | No Particle | 405 | 2.04 | 5.5 |
| 4 | 20 | 0 | n.a | Clear | No Color | No Particle | 422 | 2.03 | 5.49 |
| 1 | 0 | 1 | 40 | Clear | No Color | No Particle | n.a | 2.01 | 5.58 |
| 2 | 5 | 1 | 40 | Clear | No Color | No Particle | n.a | 2.03 | 5.59 |
| 3 | 10 | 1 | 40 | Clear | No Color | No Particle | n.a | 2.03 | 5.58 |
| 4 | 20 | 1 | 40 | Clear | No Color | No Particle | n.a | 2.03 | 5.57 |
| 1 | 0 | 4 | 5 | Clear | No Color | No Particle | n.a | 2.01 | 5.58 |
| 2 | 5 | 4 | 5 | Clear | No Color | No Particle | n.a | 2.02 | 5.57 |
| 3 | 10 | 4 | 5 | Clear | No Color | No Particle | n.a | 2.03 | 5.56 |
| 4 | 20 | 4 | 5 | Clear | No Color | No Particle | n.a | 2.01 | 5.56 |
| 1 | 0 | 4 | 25 | Clear | No Color | No Particle | n.a | 2.03 | 5.57 |
| 2 | 5 | 4 | 25 | Clear | No Color | No Particle | n.a | 2.04 | 5.58 |
| 3 | 10 | 4 | 25 | Clear | No Color | No Particle | n.a | 2.04 | 5.58 |
| 4 | 20 | 4 | 25 | Clear | No Color | No Particle | n.a | 2.02 | 5.58 |

Figure 60:
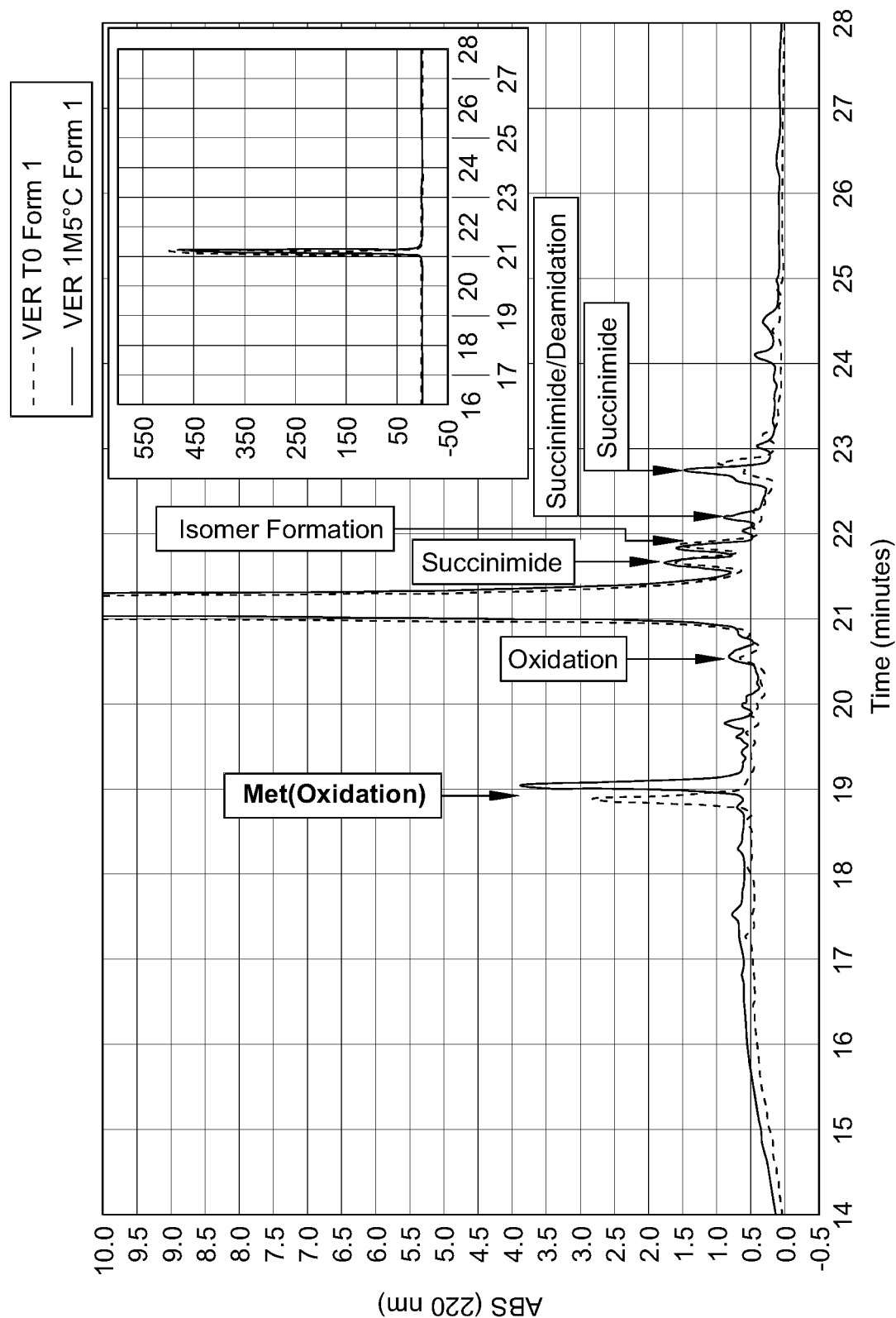
FIG. 60 depicts an exemplary RP-HPLC chromatogram with labeled peaks.
Figure 61:
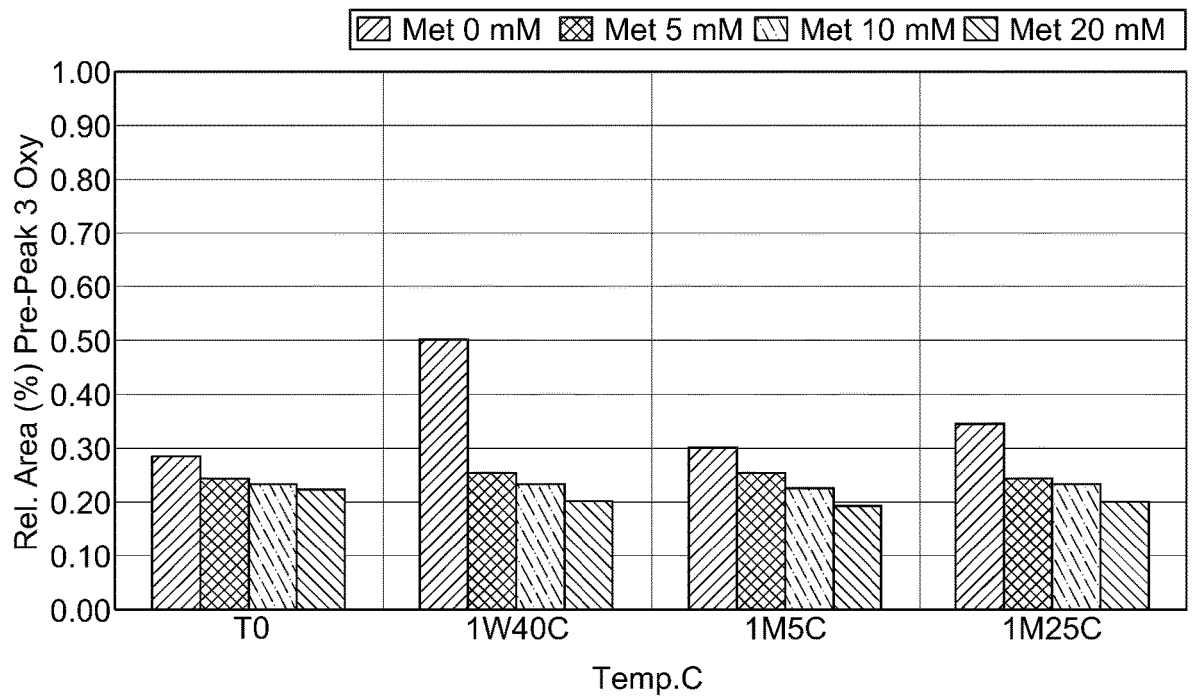
FIG. 61 depicts the relative area of the peak representing the Methionine oxidation species (pre-peak 3) for Study 5 samples at different time points, as measured by RP-HPLC.
Figure 62:
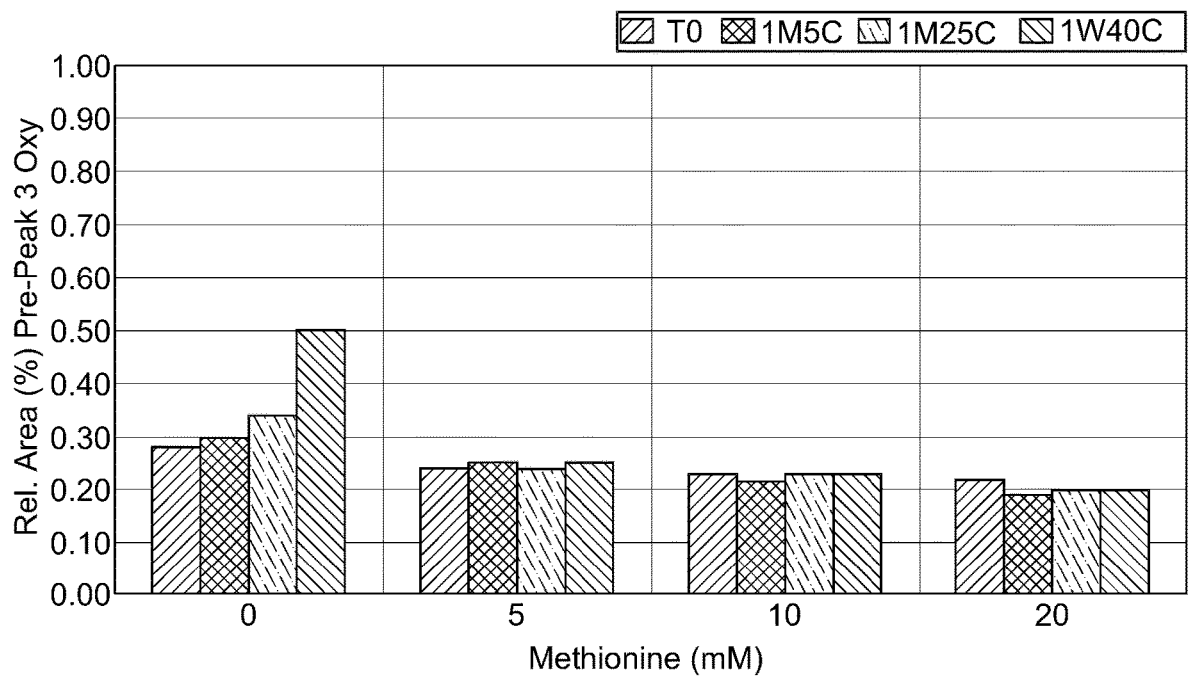
FIG. 62 depicts the relative area of the peak representing the Methionine oxidation species (pre-peak 3) for Study 5 samples at different concentrations of free Methionine, as measured by RP-HPLC.
Figure 63:
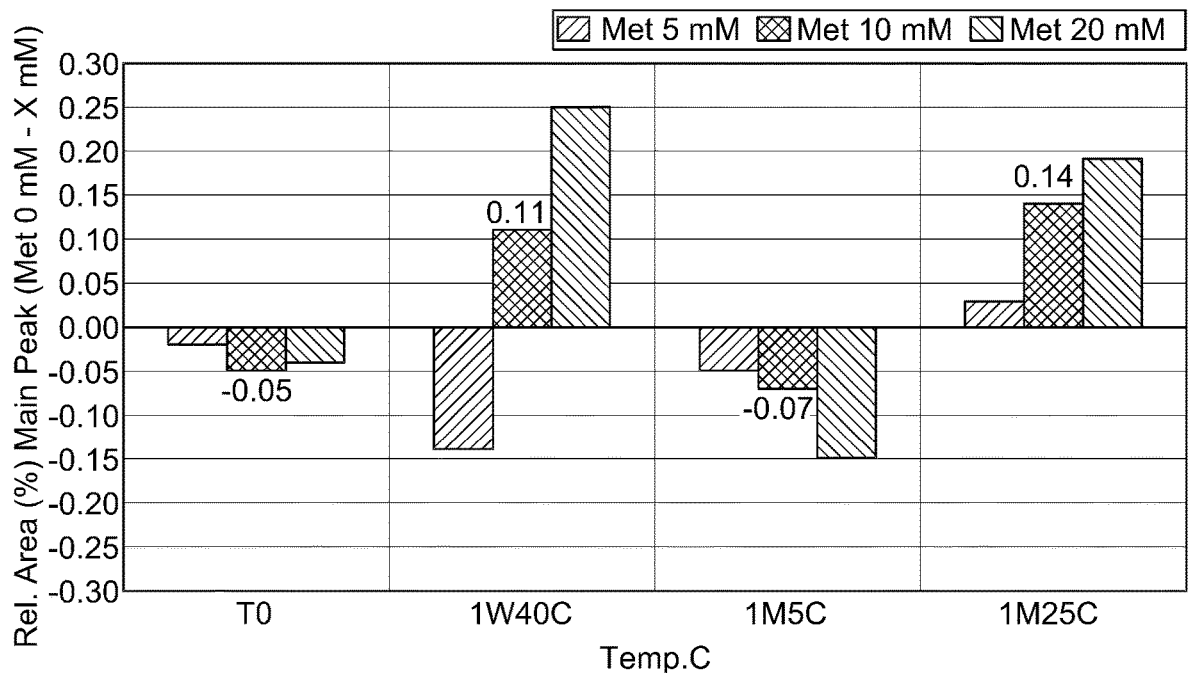
FIG. 63 depicts change in the relative area of the main peak (no Met-Met at X mM) for Study 5 samples, as measured by RP-HPLC.
Figure 64:
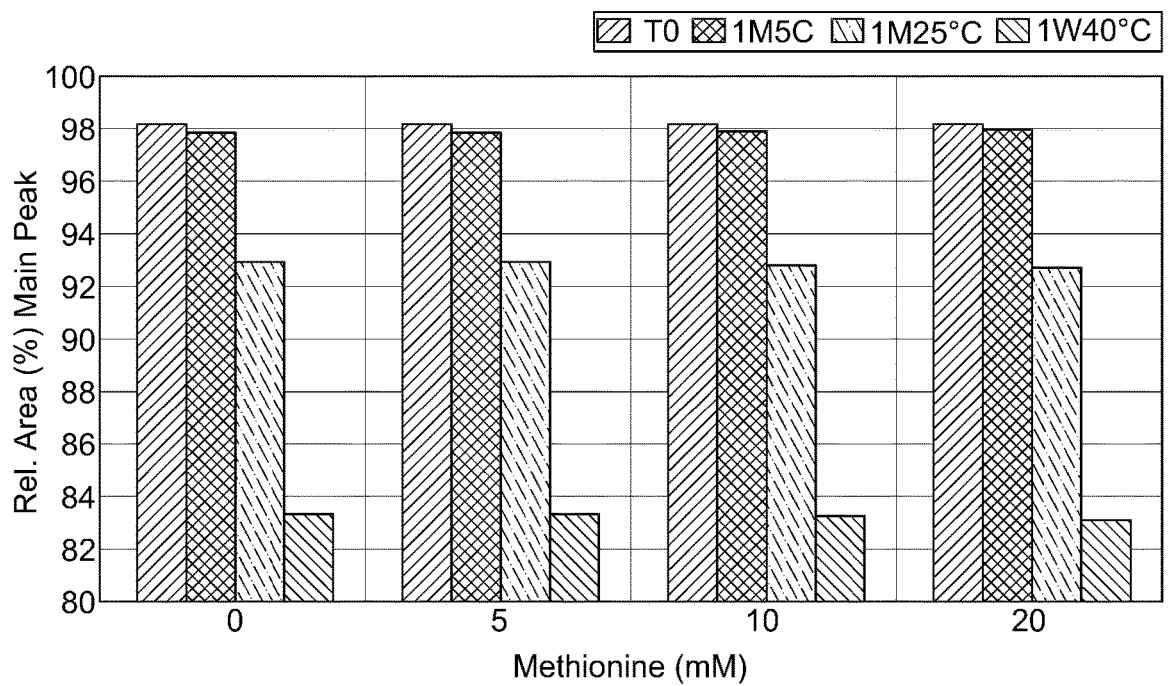
FIG. 64 depicts the relative area of the main peak as a function of Methionine concentration, as measured by RP-HPLC.
Figure 65:
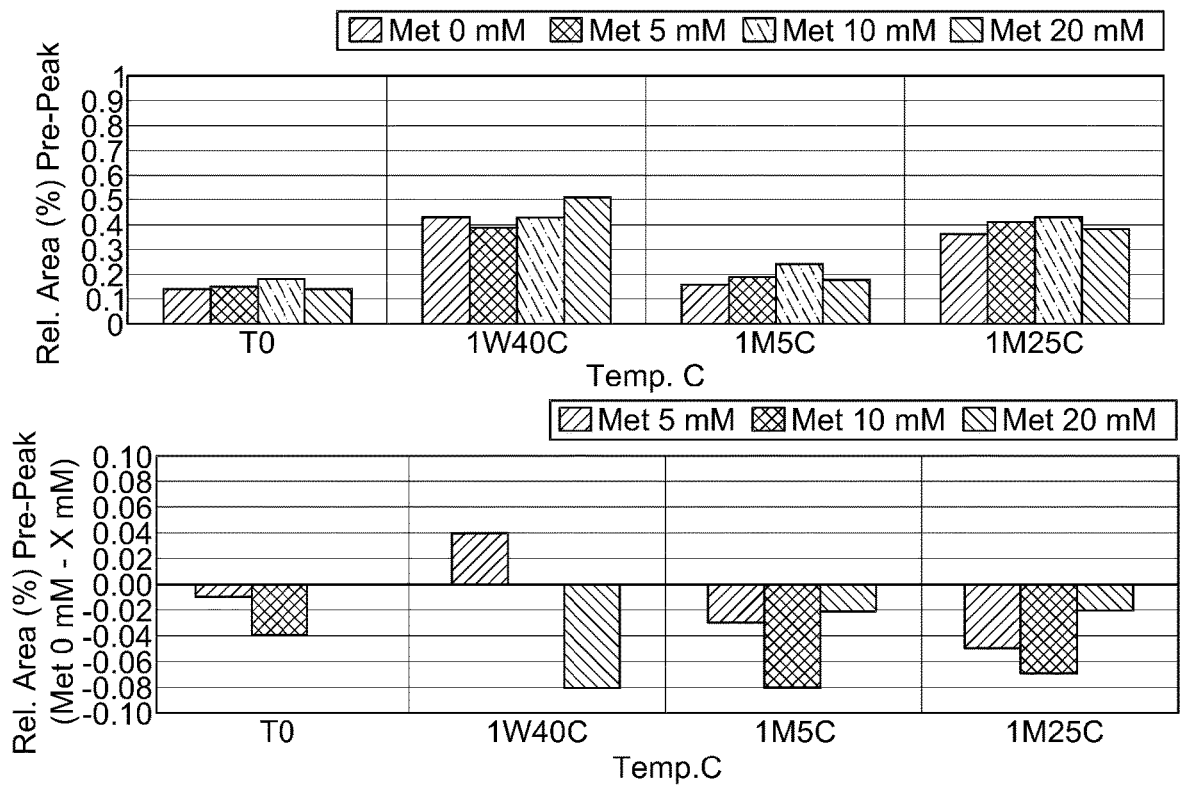
FIG. 65 depicts the relative areas of the pre-peak at different time points for Study 5 samples, as measured by SEC.
Figure 66:
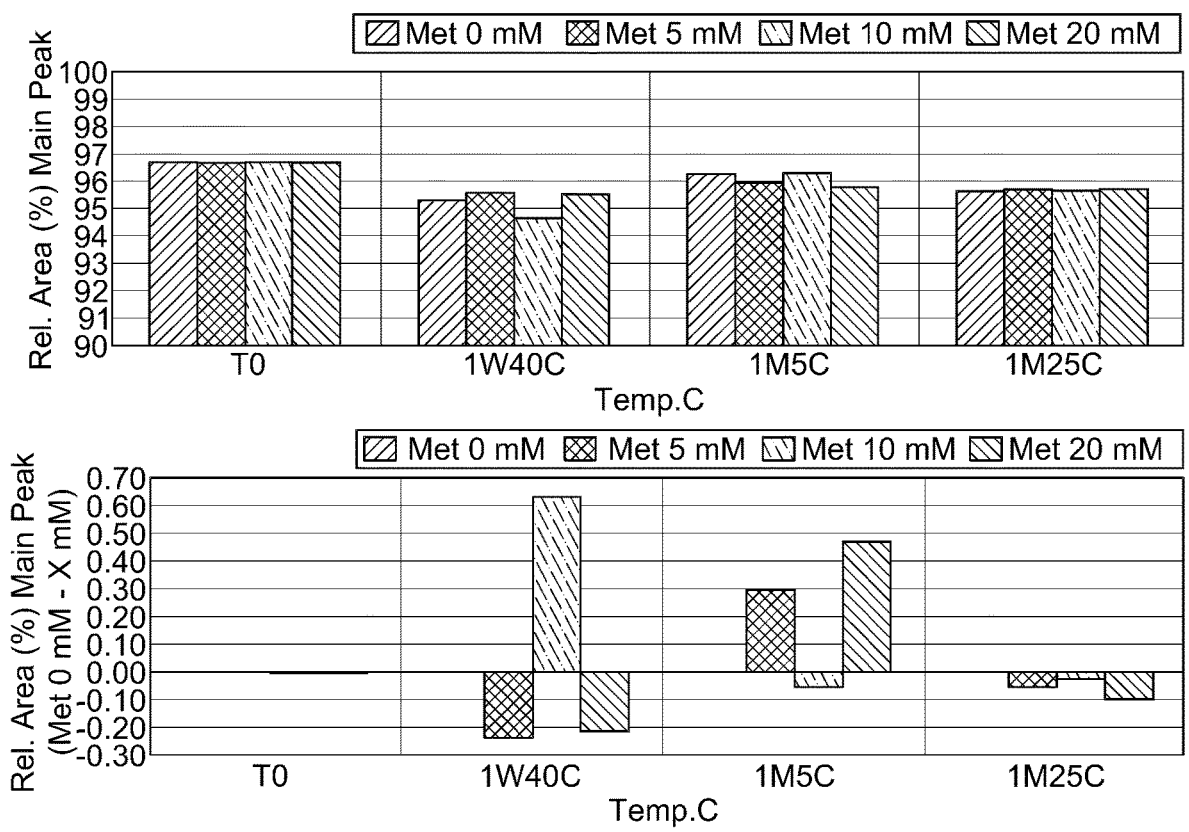
FIG. 66 depicts the relative areas of the main peak at different time points for Study 5 samples, as measured by SEC.
Figure 67:
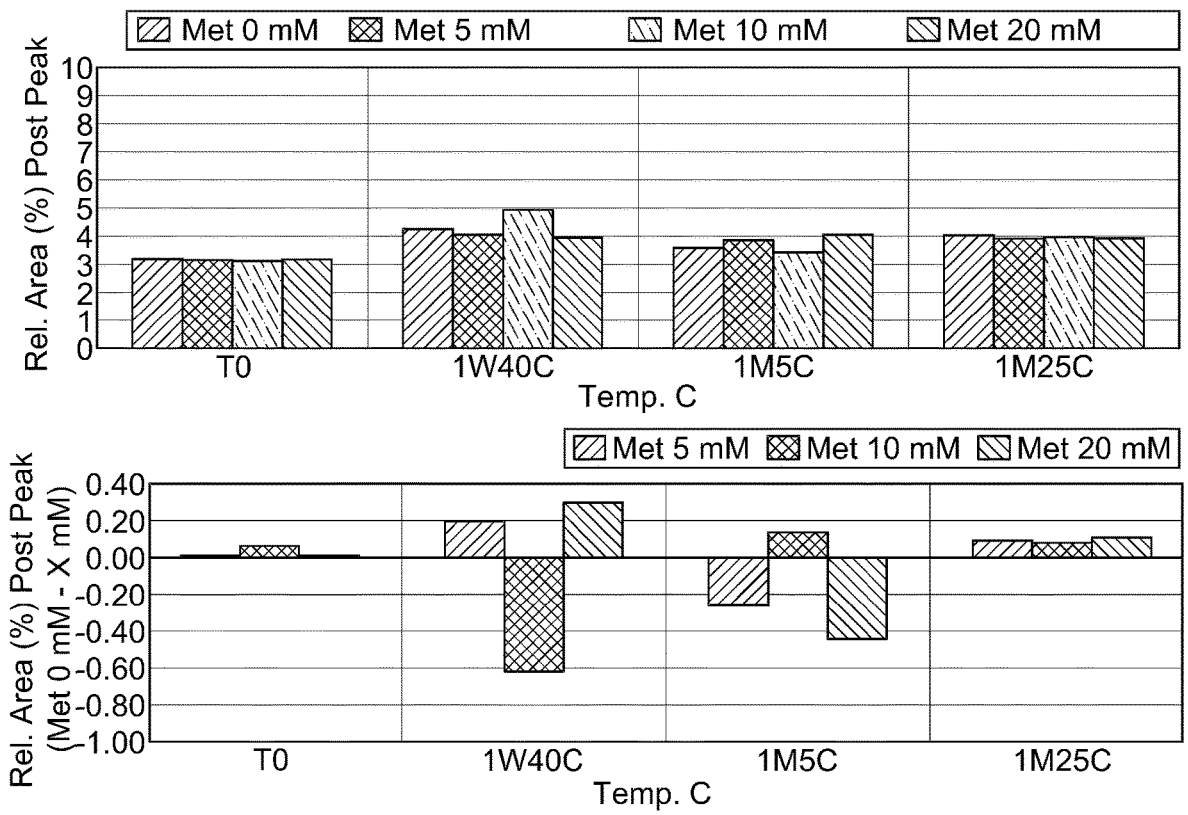
FIG. 67 depicts the relative areas of the post-peak at different time points for Study 5 samples, as measured by SEC.

Study 5 Result: Determine Methionine Oxidation of MANP by Reversed Phase Chromatography Analysis of Study 5 samples by RP-HPLC focus on maintaining overall main peak purity, but also on minimizing the Met oxidation species that elutes near 19 minutes (FIG. 60). The RP-HPLC data are summarized in Table 44. If one plots the relative area of the primary Met oxidation product as a function of free Met concentration (FIG. 61), one can see a modest, but discernible, decrease in oxidation with increasing Met content. An examination of the effect of free Met concentration shows that there is some protection of Met is added at 5 mM, but no appreciable improvement if one uses a higher concentration (FIG. 62). Similar trends are seen if one examines the main peak purity (FIG. 63 and FIG. 64).

TABLE 44

Study 5 Reversed Phase data

| Form. | Met (mM) | Time (weeks) | Temp (° C.) | Group Area (mAU * min) | Pre Peak 1 | Pre Peak 2 | Pre Peak 3 | Pre Peak 4 | Pre Peak 5 | Pre Peak 6 | Main Peak |
|---|---|---|---|---|---|---|---|---|---|---|---|
| | | | | | \multicolumn{7}{c}{Relative Area (%)} | | | | | | |
| 1 | 0 | 0 | n.a | 69.35 | 0.01 | 0.08 | 0.28 | 0.2 | 0.1 | 0.06 | 98.19 |
| 2 | 5 | 0 | n.a | 69.04 | 0.01 | 0.07 | 0.24 | 0.18 | 0.11 | 0.07 | 98.21 |
| 3 | 10 | 0 | n.a | 69.4 | 0.01 | 0.06 | 0.23 | 0.17 | 0.1 | 0.06 | 98.24 |
| 4 | 20 | 0 | n.a | 68.69 | 0.01 | 0.05 | 0.22 | 0.18 | 0.12 | 0.06 | 98.23 |
| 1 | 0 | 1 | 40 | 68.33 | 0.55 | 0.11 | 0.5 | 0.46 | 3.01 | 3.1 | 83.38 |
| 2 | 5 | 1 | 40 | 67.82 | 0.55 | 0.07 | 0.25 | 0.34 | 3.01 | 3.13 | 83.52 |
| 3 | 10 | 1 | 40 | 68.23 | 0.49 | 0.1 | 0.23 | 0.35 | 2.98 | 3.16 | 83.27 |
| 4 | 20 | 1 | 40 | 66.58 | 0.46 | 0.1 | 0.2 | 0.34 | 3.03 | 3.17 | 83.13 |
| 1 | 0 | 4 | 5 | 66.59 | 0.02 | 0.07 | 0.3 | 0.24 | 0.18 | 0.06 | 97.89 |
| 2 | 5 | 4 | 5 | 68.98 | 0.02 | 0.07 | 0.25 | 0.2 | 0.19 | 0.07 | 97.94 |
| 3 | 10 | 4 | 5 | 68.73 | 0.01 | 0.04 | 0.22 | 0.18 | 0.18 | 0.07 | 97.96 |
| 4 | 20 | 4 | 5 | 66.97 | 0.02 | 0.04 | 0.19 | 0.15 | 0.18 | 0.07 | 98.04 |
| 1 | 0 | 4 | 25 | 69.22 | 0.22 | 0.05 | 0.34 | 0.27 | 1.36 | 0.08 | 92.97 |
| 2 | 5 | 4 | 25 | 67.98 | 0.21 | 0.07 | 0.24 | 0.23 | 1.36 | 0.09 | 92.94 |
| 3 | 10 | 4 | 25 | 68.45 | 0.21 | 0.12 | 0.23 | 0.25 | 1.37 | 0.08 | 92.83 |
| 4 | 20 | 4 | 25 | 69.25 | 0.2 | 0.09 | 0.2 | 0.22 | 1.39 | 0.08 | 92.78 |

| Form. | Met (mM) | Time (weeks) | Temp (° C.) | Group Area (mAU * min) | Main Peak | Post Peak 1 | Post Peak 2 | Post Peak 3 | Post Peak 4 | Post Peak 5 | Post Peak 6 | Post Peak 7 |
|---|---|---|---|---|---|---|---|---|---|---|---|---|
| 1 | 0 | 0 | n.a | 69.35 | 98.19 | 0 | 0.31 | 0.23 | 0.29 | 0.13 | 0.06 | 0.06 |
| 2 | 5 | 0 | n.a | 69.04 | 98.21 | 0 | 0.32 | 0.24 | 0.30 | 0.14 | 0.06 | 0.05 |
| 3 | 10 | 0 | n.a | 69.4 | 98.24 | 0 | 0.30 | 0.25 | 0.28 | 0.15 | 0.07 | 0.07 |
| 4 | 20 | 0 | n.a | 68.69 | 98.23 | 0 | 0.32 | 0.25 | 0.30 | 0.15 | 0.06 | 0.06 |
| 1 | 0 | 1 | 40 | 68.33 | 83.38 | 1.25 | 5.88 | 0.14 | 1.01 | 0.44 | 0.08 | 0.11 |
| 2 | 5 | 1 | 40 | 67.82 | 83.52 | 1.23 | 6.02 | 0.14 | 1.08 | 0.44 | 0.07 | 0.16 |
| 3 | 10 | 1 | 40 | 68.23 | 83.27 | 1.22 | 6.18 | 0.15 | 1.19 | 0.46 | 0.08 | 0.13 |
| 4 | 20 | 1 | 40 | 66.58 | 83.13 | 1.26 | 6.34 | 0.14 | 1.13 | 0.45 | 0.08 | 0.17 |
| 1 | 0 | 4 | 5 | 66.59 | 97.89 | 0.00 | 0.36 | 0.17 | 0.35 | 0.21 | 0.05 | 0.09 |
| 2 | 5 | 4 | 5 | 68.98 | 97.94 | 0.00 | 0.37 | 0.19 | 0.36 | 0.22 | 0.05 | 0.09 |
| 3 | 10 | 4 | 5 | 68.73 | 97.96 | 0.00 | 0.38 | 0.20 | 0.37 | 0.23 | 0.06 | 0.10 |
| 4 | 20 | 4 | 5 | 66.97 | 98.04 | 0.00 | 0.38 | 0.19 | 0.38 | 0.23 | 0.06 | 0.07 |
| 1 | 0 | 4 | 25 | 69.22 | 92.97 | 0.96 | 2.45 | 0.07 | 0.64 | 0.42 | 0.05 | 0.12 |
| 2 | 5 | 4 | 25 | 67.98 | 92.94 | 0.94 | 2.52 | 0.08 | 0.72 | 0.45 | 0.07 | 0.10 |
| 3 | 10 | 4 | 25 | 68.45 | 92.83 | 0.95 | 2.56 | 0.08 | 0.51 | 0.59 | 0.06 | 0.16 |
| 4 | 20 | 4 | 25 | 69.25 | 92.78 | 0.98 | 2.64 | 0.08 | 0.71 | 0.45 | 0.06 | 0.11 |

Study 5 Result: Determine Methionine Oxidation of MANP by SEC

Figure 68:
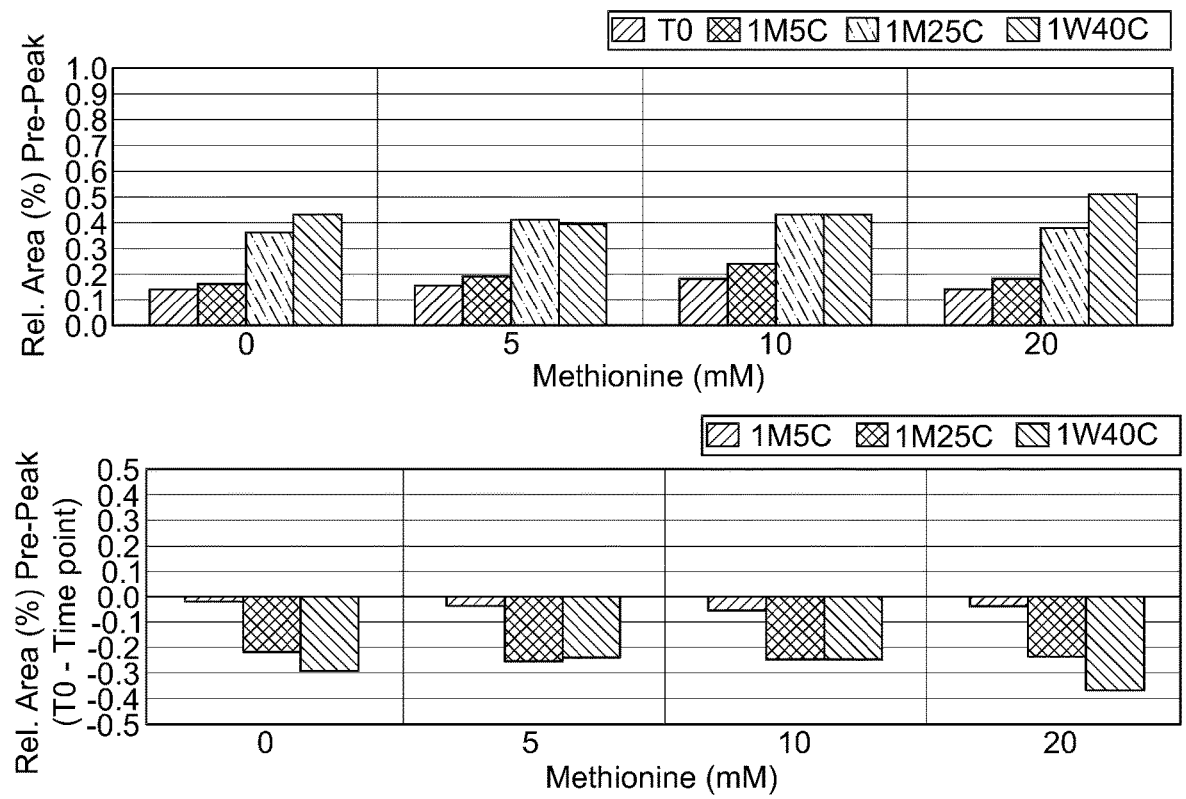
FIG. 68 depicts the relative areas of the pre-peak at different Methionine concentrations for Study 5 samples, as measured by SEC.
Figure 69:
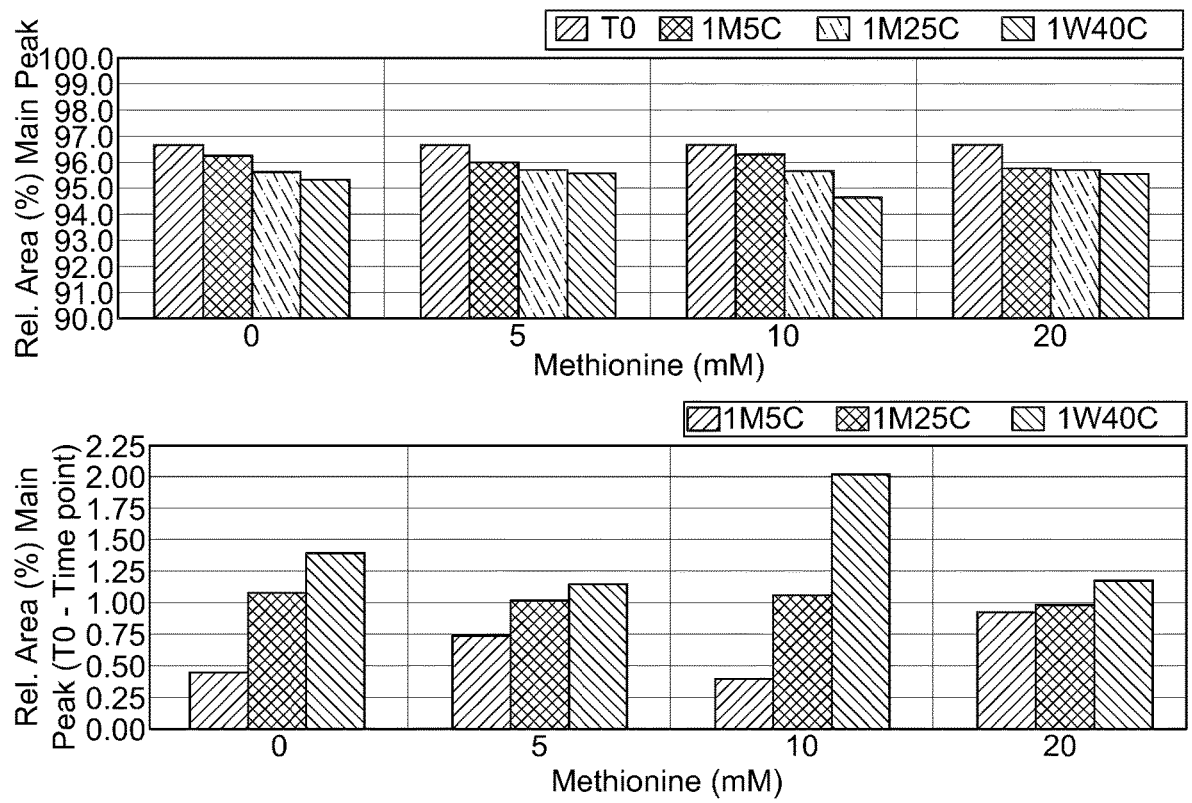
FIG. 69 depicts the relative areas of the main peak at different Methionine concentrations for Study 5 samples, as measured by SEC.
Figure 70:
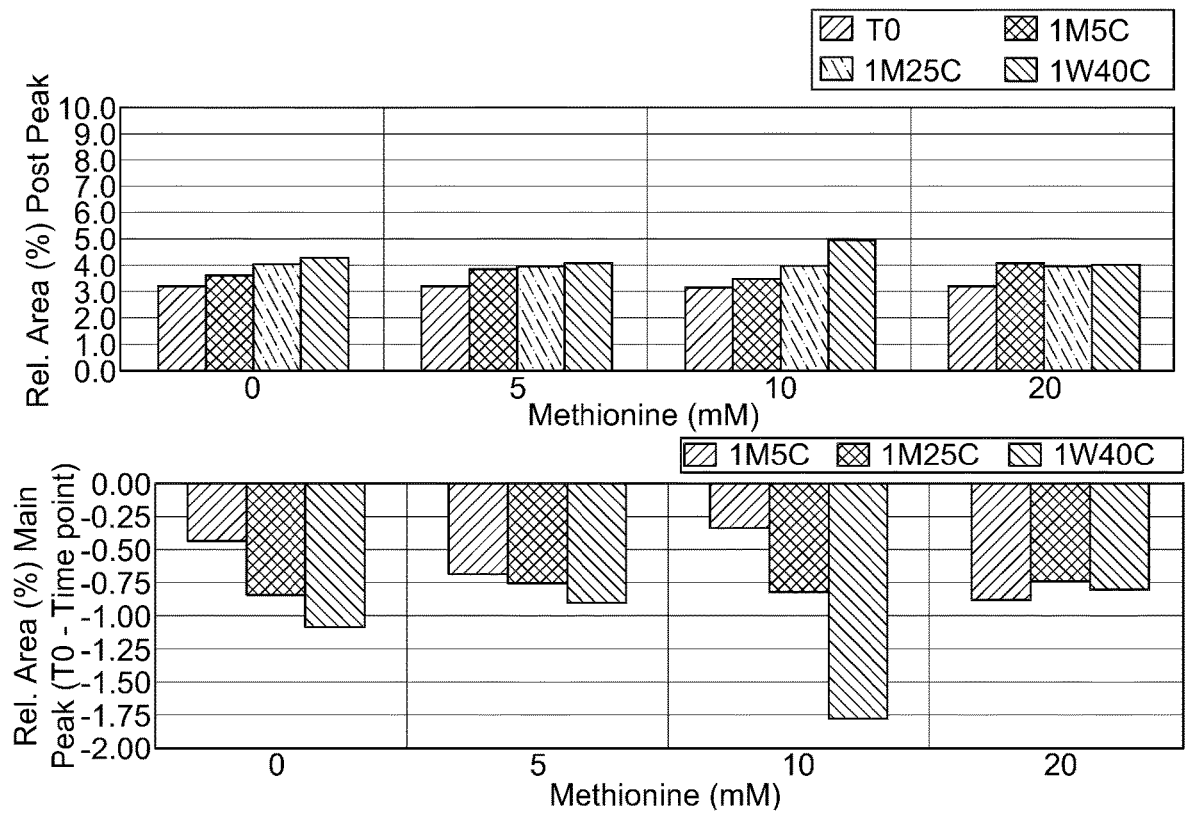
FIG. 70 depicts the relative areas of the post-peak at different Methionine concentrations for Study 5 samples, as measured by SEC.

The samples from Study 5 are also assayed using SEC, as interfacial stress often generates aggregates and higher molecular weight (HMW) species. There are some increases for HMW species, especially at 25° C. and 40° C. (Table 45). The amounts and changes in the pre-, main-, and post-peaks are graphed in FIGS. 65-70. If one looks at the effects of Met at a given time point (FIGS. 68-70), there is little impact of Met on the extent of aggregation.

TABLE 45

Study 5 SEC data

| Form. | Met (mM) | Time (weeks) | Temp (° C.) | Group Area (mAU * min) | Relative Area (%) | | |
|---|---|---|---|---|---|---|---|
| | | | | | Pre-Peak | Main Peak | Post-Peak |
| 1 | 0 | 0 | n.a | 135.45 | 0.14 | 96.67 | 3.19 |
| 2 | 5 | 0 | n.a | 135.67 | 0.15 | 96.67 | 3.18 |
| 3 | 10 | 0 | n.a | 139.46 | 0.18 | 96.68 | 3.13 |
| 4 | 20 | 0 | n.a | 133.58 | 0.14 | 96.68 | 3.18 |
| 1 | 0 | 1 | 40 | 100.16 | 0.43 | 95.29 | 4.28 |
| 2 | 5 | 1 | 40 | 101.29 | 0.39 | 95.53 | 4.08 |
| 3 | 10 | 1 | 40 | 104.01 | 0.43 | 94.66 | 4.91 |
| 4 | 20 | 1 | 40 | 99.61 | 0.51 | 95.51 | 3.98 |
| 1 | 0 | 4 | 5 | 97.62 | 0.16 | 96.23 | 3.61 |
| 2 | 5 | 4 | 5 | 101.32 | 0.19 | 95.94 | 3.87 |
| 3 | 10 | 4 | 5 | 102.57 | 0.24 | 96.29 | 3.47 |
| 4 | 20 | 4 | 5 | 99.95 | 0.18 | 95.76 | 4.06 |
| 1 | 0 | 4 | 25 | 103.90 | 0.36 | 95.60 | 4.03 |
| 2 | 5 | 4 | 25 | 104.05 | 0.41 | 95.66 | 3.94 |
| 3 | 10 | 4 | 25 | 105.75 | 0.43 | 95.63 | 3.95 |
| 4 | 20 | 4 | 25 | 104.87 | 0.38 | 95.70 | 3.92 |

Study 5 illustrates that addition of Met, even at just 5 mM, can be somewhat protective against Met oxidation of MANP. At the same time, there does not appear to be any deleterious effects of Met on the physical stability of these formulations (nor is the free Met protective against the modest levels of aggregation that occur during interfacial stress).

Conclusion

Five rounds of formulation screening are conducted on MANP. Early in the project, it was discovered that higher pH values and the use of succinate buffer are detrimental to physical stability, with precipitation and cloudiness being observed. Overall, the primary pathways for degradation are chemical instability. Under storage conditions, there is very little aggregation occurring. Even with interfacial stress (agitation, F/T cycling), the aggregation is minimal. So, limitations to shelf-life will be related to the ability to control chemical degradation, as measured by RP-HPLC.

The optimal pH appears to be near 6.0, with acetate being the preferred buffer. At this pH, an acetate concentration of 40 mM appears to be beneficial for maximizing RP-HPLC main peak purity over time at 5° C. His could serve as a backup buffer. Both mannitol and sucrose appear to be good stabilizers and can also function as tonicity modifiers. Use of electrolytes (ArgHCl, NaCl) lead to greater chemical instability. It appears that addition of small amounts of PS 20 (0.01 or 0.02%) can be protective against interfacial stress. Moreover, the addition of a small amount of free Met (5 mM) can reduce the extent of Met oxidation of MANP.

Example 2: Stability Verification Studies

Four formulations are prepared with the peptide concentration set to 2 mg/mL, with PS 20 at 0.02% and the pH ranged from 5 to 6 (Table 46). The formulations are buffered using histidine and acetate with concentrations ranging from 10 mM to 40 mM. The stabilizers/tonicity modifiers are sucrose and mannitol that range in concentration from 200 mM and 250 mM. Results of previous studies showed that HP-β-CD improved the stability of the peptide and was included in the verification study at 25 (mM).

The formulations are placed on stability up to 6 months at 5° C., 25° C. and 40° C. (Table 47). The 5° C. samples has two different orientations, non-inverted and inverted where the formulations are exposed to the caps.

TABLE 46

Verification Formulations

| Formulation No. | pH | Histidine (mM) | Acetate (mM) | Sucrose (mM) | Mannitol (mM) | HP-β-CD (mM) | PS-20 (%) |
|---|---|---|---|---|---|---|---|
| 1 | 5.0 | 40 | 0 | 200 | 0 | 0 | 0.02 |
| 2 | 6.0 | 0 | 20 | 250 | 0 | 25 | 0.02 |
| 3 | 5.5 | 0 | 40 | 0 | 250 | 0 | 0.02 |
| 4 | 5.5 | 0 | 10 | 275 | 0 | 0 | 0.02 |

TABLE 47

Temperature Studies

| Temp ° C. | T = 0 | T = 1 month | T = 3 months | T = 6 months |
|---|---|---|---|---|
| 5 | Non-inverted | Non-inverted | Non-inverted; Inverted | Non-inverted; Inverted |
| 25 | Non-inverted | Non-inverted | Non-inverted | Non-inverted |
| 40 | Non-inverted | Non-inverted | Non-inverted | — |

General Sample Preparation

A 10 mg/mL peptide solution is prepared on the day of formulation, and a 2× formulation buffer is prepared the day before. The 10 mg/mL peptide solution is prepared by weighing out the peptide into a sterile container and adding ed Milli-Q water to reach the target peptide concentration. The volume of the 10 mg/mL peptide solution is calculated based on the target sample volume. The calculated volume of the peptide is then added to a new sterile container. The volume of the 2× buffer added to the peptide solution is half the volume of the sample target volume. The pH of the peptide and the 2× buffer is then checked with a pH probe, If the pH value is outside±0.1 pH units, the sample pH is adjusted with 0.1 M of NaCl. The sample is then QS to the target sample volume with Milli-Q water, followed by measuring the pH and peptide concentration again.

The samples are sterile filtered in a clean hood that was wiped down with 70% ethanol. Each formulation is loaded into a sterile syringe with sterile filter attached. The sample is then slowly pushed through filter into a sterile container. After the samples had been sterile filtered, they are loaded into the vials.

pH Values, Osmolality and Peptide Concentrations

The verification samples are characterized by visual inspection, pH and peptide concentration, as shown in Table 48.

The pH of each formulation is checked and the measured pH of the sample is found to be within ±0.1 of the target pH. Before the start of analysis, the pH probe is calibrated with three pH standards ordered from Fisher. The pH of the formulation will be measured by inserting the pH probe into the sample and waiting until the measured value has stabilized, which can take up to 1 to 2 minutes. After the analysis the pH probe is washed with 18 MΩ water for one minute and stored in the pH storage solution.

The peptide concentration of each formulation is measured using the SoloVPE. The concentration of the sample is measured by the operator by adding 100 μL of material into a SoloVPE small UV disposable vessel. A new fibrette is installed and the sample absorbance is measured by the instrument, using an extinction coefficient of 1.58 mL*mg$^{-1}$ cm$^{-1}$, and correcting for background scattering. After analysis, the sample is removed with a pipette from the disposable vessel. The disposable vessel and fibrette are both then disposed. This procedure is repeated for each sample.

Over the course of 6 months Formulations 2, 3 and 4 show no signs of the physical instability, no change in solution color, are visually clear and no signs of particle formation are observed. Formulation 1 show no signs of physical instability up to 3 months, at 6 months a gel has formed at the bottom of the vials.

TABLE 48

Visual characterization of the verification samples

| Formulation No. | Peptide (mg/ml) | pH | Time (month) | Temp. °C. | Color | Particle | Visual |
|---|---|---|---|---|---|---|---|
| 1 | 2 | 5 | 0 | n.a | No | No | Clear |
| 2 | 2 | 6 | 0 | n.a | No | No | Clear |
| 3 | 2 | 5.5 | 0 | n.a | No | No | Clear |
| 4 | 2 | 5.5 | 0 | n.a | No | No | Clear |
| 1 | 2 | 5 | 1 | 5 | No | No | Clear |
| 2 | 2 | 6 | 1 | 5 | No | No | Clear |
| 3 | 2 | 5.5 | 1 | 5 | No | No | Clear |
| 4 | 2 | 5.5 | 1 | 5 | No | No | Clear |
| 1 | 2 | 5 | 1 | 25 | No | No | Clear |
| 2 | 2 | 6 | 1 | 25 | No | No | Clear |
| 3 | 2 | 5.5 | 1 | 25 | No | No | Clear |
| 4 | 2 | 5.5 | 1 | 25 | No | No | Clear |
| 1 | 2 | 5 | 1 | 40 | No | No | Clear |
| 2 | 2 | 6 | 1 | 40 | No | No | Clear |
| 3 | 2 | 5.5 | 1 | 40 | No | No | Clear |
| 4 | 2 | 5.5 | 1 | 40 | No | No | Clear |
| 1 | 2 | 5 | 3 | 5 | No | No | Clear |
| 2 | 2 | 6 | 3 | 5 | No | No | Clear |
| 3 | 2 | 5.5 | 3 | 5 | No | No | Clear |
| 4 | 2 | 5.5 | 3 | 5 | No | No | Clear |
| 1 | 2 | 5 | 3 | 25 | No | No | Clear |
| 2 | 2 | 6 | 3 | 25 | No | No | Clear |
| 3 | 2 | 5.5 | 3 | 25 | No | No | Clear |
| 4 | 2 | 5.5 | 3 | 25 | No | No | Clear |
| 1 | 2 | 5 | 3 | 40 | No | No | Clear |
| 2 | 2 | 6 | 3 | 40 | No | No | Clear |
| 3 | 2 | 5.5 | 3 | 40 | No | No | Clear |
| 4 | 2 | 5.5 | 3 | 40 | No | No | Clear |
| 1 | 2 | 5 | 3* | 5 | No | No | Clear |
| 2 | 2 | 6 | 3* | 5 | No | No | Clear |
| 3 | 2 | 5.5 | 3* | 5 | No | No | Clear |
| 4 | 2 | 5.5 | 3* | 5 | No | No | Clear |
| 1 | 2 | 5 | 6 | 5 | No | Yes | Clear |
| 2 | 2 | 6 | 6 | 5 | No | No | Clear |
| 3 | 2 | 5.5 | 6 | 5 | No | No | Clear |
| 4 | 2 | 5.5 | 6 | 5 | No | No | Clear |
| 1 | 2 | 5 | 6 | 25 | No | Yes | Clear |
| 2 | 2 | 6 | 6 | 25 | No | No | Clear |
| 3 | 2 | 5.5 | 6 | 25 | No | No | Clear |
| 4 | 2 | 5.5 | 6 | 25 | No | No | Clear |
| 1 | 2 | 5 | 6* | 5 | No | Yes | Clear |
| 2 | 2 | 6 | 6* | 5 | No | No | Clear |
| 3 | 2 | 5.5 | 6* | 5 | No | No | Clear |
| 4 | 2 | 5.5 | 6* | 5 | No | No | Clear |

*Sample Inverted

The pH, peptide concentration and osmotic pressure are measured for the verification samples, as shown in Table 49.

The osmotic analysis is performed using Advanced Instruments Osmo 1. At the start of analysis, a reference standard at 290 mOsm is analyzed to ensure the instrument is working properly. After the reference standard has passed the samples are then analyzed. 20 μL of material is removed and analyzed by Osmo 1, after analysis the chamber is cleared by using a chamber cleaner. This procedure is repeated for each sample.

Figure 71:
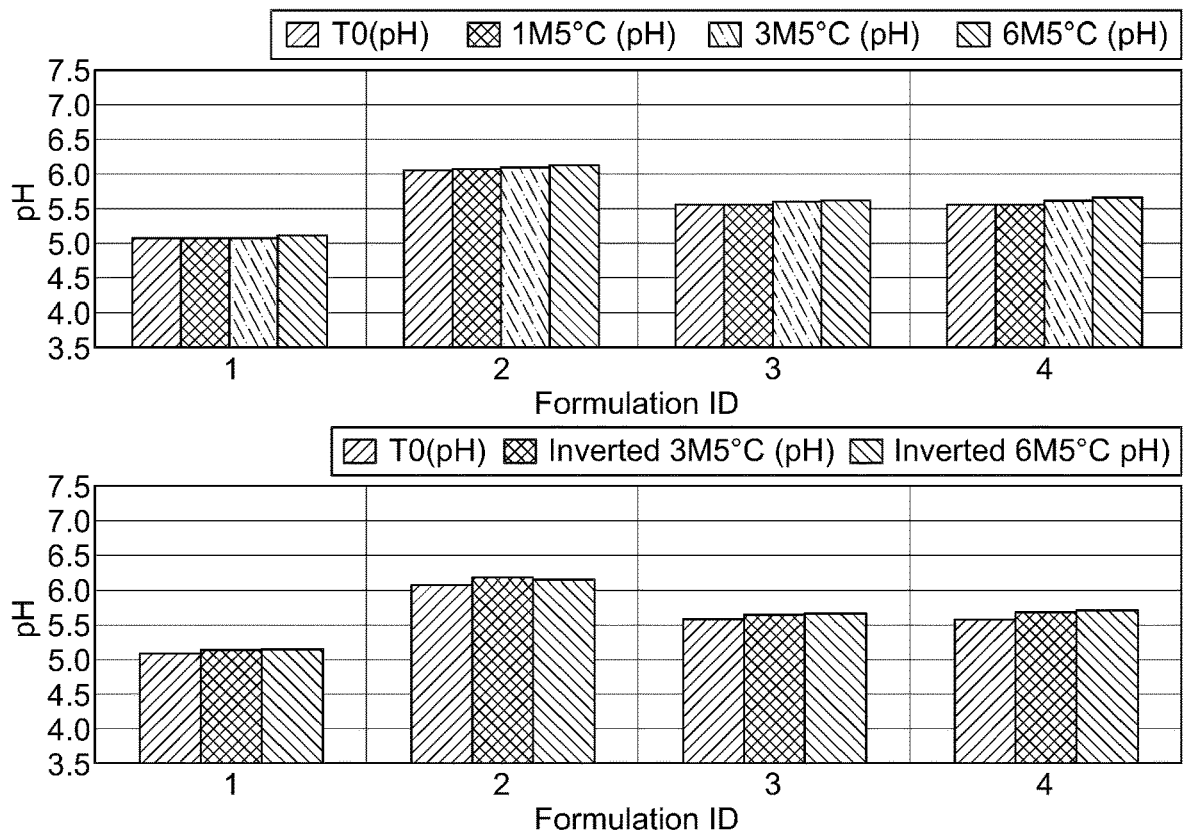
FIG. 71 depicts the pH measured for the verification samples stored at 5° C. (inverted and non-inverted).
Figure 72:
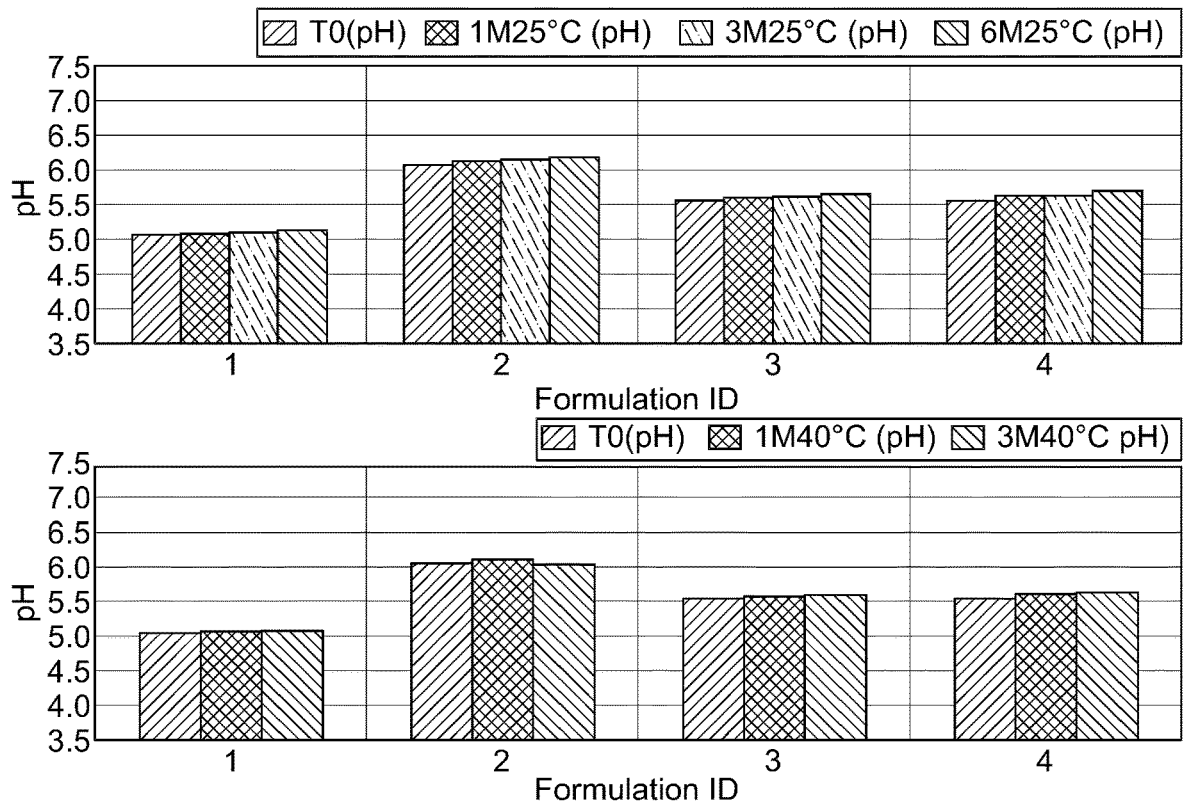
FIG. 72 depicts the pH measured for the verification samples stored at 25° C. and 40° C.

The osmolality is only measured at T=0 and ranged between 315 to 392 mOsm/kgH$_2$O. The pH for all samples varied less than 0.05 compared to the T=0 values over the course of the study, meaning no significate change is observed over the course of the study (FIG. 71 and FIG. 72).

TABLE 49 pH values, osmolality and peptide concentrations of the verification samples

| Formulation No. | Peptide (mg/ml) | pH | Time (month) | Temp. °C. | Osmolality mOSm/kgH2O | pH | Conc. mg/mL |
|---|---|---|---|---|---|---|---|
| 1 | 2 | 5 | 0 | n.a | 315 | 5.05 | 1.97 |
| 2 | 2 | 6 | 0 | n.a | 392 | 6.07 | 2.00 |
| 3 | 2 | 5.5 | 0 | n.a | 359 | 5.55 | 1.96 |
| 4 | 2 | 5.5 | 0 | n.a | 340 | 5.55 | 1.94 |
| 1 | 2 | 5 | 1 | 5 | n.a | 5.05 | 1.97 |
| 2 | 2 | 6 | 1 | 5 | n.a | 6.08 | 2.00 |
| 3 | 2 | 5.5 | 1 | 5 | n.a | 5.56 | 1.96 |
| 4 | 2 | 5.5 | 1 | 5 | n.a | 5.56 | 1.95 |
| 1 | 2 | 5 | 1 | 25 | n.a | 5.07 | 1.96 |
| 2 | 2 | 6 | 1 | 25 | n.a | 6.11 | 1.99 |
| 3 | 2 | 5.5 | 1 | 25 | n.a | 5.59 | 1.94 |
| 4 | 2 | 5.5 | 1 | 25 | n.a | 5.61 | 1.93 |
| 1 | 2 | 5 | 1 | 40 | n.a | 5.08 | 1.90 |
| 2 | 2 | 6 | 1 | 40 | n.a | 6.11 | 1.94 |
| 3 | 2 | 5.5 | 1 | 40 | n.a | 5.58 | 1.92 |
| 4 | 2 | 5.5 | 1 | 40 | n.a | 5.61 | 1.91 |
| 1 | 2 | 5 | 3 | 5 | n.a | 5.07 | 1.96 |
| 2 | 2 | 6 | 3 | 5 | n.a | 6.10 | 2.08 |
| 3 | 2 | 5.5 | 3 | 5 | n.a | 5.59 | 1.97 |
| 4 | 2 | 5.5 | 3 | 5 | n.a | 5.61 | 1.99 |
| 1 | 2 | 5 | 3 | 25 | n.a | 5.09 | 1.92 |
| 2 | 2 | 6 | 3 | 25 | n.a | 6.14 | 1.92 |
| 3 | 2 | 5.5 | 3 | 25 | n.a | 5.61 | 1.98 |
| 4 | 2 | 5.5 | 3 | 25 | n.a | 5.62 | 1.94 |
| 1 | 2 | 5 | 3 | 40 | n.a | 5.08 | 1.83 |
| 2 | 2 | 6 | 3 | 40 | n.a | 6.05 | 1.87 |
| 3 | 2 | 5.5 | 3 | 40 | n.a | 5.61 | 1.86 |
| 4 | 2 | 5.5 | 3 | 40 | n.a | 5.64 | 1.85 |
| 1 | 2 | 5 | 3* | 5 | n.a | 5.10 | 1.96 |
| 2 | 2 | 6 | 3* | 5 | n.a | 6.16 | 1.99 |
| 3 | 2 | 5.5 | 3* | 5 | n.a | 5.62 | 1.94 |
| 4 | 2 | 5.5 | 3* | 5 | n.a | 5.66 | 1.94 |
| 1 | 2 | 5 | 6 | 5 | n.a | 5.11 | 0.73 |
| 2 | 2 | 6 | 6 | 5 | n.a | 6.12 | 2.03 |
| 3 | 2 | 5.5 | 6 | 5 | n.a | 5.62 | 1.99 |
| 4 | 2 | 5.5 | 6 | 5 | n.a | 5.65 | 1.96 |
| 1 | 2 | 5 | 6 | 25 | n.a | 5.12 | 1.77 |
| 2 | 2 | 6 | 6 | 25 | n.a | 6.17 | 1.98 |
| 3 | 2 | 5.5 | 6 | 25 | n.a | 5.64 | 1.93 |
| 4 | 2 | 5.5 | 6 | 25 | n.a | 5.69 | 1.92 |
| 1 | 2 | 5 | 6* | 5 | n.a | 5.12 | 0.87 |
| 2 | 2 | 6 | 6* | 5 | n.a | 6.14 | 1.99 |
| 3 | 2 | 5.5 | 6* | 5 | n.a | 5.64 | 1.95 |
| 4 | 2 | 5.5 | 6* | 5 | n.a | 5.69 | 1.95 |

*Sample Inverted

Figure 73:
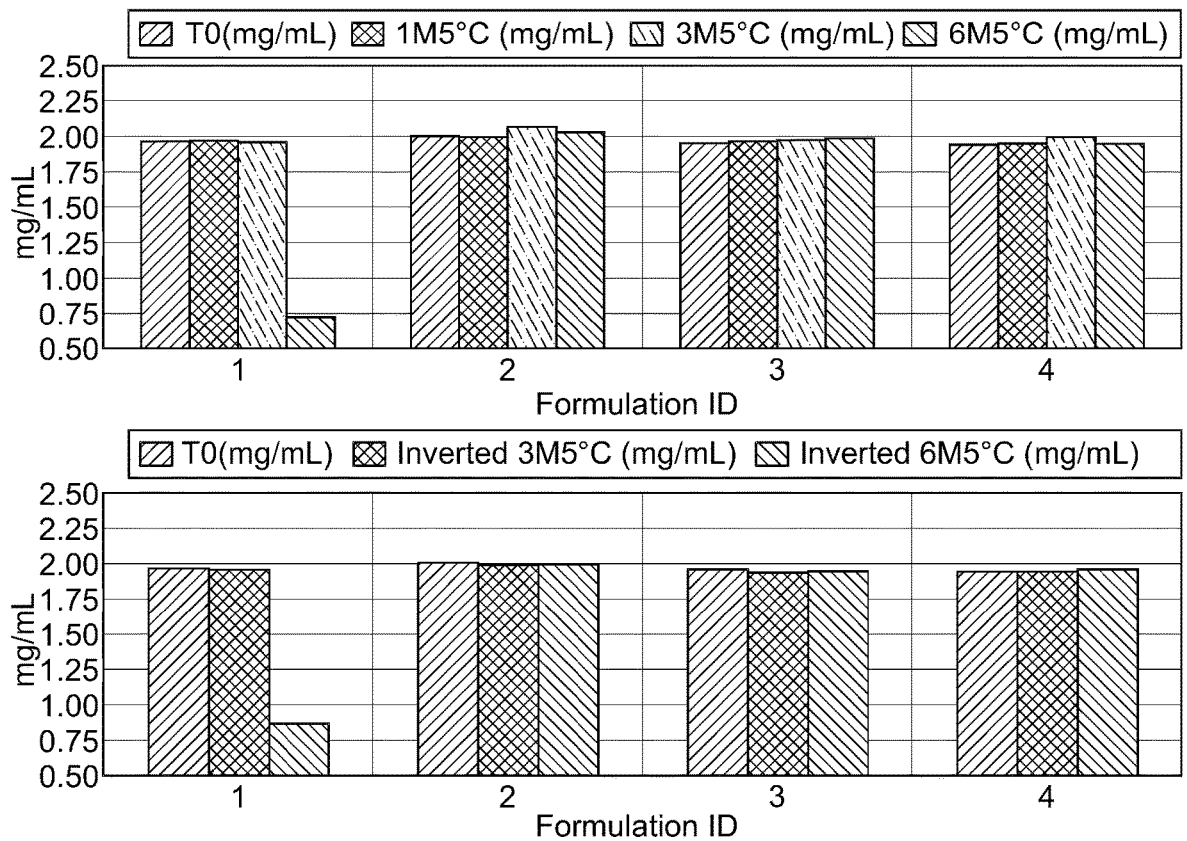
FIG. 73 depicts the peptide concentration measured for the verification sample stored at 5° C. (inverted and non-inverted).
Figure 74:
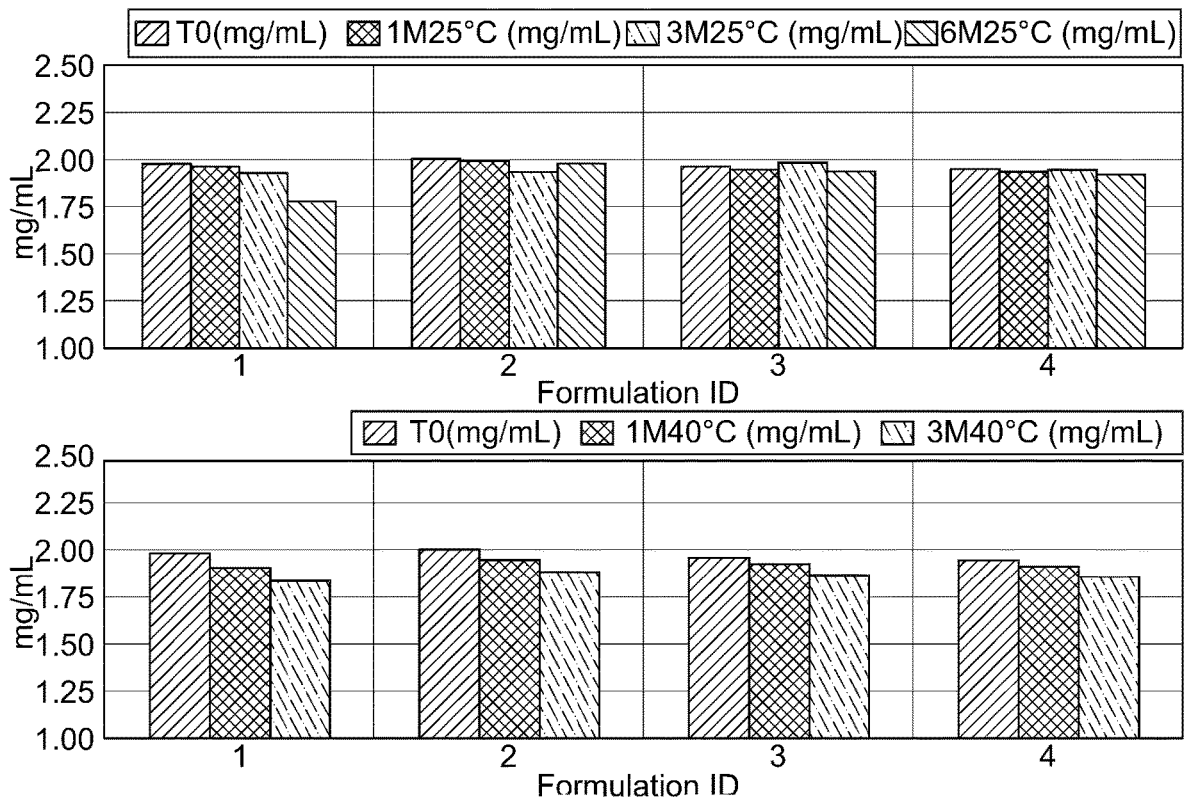
FIG. 74 depicts the peptide concentration measured for the verification samples stored at 25° C. and 40° C.

The peptide concentration for Formulations 2, 3, and 4 at 5° C. changes less than 10% after 6 months at 5° C. (FIG. 73 and FIG. 74). The peptide concentration is decreasing for all formulations when stored at 40° C. over 3 months, which is not observed at 5° C. and 25° C. (FIG. 74). Formulation 1 at 5° C. after 6 months on stability does experience a significate drop in peptide concentration from ~2 mg/mL to ~ 0.8 mg/mL (FIG. 73), unlike the other formulations. The loss of peptide concentration for Formulation 1 at 5° C. appears to be due to the peptide forming a gel at the 6-month timepoint.

Figure 75:
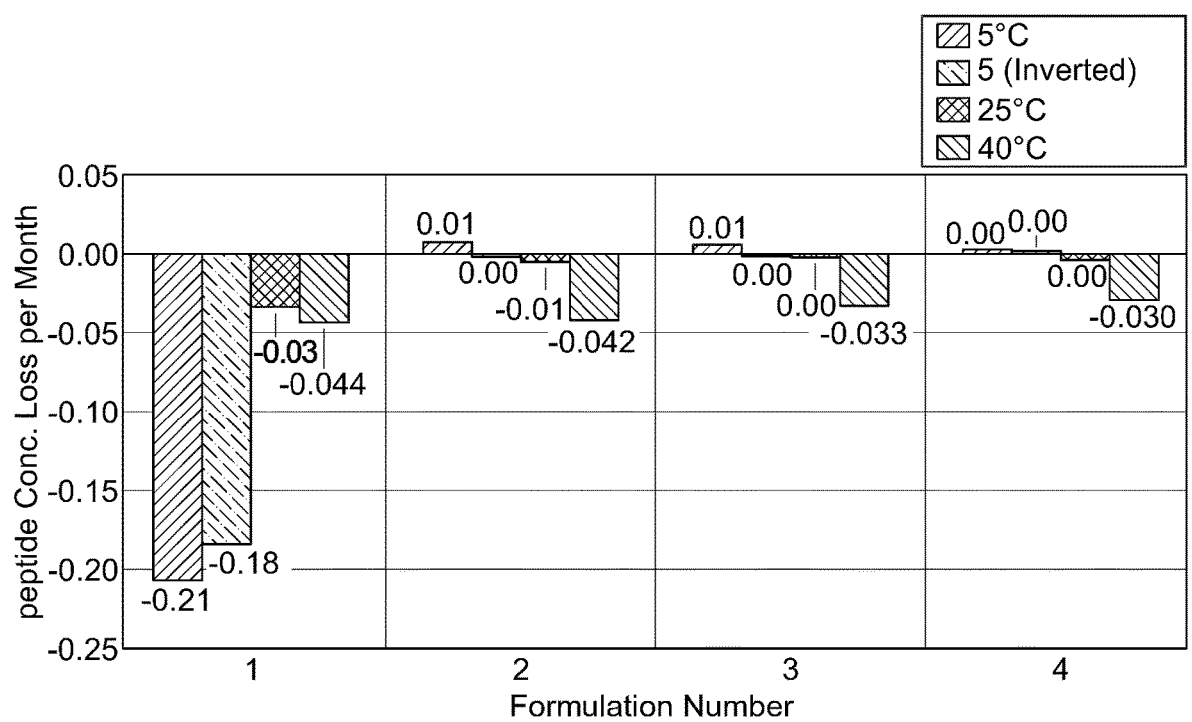
FIG. 75 depicts the peptide concentration loss per month for the verification samples stored at 5° C., 25° C., and 40° C.

When the predicting the loss of peptide concentration per month for the three temperatures, Formulation 1 is losing the most compared to the other formulations (FIG. 75). The peptide concentration for Formulation 4 is predicted to not to change when the peptide was stored at 5° C. and 25° C.

Reverse Phase High Performance Liquid Chromatography (RP-HPLC)

Figure 76:
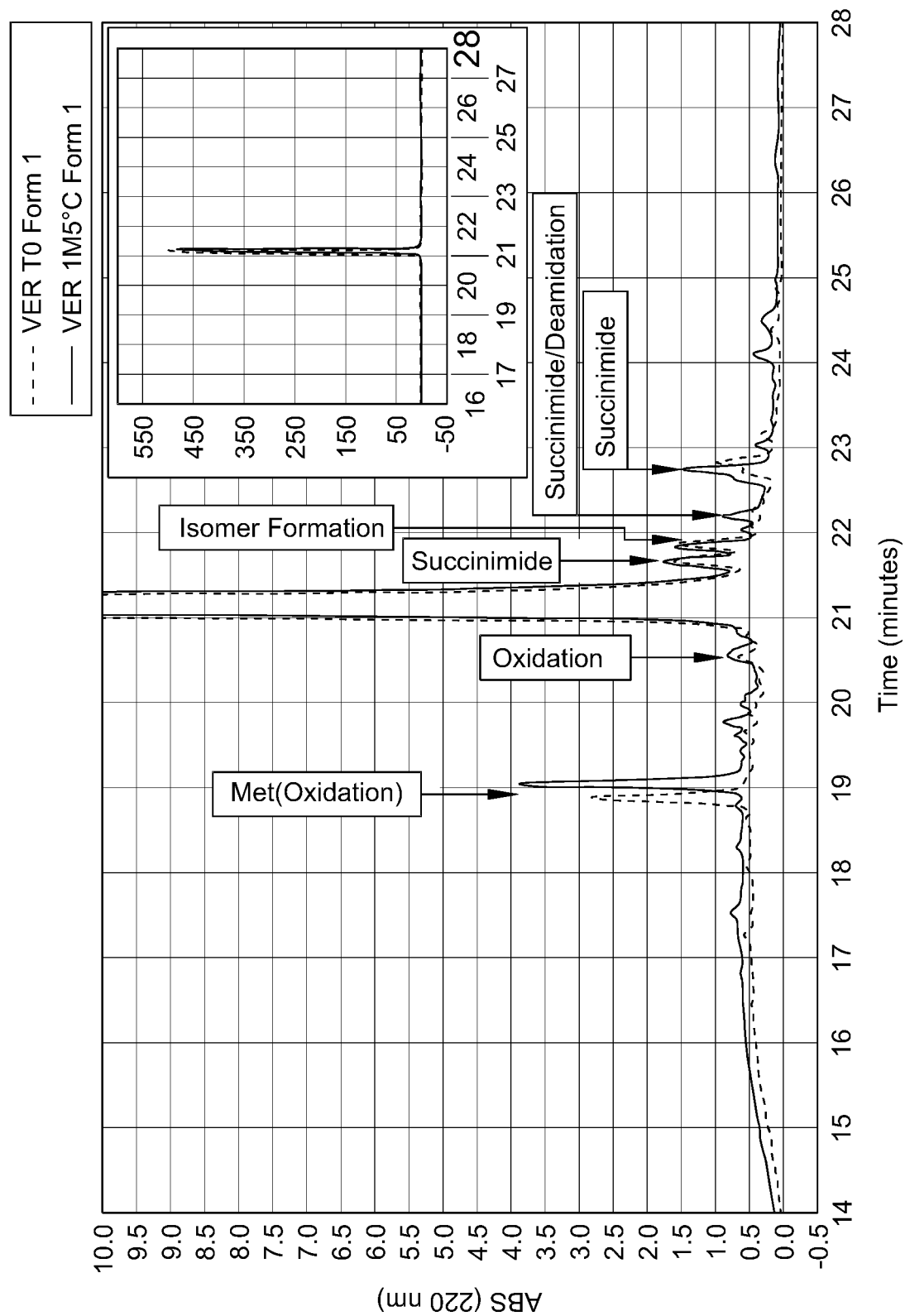
FIG. 76 depicts an exemplary RP-HPLC chromatogram with suggested peak identification.

The reversed phase (RP) HPLC method was developed for conducting the formulation work, as it is able to detect and quantify up a number degradation products (FIG. 76). Thus, it provides a reliable indication of chemical purity of MANP. Briefly, the parameters used for RP-HPLC analysis are as follows:

Column: XSelect CSH, C18, 3.5 μm, 4.6 mm×150 mm, from Waters (Part No. 186005270),
Mobile Phase A: 15% Acetonitrile, 85% Water, 0.1% TFA,
Mobile Phase B: 30% Acetonitrile, 70% Water, 0.1% TFA,
Mobile Phase C: 80% Acetonitrile, 20% Water, 0.1% TFA,
Sample Concentration (mg/mL): 2 mg/mL injected neat,
Autosampler Temp: 8±3° C.,
Column Temp.: 40° C.° C.,
Flow Rate: 0.4 mL/minute,
Injection Vol: 1.25 μL,
UV Setting: 220 nm, and
Data Collection Time: 10 Hz.

TABLE 50

Reversed Phase Mobile Phase Gradients

| Time (Min) | Flow Rate (mL/min) | Mobile Phase B (%) | Mobile Phase C (%) |
|---|---|---|---|
| 0.5 | 0.4 | 10 | 0 |
| 30.0 | 0.4 | 85 | 0 |
| 30.1 | 0.4 | 85 | 0 |
| 40.0 | 0.4 | 0 | 100 |
| 42.0 | 0.4 | 0 | 100 |
| 42.1 | 0.4 | 10 | 0 |
| 45.1 | 0.4 | 10 | 0 |
| 60 | 0.4 | 10 | 0 |

FIG. 76 shows an exemplary reverse phase chromatogram with suggested peak identification. The results of the RP-HPLC analysis of the verification study samples over the course of 6 months are listed in Tables 51-54.

TABLE 51

RP-HPLC data for T = 0 and T = 1 month

| Form. No. | Temp. ° C. | Group Area (mAU * min) | Rel. Area (%) Pre-Peak | | | | | | Rel. Area (%) Main Peak | Rel. Area (%) Post Peak | | | | | | |
|---|---|---|---|---|---|---|---|---|---|---|---|---|---|---|---|---|
| | | | 1 | 2 | 3 (Oxy) | 4 | 5 | 6 | | 1 | 2 | 3 | 4 | 5 | 6 | 7 |
| 1 | n.a | 67.18 | 0.02 | 0.07 | 0.44 | 0.24 | 0.16 | n.a. | 98.06 | 0.00 | 0.30 | 0.27 | 0.23 | 0.15 | 0.04 | 0.03 |
| 2 | n.a | 67.07 | 0.02 | 0.03 | 0.42 | 0.18 | 0.37 | n.a. | 97.95 | 0.00 | 0.38 | 0.11 | 0.30 | 0.04 | 0.04 | 0.17 |
| 3 | n.a | 65.69 | 0.02 | 0.05 | 0.38 | 0.18 | 0.16 | n.a. | 98.18 | 0.00 | 0.31 | 0.25 | 0.23 | 0.15 | 10.05 | 0.04 |
| 4 | n.a | 66.57 | 0.02 | 0.01 | 0.35 | 0.16 | 10.21 | n.a. | 98.16 | 0.00 | 0.33 | 0.27 | 0.27 | 0.13 | 0.04 | 0.05 |

TABLE 52

RP-HPLC data for T = 1 month

| Form. No. | Temp. ° C. | Group Area (mAU * min) | Rel. Area (%) Pre-Peak | | | | | | Rel. Area (%) Main Peak | Rel. Area (%) Post Peak | | | | | | |
|---|---|---|---|---|---|---|---|---|---|---|---|---|---|---|---|---|
| | | | 1 | 2 | 3 (Oxy) | 4 | 5 | 6 | | 1 | 2 | 3 | 4 | 5 | 6 | 7 |
| 1 | 5 | 66.12 | 0.02 | 0.10 | 0.58 | 0.29 | 0.21 | 0.00 | 97.65 | 0.00 | 0.33 | 0.00 | 0.53 | 0.21 | 0.04 | 0.05 |
| 2 | 5 | 67.36 | 0.02 | 0.10 | 1.01 | 0.23 | 0.44 | 0.00 | 96.79 | 0.00 | 0.53 | 0.00 | 0.54 | 0.08 | 0.07 | 0.18 |
| 3 | 5 | 66.48 | 0.02 | 0.10 | 0.51 | 0.30 | 0.23 | 0.00 | 97.70 | 0.00 | 0.33 | 0.00 | 0.49 | 0.20 | 0.04 | 0.07 |
| 4 | 5 | 65.46 | 0.01 | 0.08 | 0.45 | 0.31 | 0.26 | 0.00 | 97.80 | 0.00 | 0.35 | 0.00 | 0.45 | 0.17 | 0.03 | 0.08 |
| 1 | 25 | 66.98 | 0.08 | 0.16 | 0.64 | 0.59 | 0.86 | 0.00 | 93.44 | 1.29 | 1.08 | 0.00 | 0.75 | 0.98 | 0.05 | 0.09 |
| 2 | 25 | 66.80 | 0.17 | 0.08 | 0.69 | 0.39 | 1.18 | 10.77 | 92.13 | 0.00 | 3.58 | 10.00 | 0.68 | 0.14 | 0.06 | 0.14 |
| 3 | 25 | 65.54 | 0.13 | 0.08 | 0.54 | 0.36 | 1.16 | 0.59 | 93.31 | 0.76 | 1.91 | 0.00 | 0.60 | 0.41 | 0.05 | 0.10 |
| 4 | 25 | 63.66 | 0.13 | 0.08 | 0.52 | 0.27 | 1.06 | 0.63 | 93.55 | 0.68 | 2.04 | 0.00 | 0.59 | 0.31 | 0.05 | 0.09 |
| 1 | 40 | 61.79 | 1.76 | 1.05 | 4.87 | 2.67 | 4.92 | 4.73 | 70.09 | 2.81 | 4.32 | 0.00 | 1.21 | 1.44 | 0.10 | 0.03 |
| 2 | 40 | 62.63 | 2.33 | 0.36 | 1.33 | 1.42 | 5.18 | 4.51 | 62.84 | 1.38 | 16.13 | 3.48 | 0.24 | 0.31 | 0.46 | 0.03 |
| 3 | 40 | 65.07 | 0.99 | 0.45 | 0.96 | 0.75 | 5.75 | 5.21 | 72.03 | 1.60 | 10.51 | 0.59 | 0.60 | 0.32 | 0.20 | 0.03 |
| 4 | 40 | 64.01 | 1.60 | 0.30 | 1.08 | 0.74 | 5.26 | 5.01 | 71.38 | 1.50 | 11.01 | 1.57 | 0.27 | 0.20 | 0.05 | 0.04 |

TABLE 53

RP-HPLC data for T = 3 month

| Form. | Temp. °C. | Group Area (mAU * min) | Rel. Area (%) Pre-Peak | | | | | | Rel. Area (%) Main Peak | Rel. Area (%) Post Peak | | | | | | |
|---|---|---|---|---|---|---|---|---|---|---|---|---|---|---|---|---|
| | | | 1 | 2 | 3 (Oxy) | 4 | 5 | 6 | | 1 | 2 | 3 | 4 | 5 | 6 | 7 |
| 1 | 5 | 63.65 | 0.02 | 0.05 | 0.56 | 0.32 | 0.00 | 0.26 | 97.28 | 0.00 | 0.39 | 10.22 | 0.38 | 0.34 | 0.04 | 0.14 |
| 2 | 5 | 68.10 | 0.05 | 0.09 | 1.25 | 0.35 | 0.51 | 0.00 | 96.04 | 0.00 | 0.76 | 0.08 | 0.47 | 0.10 | 0.07 | 0.23 |
| 3 | 5 | 67.31 | 0.05 | 0.10 | 0.52 | 0.29 | 0.29 | 0.00 | 97.43 | 0.00 | 0.16 | 10.42 | 0.30 | 0.24 | 0.04 | 0.15 |
| 4 | 5 | 65.44 | 0.04 | 0.06 | 0.45 | 0.24 | 0.31 | 0.00 | 97.62 | 0.00 | 0.44 | 0.14 | 0.29 | 0.20 | 0.04 | 0.18 |
| 1 | 25 | 65.12 | 0.38 | 0.23 | 0.67 | 0.60 | 2.30 | 0.00 | 88.88 | 1.97 | 2.76 | 0.12 | 0.75 | 1.18 | 0.07 | 0.11 |
| 2 | 25 | 66.03 | 0.98 | 0.26 | 0.87 | 0.81 | 2.26 | 2.48 | 81.99 | 0.00 | 8.59 | 0.00 | 1.03 | 0.19 | 0.36 | 0.17 |
| 3 | 25 | 65.91 | 0.48 | 0.15 | 0.58 | 0.50 | 2.52 | 2.30 | 86.35 | 1.06 | 4.69 | 0.10 | 0.68 | 0.41 | 0.09 | 0.12 |
| 4 | 25 | 64.05 | 0.48 | 0.15 | 0.61 | 0.53 | 2.35 | 2.27 | 86.31 | 0.97 | 4.95 | 0.10 | 0.75 | 0.27 | 0.13 | 0.14 |
| 1 | 40 | 61.00 | 5.78 | 3.56 | 4.73 | 7.40 | 9.47 | 11.30 | 42.58 | 3.90 | 7.78 | 0.51 | 1.68 | 0.97 | 0.33 | 0.00 |
| 2 | 40 | 55.88 | 4.02 | 0.77 | 1.95 | 4.12 | 6.16 | 10.42 | 29.96 | 5.94 | 25.55 | 0.00 | 8.23 | 1.12 | 1.64 | 0.12 |
| 3 | 40 | 60.03 | 3.23 | 0.86 | 1.66 | 3.52 | 8.74 | 12.23 | 41.83 | 4.63 | 18.80 | 0.65 | 2.53 | 0.43 | 0.89 | 0.00 |
| 4 | 40 | 59.95 | 3.58 | 1.04 | 1.91 | 3.73 | 7.84 | 11.66 | 40.15 | 4.50 | 19.08 | 0.97 | 4.27 | 0.32 | 0.94 | 0.00 |
| 1 | 5* | 66.96 | 0.03 | 0.02 | 0.53 | 0.35 | 0.27 | 0.00 | 97.38 | 0.00 | 0.39 | 0.21 | 0.34 | 0.29 | 0.03 | 0.14 |
| 2 | 5* | 67.10 | 0.03 | 0.11 | 0.85 | 0.30 | 0.00 | 0.47 | 96.59 | 0.00 | 0.74 | 0.07 | 0.43 | 0.11 | 0.07 | 0.23 |
| 3 | 5* | 65.65 | 0.05 | 0.06 | 0.47 | 0.25 | 0.29 | 0.00 | 97.51 | 0.00 | 0.42 | 0.17 | 0.32 | 0.24 | 0.05 | 0.17 |
| 4 | 5* | 65.90 | 0.03 | 0.06 | 0.46 | 0.24 | 0.33 | 0.00 | 97.46 | 0.00 | 0.46 | 0.17 | 0.35 | 0.23 | 0.05 | 0.17 |

TABLE 54

RP-HPLC data for T = 6 month

| Form. | Temp. °C. | Group Area (mAU * min) | Rel. Area (%) Pre-Peak | | | | | | Rel. Area (%) Main Peak | Rel. Area (%) Post Peak | | | | | | |
|---|---|---|---|---|---|---|---|---|---|---|---|---|---|---|---|---|
| | | | 1 | 2 | 3 (Oxy) | 4 | 5 | 6 | | 1 | 2 | 3 | 4 | 5 | 6 | 7 |
| 1 | 5 | 22.55 | 0.04 | 0.07 | 0.66 | 0.61 | 0.99 | n.a. | 93.53 | 0.99 | 1.12 | 0.42 | 0.76 | 0.74 | 0.02 | 0.04 |
| 2 | 5 | 67.08 | 0.06 | 0.07 | 1.16 | 0.23 | 0.59 | n.a. | 95.76 | n.a. | 1.23 | 0.05 | 0.47 | 0.12 | 0.06 | 0.20 |
| 3 | 5 | 67.62 | 0.05 | 0.04 | 0.48 | 0.27 | 0.49 | n.a. | 96.90 | n.a. | 0.69 | 0.14 | 0.42 | 0.33 | 0.05 | 0.13 |
| 4 | 5 | 65.37 | 0.03 | 0.03 | 0.49 | 0.27 | 0.53 | n.a. | 96.98 | n.a. | 0.71 | 0.11 | 0.39 | 0.25 | 0.04 | 0.17 |
| 1 | 25 | 57.87 | 1.51 | n.a. | 0.87 | 1.17 | 4.96 | 5.14 | 76.64 | 2.33 | 4.96 | 0.60 | 0.63 | 1.09 | 0.08 | n.a. |
| 2 | 25 | 61.90 | 1.45 | 0.19 | 1.18 | 1.07 | 3.77 | 4.94 | 68.70 | 1.17 | 15.65 | 0.20 | 1.28 | 0.15 | 0.16 | 0.08 |
| 3 | 25 | 64.31 | 0.93 | 0.19 | 0.70 | 0.50 | 4.98 | 5.44 | 75.38 | 1.38 | 8.91 | 0.14 | 0.86 | 0.43 | 0.09 | 0.06 |
| 4 | 25 | 62.55 | 1.35 | 0.18 | 0.82 | 0.58 | 4.48 | 5.10 | 75.09 | 1.27 | 9.42 | 0.18 | 1.02 | 0.42 | n.a. | 0.09 |
| 1 | 5* | 28.02 | 0.06 | 0.06 | 0.54 | 0.52 | 0.80 | n.a. | 94.49 | 0.97 | 0.93 | 0.33 | 0.65 | 0.66 | n.a. | n.a. |
| 2 | 5* | 67.99 | 0.05 | 0.09 | 0.85 | 0.37 | 0.65 | n.a. | 95.87 | n.a. | 1.23 | 0.07 | 0.49 | 0.11 | 0.05 | 0.17 |
| 3 | 5* | 65.45 | 0.08 | 0.01 | 0.46 | 0.19 | 0.40 | 0.06 | 97.18 | n.a. | 0.65 | 0.11 | 0.30 | 0.37 | 0.04 | 0.15 |
| 4 | 5* | 66.67 | 0.04 | 0.01 | 0.47 | 0.23 | 0.49 | n.a. | 97.05 | n.a. | 0.71 | 0.11 | 0.42 | 0.27 | 0.05 | 0.14 |

*Sample Inverted

Figure 77:
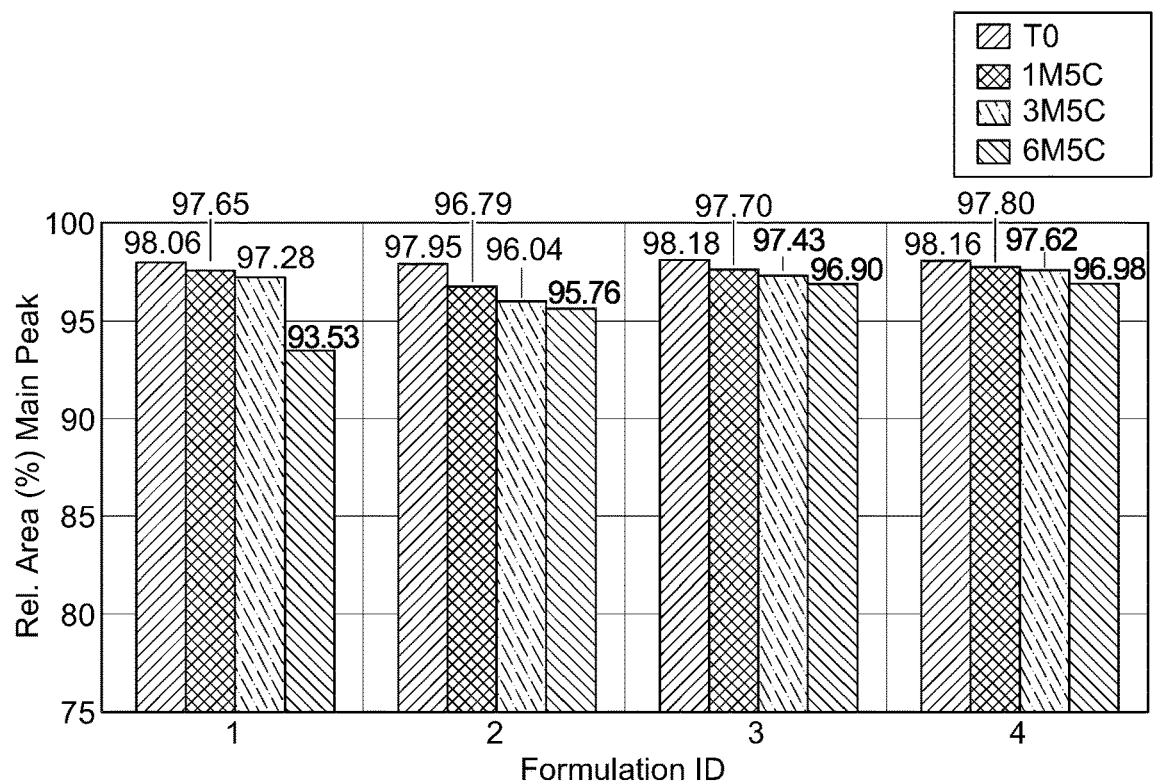
FIG. 77 depicts the relative areas of the main peak for verification samples stored at 5° C. over time, as measured by RP-HPLC (non-inverted).
Figure 78:
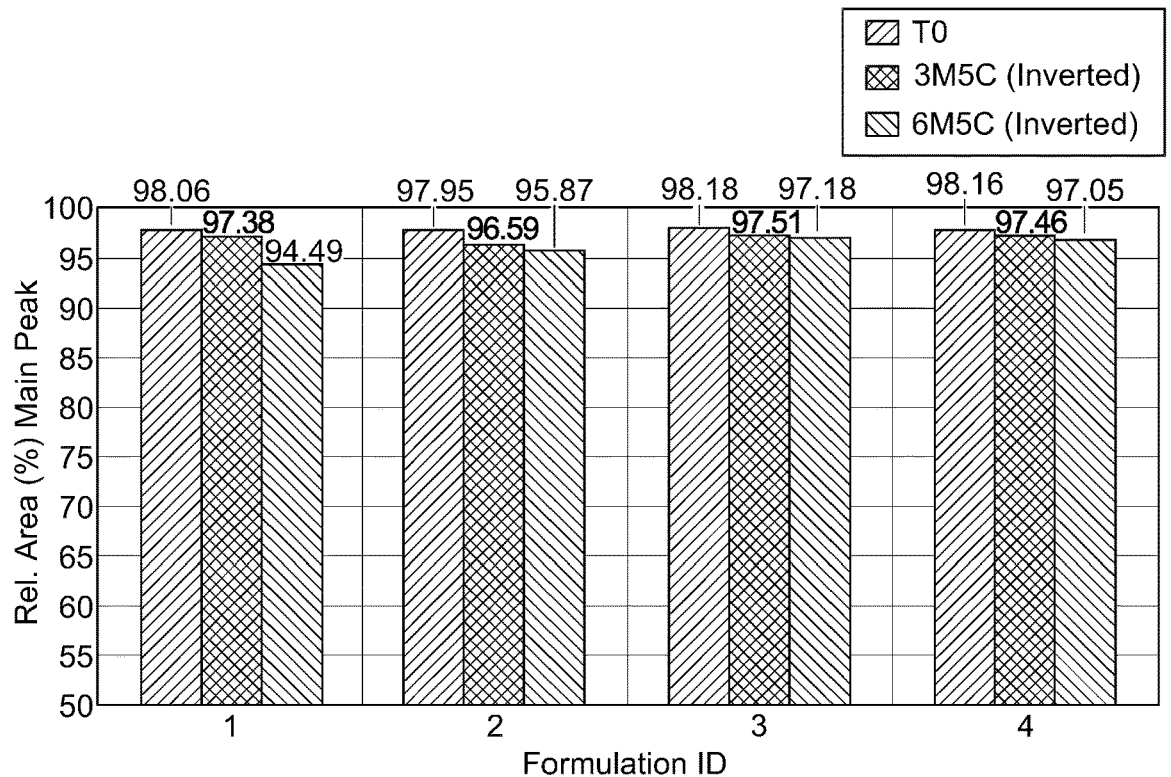
FIG. 78 depicts the relative areas of the main peak for verification samples stored at 5° C. over time, as measured by RP-HPLC (inverted).
Figure 79:
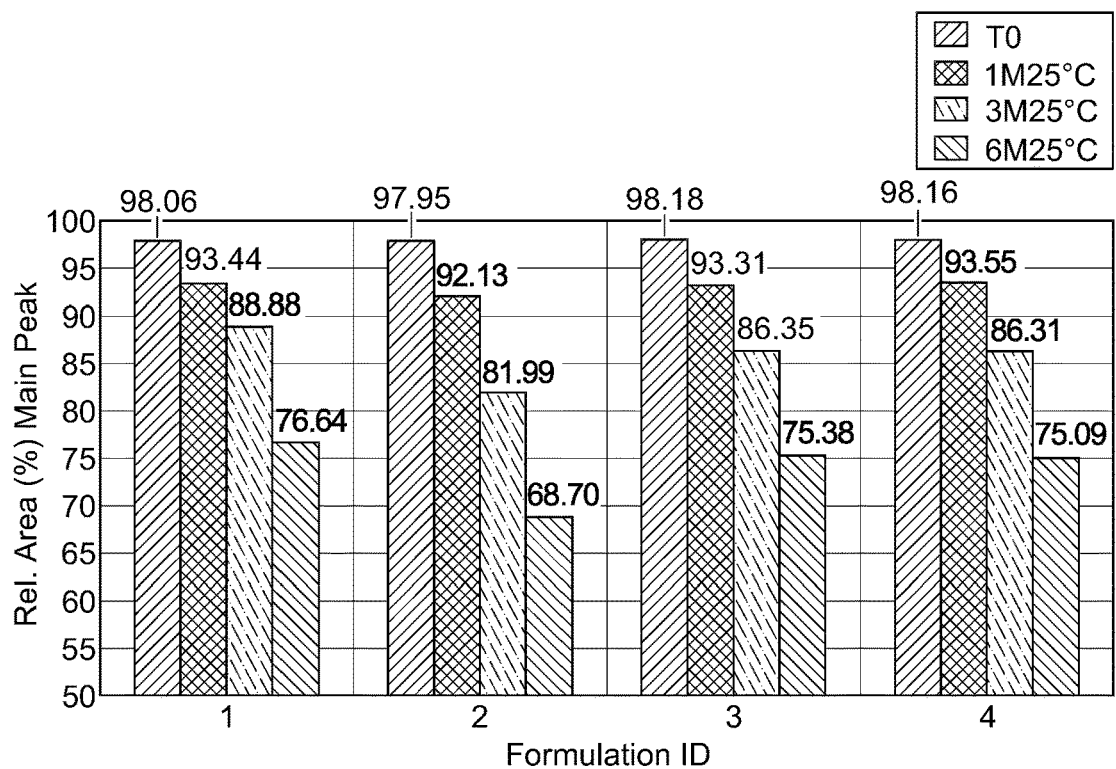
FIG. 79 depicts the relative areas of the main peak for verification samples stored at 25° C. over time, as measured by RP-HPLC (non-inverted).
Figure 80:
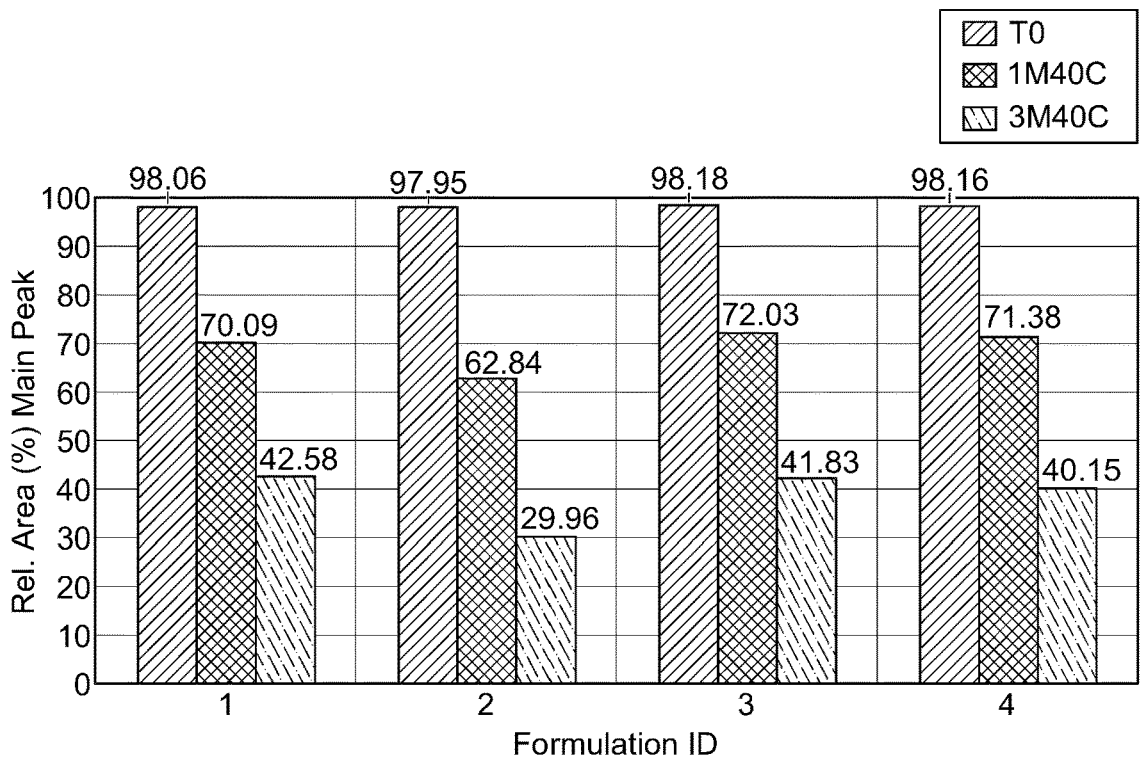
FIG. 80 depicts the relative areas of the main peak for verification samples stored at 40° C. over time, as measured by RP-HPLC (non-inverted).

The results show that over the course of 6 months at 5° C., Formulation 4 is losing 0.18% of the main peak per month (the best performing) compared to Formulation 1 which is losing 0.74% per month (least stable formulation) (FIG. 77). Similar results are observed when the samples are inverted (FIG. 78). The loss of the relative area of the main peak increases to 3.5 to 4% when the samples are stored at 25° C. (FIG. 79). When the samples are stored at 40° C., the loss of the relative area of the main peak increases to 18 to 22% (FIG. 80).

Figure 81:
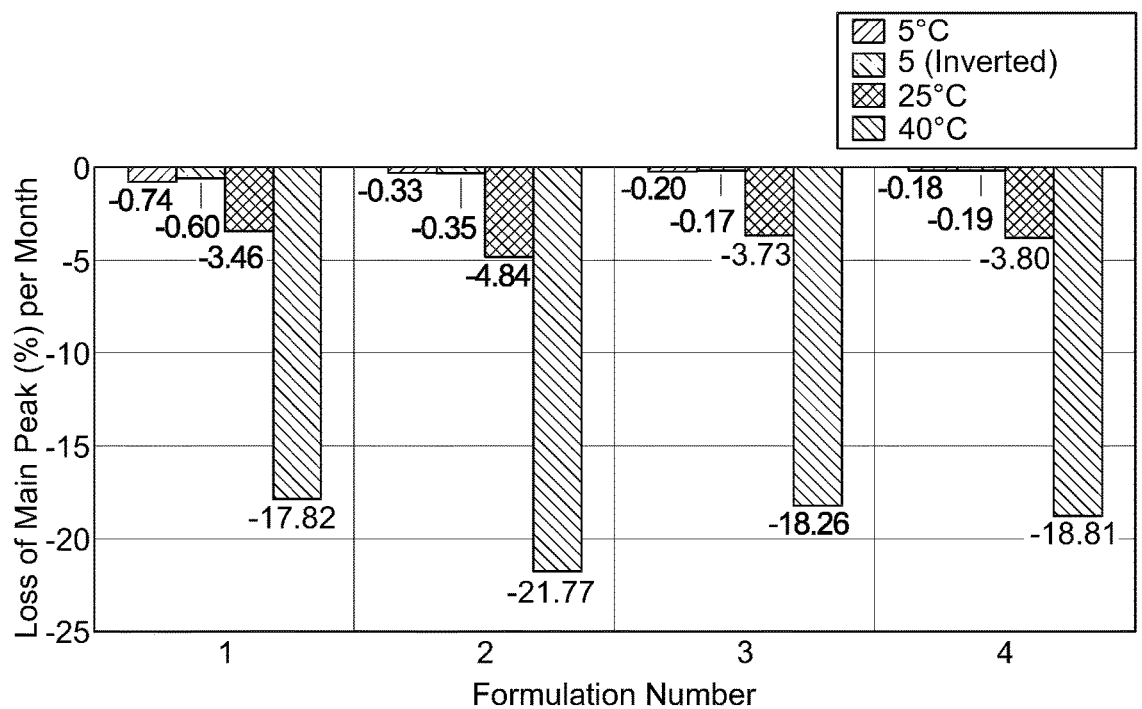
FIG. 81 depicts the change per month of relative areas of the main peak for verification samples at different temperatures, as measured by RP-HPLC.
Figure 82:
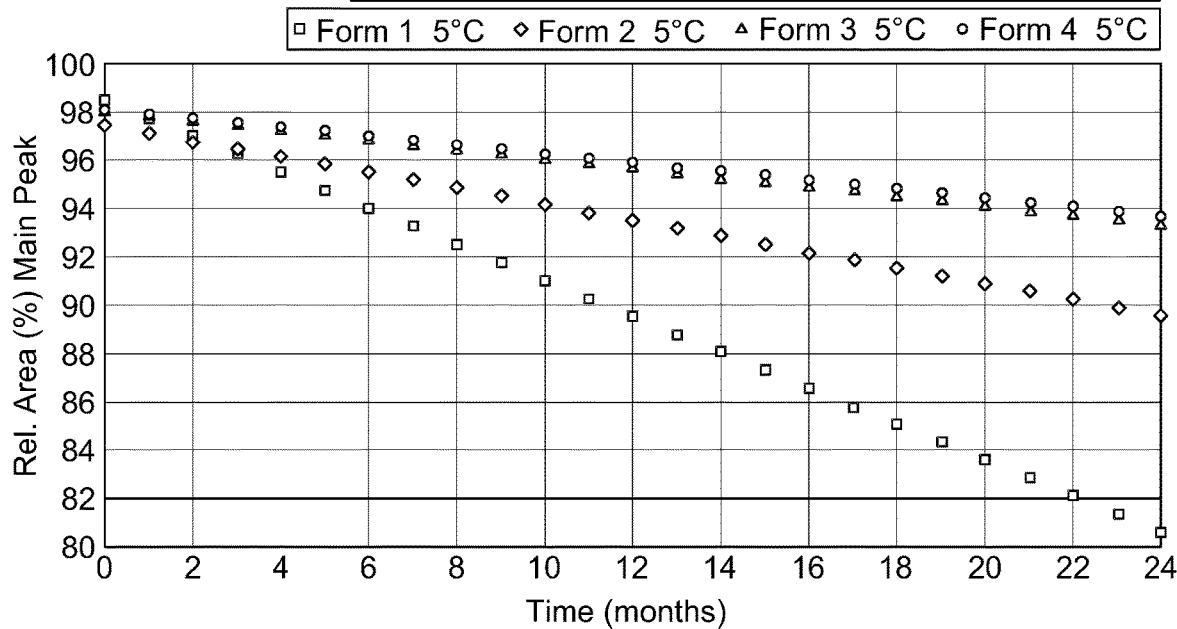
FIG. 82 depicts the predicted change per month of relative areas of the main peak for verification samples stored at 5° C., as measured by RP-HPLC (non-inverted).
Figure 83:
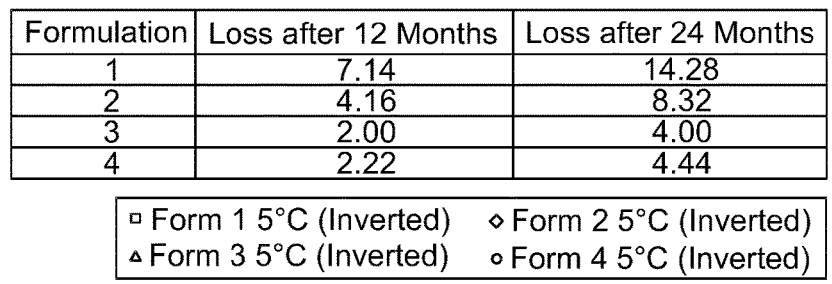
FIG. 83 depicts the predicted change per month of relative areas of the main peak for verification samples stored at 5° C., as measured by RP-HPLC (inverted).
Figure 83:
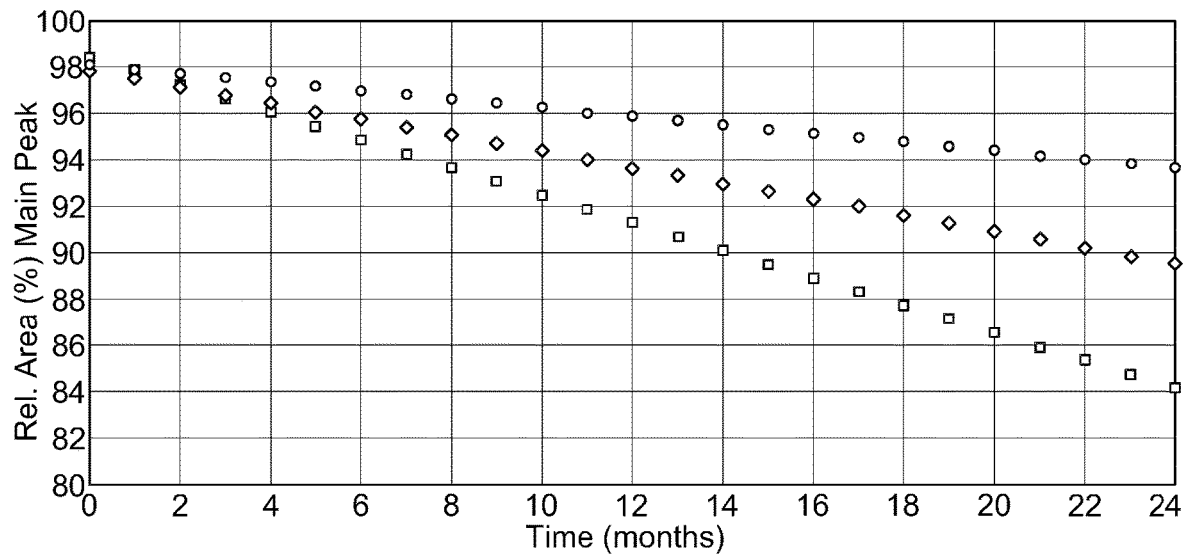
Figure 84:
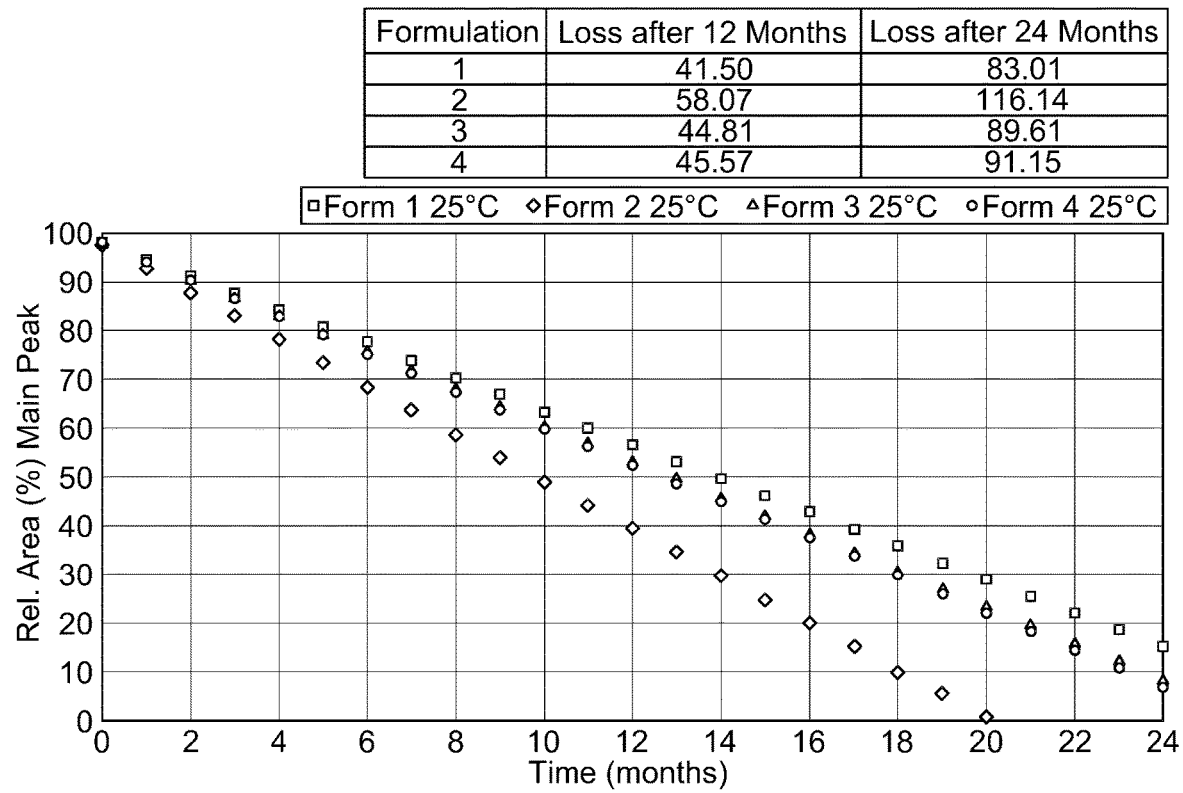
FIG. 84 depicts the predicted change per month of relative areas of the main peak for verification samples stored at 25° C., as measured by RP-HPLC.
Figure 85:
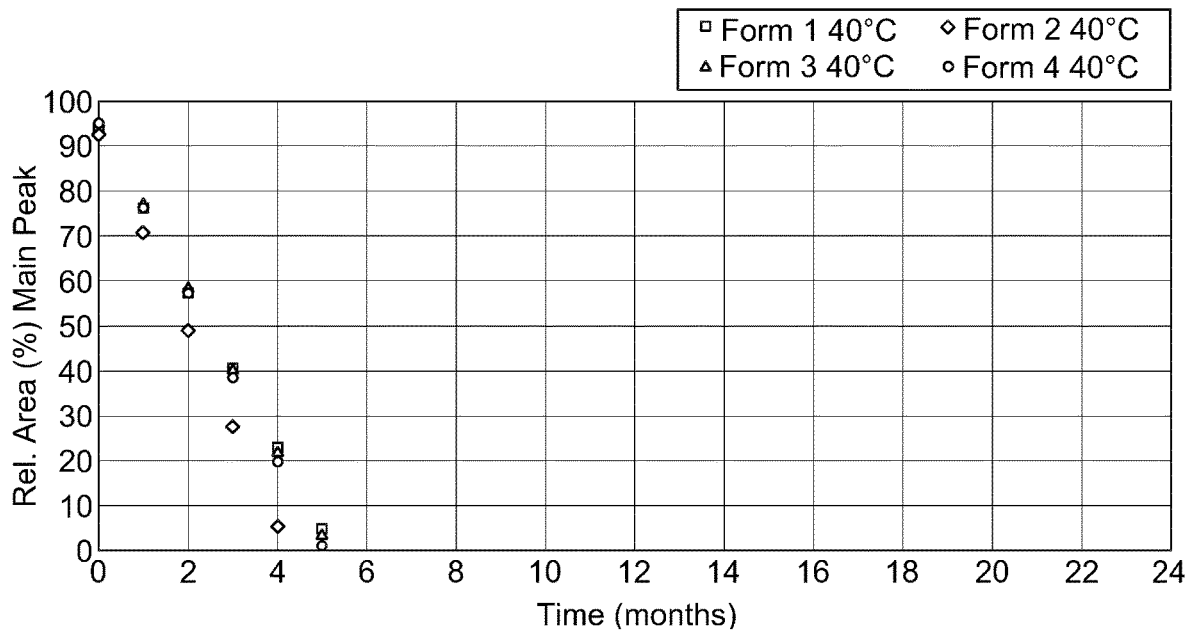
FIG. 85 depicts the predicted change per month of relative areas of the main peak for verification samples stored at 40° C., as measured by RP-HPLC.
Figure 86:
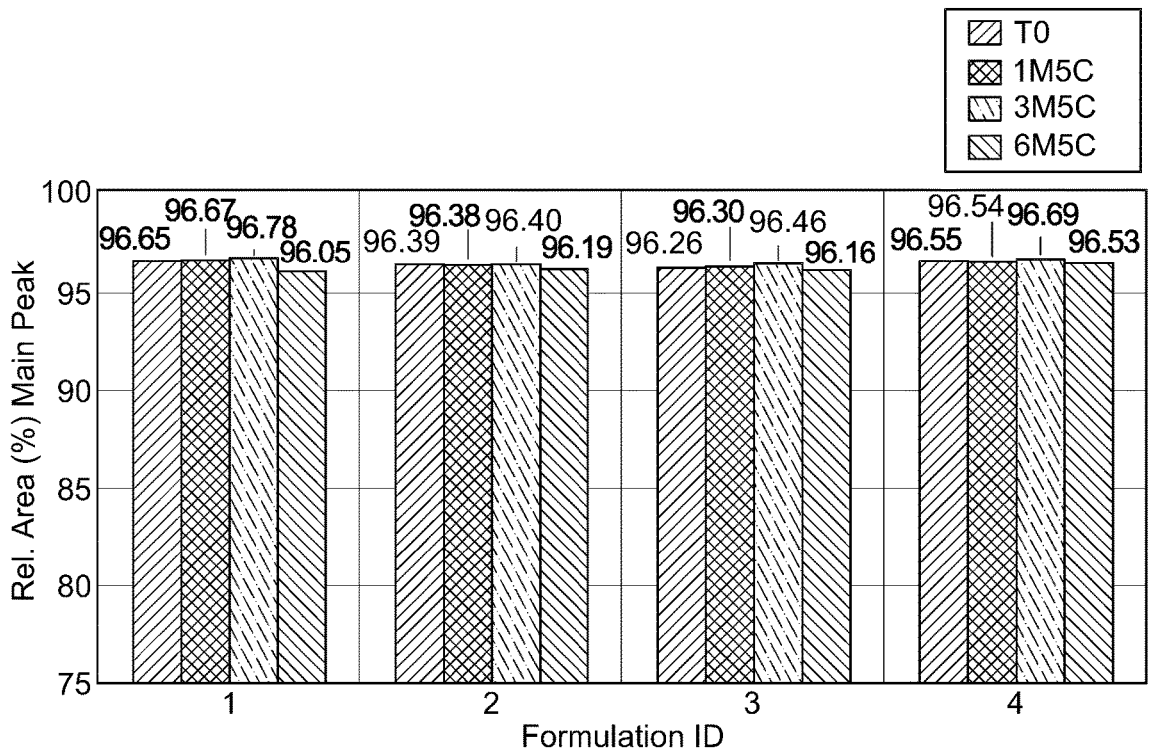
FIG. 86 depicts the relative areas of the main peak for verification samples stored at 5° C. over time, as measured by SEC (non-inverted).
Figure 87:
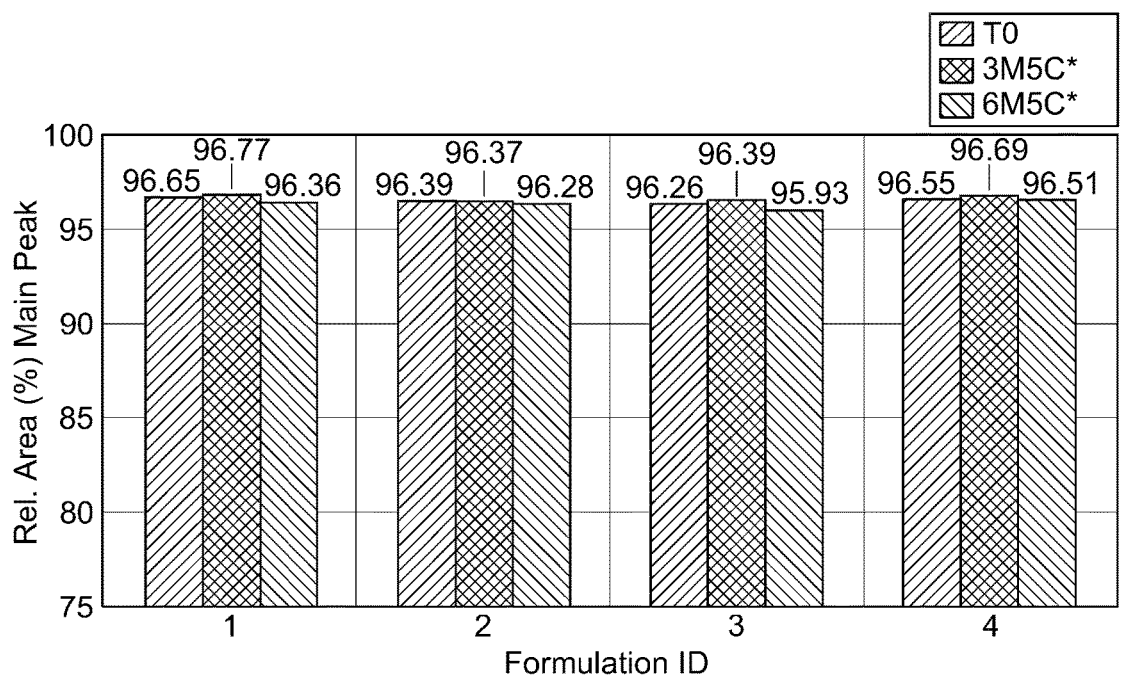
FIG. 87 depicts the relative areas of the main peak for verification samples stored at 5° C. over time, as measured by SEC (inverted).
Figure 88:
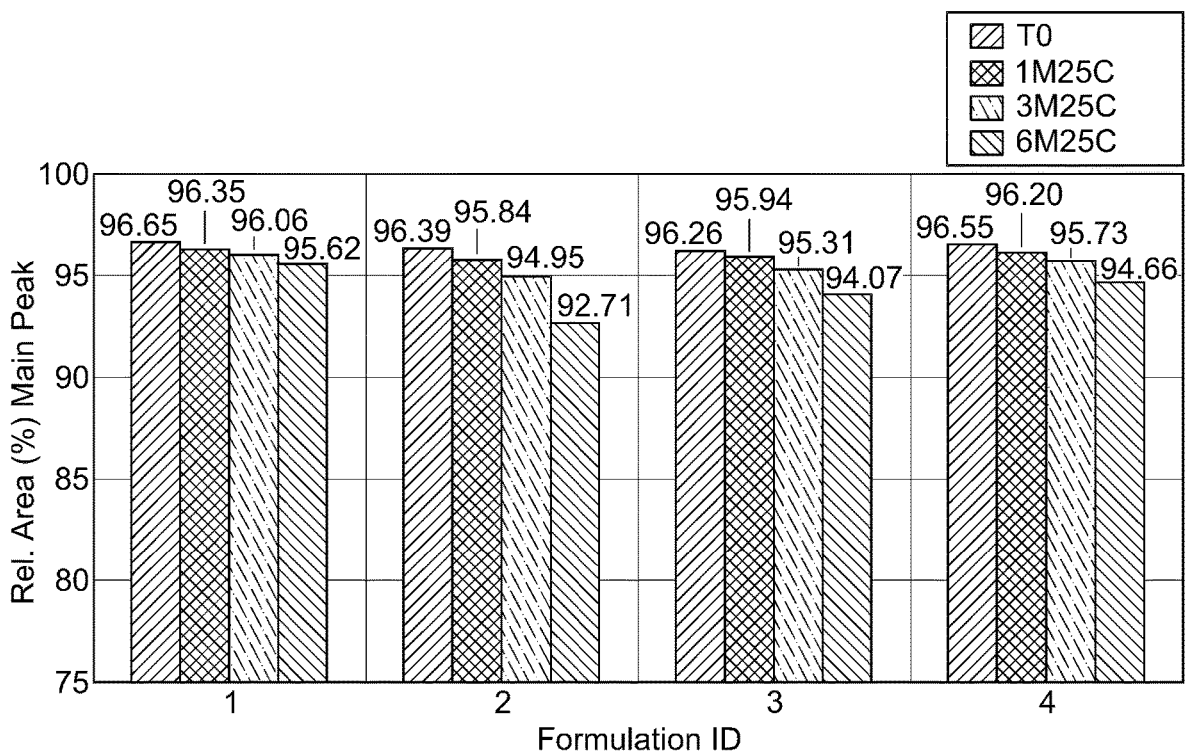
FIG. 88 depicts the relative areas of the main peak for verification samples stored at 25° C. over time, as measured by SEC (non-inverted).
Figure 89:
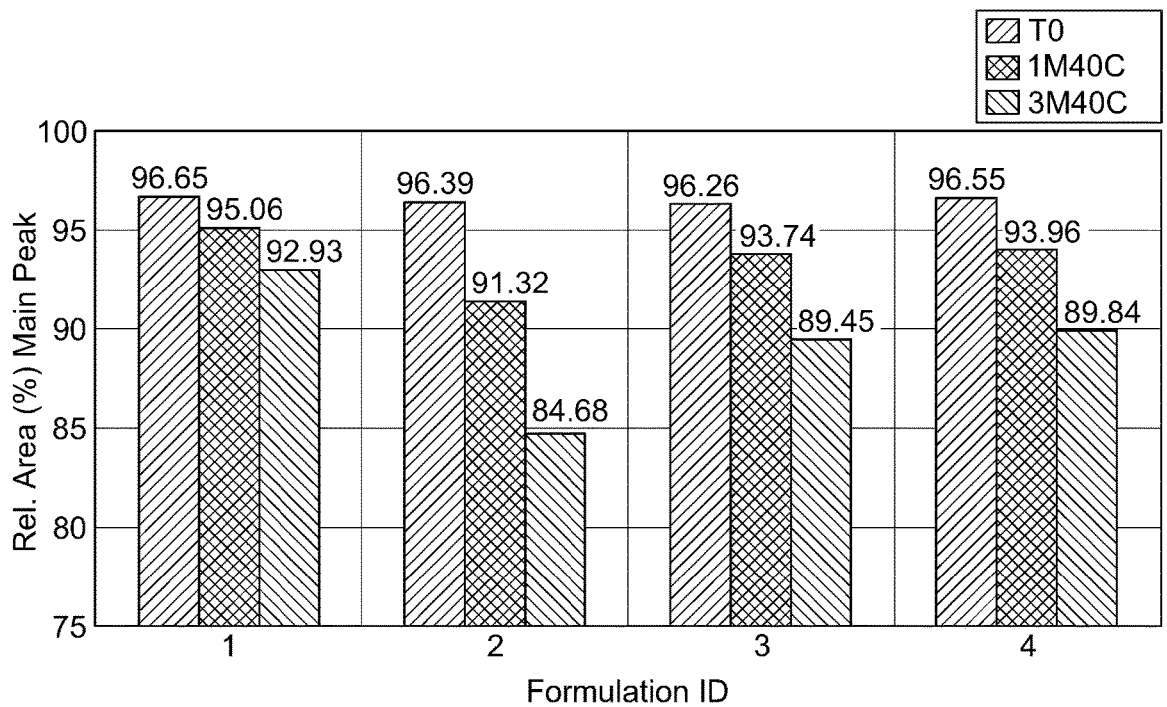
FIG. 89 depicts the relative areas of the main peak for verification samples stored at 40° C. over time, as measured by SEC (non-inverted).

FIG. 81 shows the predicted loss of main peak per month. When predicting the relative area of the main peak at 12 months at 5° C. by RP-HPLC, Formulation 1 has lost 8.93% (FIG. 82). By comparison, the loss for Formulation 4 after 12 months is only 2.21%. Formulation 3 is only slightly less stable than this, based on the RP-HPLC data at 5° C. Storing the vials in the inverted position does not change the estimated degradation rates appreciably (FIG. 83). Degradation of these most stable formulation increases dramatically (more than 20-fold) at 25° C. (FIG. 84). Degradation of these most stable formulation also increases dramatically at 40° C. (FIG. 85).

Size Exclusion Chromatography

Figure 90:
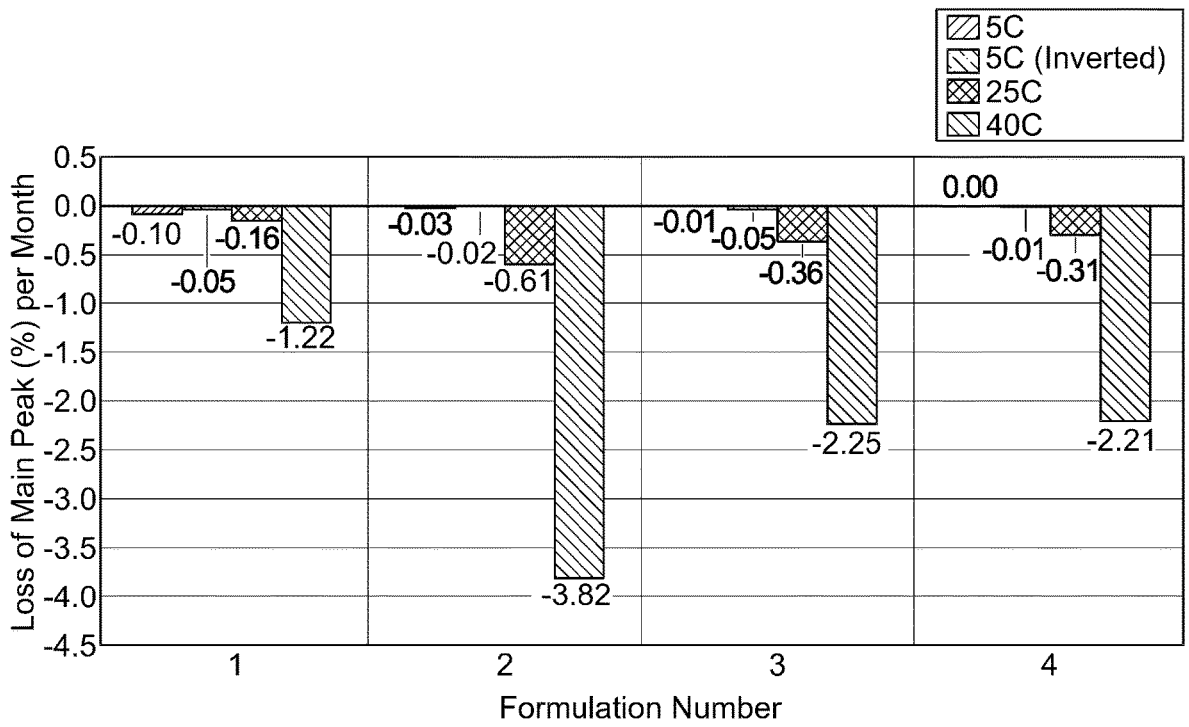
FIG. 90 depicts the change per month of relative areas of the main peak for verification samples at different temperatures, as measured by SEC.
Figure 91:
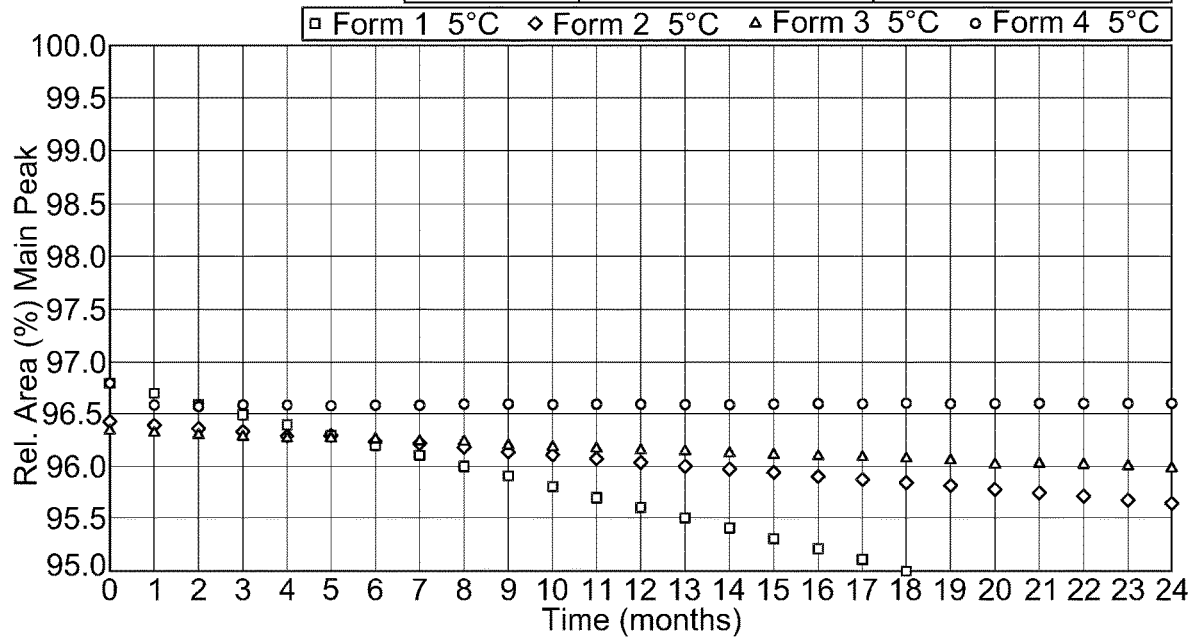
FIG. 91 depicts the predicted change per month of relative areas of the main peak for verification samples stored at 5° C., as measured by SEC (non-inverted).
Figure 92:
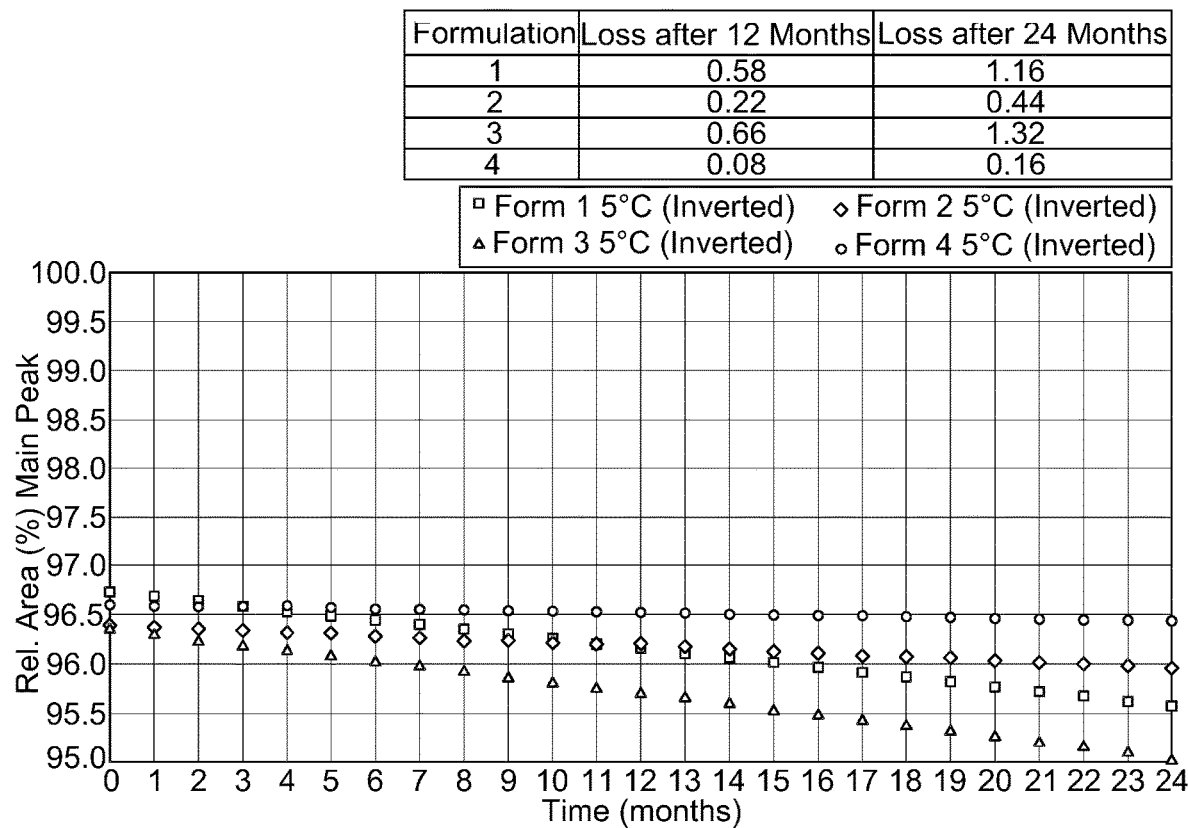
FIG. 92 depicts the predicted change per month of relative areas of the main peak for verification samples stored at 5° C., as measured by SEC (inverted).
Figure 93:
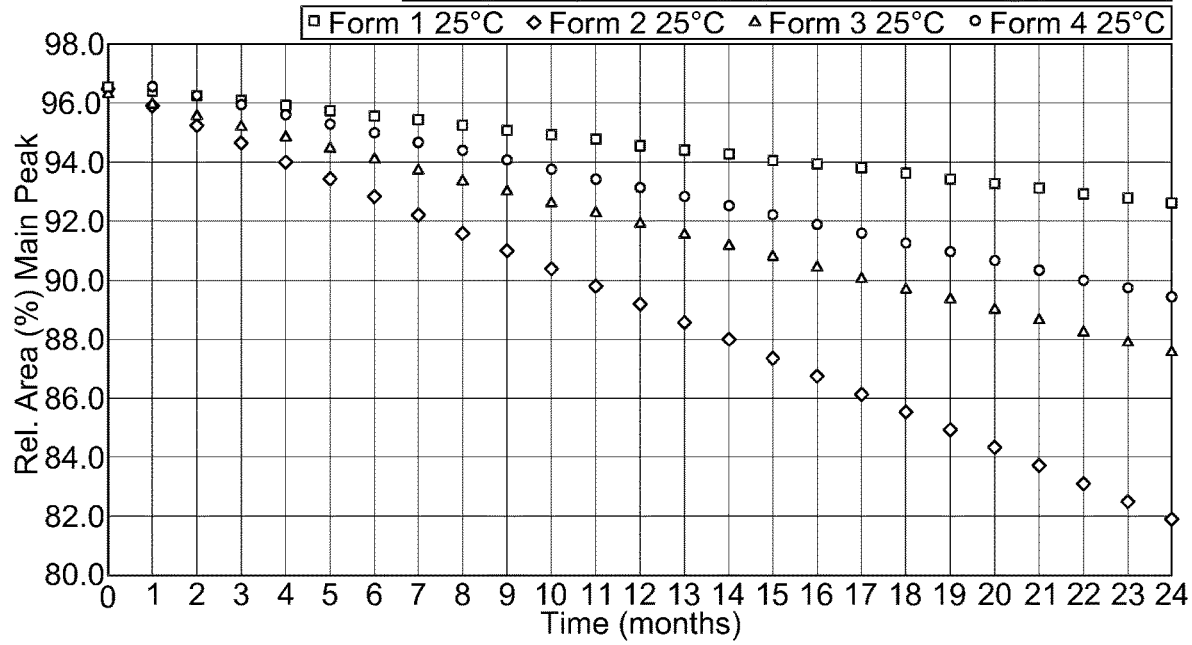
FIG. 93 depicts the predicted change per month of relative areas of the main peak for verification samples stored at 25° C., as measured by SEC.
Figure 94:
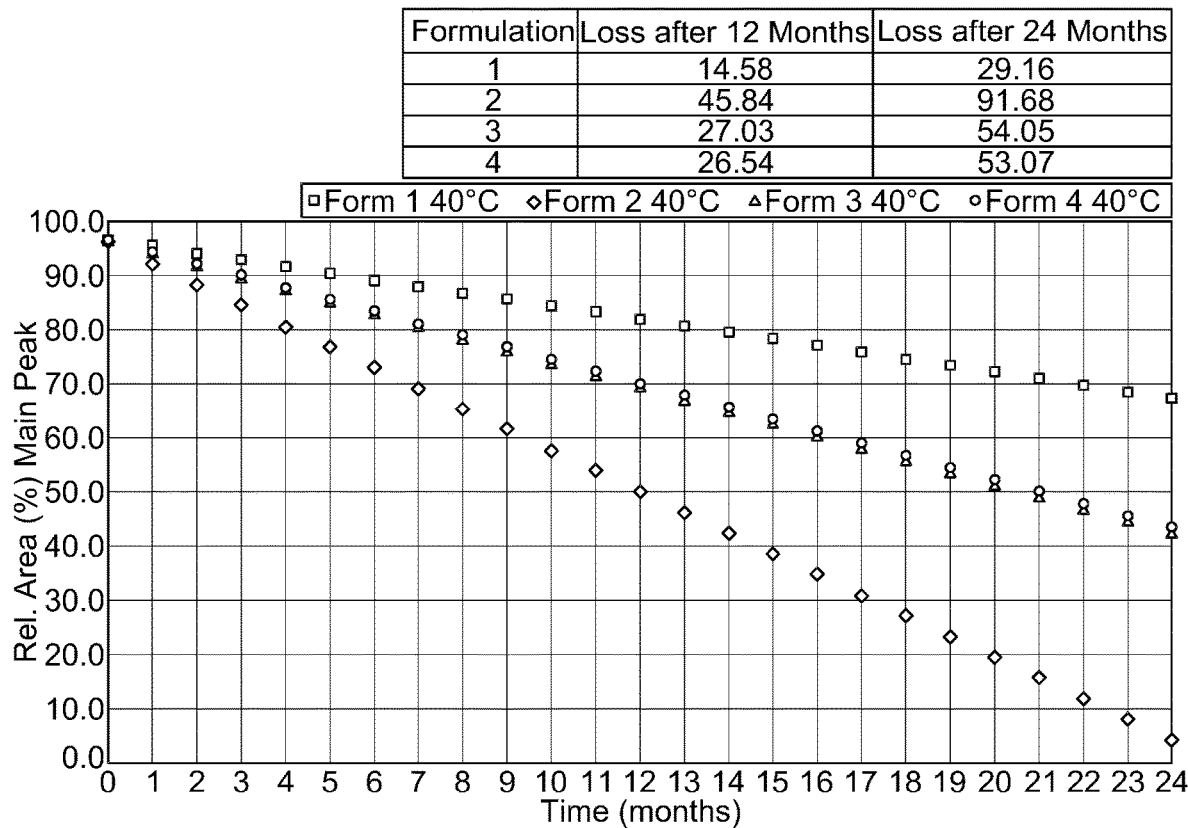
FIG. 94 depicts the predicted change per month of relative areas of the main peak for verification samples stored at 40° C., as measured by SEC.

Stability is also monitored using SEC, although the formulation screening clearly indicates that the primary degradation processes are related to chemical instability. The higher molecular weight (HMW) species, labeled as the pre-peak in SEC, is ≤0.50% at T0 (Table 55). After six months at 5° C., none of the formulations exhibits HMW levels ≥0.50% (Table 57). Graphical descriptions of the monomer loss by SEC under different storage conditions are shown in FIGS. 86-89. Based on these results, the loss per month is estimated at different storage temperatures (FIG. 90). From these data, it appears that Formulation 1 is the least stable and Formulation 4 is the most stable, especially when held at 5° C. (FIGS. 91-94).

TABLE 55

Size Exclusion Chromatography Data for T = 0 and T = 1 month

| Form. | Time (Months) | Temp. ° C. | Group Area (mAU * min) | Rel. Area (%) Pre Peaks | Rel. Area (%) Main Peak | Rel. Area (%) Post Peaks |
|---|---|---|---|---|---|---|
| 1 | 0 | n.a. | 99.163 | 0.27 | 96.65 | 3.08 |
| 2 | 0 | n.a | 104.085 | 0.50 | 96.39 | 3.12 |
| 3 | 0 | n.a | 104.437 | 0.30 | 96.26 | 3.44 |
| 4 | 0 | n.a | 102.186 | 0.29 | 96.55 | 3.16 |
| 1 | 1 | 5 | 102.378 | 0.27 | 96.67 | 3.05 |
| 2 | 1 | 5 | 102.694 | 0.48 | 96.38 | 3.14 |
| 3 | 1 | 5 | 101.017 | 0.30 | 96.30 | 3.40 |
| 4 | 1 | 5 | 101.275 | 0.31 | 96.54 | 3.15 |
| 1 | 1 | 25 | 100.942 | 0.43 | 96.35 | 3.21 |
| 2 | 1 | 25 | 102.433 | 0.59 | 95.84 | 3.57 |
| 3 | 1 | 25 | 102.411 | 0.41 | 95.94 | 3.65 |
| 4 | 1 | 25 | 99.105 | 0.37 | 96.20 | 3.43 |
| 1 | 1 | 40 | 98.682 | 0.83 | 95.06 | 4.12 |
| 2 | 1 | 40 | 101.862 | 2.02 | 91.32 | 6.66 |
| 3 | 1 | 40 | 100.943 | 0.87 | 93.74 | 5.39 |
| 4 | 1 | 40 | 99.932 | 0.80 | 93.96 | 5.24 |

TABLE 56

Size Exclusion Chromatography Data for T = 3 months

| Form. | Time (Months) | Temp. ° C. | Group Area (mAU * min) | Rel. Area (%) Pre Peak | Rel. Area (%) Main Peak | Rel. Area (%) Post Peak |
|---|---|---|---|---|---|---|
| 1 | 3 | 5 | 130.54 | 0.33 | 96.78 | 2.88 |
| 2 | 3 | 5 | 138.90 | 0.47 | 96.40 | 3.13 |
| 3 | 3 | 5 | 134.68 | 0.37 | 96.46 | 3.17 |
| 4 | 3 | 5 | 135.66 | 0.37 | 96.69 | 2.95 |
| 1 | 3 | 25 | 135.19 | 0.57 | 96.06 | 3.37 |
| 2 | 3 | 25 | 132.49 | 0.77 | 94.95 | 4.28 |
| 3 | 3 | 25 | 122.85 | 0.51 | 95.31 | 4.18 |
| 4 | 3 | 25 | 131.41 | 0.49 | 95.73 | 3.78 |
| 1 | 3 | 40 | 127.00 | 1.20 | 92.93 | 5.87 |
| 2 | 3 | 40 | 128.72 | 5.21 | 84.68 | 10.11 |
| 3 | 3 | 40 | 127.76 | 1.95 | 89.45 | 8.59 |
| 4 | 3 | 40 | 130.34 | 2.04 | 89.84 | 8.12 |
| 1 | 3 | 5* | 135.04 | 0.35 | 96.77 | 2.88 |
| 2 | 3 | 5* | 138.72 | 0.48 | 96.37 | 3.15 |
| 3 | 3 | 5* | 130.46 | 0.35 | 96.39 | 3.27 |
| 4 | 3 | 5* | 122.50 | 0.36 | 96.69 | 2.95 |

TABLE 57

Size Exclusion Chromatography Data for T = 6 months

| Form. | Time (Months) | Temp. ° C. | Group Area (mAU * min) | Rel. Area (%) Pre Peak | Rel. Area (%) Main Peak | Rel. Area (%) Post Peak |
|---|---|---|---|---|---|---|
| 1 | 6 | 5 | 33.66 | 0.31 | 96.05 | 3.64 |
| 2 | 6 | 5 | 103.45 | 0.45 | 96.19 | 3.35 |
| 3 | 6 | 5 | 102.38 | 0.30 | 96.16 | 3.54 |
| 4 | 6 | 5 | 98.88 | 0.35 | 96.53 | 3.12 |
| 1 | 6 | 25 | 90.52 | 0.55 | 95.62 | 3.83 |
| 2 | 6 | 25 | 101.30 | 1.21 | 92.71 | 6.09 |
| 3 | 6 | 25 | 100.29 | 0.62 | 94.07 | 5.31 |
| 4 | 6 | 25 | 96.01 | 0.62 | 94.66 | 4.72 |
| 1 | 6 | 5* | 41.91 | 0.25 | 96.36 | 3.39 |
| 2 | 6 | 5* | 101.23 | 0.43 | 96.28 | 3.30 |
| 3 | 6 | 5* | 98.72 | 0.31 | 95.93 | 3.76 |
| 4 | 6 | 5* | 101.56 | 0.35 | 96.51 | 3.13 |

*Sample Inverted

Subvisible Particle Analysis (Flow Cam)

The levels of subvisible particles (SVPs) are measured for these verification samples, as summarized in Table 58. While some samples arrived at GLB in the thawed state, the six-month samples were intact, being shipped on dry ice. The data clearly show a greatly increased level of SVPs for Formulation 1 compared to the other samples. The other three compositions have modest levels of SVPs in the larger size bins, and all within typical USP limits. Possibly, Formulation 3 has slightly lower levels of SVPs, but all were markedly more stable than Formulation 1.

TABLE 58

Flow Cam (Particle Analysis) Data for T = 0 to T = 6 months

| Form. No. | Time (month) | Temp. °C. | GTE 2 μm | GTE 3 μm | GTE 5 μm | GTE 10 μm | GTE 25 μm |
|---|---|---|---|---|---|---|---|
| 1 | 0 | n.a | 6291 | 3394 | 1417 | 588 | 93 |
| 2 | 0 | n.a | 1649 | 622 | 101 | 43 | 29 |
| 3 | 0 | n.a | 21426 | 12136 | 7280 | 2803 | 224 |
| 4 | 0 | n.a | 1820 | 690 | 319 | 216 | 60 |
| 1 | 1 | 5 | 9059 | 4064 | 2111 | 1169 | 249 |
| 2 | 1 | 5 | 5490 | 2420 | 1136 | 288 | 96 |
| 3 | 1 | 5 | 14700 | 2990 | 1091 | 477 | 250 |
| 4 | 1 | 5 | 11989 | 3763 | 1576 | 988 | 311 |
| 1 | 1 | 25 | 15236 | 8509 | 5025 | 2472 | 805 |
| 2 | 1 | 25 | 7226 | 3163 | 1492 | 614 | 63 |
| 3 | 1 | 25 | 15808 | 7182 | 3630 | 2053 | 899 |
| 4 | 1 | 25 | 20007 | 6515 | 2391 | 739 | 335 |
| 1 | 1 | 40 | 22015 | 7995 | 3175 | 1155 | 452 |
| 2 | 1 | 40 | 7396 | 2760 | 833 | 243 | 52 |
| 3 | 1 | 40 | 6337 | 1798 | 713 | 230 | 77 |
| 4 | 1 | 40 | 26202 | 9146 | 3049 | 709 | 360 |
| 1 | 3 | 5 | 19854 | 13183 | 7055 | 2752 | 272 |
| 2 | 3 | 5 | 1140 | 693 | 493 | 308 | 154 |
| 3 | 3 | 5 | 1788 | 556 | 208 | 122 | 17 |
| 4 | 3 | 5 | 3414 | 1750 | 882 | 289 | 87 |
| 1 | 6 | 6 | 255149 | 180089 | 114576 | 39815 | 2386 |
| 2 | 6 | 6 | 6909 | 3280 | 1043 | 235 | 47 |
| 3 | 6 | 6 | 394880 | 49375 | 122 | 122 | 46 |
| 4 | 6 | 6 | 64563 | 22505 | 4476 | 238 | 52 |
| 1 | 6 | 25 | 218383 | 153044 | 100930 | 41656 | 5924 |
| 2 | 6 | 25 | 3354 | 1607 | 835 | 405 | 101 |
| 3 | 6 | 25 | 3118 | 1553 | 645 | 191 | 65 |
| 4 | 6 | 25 | 1067 | 553 | 308 | 193 | 77 |
| 1* | 6 | 5 | 28302 | 18198 | 10970 | 4640 | 695 |
| 2* | 6 | 5 | 1102 | 608 | 350 | 185 | 62 |
| 3* | 6 | 5 | 3661 | 2069 | 1035 | 466 | 159 |
| 4* | 6 | 5 | 1343 | 836 | 518 | 224 | 47 |

*Sample Inverted

Conclusion

Four different formulations of MANP are placed on stability for six months at 5° C., 25° C., and 40° C. There are minimal, if any changes, in visual appearance, peptide content and pH values over the course of the study. Two different HPLC methods are used to monitor stability: RP-HPLC and SEC. MANP is much more sensitive to chemical instability, so RP-HPLC provides the most sensitive and detailed assessment of stability. Those results show that Formulation 4 is the most stable, with Formulation 3 providing almost as good of a stability profile. Both are formulated at pH 5.5 using acetate buffer. Formulation 1 is clearly less stable than the others, which is also seen by SEC. Formulation 1 also displays the highest levels of SVPs as well. Thus, the lead candidate is Formulation 4 containing sucrose as the stabilizer at pH 5.5, with Formulation 3 being the best backup candidate.

EMBODIMENTS

From the foregoing, it will be appreciated that aspects of the disclosure can be embodied in various ways, which include but are not limited to the following:

Embodiment 1: A composition comprising MANP, acetate, sucrose, and polysorbate 20.

Embodiment 2: The composition of embodiment 1, wherein the concentration of MANP is about 2 mg/ml.

Embodiment 3: The composition of embodiment 1, wherein the MANP consists essentially of SEQ ID NO: 1.

Embodiment 4: The composition of embodiment 1, wherein the concentration of acetate is in the range of about 10 mM to about 40 mM.

Embodiment 5: The composition of embodiment 1, wherein the concentration of acetate is about 10 mM.

Embodiment 6: The composition of embodiment 1, wherein the concentration of sucrose is in the range of about 250 mM to about 275 mM.

Embodiment 7: The composition of embodiment 1, wherein the concentration of sucrose is about 275 mM.

Embodiment 8: The composition of embodiment 1, wherein the concentration of polysorbate 20 is about 0.02%.

Embodiment 9: The composition of embodiment 1, wherein the pH is about 5.5.

Embodiment 10: The composition of embodiment 1, wherein the osmolality is about 300-420 mOsm/kgH$_2$O.

Embodiment 11: The composition of embodiment 1, wherein the osmolality is about 310-390 mOsm/kgH$_2$O.

Embodiment 12: A composition comprising MANP, acetate, mannitol, and polysorbate 20.

Embodiment 13: The composition of embodiment 12, wherein the concentration of MANP is about 2 mg/ml.

Embodiment 14: The composition of embodiment 12, wherein the MANP consists essentially of SEQ ID NO: 1.

Embodiment 15: The composition of embodiment 12, wherein the concentration of acetate is in the range of about 10 mM to about 40 mM.

Embodiment 16: The composition of embodiment 12, wherein the concentration of acetate is about 40 mM.

Embodiment 17: The composition of embodiment 12, wherein the concentration of mannitol is in the range of about 250 mM to about 275 mM.

Embodiment 18: The composition of embodiment 12, wherein the concentration of mannitol is about 250 mM.

Embodiment 19: The composition of embodiment 12, wherein the concentration of polysorbate 20 is about 0.02%.

Embodiment 20: The composition of embodiment 12, wherein the pH is about 5.5.

Embodiment 21: The composition of embodiment 12, wherein the osmolality is about 300-420 mOsm/kgH$_2$O.

Embodiment 22: The composition of embodiment 12, wherein the osmolality is about 310-390 mOsm/kgH$_2$O.

Embodiment 23: A composition for use in the treatment of hypertension, comprising MANP, acetate, sucrose, and polysorbate 20.

Embodiment 24: The composition of embodiment 23, wherein the concentration of MANP is about 2 mg/ml.

Embodiment 25: The composition of embodiment 23, wherein the MANP consists essentially of SEQ ID NO: 1.

Embodiment 26: The composition of embodiment 23, wherein the concentration of acetate is in the range of about 10 mM to about 40 mM.

Embodiment 27: The composition of embodiment 23, wherein the concentration of acetate is about 10 mM.

Embodiment 28: The composition of embodiment 23, wherein the concentration of sucrose is in the range of about 250 mM to about 275 mM.

Embodiment 29: The composition of embodiment 23, wherein the concentration of sucrose is about 275 mM.

Embodiment 30: The composition of embodiment 23, wherein the concentration of polysorbate 20 is about 0.02%.

Embodiment 31: The composition of embodiment 23, wherein the pH is about 5.5.

Embodiment 32: The composition of embodiment 23, wherein the osmolality is about 300-420 mOsm/kgH$_2$O.

Embodiment 33: The composition of embodiment 23, wherein the osmolality is about 310-390 mOsm/kgH$_2$O.

Embodiment 34: A composition for use in the treatment of hypertension, comprising MANP, acetate, mannitol, and polysorbate 20.

Embodiment 35: The composition of embodiment 34, wherein the concentration of MANP is about 2 mg/ml.

Embodiment 36: The composition of embodiment 34, wherein the MANP consists essentially of SEQ ID NO: 1.

Embodiment 37: The composition of embodiment 34, wherein the concentration of acetate is in the range of about 10 mM to about 40 mM.

Embodiment 38: The composition of embodiment 34, wherein the concentration of acetate is about 40 mM.

Embodiment 39: The composition of embodiment 34, wherein the concentration of mannitol is in the range of about 250 mM to about 275 mM.

Embodiment 40: The composition of embodiment 34, wherein the concentration of mannitol is about 250 mM.

Embodiment 41: The composition of embodiment 34, wherein the concentration of polysorbate 20 is about 0.02%.

Embodiment 42: The composition of embodiment 34, wherein the pH is about 5.5.

Embodiment 43: The composition of embodiment 34, wherein the osmolality is about 300-420 mOsm/kgH$_2$O.

Embodiment 44: The composition of embodiment 34, wherein the osmolality is about 310-390 mOsm/kgH$_2$O.

Embodiment 45: A pharmaceutical composition, comprising about 2 mg/ml MANP, about 10 mM acetate, about 275 mM sucrose, and about 0.02% polysorbate 20.

Embodiment 46: A pharmaceutical composition, comprising about 2 mg/ml MANP, about 40 mM acetate, about 250 mM mannitol, and about 0.02% polysorbate 20.

Embodiment 47: A pharmaceutical composition, comprising about 2 mg/ml MANP, about 10 mM acetate, about 275 mM sucrose, and about 0.02% polysorbate 20, wherein less than 0.5% of monomers aggregate after 24 months when stored at 2-8° C., as measured by the relative area of the main peak obtained via size exclusion chromatography.

Embodiment 48: A pharmaceutical composition, comprising about 2 mg/ml MANP, about 10 mM acetate, about 275 mM sucrose, and about 0.02% polysorbate 20, wherein the composition loses less than 1% purity after 6 months when stored at 5° C., as measured by the height of the main peak obtained via reversed phase HPLC.

Embodiment 49: The pharmaceutical composition of embodiment 48, wherein the composition loses less than 0.5% purity after 6 months when stored at 5° C., as measured by the height of the main peak obtained via reversed phase HPLC.

Embodiment 50: The pharmaceutical composition of embodiment 48, wherein the composition loses less than 0.2% purity after 6 months when stored at 5° C., as measured by the height of the main peak obtained via reversed phase HPLC.

Embodiment 51: A pharmaceutical composition, comprising about 2 mg/ml MANP, about 10 mM acetate, about 275 mM sucrose, and about 0.02% polysorbate 20, wherein the composition loses less than 10% purity after 12 months when stored at 5° C., as measured by the relative area of the main peak obtained via reversed phase HPLC.

Embodiment 52: The pharmaceutical composition of embodiment 51, wherein the composition loses less than 5% purity after 12 months when stored at 5° C., as measured by the relative area of the main peak obtained via reversed phase HPLC.

Embodiment 53: The pharmaceutical composition of embodiment 51, wherein the composition loses less than 3% purity after 12 months when stored at 5° C., as measured by the relative area of the main peak obtained via reversed phase HPLC.

Embodiment 54: A pharmaceutical composition, comprising about 2 mg/ml MANP, about 10 mM acetate, about 275 mM sucrose, and about 0.02% polysorbate 20, wherein the composition loses less than 10% purity after 24 months when stored at 5° C., as measured by the relative area of the main peak obtained via reversed phase HPLC.

Embodiment 55: The pharmaceutical composition of embodiment 54, wherein the composition loses less than 5% purity after 24 months when stored at 5° C., as measured by the relative area of the main peak obtained via reversed phase HPLC.

Embodiment 56: A pharmaceutical composition, comprising about 2 mg/ml MANP, about 10 mM acetate, about 275 mM sucrose, and about 0.02% polysorbate 20, wherein the composition loses less than 0.2% purity after 12 months when stored at 5° C., as measured by the relative area of the main peak obtained via size exclusion chromatography.

Embodiment 57: The pharmaceutical composition of embodiment 56, wherein the composition loses less than 0.18% purity after 12 months when stored at 5° C., as measured by the relative area of the main peak obtained via size exclusion chromatography.

Embodiment 58: A pharmaceutical composition, comprising about 2 mg/ml MANP, about 10 mM acetate, about 275 mM sucrose, and about 0.02% polysorbate 20, wherein the composition loses less than 0.5% purity after 24 months when stored at 5° C., as measured by the relative area of the main peak obtained via size exclusion chromatography.

Embodiment 59: The pharmaceutical composition of embodiment 58, wherein the composition loses less than 0.35% purity after 24 months when stored at 5° C., as measured by the relative area of the main peak obtained via size exclusion chromatography.

Embodiment 60: A composition comprising MANP, a buffer, a stabilizer/tonicity agent, and a non-ionic surfactant.

Embodiment 61: The composition of embodiment 60, wherein the buffer is selected from the group consisting essentially of acetate, acetic acid, alanine, arginine, aspartic acid, bicarbonate, bicine, carbonate, citrate, citric acid, glycine, glycylglycine, glutamic acid, histidine, lysine, malic acid, potassium phosphate, sodium acetate, sodium citrate, sodium dihydrogen phosphate, disodium hydrogen phosphate, sodium phosphate, sodium succinate, succinic acid, sulphate, nitrate, maleic acid, fumaric acid, tartaric acid, aspartic acid, tricine, tris(hydroxymethyl)-aminomethane, and tromethamine.

Embodiment 62: The composition of embodiment 61, wherein the buffer is acetate.

Embodiment 63: The composition of embodiment 62, wherein the concentration of acetate is in the range of about 10 mM to 40 mM.

Embodiment 64: The composition of embodiment 62, wherein the concentration of acetate is about 10 mM.

Embodiment 65: The composition of embodiment 62, wherein the concentration of acetate is about 40 mM.

Embodiment 66: The composition of embodiment 60, wherein the stabilizer/tonicity agent is selected from the group consisting essentially of albumin, arginine, Brij 30, Brij 35, dextrose, dimethylsulfon, ethylenediaminetetraacetic acid, glycerol, glycerin, glycine, guanine, hydroxypropyl-b-cyclodextrin, lactose monohydrate, magnesium chloride, maltose, mannitol, methionine, 2-methylthioethanol, monothioglycerol, myo-inositol, potassium chloride, polaxamers, polyethylene glycols, polysorbate 20, polysorbate 80, polyvinyl alcohol, polyvinylpyrrolidone, propylene glycol, protamine sulfate, sodium chloride, sorbitol, sucrose, thioglycolic acid, trehalose, and Triton.

Embodiment 67: The composition of embodiment 60, wherein the stabilizer/tonicity agent is sucrose.

Embodiment 68: The composition of embodiment 67, wherein the concentration of sucrose is about 275 mM.

Embodiment 69: The composition of embodiment 60, wherein the stabilizer/tonicity agent is mannitol.

Embodiment 70: The composition of embodiment 69, wherein the concentration of mannitol is about 250 mM.

Embodiment 71: The composition of embodiment 60, wherein the non-ionic surfactant is selected from the group consisting essentially of behenoyl polyoxylglycerides, polysorbate 20, polysorbate 40, docusate sodium, polysorbate 60, polysorbate 80, benzalkonium chloride, caprylocaproyl polyoxylglycerides, cetylpyridinium chloride, lauroyl polyoxylglycerides, linoleoyl polyoxylglycerides, octoxynol 9, oleoyl polyoxylglycerides, poloxamer, polyoxyl 10 oleyl ether, polyoxyl 15 hydroxystearate, nonoxynol 9, polyoxyl 20 cetostearyl ether, polyoxyl 40 stearate, pullulan, polyoxyl lauryl ether, polyoxyl stearyl ether, sodium lauryl sulfate, sorbitan monolaurate, sorbitan monooleate, polyoxyl stearate, sorbitan monopalmitate, sorbitan monostearate, stearoyl polyoxylglycerides, sorbitan sesquioleate, sorbitan trioleate, and tyloxapol.

Embodiment 72: The composition of embodiment 60, wherein the non-ionic surfactant is polysorbate 20.

Embodiment 73: The composition of embodiment 71, wherein the concentration of polysorbate 20 is about 0.2%.

Embodiment 74: The composition of embodiment 60, wherein the pH is about 5.5.

Embodiment 75: The composition of embodiment 60, wherein the osmolality is about 300-420 mOsm/kgH$_2$O.

Embodiment 76: The composition of embodiment 60, wherein the osmolality is about 310-390 mOsm/kgH$_2$O.

Embodiment 77: A vial containing a formulation comprising MANP, acetate, sucrose, and polysorbate 20.

Embodiment 78: The vial of embodiment 77, wherein the concentration of MANP is about 2 mg/ml.

Embodiment 79: The vial of embodiment 77, wherein the MANP consists essentially of SEQ ID NO: 1.

Embodiment 80: The vial of embodiment 77, wherein the concentration of acetate is in the range of about 10 mM to about 40 mM.

Embodiment 81: The vial of embodiment 77, wherein the concentration of acetate is about 10 mM.

Embodiment 82: The vial of embodiment 77, wherein the concentration of sucrose is about 275 mM.

Embodiment 83: The vial of embodiment 77, wherein the concentration of polysorbate 20 is about 0.02%.

Embodiment 84: The vial of embodiment 77, wherein the pH is about 5.5.

Embodiment 85: The vial of embodiment 77, wherein the osmolality is about 300-420 mOsm/kgH$_2$O.

Embodiment 86: The vial of embodiment 77, wherein the osmolality is about 310-390 mOsm/kgH$_2$O.

Embodiment 87: A lyophilized powder made according to the steps of:
  (a) combining in a liquid solution: MANP, acetate, sucrose, and polysorbate 20; and
  (b) lyophilizing the combination of step (a)

Embodiment 88: The lyophilized powder of embodiment 87, wherein the concentration of MANP in the liquid composition is about 2 mg/ml.

Embodiment 89: The lyophilized powder of embodiment 87, wherein the MANP consists essentially of SEQ ID NO: 1.

Embodiment 90: The lyophilized powder of embodiment 87, wherein the concentration of acetate in the liquid composition is in the range of about 10 mM to about 40 mM.

Embodiment 91: The lyophilized powder of embodiment 87, wherein the concentration of acetate in the liquid composition is about 10 mM.

Embodiment 92: The lyophilized powder of embodiment 87, wherein the concentration of sucrose in the liquid composition is in the range of about 250 mM to about 275 mM.

Embodiment 93: The lyophilized powder of embodiment 87, wherein the concentration of sucrose in the liquid composition is about 275 mM.

Embodiment 94: The lyophilized powder of embodiment 87, wherein the concentration of polysorbate 20 in the liquid composition is about 0.02%.

Embodiment 95: The lyophilized powder of embodiment 87, wherein the pH of the liquid composition is about 5.5.

Embodiment 96: The lyophilized powder of embodiment 87, wherein the osmolality of the liquid composition is about 300-420 mOsm/kgH$_2$O.

Embodiment 97: The lyophilized powder of embodiment 87, wherein the osmolality of the liquid composition is about 310-390 mOsm/kgH$_2$O.

Embodiment 98: A lyophilized powder made according to the steps of:
  a. combining in a liquid solution: MANP, acetate, mannitol, and polysorbate 20; and
  b. lyophilizing the combination of step (a).

Embodiment 99: The lyophilized powder of embodiment 98, wherein the concentration of MANP in the liquid composition is about 2 mg/ml.

Embodiment 100: The lyophilized powder of embodiment 98, wherein the MANP consists essentially of SEQ ID NO: 1.

Embodiment 101: The lyophilized powder of embodiment 98, wherein the concentration of acetate in the liquid composition is in the range of about 10 mM to about 40 mM.

Embodiment 102: The lyophilized powder of embodiment 98, wherein the concentration of acetate in the liquid composition is about 40 mM.

Embodiment 103: The lyophilized powder of embodiment 98, wherein the concentration of mannitol in the liquid composition is in the range of about 250 mM to about 275 mM.

Embodiment 104: The lyophilized powder of embodiment 98, wherein the concentration of mannitol in the liquid composition is about 250 mM.

Embodiment 105: The lyophilized powder of embodiment 98, wherein the concentration of polysorbate 20 in the liquid composition is about 0.02%.

Embodiment 106: The lyophilized powder of embodiment 98, wherein the pH of the liquid composition is about 5.5.

Embodiment 107: The lyophilized powder of embodiment 98, wherein the osmolality of the liquid composition is about 300-420 mOsm/kgH$_2$O.

Embodiment 108: The lyophilized powder of embodiment 98, wherein the osmolality of the liquid composition is about 310-390 mOsm/kgH$_2$O.

Embodiment 109: A dry powder composition comprising MANP, acetate, sucrose, and polysorbate 20.

Embodiment 110: A powder made by spray drying, wherein the spray drying comprises the steps of:
a. providing a liquid comprising MANP, acetate, sucrose, and polysorbate 20; and
b. spray-drying the liquid of step (a) with a spray-drying device.

Embodiment 111: A lyophilized powder made by freeze-drying, wherein the freeze-drying comprises the steps of:
a. providing a liquid comprising MANP, acetate, sucrose, and polysorbate 20; and
b. freeze-drying the liquid of step (a) at a temperature for a length of time sufficient to transform the liquid formation into a solid state.

Embodiment 112: A lyophilized powder made by a method comprising the steps of:
a. providing a liquid comprising MANP, acetate, sucrose, and polysorbate 20; and
b. lyophilizing the liquid of step (a).

Embodiment 113: A pre-filled syringe containing MANP, acetate, sucrose, and polysorbate 20.

Embodiment 114: The pre-filled syringe of embodiment 113, wherein the concentration of MANP is about 2 mg/ml.

Embodiment 115: The pre-filled syringe of embodiment 113, wherein the MANP consists essentially of SEQ ID NO: 1.

Embodiment 116: The pre-filled syringe of embodiment 113, wherein the concentration of acetate is in the range of about 10 mM to about 40 mM.

Embodiment 117: The pre-filled syringe of embodiment 113, wherein the concentration of acetate is about 10 mM.

Embodiment 118: The pre-filled syringe of embodiment 113, wherein the concentration of sucrose is about 275 mM.

Embodiment 119: The pre-filled syringe of embodiment 113, wherein the concentration of polysorbate 20 is about 0.02%.

Embodiment 120: The pre-filled syringe of embodiment 113, wherein the pH is about 5.5.

Embodiment 121: The pre-filled syringe of embodiment 113, wherein the osmolality is about 300-420 mOsm/kgH$_2$O.

Embodiment 122: The pre-filled syringe of embodiment 113, wherein the osmolality is about 310-390 mOsm/kgH$_2$O.

While the invention has been described with reference to particular aspects, it will be understood by those skilled in the art that various changes may be made and equivalents may be substituted for elements thereof without departing from the scope of the invention. In addition, many modifications may be made to a particular situation or material to the teachings of the invention without departing from the scope of the invention. Therefore, it is intended that the invention not be limited to the particular aspects disclosed but that the invention will include all aspects falling within the scope and spirit of the appended claims.

---

---

The invention claimed is:

1. A pharmaceutical composition, comprising about 2 mg/ml modified atrial natriuretic peptide (MANP), about 10 mM acetate, about 275 mM sucrose, and about 0.02% polysorbate 20, wherein the pH is 4.4-6.6.

2. The pharmaceutical composition of claim 1, wherein the MANP consists essentially of SEQ ID NO: 1.

3. The pharmaceutical composition of claim 1, wherein the pH is 4.4-4.6 about 5.5.

4. The pharmaceutical composition of claim 1, wherein the osmolality is about 300-420 mOsm/kgH$_2$O.

5. The pharmaceutical composition of claim 1, wherein the osmolality is about 310-390 mOsm/kgH$_2$O.

6. The pharmaceutical composition of claim 1, wherein the pH is 4.6-4.8.

7. The pharmaceutical composition of claim 1, wherein the pH is 4.8-5.0.

8. The pharmaceutical composition of claim 1, wherein the pH is 5.0-5.5.

9. The pharmaceutical composition of claim 1, wherein the pH is 5.5-6.0.

10. The pharmaceutical composition of claim 1, wherein the pH is 4.5.

11. The pharmaceutical composition of claim 1, wherein the pH is 5.0.

12. The pharmaceutical composition of claim 1, wherein the pH is 5.5.

13. A vial containing a formulation comprising about 2 mg/ml modified atrial natriuretic peptide (MANP), about 10 mM acetate, about 275 mM sucrose, and about 0.02% polysorbate 20, wherein the pH is 4.4-6.6.

14. The vial of claim 13, wherein the MANP consists essentially of SEQ ID NO: 1.

15. The vial of claim 13, wherein the pH is 4.4-4.6.

16. The vial of claim 13, wherein the osmolality is about 300-420 mOsm/kgH$_2$O.

17. The vial of claim 13, wherein the osmolality is about 310-390 mOsm/kgH$_2$O.

18. The vial of claim 13, wherein the pH is 4.6-4.8.

19. The vial of claim 13, wherein the pH is 4.8-5.0.

20. The vial of claim 13, wherein the pH is 5.0-5.5.

21. The vial of claim 13, wherein the pH is 5.5-6.0.

22. A pre-filled syringe containing about 2 mg/ml modified atrial natriuretic peptide (MANP), about 10 mM acetate, about 275 mM sucrose, and about 0.02% polysorbate 20, wherein the pH is 4.4-6.6.

23. The pre-filled syringe of claim 22, wherein the MANP consists essentially of SEQ ID NO: 1.

24. The pre-filled syringe of claim 22, wherein the pH is 4.4-4.6.

25. The pre-filled syringe of claim 22, wherein the pre-filled syringe is configured as an injection device with an auto-injector.

26. The pre-filled syringe of claim 22, wherein the osmolality is about 310-390 mOsm/kgH$_2$O.

27. The pre-filled syringe of claim 22, wherein the pH is 4.6-4.8.

28. The pre-filled syringe of claim 22, wherein the pH is 4.8-5.0.

29. The pre-filled syringe of claim 22, wherein the pH is 5.0-5.5.

30. The pre-filled syringe of claim 22, wherein the pH is 5.5-6.0.

31. A method of treating hypertension in a patient in need thereof, comprising administering to said patient a composition comprising about 2 mg/ml modified atrial natriuretic peptide (MANP), about 10 mM acetate, about 275 mM sucrose, and about 0.02% polysorbate 20, wherein the pH is 4.4-6.6.

32. The method of claim 31, wherein the MANP consists essentially of SEQ ID NO: 1.

33. The method of claim 31, wherein the pH is 4.4-4.6.

34. The method of claim 31, wherein the osmolality is about 300-420 mOsm/kgH$_2$O.

35. The method of claim 31, wherein the osmolality is about 310-390 mOsm/kgH$_2$O.

36. The method of claim 31, wherein the pH is 4.6-4.8.

37. The method of claim 31, wherein the pH is 4.8-5.0.

38. The method of claim 31, wherein the pH is 5.0-5.5.

39. The method of claim 31, wherein the pH is 5.5-6.0.

* * * * *

UNITED STATES PATENT AND TRADEMARK OFFICE
CERTIFICATE OF CORRECTION

PATENT NO. : 12,427,185 B2
APPLICATION NO. : 18/824445
DATED : September 30, 2025
INVENTOR(S) : Jesse Crowne et al.

Page 1 of 1

It is certified that error appears in the above-identified patent and that said Letters Patent is hereby corrected as shown below:

In the Claims

In Claim 3, Column 89, Lines 49-50 should read:
3. The pharmaceutical composition of claim 1, wherein the pH is 4.4-4.6.

Signed and Sealed this
Eleventh Day of November, 2025

John A. Squires
*Director of the United States Patent and Trademark Office*